(12) United States Patent
Duvick et al.

(10) Patent No.: US 6,639,132 B1
(45) Date of Patent: Oct. 28, 2003

(54) ALTERED FATTY-ACID, PROTEIN, OIL, AND STARCH CORN LINES AND METHOD FOR PRODUCING SAME

(75) Inventors: Susan A. Duvick, Madrid, IA (US); Linda M. Pollak, Guthrie Center, IA (US); Pamela J. White, Ames, IA (US)

(73) Assignees: The United States of America as represented by the Secretary of Agriculture, Washington, DC (US); Iowa State University Research Foundation, Ames, IA (US)

( * ) Notice: Subject to any disclaimer, the term of this patent is extended or adjusted under 35 U.S.C. 154(b) by 0 days.

(21) Appl. No.: 09/285,368

(22) Filed: Apr. 2, 1999

Related U.S. Application Data

(60) Provisional application No. 60/080,406, filed on Apr. 2, 1998.

(51) Int. Cl.$^7$ .............................. A01H 5/00; A01H 5/10; A01H 1/00; C12N 5/04

(52) U.S. Cl. .................... 800/320.1; 800/263; 800/264; 800/269; 800/270; 800/275; 435/412; 435/421; 435/424; 435/430; 435/430.1

(58) Field of Search .............................. 800/320.1, 269, 800/270, 275, 264, 263; 435/412, 421, 424, 430, 430.1

(56) References Cited

U.S. PATENT DOCUMENTS 5,082,991 A * 1/1992 Cavanah .................... 800/320.1
5,330,547 A * 7/1994 Eubanks et al. ................ 47/58

FOREIGN PATENT DOCUMENTS

WO    WO 92/01367    * 2/1992   ............ A01H/1/02

OTHER PUBLICATIONS

Bates et al. 1974. Wide Crosses. pp 5–1B to 5–7B, In: Proc. of World–Wide Maize Improvement in the &0's and the Role of CIMMT, Apr. 22–26, CIMMYT, El Batan, Mexico.*
Eubanks et al. 1995. A cross between two maize relatives: Tripsacum dactyloides and Zea diploperennis. Economic Botany 49(2):172–182.*
Eubanks et al. 1997. Molecular analysis of crosses between Tripsacum dactyloides and Zea diploperennis. Theor. Appl. Genet. 94:707–712.*
Harlan et al. 1977. Pathways of genetic transfer from Tripsacum to Zea mays. Proc. Natl. Acad. Sci. (USA) 74(8)3494–3497.*
Galinat et al. 1977. The origin of corn. Pp27–39, In: Corn and corn improvement. Agronomy Monograph No. 18. Ed. G.F. Sprague. American Soc. of Agronomy, Madison, WI.*
Kraft et al. 2000. Linkage disequilibrium in sugarbeet. Theor. Appl. Genet. 101:323–326.*
Viands et al. 1988. Chapter 30, Pollination control: mechanical and sterility. pp 931–960, In: Alfalfa and alfalfa improvement, Agronomy Monograph No. 29. Crop Sci. Soc. of America, Madison, WI.*
Eshed et al. 1996. Less–than–additive epistatic interactions of quantitative trait loci in tomato. Genetics 143:1807–1817.*
Lubberstedt et al. 1997. QTL mapping in testcrosses of European flint lines of maize. II. Comparison of different testers fro forage quality traits. Crop Sci. 37:1913–1922.*
Watson et al. 1975. Breeding corn for increased oil content. Proc. 13$^{th}$ Annual Corn and Sorghum Res. Conf 30:251–275.*
Weber et al. 1975. Breeding for lipid composition in corn. J. Am. Oil Chem Soc. 52(9):370–373.*
Berthaud et al. 1989. Genetic resources and gene transfer to maize. Pp 121–131, In:2nd International Symposium on Genetic Manipulation in Crops, Aug. 29–31, 1998, El batan, Mexico. International Maize and Wheat Improvement Center, Lisboa Mexico.*
Kindiger, B., et al., "Cytological Evidence Supporting a Procedure for Directing and Enhancing Pairing Between Maize and Tripsacum", *Genome*, 1990, vol. 33, pp. 495–500.
Branson, T. F., et al., "Potential for Utilizing Resistance fromRelatives of Cultivated Crops" Proceed. North Central Branch–ESA, 1972, vol. 27, pp. 91–94.

(List continued on next page.)

*Primary Examiner*—David T. Fox
(74) *Attorney, Agent, or Firm*—John D. Fado; Curtis P. Ribando

(57) ABSTRACT

Improved corn lines having high protein and/or oil content and a method for producing such a lines. In another embodiment, improved corn lines having high oleic fatty-acid content, and/or either elevated or lowered saturated fat content, and a method for producing such a lines. In yet another embodiment, improved corn lines having a starch composition including starch components having a lower peak onset, having lower or higher enthalpy of gelatinization (cal/g), having lower or higher range of gelatinization (° C.), and/or having lower or higher percentage retrogradation. According to the present invention, new genes are introduced from a novel source, viz. *Tripsacum dactyloides L.*, into the Corn-Belt genome or other conventional corn lines and thus the genetic diversity is increased and germplasm and value-added trait enhancement are allowed through traditional plant breeding practices. Introgression merges Tripsacum genetic material into the corn breeding stock. Selection for lines having desired characteristics from the corn lines as well as having improved protein, oil, and/or starch characteristics provides the improved breeding stock of the present invention. In one embodiment, selection is based on near-infrared reflectance measurement of protein, oil, and/or starch of seed. In another embodiment, selection is based on differential scanning calorimetry measurement of starch thermal characteristics. In yet another embodiment, selection is based on gas chromatographic measurement of fatty-acid oil composition of seed. In some embodiments, particular types of fatty acids are selected for in the breeding process.

21 Claims, 8 Drawing Sheets

OTHER PUBLICATIONS

Farquharson, L. I. (1957), "Hybridization of Tripsacum and Zea", Journal of Heredity, vol. 40, pp. 295–299.

Galinat, Walton C., "Chapter 1 The Origin of Corn", *Corn and Corn Improvement* #18 Agronomy, Am. Soc. of Agron. 1977, pp. 1–47.

Poehlman, J. M., "18 Breeding Corn (Maize)", *Breeding Field Crops*, 3rd Ed., AVI Pub. Co., Inc., 1987, pp. 451–453.

MacNeish, R. S., "The Origins of New World Civilization", *Plant Agriculture* with Freeman and Co., 1964 pp. 13–21.

Mangelsdorf, P. C., "Corn Its Origin Evolution and Improvement", 1974, TheBelknap Press of Howard University Press, Cambridge, Mass. pp. 58–70.

Pasupaleti, G. V., et al., "The Cytology of the Trigernomic Hybrid", Maize Genetics Cooperation Newsletter 60, 1986, p. 133.

* cited by examiner

ALTERED FATTY-ACID, PROTEIN, OIL, AND STARCH CORN LINES AND METHOD FOR PRODUCING SAME

This application claims the benefit of provisional Application No. 60/080,406, filed Apr. 2, 1998.

FIELD OF THE INVENTION

This invention relates to the field of corn plants, and more specifically to improved corn lines having improved nutrative content and to a method for producing such lines.

BACKGROUND OF THE INVENTION

Corn is the major crop on the cultivated land of the United States, where over 70 million acres were planted in 1995. U.S. corn production, accounting for about half of the world's annual production, added over $23.5 billion of value to the American economy in 1995 as a raw material. Products derived from corn are used for human consumption, as raw material for industry and as raw material for the production of ethanol. The primary use of farmer-produced field corn is as livestock feed. This includes feed for hogs, beef cattle, dairy cows and poultry. About 60 percent of corn production is used for feeding livestock and poultry. A small increase in value to this 60% segment of the corn market, such as an increase of 10 cents per bushel, would increase its annual value by $480 million for an eight-billion bushel total corn harvest.

Human consumption of corn includes direct consumption of sweet corn, and consumption of processed-corn products such as cereals and snacks whose manufacture involves extruder cooking (e.g., Cheetos™), ground corn eaten as grits, corn meal and corn flour. Corn oil is also used as a high-grade cooking oil and salad oil, and in margarine. Corn is used in the production of some starches, sugars (e.g., fructose) and syrups. Another important use is in the production of sweeteners, such as corn syrup used in soft drinks.

Wet-milling and dry-milling processes also produce corn starch and corn flour that have applications in industry. These include use as elements of building materials, and in products used in the paper industry and in the manufacture of textiles and starches.

The seed of an inbred corn line, the plant produced by the inbred seed, hybrid seed produced from the crossing of the inbred to another inbred, the hybrid corn plant grown from said seed, and various parts of the inbred and hybrid corn plant can thus be utilized for human food, livestock feed, and as a raw material in industry.

Theories About the Origin of Corn

According to Dr. Beryl B. Simpson of the University of Texas at Austin, there are three main theories on the origin of corn.

1. Tripartite Theory (Mangelsdorf):

The Tripartite Theory suggested in 1939 by Mangelsdorf (Mangelsdorf, P. C. and Reeves, R. G., 1939, The origin of Indian corn and its relatives, Texas Agric. Exp. Stn. Bull. 574:1–315) stated:
  A. The ancestor of cultivated maize was both a popcorn and a pod corn. (This point has been borne out by the archaeological record.)
  B. Teosinte is not the direct ancestor of maize but instead a taxon produced by hybridization of maize and Tripsacum.

This point in Mangelsdorf's original tripartite theory is controverted by more recent findings indicating that annual teosinte resulted from a hybridization between maize and perennial teosinte *Zea diploperennis*.
  C. Many modern varieties of maize have undergone genetic introgression from teosinte or Tripsacum or, both either directly or via hybridization with other land races that hold different and distinct genetic blocks or DNA sequences. (Introgression involves incorporation of foreign genetic material into a line of breeding stock.) This notion of the role of introgression has greatly increased understanding of racial variation in maize.

2. "Teosinte as an Ancestor" Hypothesis (Galinat, Beadle)

In this theory, the female "cob" of teosinte became the cob of modern corn and the male inflorescence (tassel) of teosinte is the equivalent of the modern tassel of corn. Galinat has suggested that the differences between corn and teosinte can be reduced to three distinguishing features that separate the teosinte ear from that of a maize cob: a single spikelet per cupule versus two kernels in each cupule in maize, a two-ranked arrangement in teosinte (but appearing single by abortion in the "cob") as opposed to many-ranked (multiple rows of kernels) in maize, and shattering rachis (cob) in teosinte vs. fused rachis (cob) in maize. The changes in teosinte that led to maize are a consequence of both lateral branch condensation (reduction) and genetic mutations that were favored by humans in the process of domestication.

Galinat has proposed a series of stages leading from teosinte to the primitive maize cob. He discovered them by studying the anatomical origin of the cupule in the maize cob and by breeding teosinte against a background of Nal-Tel corn. Further breeding of the F2 population with teosinte and Nal-Tel resulted in an assorted group of plants including potential ancestral forms. Doebley has recently demonstrated the numbers and locations of the genes responsible for the major differences between corn and teosinte. There are five major genes and some pleiotropic genes involved.

3. CSTT or Catastrophic Sexual Transmutation Theory (Iltis)

According to this theory devised by Hugh Iltis, the modern corn cob is a transformed male teosinte rachis. The socket for the male flower evolved into a cupule to provide support for two developing kernels. Each teosinte spikelet consists of a pair of a fertile and a sterile floret. In the process of sexual transformation, the sterile floret became sexual again, producing two kernels (two-ranked) in each cupule leading to an expressed two-ranked condition. The size of the cob can expand because the male tassel has numerous rachises holding the florets (teosinte fruits are single ranked and pressed to the single rachis). As each tassel branch becomes fertile a longer cob is possible. Furthermore, the initial cob should have four kernel rows as a result of the alternation of floral segments. If these twist around, then the row number increases as the ear becomes more compact. None of these morphological changes require new genes, merely a switch in the development pattern—a switch that is sometimes seen in abnormal corn male tassels.

Recently Etis has modified his view of the "transformation" of male into female inflorescences (still Catastrophic Sexual Transmutation Theory). However, John Doebley has genetic data that show which genes control the characters that cause the differences in the ears of teosinte and maize.

Corn Breeding

Modern commercial corn is generally a hybrid maize plant (*Zea mays L.*) grown from seed of a cross of two inbred lines. Other sources of corn have been neglected because of the vastly superior yield that has developed over time by various breeding programs. Typically, a modern maize inbred line is self-pollinated, sib-crossed, and/or back-crossed in order to concentrate reliably inheritable characteristics into that inbred line.

According to U.S. Pat. No. 5,728,922 issued Mar. 17, 1998 to Albert R. Hornbrook (which is incorporated herein by reference), maize is a highly variable species. For hundreds of years, maize breeding consisted of isolation and selection of open-pollinated varieties. Native Americans developed many different varieties since the domestication of maize in prehistory. Theories about such domestication are described above. During the course of the nineteenth century, North American farmers and seedsmen developed a wide array of open-pollinated varieties, many of which resulted from an intentional or an accidental cross between two very different types of maize: the Southern Dents, which resemble varieties still grown in Mexico, and the Northern Flints, which seem to have moved from the Guatemalan highlands into the northerly parts of the United States and into Canada. The open-pollinated varieties which were developed during this time were maintained by selection of desirable ears from within the variety for use as foundation seed stock. The only pollination control which was practiced to generate the seed was isolation of the seed crop from pollen from other varieties. Experimentation with inbreeding in open-pollinated varieties showed that it invariably led to a marked reduction in plant vigor and stature, as well as in productivity.

In the early twentieth century, researchers discovered that vigor was restored when an inbred line from an open-pollinated variety was crossed to another, usually unrelated, inbred line, and that the resulting hybrids were not only more uniform than open-pollinated varieties, but in many cases were more productive as well. Many of the inbreds developed from open-pollinated varieties were remarkably unproductive, however, which made F1 seed quite expensive to produce in any volume. By the 1930's seedsmen were offering four-way (or double) crosses to growers. These consisted of a cross between two single crosses, which in turn were each crosses between two inbred lines. In this way, only a small quantity of single-cross seed was required, and the seed sold to growers was produced on F1 hybrids. Four-way crosses dominated the seed industry until the late 1950's, when three-way crosses were offered to growers, consisting of seed produced on a single-cross hybrid with an inbred line as the pollinator. Through the efforts of public and private maize breeders, inbred lines were selected to be more productive and vigorous than the earlier selections from the open-pollinated varieties, and by the early 1970's, single-cross seed was readily available to growers. Presently, the overwhelming majority of hybrid corn seed sold in the United States is single-cross maize seed.

Among the major reasons for the economic importance of corn and the large acreages planted with the crop are the successful hybridization of the maize plant and the continued improvement, by researchers, of the genetic stock that is used to produce the seed grown by farmers. This process has been on-going since its beginning in the early part of the century. The average bushel-per-acre yield for the American farmer has gone from around 30 in the middle of the 1930's (before hybrids became dominant) to the present average of close to 120. While not all of this four-fold increase can be attributed to genetic improvement (availability of relatively cheap nitrogen and improvements in farming practices are two other components), a good share of it can.

The physical structure of the maize plant provides the maize breeder with opportunities either to cross a plant with another plant or to self-pollinate a given plant. Since the male inflorescence (the tassel) and the female inflorescence (the ear) are physically separated from each other on the plant, the breeder has the ability to mate plants as desired with relative ease. Similar physical manipulations are used both for cross-pollinating and for self-pollinating a maize plant. The silks (stigmae of maize female florets) are protected from pollination until pollen is collected from the male inflorescence. For cross-pollination, pollen from one plant is distributed on the silks of another plant, while for self-pollination, pollen from a plant is distributed on silks of the same plant. Sib-pollination is a type of cross-pollination in which both plants are closely related genetically. Cross-pollinating and self-pollinating techniques are used in the development of inbreds which, when crossed, produce seed of commercially available maize hybrids. Self-pollination and sib-pollination increase the level of inbreeding in progeny plants, leading to fixation of alleles.

With continued inbreeding comes a large reduction in vigor and productivity. This phenomenon is know as inbreeding depression. The progeny from the crossing of two inbred lines is a first-generation (F1) hybrid, which has better productivity and agronomic characteristics than either of the inbred parents. This phenomenon is called hybrid vigor or heterosis. Heterosis is reduced markedly in succeeding generations (F2, F3, etc.), making it economically justifiable for the farmer to obtain F1 seed each year for planting. As a result, the hybrid maize seed industry benefits both farmers and producers of hybrid maize seed.

The method of hybridization in maize first involves the development of inbred lines. Inbred lines are commonly developed through some variation of pedigree breeding, wherein the plant breeder maintains the identity of each new line throughout the inbreeding process. To initiate the pedigree breeding process, the breeder may make an F1 cross between two existing inbred lines which complement each other for traits for which improvement is desired, and which cross well with other inbreds from other genetic backgrounds to make commercial hybrids. The F1 is selfed to provide F2 seed (also called the S1 seed), which is planted and selfed to produce the S2 or F3 generation. S2 lines are planted ear-to-row, and self-pollinations are made within individual rows. Rows which do not provide a desirable phenotype are discarded. Selected ears are planted ear-to-row, and this process repeats until substantial homozygosity is attained, usually by the S6 or S7 generation. Once homozygosity is attained, the inbred can be maintained in open-pollinated isolations. At some point during the breeding process, the inbred lines are crossed to a tester inbred line of a different genetic background and evaluated in replicated yield tests. Lines that result in inferior crosses with the tester inbred line are discarded.

Maize breeders, in general, structure their efforts to take advantage of known heterotic patterns; that is, they use their knowledge of which inbreds make good hybrids with which other inbreds, and they ensure that genetic material from these heterotic pools does not cross over into opposing pools. A highly successful heterotic pattern in the United States Corn-Belt has been to use lines from a population known as Iowa Stiff Stalk Synthetic crossed with lines having more or less of a Lancaster background to provide hybrids for growers (Lancaster was a relatively unimportant open-pollinated variety, until it was discovered in the early years of inbred/hybrid development that it provided an outstanding source of lines with good general combining ability). Other heterotic patterns have also been developed, primarily for the northern and southern regions of the United States. Breeders have understandably been reluctant to use competitive private company hybrids as source material, because, in such instances, usually it will not be known where derived lines fit in a heterotic pattern (Hallauer et al., "Corn Breeding", Corn and Corn Improvement pp. 463–564, (1988)). As well, using competitors' hybrids as source germplasm risks the dispersal of existing heterotic patterns: many breeders feel that introducing, for example, Lancaster material into an Iowa Stiff Stalk background would lessen their ability to develop lines which could be crossed to Lancaster-derived inbreds. Unless it is known that a competitor's hybrid was genetically distinct from a breeder's own material, it is considered to be a more risky approach to improvement of a heterotic pool than utilizing known material.

While a maize breeder might anticipate that a source population is capable of providing a certain degree of variation, that variation first has actually to occur, and then to be identified by the breeder. Most variants are expected to fall between the parental values for any given trait; only very exceptional individuals will exceed the better parent (or be worse than the worse parent) for a trait. This is especially true when a trait is determined by a large number of genes, each having a relatively small effect on the trait. Most traits of interest to the maize breeder, including productivity, maturity, and stalk and root quality, are such traits. To complicate matters further, high negative correlations occur in maize between productivity, maturity, and stalk quality. A breeder may be able to improve yield, but at the expense of stalk quality or later maturity. The occurrence of an individual with a combination of superior traits is very rare. Even if the individual does occur in a sample of the source population, the breeder often lacks the resources required to identify that individual. Traits of low heritability, such as productivity, must be evaluated in several locations to be accurately evaluated. Only a very limited number of genotypes can be tested because of constraints upon resources. Thus, a breeder may miss the desired individual, simply because he cannot evaluate all genotypes produced by the source population.

A valuable lesson was learned years ago about the expectation of the success of progeny improvement methods. The inbred Wf9 was developed in Indiana, and released to seed growers in the mid-1930's. Despite having several agronomic deficiencies, it became the most widely used inbred during the double-cross era of maize seed production. It naturally became the basis for numerous public improvement projects. Despite having abundant resources applied to the objective of developing an improved Wf9, no inbred from the public sector with a Wf9 background ever supplanted Wf9 in seed-production fields. A similar story can be told about A632, at one time the predominant seed line for Northern Corn-Belt hybrids. Many public breeders tried to improve on A632, but no A632-derived line from the public sector achieved the prominence of A632, and it was eventually supplanted by a completely unrelated inbred. More recently, B73 improvement programs have been tried, and a number of B73-derived progenies have been commercially accepted. Many modern stiff-stalk commercial lines are improved B73's, at least for pest resistance.

The objective of a plant breeder when developing a new inbred line of maize is to combine the highest number of desirable alleles into a single isolate as possible. No parent line contains all desirable alleles at all loci, and the breeder hopes to introgress a higher frequency of favorable alleles into resulting progenies. However, with the current state of the art, a breeder is generally not able to define which allele at any given locus is desirable, and for most traits of interest, he does not have information about which genetic loci are involved in influencing the trait. His primary tool to measure the genotypes of progenies is phenotypic evaluation. The phenotype of a plant is influenced both by its genotype and the environment in which it is grown, so the phenotypic measure of a plant is only an indirect measure of its genotype. When environmental effects are large relative to the genotypic effects, it is said that the trait has low heritability. The breeder must evaluate traits of low heritability in many different environments in order to be reasonably sure that he has an accurate estimate of the genotypic effect. Productivity of marketable grain is such a trait, according to years of breeding experience and numerous scientific publications.

The requirement of evaluating genotypes in different environments places serious restraints on the maize breeder in terms of the number of genotypes the breeder will be able to evaluate. The large number of possible genotypes, coupled with the small sample size from a segregating population, make it uncertain that a breeder will be able to invent a new maize inbred line which is a measurable improvement over its parents. The invention of new inbred lines and of new hybrids is extremely important to the companies in the hybrid seed maize industry that have investments in research. Much effort is given to the research and development of these inbreds and hybrids. The breeding and selection of inbred lines involves many years of inbreeding, skilled selection, correct statistical testing, and decision making.

According to U.S. Pat. No. 5,330,547 issued Jul. 19, 1994 to Mary W. Eubanks (which is incorporated herein by reference), maize is a monoecious grass, i.e., it has separate male and female flowers. The staminate, i.e., pollen-producing, flowers are produced in the tassel and the pistillate or female flowers are produced on the shoot. Pollination is accomplished by the transfer of pollen from the tassel to the silks. Since maize is naturally cross-pollinated, controlled pollination, in which pollen collected from the tassel of one plant is transferred by hand to the silks of another plant, is a technique used in maize breeding. The steps involved in making controlled crosses and self-pollinations in maize are as follows: (1) the ear emerging from the leaf shoot is covered with an ear shoot bag one or two days before the silks emerge to prevent pollination; (2) on the day before making a pollination, the ear shoot bag is removed momentarily to cut back the silks, then is immediately placed back over the ear; (3) on the day before making a pollination, the tassel is covered with a tassel bag to collect pollen; (3) on the day of pollination, the tassel bag with the desired pollen is carried to the plant for crossing, the ear shoot bag is removed and the pollen dusted on the silk brush, the tassel bag is then immediately fastened in place over the shoot to protect the developing ear.

Wild relatives of crop plants are an important source of genetic diversity and genes well adapted to many different stresses. The wild relatives of maize include annual teosinte (*Zea mexicana*), perennial teosinte and Tripsacum. Tripsacum is a more distant relative of maize with a different haploid chromosome number (n=18). The progeny of (maize X Tripsacum) obtained by artificial methods are thought to be all male sterile and have limited female fertility when pollinated by maize pollen. Cytogenetic studies of maize-Tripsacum hybrids show partial chromosome pairing and homology between segments of Tripsacum and maize chromosomes (Maguire, M. P., 1961, Evolution 15:394–400; Maguire, M. P., 1963, Genetics 48:1185–1194; Chaganti, R.

S. K., 1965, Bussey Inst. Harv. Univ., 93p.; Galinat, W. C., 1974, Evolution 27:644–655). In spite of strong cross-incompatibility, the fact that maize and Tripsacum chromosomes can occasionally pair with one another enables limited transfer of Tripsacum genes into maize.

Successful introgression of Tripsacum genetic material into maize heretofore has required years of complicated, high-risk breeding programs that involve many backcross generations to stabilize desirable Tripsacum genes in maize. According to Kindiger and Beckett: "Tripsacum may be expected to contain valuable agronomic characters . . . that could be exploited for the overall improvement of maize. An effective procedure to transfer Tripsacum germ plasm into maize has been needed by maize breeders and geneticists for many years" (1990, p. 495). Beneficial traits that may be derived from Tripsacum include heat and drought tolerance (Reeves, R. G. and Bockholt, A. J., 1964, Crop Sci. 4:7–10), elements of apomixis, increased heterosis (Reeves and Bockholt 1964; Cohen, J. I. and Galinat, W. C., 1984, Crop. Sci. 24:1011–1015), resistance to corn root worm (Branson, T. F., 1971, Ann. Entomol. Soc. Am. 64:861–863), corn leaf aphid, northern and southern leaf blight, common rust, anthracnose, fusarium stalk rot and Stewart's bacterial blight (Berquist, R. R., 1981, Sci. Monogr. Univ. Wyo. Agric. Exp. Stn., The Station 71:518–520; de Wet, J. M. J., 1979, Broadening the Genetic base of crops, PUDOC, Center for Agricultural Publishing and Documentation, 203–210, Zevon, A. C. and van Harten, A. M. (eds.), Wageningen, Netherlands). Plant breeders acknowledge Tripsacum has significant potential for improving corn by expanding its genetic diversity (Cohen, J. I. and Galinat, W. C., 1984; Poehlman, J. M., 1987, Breeding Field Crops, $3^{rd}$ Ed., AVI Pub. Co., 451–453). The limited fertility of maize-Tripsacum hybrids presents a significant biological barrier to gene flow between these species.

*Zea mays* X Tripsacum plants have unreduced gametes with 28 chromosomes, one set of 10 Zea chromosomes and one set of 18 Tripsacum chromosomes. There has been one report of a successful reciprocal cross of Tripsacum pollinated by maize in which embryo culture techniques were used to bring the embryo to maturity. The plants were sterile (Farquharson 1957). This (Tripsacura X maize) plant was employed by Branson and Guss (1972) in tests for rootworm resistance in maize-Tripsacum hybrids. When the (maize X Tripsacura) hybrid has been crossed with either annual teosinte or diploperennis, a trigenomic hybrid has been produced that has a total of 38 chromosomes; 10 from maize, 18 from Tripsacum and 10 from teosinte. The resulting trigenomic plants were all male sterile and had a high degree of female infertility.

What are needed are corn lines having compositions of protein, oil, and starch that are significantly different from the compositions found in conventional corn lines.

SUMMARY OF THE INVENTION

According to the invention, there are provided novel introgressed corn lines containing genetic material from *Tripsacum dactyloides L.*, wherein, in the breeding procedure, selections have been made both for yield, kernel size, stalk strength, pest resistance, and other maize-like qualities, as well as selecting for desirable new traits, such as high protein content, high oil content, high oleic acid content, high or low saturated oil content, and/or starch having unique thermal characteristics. The desirable new traits are contributed by the introgression of Tripsacum genetic material into corn lines and the selection process.

Summary of High-protein and/or High-oil Corn Lines

According to one embodiment of the invention, there is provided a novel inbred (maize) corn line, designated GC, that provides higher protein content than conventional corn lines, higher oil content than conventional corn lines, or both higher protein and higher oil than conventional corn lines. (In the present description, the general designation "GC" followed by "#" and a four-digit plant line number will refer to any of the specific corn lines that are listed in the next paragraph.) This invention thus relates to the seeds of a GC inbred maize line, to the plants of a GC inbred maize line, to the pollen of a GC inbred maize line, and to methods for producing a maize plant produced by crossing a GC inbred line with itself, another GC line or another maize line. This invention further relates to hybrid maize seeds and plants produced by crossing a GC inbred line with either another GC line or with another maize line.

According to one embodiment of the invention, there are provided corn lines based on introgressions between and among selected recovered lines of maizexTripsacum material (said recovered lines including #5S1, #13S1, #15S1), and publicly available inbred lines including A632, B73, W153R, and Mo17. At least some of the selections were based initially on high oleic-acid content and high saturated-fatty-acid content.

Another aspect of the present invention provides seed of high-protein inbred corn lines designated GC#3892, GC#3805, GC#3978, GC#3728, GC#3963, GC#3642, GC#3781, or GC#3663, high-oil inbred corn lines designated GC#4066, GC#3886, GC#3831, GC#3833, GC#3641, GC#3839, GC#3822, GC#3930, GC#3969, GC#3696, GC#3829, GC#3713, GC#4037, GC#3700, GC#3901, GC#3809, GC#3689, GC#3640, GC#3723, GC#3821, GC#3892, GC#3697, GC#4053, GC#3711, GC#3712, GC#3823, GC#3694, GC#3838, GC#3717, GC#3687, GC#3968, GC#4151, GC#3941, GC#3695, GC#3806, GC#3926, GC#3896, GC#3808, GC#3927, GC#3719, or GC#3810, or high-protein-and high-oil inbred corn lines designated GC#3847, GC#3763, GC#3913, GC#3753, GC#3820, GC#3905, GC#3815, GC#3911, GC#3646, GC#3951, GC#4026, GC#3692, GC#3929, GC#3978, GC#3807, GC#3643, GC#4090, GC#3961, GC#3922, GC#3631, GC#3812, GC#3716, GC#3691, GC#3674, GC#3714, GC#4020, GC#3636, GC#1330, GC#3747, GC#3933, GC#3932, GC#3924, GC#3762, GC#3971, GC#3904, GC#3956, GC#4158, GC#3964, GC#4030, GC#4054, or GC#1324 (collectively, "GC inbred maize lines"). In one embodiment, the present invention provides a "first" corn plant produced by said seed or regenerable parts of said seed (the term "first" corn plant refers to an arbitrary plant produced by said seed or regenerable parts of said seed).

In another embodiment, the present invention provides seed of the first corn plant. In yet another embodiment, the present invention provides pollen of the first corn plant. In one such embodiment, the present invention provides seed of a corn plant pollinated by such pollen.

In another embodiment, the present invention provides an ovule of the first corn plant produced by said seed or regenerable parts of said seed.

In yet another embodiment, the present invention provides a corn plant having all the physiological and morphological characteristics of the first corn plant.

Another aspect of the present invention provides a tissue culture of regenerable cells, wherein the cells include genetic material derived, in whole or in part, from high-protein and/or high-oil inbred corn lines of the invention as designated above, and wherein the cells are regenerable into plants having the morphological and physiological characteristics of the respective GC inbred corn lines.

In yet another embodiment, the present invention provides a tissue culture comprising cultured cells derived, in whole or in part, from a plant part of a plant of the present invention, wherein the plant part is selected from the group consisting of leaves, roots, root tips, root hairs, anthers, pistils, stamens, pollen, ovules, flowers, seeds, embryos, stems, buds, cotyledons, hypocotyls, cells and protoplasts. In one such embodiment, a corn plant is regenerated from the tissue culture, the corn plant having all the morphological and physiological characteristics of the respective GC inbred corn lines.

In yet another embodiment, the present invention provides a method for producing high-protein content or high-oil content or high-protein and high-oil content corn seed comprising the step: crossing a first parent corn plant with a second parent corn plant and harvesting resultant first-generation (F1) hybrid corn seed, wherein said first or second parent corn plant is the first corn plant described above.

Another aspect of the present invention provides a method for breeding and selecting corn including the steps of: (a) introgressing plants of a corn line with plants of genus Tripsacum, to obtain genetic material; (b) growing corn plants from the genetic material resulting from the introgressing step of step (a) to obtain seeds; and (c) selecting from among the seed of the corn plants of step (b) those seeds having superior protein content or oil content or both.

In one such embodiment, the method further includes the step of: (d) creating an inbred corn line derived from the selected seeds of step (c). In another such embodiment, the method further includes the step of: (e) crossing the inbred corn line with another inbred corn line to obtain hybrid seeds. In yet another such embodiment, the method further includes the step of: (f) generating plants from the hybrid seeds resulting from step (e). In still another such embodiment, the method further includes the step of: (g) generating a tissue culture of regenerable cells from genetic material derived from the plants resulting from step (b), said tissue culture derived, in whole or in part, from a plant part selected from the group consisting of leaves, roots, root tips, root hairs, anthers, pistils, stamens, pollen, ovules, flowers, seeds, embryos, stems, buds, cotyledons, hypocotyls, cells and protoplasts.

Yet another aspect of the present invention provides seed of a corn variety, said variety having greater than or equal to about 10% protein at 0% moisture content. In one embodiment, the seed have greater than or equal to about 15% protein at 0% moisture content, and greater than or equal to about 12% protein at 15% moisture content. In another embodiment, the seed have greater than or equal to about 17% protein at 0% moisture content, and greater than or equal to about 14% protein at 15% moisture content. In yet another embodiment, the seed have greater than or equal to about 4% oil at 0% moisture content, and greater than or equal to about 3.5% oil at 15% moisture content.

In one such embodiment, said corn variety has genetic material derived from a plant of genus Tripsacum. In another such embodiment, the corn variety has genetic material derived from a plant of *Tripsacum dactyloides L.*

Another aspect of the present invention provides a second corn plant, or its parts, produced by such seed or regenerable parts of said seed. In another embodiment, the present invention provides seed of the second corn plant. In yet another embodiment, the present invention provides pollen of the second corn plant. In still another embodiment, the present invention provides seed of a corn plant pollinated by the pollen of the second corn plant.

Summary of High-oleic Acid High-oil Corn Lines

A. In one embodiment, the present invention provides a corn seed having an oleic acid content of approximately 50% or greater, relative to the total fatty acid content of said seed, and having a weight per seed of greater than about 0.15 gram.

B. In one embodiment, the present invention provides a corn seed having an oleic acid content of approximately 50% or greater, relative to the total fatty acid content of said seed, and having a weight per seed of greater than about 0.15 gram, wherein said seed is the product of a cross between (A) a first parent from a corn line that is true-breeding for said oleic acid content and (B) a parent from a second corn line.

C. In one embodiment, the present invention provides a corn seed having an oleic acid content of approximately 50% or greater, relative to the total fatty acid content of said seed, and having a weight per seed of greater than about 0.15 gram, wherein said seed is the product of a cross between (A) a first parent from a corn line that is true-breeding for said oleic acid content and (B) a parent from a second corn line, wherein said oleic acid content is about 60% or greater.

D. In one embodiment, the present invention provides a corn seed having an oleic acid content of approximately 50% or greater, relative to the total fatty acid content of said seed, and having a weight per seed of greater than about 0.15 gram, wherein said seed is the product of a cross between (A) a first parent from a corn line that is true-breeding for said oleic acid content and (B) a parent from a second corn line, wherein said oleic acid content is about 60% or greater, wherein said oleic acid content is about 65% or greater.

E. In one embodiment, the present invention provides a corn seed having an oleic acid content of approximately 50% or greater, relative to the total fatty acid content of said seed, and having a weight per seed of greater than about 0.15 gram, wherein said seed is the product of a cross between (A) a first parent from a corn line that is true-breeding for said oleic acid content and (B) a parent from a second corn line, wherein said oleic acid content is about 60% or greater, wherein said oleic acid content is about 70% or greater.

F. In one embodiment, the present invention provides a corn seed having an oleic acid content of approximately 50% or greater, relative to the total fatty acid content of said seed, and having a weight per seed of greater than about 0.15 gram, wherein said oleic acid content is between about 60% and about 70%.

G. In one embodiment, the present invention provides a corn seed having an oleic acid content of approximately 50% or greater, relative to the total fatty acid content of said seed, and having a weight per seed of greater than about 0.15 gram, said seed being the product of a corn plant having the characteristics of a GC inbred corn line.

I. In one embodiment, the present invention provides a corn seed comprising a yellow seed coat and having an oleic acid content of approximately 50% or greater, relative to the total fatty acid content of said seed, said seed being the product of a cross between (A) a first parent from a corn line that is true-breeding for said oleic acid content and for said yellow seed coat and (B) a second parent, wherein said first parent comprises germplasm encoding said oleic acid content and said second parent comprises a genetic determinant for yellow or white seed color.

J. In one embodiment, the present invention provides a corn seed comprising a yellow seed coat and having an oleic acid content of approximately 50% or greater, relative to the total fatty acid content of said seed, said seed being the product of a cross between (A) a first parent from a corn line that is true-breeding for said oleic acid content and for said yellow seed coat and (B) a second parent, wherein said first parent comprises germplasm encoding said oleic acid content and said second parent comprises a genetic determinant for white seed color, wherein said first parent is from a GC inbred corn line.

K. In one embodiment, the present invention provides a corn seed comprising a yellow seed coat and having an oleic acid content of approximately 50% or greater, relative to the total fatty acid content of said seed, said seed being the product of a cross between (A) a first parent from a corn line that is true-breeding for said oleic acid content and for said yellow seed coat and (B) a second parent, wherein said first parent comprises germplasm encoding said oleic acid content and said second parent comprises a genetic determinant for white seed color, said seed being the product of a corn plant having the characteristics of a line selected from the group consisting of a GC inbred corn line and a corn line based on a GC inbred corn line.

L. In one embodiment, the present invention provides a corn seed comprising a yellow seed coat and having an oleic acid content of approximately 50% or greater, relative to the total fatty acid content of said seed, said seed being the product of a cross between (A) a first parent from a corn line that is true-breeding for said oleic acid content and for said yellow seed coat and (B) a second parent, wherein said first parent comprises germplasm encoding said oleic acid content and said second parent comprises a genetic determinant for white seed color, said seed being the product of a corn plant having the characteristics of a line selected from the group consisting of a GC inbred corn line and a corn-line based on a GC inbred corn line.

M. In one embodiment, the present invention provides a corn seed comprising a white seed coat and having oleic acid content of approximately 60% or greater, relative to the total fatty acid content of said seed, said seed being the product of a cross between (A) a first parent from a corn line that is true-breeding for said oleic acid content and (B) a second parent.

N. In one embodiment, the present invention provides a corn seed comprising a white seed coat and having oleic acid content of approximately 60% or greater, relative to the total fatty acid content of said seed, said seed being the product of a cross between (A) a first parent from a corn line that is true-breeding for said oleic acid content and (B) a second parent, wherein one of said first and second parents comprises a genetic determinant for white seed color.

O. In one embodiment, the present invention provides a corn seed comprising a white seed coat and having oleic acid content of approximately 60% or greater, relative to the total fatty acid content of said seed, said seed being the product of a cross between (A) a first parent from a corn line that is true-breeding for said oleic acid content and (B) a second parent, wherein one of said first and second parents comprises a genetic determinant for white seed color, wherein said second parent is from a corn line that is true-breeding for said oleic acid content.

P. In one embodiment, the present invention provides a corn plant that produces seeds that have an oleic acid content of approximately 50% or greater, relative to the total fatty acid content of said seed, and that have a weight per seed of greater than about 0.15 gram.

Q. In one embodiment, the present invention provides a corn plant that produces seeds that have an oleic acid content of approximately 50% or greater, relative to the total fatty acid content of said seed, and that have a weight per seed of greater than about 0.15 gram, wherein said oleic acid content is between about 60% and about 70%.

R. In one embodiment, the present invention provides a method for producing a yellow-coated corn seed having an oleic acid content of approximately 50% or greater by weight, comprising the step of crossing (A) a first parent that comprises Tripsacum germplasm encoding said oleic acid content with (B) a second parent that comprises a genetic determinant for yellow seed color.

S. In one embodiment, the present invention provides a method for producing a yellow-coated corn seed having an oleic acid content of approximately 50% or greater by weight, comprising the step of crossing (A) a first parent that comprises Tripsacum germplasm encoding said oleic acid content with (B) a second parent that comprises a genetic determinant for yellow seed color, wherein both of said first and second parents are true-breeding for said yellow seed color.

T. In one embodiment, the present invention provides a method for producing a white-coated corn seed having an oleic acid content of approximately 50% or greater by weight, comprising the step of crossing (A) a first parent that yields white seed with (B) a second parent that comprises Tripsacum germplasm encoding, and that is true-breeding for, said oleic acid content.

U. In one embodiment, the present invention provides a product consisting of a substantially homogeneous assemblage of corn seeds that has an oleic acid content of approximately 50% or greater, relative to the total fatty acid content of said seeds.

V. In one embodiment, the present invention provides a corn-seed product consisting of a substantially homogeneous assemblage of corn seeds that have an oleic acid content of approximately 60% or greater, relative to the total fatty acid content of said seeds, said seeds being the product of a cross between (A) parents from a first corn line that is true-breeding for said oleic acid content and (B) parents from a second corn line.

W. In one embodiment, the present invention provides a corn-seed product consisting of a substantially homogeneous assemblage of corn seeds that have an oleic acid content of approximately 60% or greater, relative to the total fatty acid content of said seeds, said seeds being the product of a cross between (A) parents from a first corn line that is true-breeding for said oleic acid content and (B) parents from a second corn line, wherein said oleic acid content is about 60% or greater.

X. In one embodiment, the present invention provides a corn-seed product consisting of a substantially homogeneous assemblage of corn seeds that have an oleic acid content of approximately 60% or greater, relative to the total fatty acid content of said seeds, said seeds being the product of a cross between (A) parents from a first corn line that is true-breeding for said oleic acid content and (B) parents from a second corn line, wherein said oleic acid content is about 65% or greater.

Y. In one embodiment, the present invention provides a corn-seed product consisting of a substantially homogeneous assemblage of corn seeds that have an oleic acid content of approximately 60% or greater, relative to the total fatty acid content of said seeds, said seeds being the product of a cross between (A) parents from a first corn line that is true-breeding for said oleic acid content and (B) parents from a second corn line, wherein said oleic acid content is about 70% or greater.

Z. In one embodiment, the present invention provides a corn-seed product consisting of a substantially homogeneous assemblage of corn seeds that have an oleic acid content of approximately 60% or greater, relative to the total fatty acid content of said seeds, said seeds being the product of a cross between (A) parents from a first corn line that is true-breeding for said oleic acid content and (B) parents from a second corn line, wherein said seeds each comprise a white seed coat.

AA. In one embodiment, the present invention provides a corn-seed product consisting of a substantially homogeneous assemblage of corn seeds that have an oleic acid content of approximately 60% or greater, relative to the total fatty acid content of said seeds, said seeds being the product of a cross between (A) parents from a first corn line that is true-breeding for said oleic acid content and (B) parents from a second corn line, wherein said seeds each comprise a yellow seed coat.

BB. In one embodiment, the present invention provides a corn-seed product consisting of a substantially homogeneous assemblage of corn seeds that have an oleic acid content of approximately 60% or greater, relative to the total fatty acid content of said seeds, said seeds being the product of a cross between (A) parents from a first corn line that is true-breeding for said oleic acid content and (B) parents from a second corn line, wherein said corn seeds, when grown under temperature conditions ranging from those of a northern climate to those of a southern climate, yield plants that produce seeds displaying a variation in said oleic acid content of about 4 to 5% by weight or less.

CC. In one embodiment, the present invention provides a corn line consisting of a substantially uniform population of *Zea Mays L*. plants that produce seeds having an oleic acid content of approximately 60% or greater, relative to the total fatty acid content of said seeds, said line being true-breeding for said oleic acid content.

DD. In one embodiment, the present invention provides a corn line consisting of a substantially uniform population of *Zea Mays L*. plants that produce seeds having an oleic acid content of approximately 60% or greater, relative to the total fatty acid content of said seeds, said line being true-breeding for said oleic acid content, wherein said oleic acid content is about 60% or greater.

EE. In one embodiment, the present invention provides a corn line consisting of a substantially uniform population of *Zea Mays L*. plants that produce seeds having an oleic acid content of approximately 60% or greater, relative to the total fatty acid content of said seeds, said line being true-breeding for said oleic acid content, wherein said oleic acid content is about 65% or greater.

FF. In one embodiment, the present invention provides a corn line consisting of a substantially uniform population of *Zea Mays L*. plants that produce seeds having an oleic acid content of approximately 60% or greater, relative to the total fatty acid content of said seeds, said line being true-breeding for said oleic acid content, wherein said oleic acid content is about 70% or greater.

GG. In one embodiment, the present invention provides a corn line consisting of a substantially uniform population of *Zea Mays L*. plants that produce seeds having an oleic acid content of approximately 60% or greater, relative to the total fatty acid content of said seeds, said line being true-breeding for said oleic acid content, wherein said seeds each comprise a white seed coat.

HH. In one embodiment, the present invention provides a corn line consisting of a substantially uniform population of *Zea Mays L*. plants that produce seeds having an oleic acid content of approximately 60% or greater, relative to the total fatty acid content of said seeds, said line being true-breeding for said oleic acid content, wherein said seeds each comprise a yellow seed coat.

II. In one embodiment, the present invention provides a corn seed having an oleic acid content of approximately 50% or greater, relative to the total fatty acid content of said seed, and having a weight per seed of greater than about 0.15 gram, wherein said corn seed is true-breeding for said oleic acid content.

DESCRIPTION OF PREFERRED EMBODIMENTS

In the following detailed description of the preferred embodiments, reference is made to the accompanying drawings that form a part hereof, and in which are shown by way of illustration specific embodiments in which the invention may be practiced. It is understood that other embodiments may be utilized and structural changes may be made without departing from the scope of the present invention.

The present invention is directed to a corn plant that includes genetic material from Tripsacum, and in particular, *Tripsacum dactyloides L*. (common name Eastern Gamagrass, or Fakahatchee Grass.) More particularly, the seed from the invented corn plant of one embodiment is significantly higher in protein and/or oil content than conventional Corn-Belt lines.

Figures 1A, 1B, 1C:
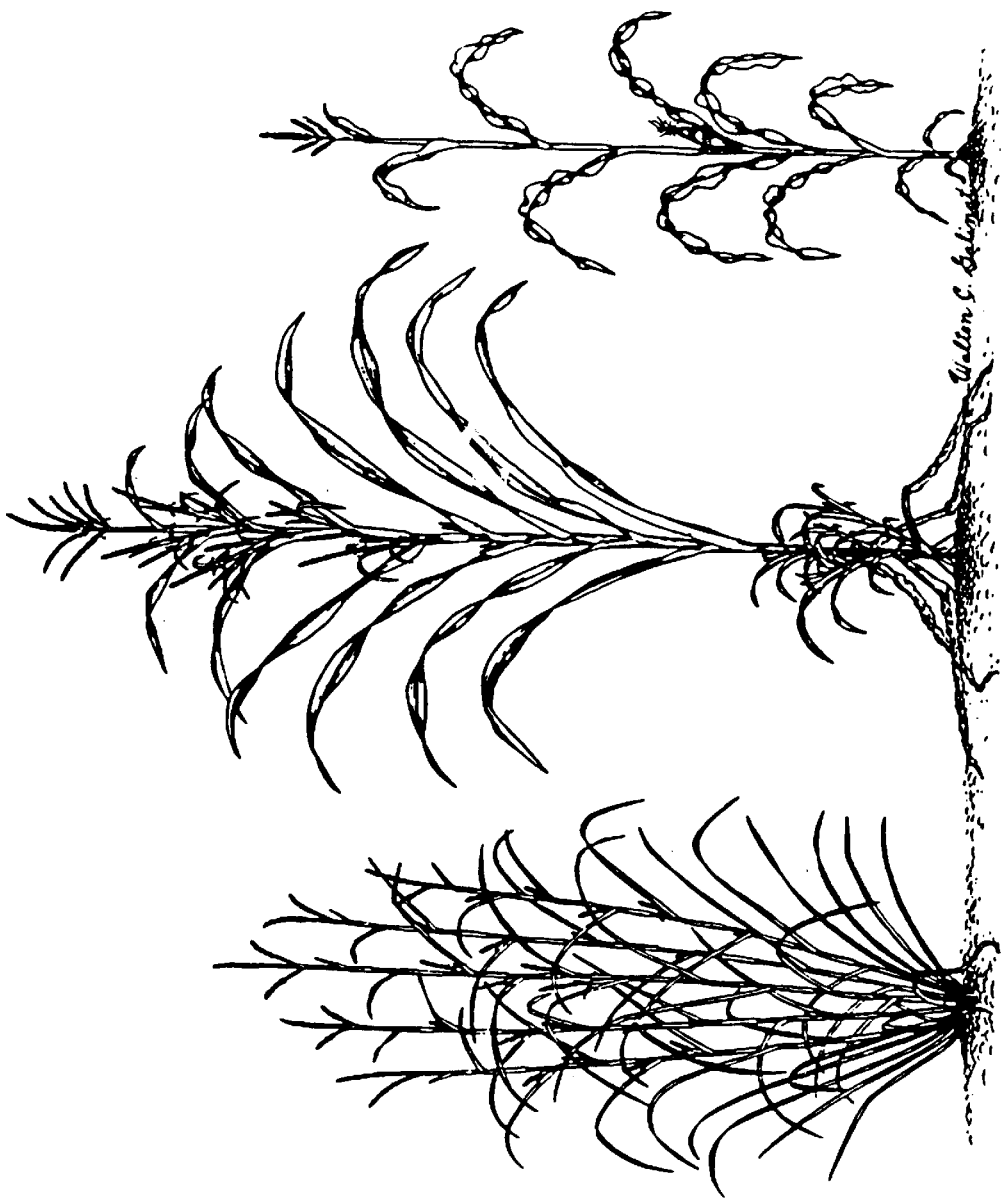
FIG. 1A shows a *Tripsacum dactyloides* plant at ca. 365 days.
FIG. 1B shows a corn×*Tripsacum dactyloides* F1 hybrid plant at ca. 284 days.
FIG. 1C shows a corn plant of the type used as a parent of the plant in FIG. 1B.

FIG. 1A shows a *Tripsacum dactyloides* plant at ca. 365 days. FIG. 1B shows a corn×*Tripsacum dactyloides* F1 hybrid plant at ca. 284 days. FIG. 1C shows a corn plant of the type used as a parent of the plant in FIG. 1B. Increased Genetic Diversity for the Present Invention To find sources of genetic variability, corn lines introgressed with genes from Tripsacum, a wild relative of corn, were evaluated for grain and oil quality traits. The original Tripsacumxmaize introgressed lines had numerous shortcomings such as poor yield, stalk problems, unusual grain color, etc. The phenotypic description of the original Tripsacumxmaize introgressed population is as follows: there was a large variation in plant height (range 5–8 feet), the ears were small (1–3 inches), and there was a wide variation in kernel color (various ears were entirely brown, copper, yellow, orange, purple, black, orange or tan, some ears had kernels that were two tone, e.g., yellow with areas of tan). There were many male-sterile plants (the tassels had no anthers, or the anthers had no pollen. There were also many female-sterile plants (the ears had silk, but no seed was produced when pollinated). Some plants had tassel ears (i.e., seeds were produced in the tassels) and other plants had ear tassels (pollen-generating structures in the ears), both of which are considered undesirable. Almost all the plants had skinny stalks, not substantial enough to hold the plant upright, especially if the plant had one or more large ears of corn. Many plants had massive tillering (multiple stalks branching from the base of the plant—see FIG. 1A, these multiple stalks can lodge (fall over) or jam in the harvesting machinery). The original population had a wide range of oleic acid content. Seeds were measured, segregating for fatty acid composition, e.g., oleic acid values ranged from 19.56% to 57.9%. Other shortcomings of the original Tripsacumxmaize introgressed population included very poor overall agronomic traits, e.g., it was disease- and insect-damage susceptible. The ear heights on the plants varied from plant-to-plant; farmers prefer to have ear heights uniform to facilitate machine harvest. The kernels were colored; customers prefer to have a yellow grain color. The weak stalks fell over (lodged), unable to support the weight of the much larger ear that resulted from introgressing and backcrossing maize genetics. There were branched (forked) clusters of ear; farmers prefer to have one unbranched ear for automated harvesting and removal of the seed from the ear. The ears were small, and the kernels on the ears were small. Finally, the flowering dates among the population were nonuniform between plants. It is preferable to have a short flowering period, so that plants will mature at the same time for harvest.

This invention is also directed to methods for producing a corn plant by crossing a first parent corn plant with a second parent corn plant wherein the first or second corn plant is an inbred corn plant from a GC inbred line. Further, both first and second parent corn plants may be from either GC inbred line. Thus, any methods using the GC inbred corn line are part of the invention, including backcrosses, hybrid breeding, and crosses to other populations. Any plants produced using a GC inbred corn line as a parent are within the scope of this invention. One preferred use of the GC inbred corn line is for the production of first-generation (F1) corn hybrid seeds which produce plants with superior characteristics, by crossing GC (either as a seed line or as a pollen line) to another, distinct inbred line, both for sale to growers to produce market grain, and for inbreeding and development of improved inbred lines by its proprietors. A second important use of this inbred line is for the production of GC inbred seed, by crossing GC with another plant of GC, or by directly self-pollinating a plant of a GC inbred corn line.

As used herein, the term "plant" includes one or more plant cells, plant protoplasts, plant cells of tissue culture from which corn plants can be regenerated, plant calli, plant clumps, and plant cells that are intact in plants or parts of plants, such as pollen, flowers, kernels, ears, cobs, leaves, husks, stalks, and the like. Thus another aspect of this invention is to provide for cells which upon growth and differentiation produce the inbred lines that are cited here by the general designation GC.

Transformation, a technique from molecular biology, now offers opportunity for the asexual transfer of genes that heretofore could only be achieved by crossing different plant strains. In order for breeders to employ gene transfer via transformation, they first have to be able to achieve plant regeneration from calli or protoplasts. Although transformation has been successfully performed in maize (Gordan-Kamm et al. 1990), there is limitation in developing transgenic maize due to the difficulties of plant regeneration from maize protoplasts (Potrykus, I., 1990, Bio/Technol. 8:535–542). The problem is that there are very few maize lines that can be successfully regenerated from maize protoplasts. In order for transformation to be useful for commercial hybrid seed production, it will be necessary to have inbred lines amenable to the transgenic process that can be regenerated by tissue culture.

Techniques involving the tissue culture of maize cells and plant parts have been developed to the point that it is now possible to regenerate plants from nearly all genotypes, by varying the culture media in which the cells or parts are cultured. Based upon experience with other inbreds with somewhat similar genetic background, it is anticipated that inbred corn line GC, the invention to be described next, will readily provide regenerable cells in culture of cells or plant parts.

Corn oil from Corn-Belt lines has a very narrow range for fatty acid composition. Historically, this narrow-range resulted from using genetically uniform material to create the modern Corn-Belt hybrids. According to the present invention, new genes from a novel source, viz. *Tripsacum dactyloides L.*, are introduced into the Corn-Belt genome and thus genetic diversity is increased and germplasm and value-added trait enhancement are allowed through traditional plant-breeding practices.

As used herein "introgression" involves conventional pollination breeding techniques to incorporate foreign genetic material into a line of breeding stock. A population of corn introgressed with genes from related species was screened for unique value-added traits. The introgressed lines with useful oil quality traits were crossed to Corn-Belt inbreds in an attempt to alter the fatty acid composition of the Corn-Belt material. Recovered parental introgressed corn lines with desirable fatty acid profiles were reciprocally crossed to Corn-Belt inbreds. These breeding crosses were self-pollinated and backcrossed for several generations to create new inbreds with enhanced oil quality. The fatty acids targeted for improvement were oleic acid and total saturated fatty acids (palmitic and stearic acids). The breeding program successfully resulted in markedly higher oleic acid composition and significantly lower total saturated fatty acid composition.

Corn lines with both high protein and high oil compositions were created using traditional plant breeding techniques of cross- and self-pollination with public Corn-Belt inbred lines and corn lines introgressed with *Tripsacum dactyloides L*. These lines can be used as breeding lines in a commercial corn breeding program to develop elite proprietary lines with higher levels of both protein and oil. The elite lines would be parents in high-yielding commercial hybrids designed for feed use.

Diploid *Tripsacum dactyloides* is (2n=36). Diploid maize is (2n=20). When these two species are crossed, n=18 chromosomes are contributed by the Tripsacum, and n=10 chromosomes are contributed by the maize. Such first-generation (F1) hybrids are commercially unsatisfactory from a number of standpoints, such as appearance, color, stalk, etc.; however, they are used for such purposes as colored ornamental corn, or as sources for corn apomixis (a sexual generation of seed in a field-grown ear wherein the seed having approximately 100% genetic material from the mother plant, in order to achieve plants that breed true without the trouble of generating hybrids from inbred lines). Colored ornamental corn is unsatisfactory for a number of industrial food purposes for which white or lightly colored ingredients are preferred. On the other hand, for purposes in which colored corn ingredients are wanted, such as for red or blue corn chips, it is contemplated by the present invention to select for seed that produce such characteristics.

A self-cross of a (2n=28) F1 maize-Tripsacum hybrid to itself causes some amount of Tripsacum genetic material to cross over to maize chromosomes. A backcross of a (2n=28) F1 maize-Tripsacum hybrid to a maize parent line also causes some amount of Tripsacum genetic material to cross over to maize chromosomes. Further, such backcross operations, when repeated over several generations, tend to eventually result in (2n=20) corn lines.

In one embodiment, the present invention uses introgression involving self-crosses of maize-Tripsacum hybrids and backcrosses of maize-Tripsacum hybrids to an inbred maize or corn line to incorporate Tripsacum genetic material into a line of corn breeding stock. Introgression of quantitative traits from one germplasm to another involves the identification and segregation of favorable genotypes in isolated generations, followed by repeated backcrossing to commercially acceptable cultivars. In one embodiment, the present invention provides selection by observation of plants having acceptable yield and field characteristics such as stalk strength and compatibility with conventional harvesting machinery, as well as having measurable quantitative traits such as high protein and/or oil content. In one embodiment, particular fatty acid components are selected for, such as palmitic or oleic acids.

This selection procedure is generally quite feasible for simply inherited quantitative traits such as are sought in the present invention, but as the number of genes controlling a trait increases, screening the number of F2 segregants required to identify at least one individual which represents the ideal (homozygous) genotype quickly becomes a prohibitively complex and costly task. For example, with one gene and two alleles of equal frequency, the probability of recovering a desirable genotype in the F2 generation is 1/4. However, if the number of genes is increased to 5 or 10, the probability of recovering an ideal genotype in the F2 population is reduced to approximately one in one thousand and one in one million, respectively. Thus, to identify desirable segregants, one must either reduce the number of segregants needed or have available very efficient screening procedures. Additionally, in situations where environmental effects interfere with the ability to draw accurate genotypic information from the phenotype, large allocations of time and resources are required to evaluate progeny in replicated trials within several target environments. Thus, other methods of selection for introgression and expression of the desired quantitative traits into corn lines are also contemplated by the present invention. For example, the use of restriction fragment length polymorphisms (RFLPs) to dissect multigenic traits into their individual genetic components is contemplated, as described in U.S. Pat. No. 5,385,835 issued Jan. 31, 1995 to Timothy Helentjaris, et al. (entitled "*Identification and localization and introgression into plants of desired multigenic traits*"), which is incorporated herein by reference. A genome, or portion thereof, saturated with RFLPs or probed with select RFLP markers, all of which can be evaluated together in individual plants, has been found to give the resolution necessary to break down traits of complex inheritance into individual loci, even traits significantly influenced by environment.

One source of genetic material used for one embodiment of the present invention includes a pool of introgressed lines of maize-*Tripsacum dactyloides* seeds generally attributed to Harlan and DeWet (Harlan J. R., De Wet J. M. J., Naik S. M. and Lambert R. J., 1970—Chromosome pairing within genomes in maize x Tripsacum hybrids; *Science*. 167:1247–1248). The Zea mays parent used in the original crosses to *Tripsacum dactyloides* by Harlan and DeWet is said to be a standard purple maize inbred line, viz. Ul1974, which has purple aleurone and exhibits purple kernels and purple plants. In one embodiment, this Harlan and DeWet source of genetic material is introgressed with one or more standard Corn-Belt varieties to obtain inbred lines that retain the desirable characteristics of the maize parent lines such as stiff stalks, large ears, pest resistance, and high yield, while also obtaining the desired characteristics of the Tripsacum, e.g., high protein content, high oil content, or a combination of high oil and high protein content. In other embodiments, additional desirable characteristics (such as particular types of fatty acid content in the oil, or pest resistance, or plants that generate seed by apomixis, or color) conferred from the Tripsacum are also selected for. Seeds from individual plants are tested (in one embodiment, by gas chromatography; in another embodiment, selection is based on near-infrared reflectance measurement of protein, oil, and/or starch of seed) for protein and/or oil content and/or starch (and/or other desired characteristic), and seeds are selected for further breeding based on the results of the testing. In this way, corn lines are developed that retain satisfactory characteristics from the maize lines, while also acquiring superior characteristics contributed by the addition of Tripsacum genetic material.

Source of Genetic Contribution in Original Population

Accurate chromosome counts have not as of yet been performed on the lines of the present invention. The genetic contribution which resulted in the advantageous traits in the seed from crosses of Corn Belt lines with the Tripsacum introgressed lines of the present invention is believed to have come from the Tripsacum contribution, because the self-pollinated plants from the original population had Tripsacum traits including massive tillering, thin leaves, tassel ears, ear tassels, small ears, small grain, and thin stalks and a generally grassy appearance. It is also possible that the traits of interest came from some other genetic source, e.g., via stray pollen since open pollination occurred in the parent lines.

Most commercial hybrids have less than optimum protein and oil compositions. Commercial hybrids have an average of 7.4% protein and 3.3% oil on a 0% moisture basis. The high-protein and -oil lines according to the present invention have up to 18.1% protein and 5.4% oil. End users in the feed and food industries must supplement conventional corn with protein and oil from other high-priced sources. Corn hybrids with optimum (i.e., elevated) levels of protein and oil of the present invention would not need to be supplemented to meet end-user needs, or would require supplementing to a lesser extent, thus reducing cost. Corn with desirable nutrient content increases profitability for corn producers, has a major profitability advantage for producers who feed livestock with their own corn, and increases profitability in the feed and livestock industries. Through feeding livestock, most of the U.S. corn crop is processed into meat and dairy products that affect everyone in our society. An economic advantage of corn as a higher-value feed product could be passed along to consumers in lower prices or higher-quality products at a given price. Lines with high protein and oil may also have an advantage in the export market for buyers concerned with feed and food quality. They also have an advantage in the food industry, for marketing nutritious food products and stimulating the development of new food products. More protein means better nutritional value for the product. High corn oil content in seeds yields greater amounts of corn oil when such grain is processed into corn oil, and provides an economic advantage to starch wet milling. In varieties of the present invention that provide high oleic content, the value of corn oil processed from such grain tends be higher than that of normal corn oil.

For example, at $214/ton for 44%-protein soybean meal, the value of a 1% increase in corn protein content (e.g., from 8% to 9%) is about 12 cents per bushel more in value. Likewise, a 1% increase in oil content yields about 14 cents per bushel more in value. About 20 percent of U.S. corn production is exported each year, providing a positive contribution to the nation's trade balance, and much of this corn is used for feed. High-quality end-user products would have a favorable impact on exports. High-protein and/or high-oil corn lines have clear commercial advantages in the feed industry. Currently, corn used for feed is deficient in the amount of protein and oil required to make an optimum feed product, and supplementation is therefore required. These supplements increase cost and labor. Corn with optimum feed value would favorably impact corn growers who feed their grain to their livestock. For example, an estimated 1.064 million farmers and ranchers raise beef cattle, and many of these farmers grow and use their own feed corn. There are about 150,000 pork producers, most of whom grow their own corn for feed. Optimal feed corn hybrids would increase their profitability.

Table 1 shows protein, oil, and starch content as measured for a number of commercial corn sources. Each of these three parameters is shown for 0% moisture and for 15% moisture. The EPV (economic premium value) column shows an estimation of the relative economic value provided by the combination of measured parameters for each variety. The last column shows an estimation of the incremental (or decremental) value per bushel. The last row shows the averages for each measurement. In these measurements of these conventional hybrids, the average protein content was 7.4% at 0% moisture, and 6.3% at 15% moisture. In these measurements, the average oil content across all these conventional hybrids was 3.3% at 0% moisture, and 2.8% at 15% moisture. In these measurements, the average starch content was 61.1% at 0% moisture, and 51.9% at 15% moisture. Other reports indicate an average protein content for corn as 10% protein, and an average oil content for corn as less than 5%.

Table 2 shows protein, oil, and starch content as measured for a number of corn lines according to the present invention that were selected for their high protein content. Table 3 shows protein, oil, and starch content as measured for a number of corn lines according to the present invention that were selected for their high oil content. Table 4 shows protein, oil, and starch content as measured for a number of corn lines according to the present invention that were selected for their combined high protein and oil content. The corn lines shown in Table 4 were the result of crossing to commercial line Mo17 which is publicly available. These crosses were grown in replicated yield tests.

TABLE 1

Commercial Hybrids*

| | | Moisture Content for Each Composition** | | | | | | | Premium over current price |
|---|---|---|---|---|---|---|---|---|---|
| Company | Hybrid | 0% Protein | 0% Oil | 0% Starch | 15% Protein | 15% Oil | 15% Starch | Feed EPV | $/bu @ $2.72/bu |
| Cargill | 5677 | 7.5 | 3.1 | 61.2 | 6.4 | 2.6 | 52.0 | 2.57 | −0.15 |
| DeKalb | DK566 | 7.6 | 3.4 | 60.7 | 6.5 | 2.9 | 51.6 | 2.57 | −0.15 |
| DeKalb | DK580 | 7.3 | 3.4 | 61.1 | 6.2 | 2.9 | 51.9 | 2.56 | −0.16 |
| Mycogen | 2595 | 6.9 | 3.3 | 61.3 | 5.9 | 2.8 | 52.1 | 2.52 | −0.20 |
| Mycogen | 2674 | 7.9 | 3.4 | 61.0 | 6.7 | 2.9 | 51.9 | 2.60 | −0.12 |
| DeKalb | DK604 | 7.5 | 3.3 | 61.0 | 6.4 | 2.8 | 51.9 | 2.57 | −0.15 |
| Pioneer | 3394 | 7.5 | 3.2 | 61.4 | 6.4 | 2.7 | 52.2 | 2.57 | −0.15 |
| DeKalb | DK591 | 7.6 | 3.5 | 60.5 | 6.5 | 3.0 | 51.4 | 2.57 | −0.15 |
| Cargill | 6303 | 7.7 | 3.3 | 60.9 | 6.5 | 2.8 | 51.8 | 2.58 | −0.14 |
| Middlekoop | M711 | 7.2 | 3.2 | 61.4 | 6.1 | 2.7 | 52.2 | 2.55 | −0.17 |
| Wyffels | W552 | 7.1 | 3.2 | 61.6 | 6.0 | 2.7 | 52.4 | 2.54 | −0.18 |
| Ottlie | 2453 | 7.3 | 3.2 | 61.4 | 6.2 | 2.7 | 52.2 | 2.56 | −0.16 |
| ICI/Garst | 8541 | 7.4 | 3.5 | 60.8 | 6.3 | 3.0 | 51.7 | 2.57 | −0.15 |
| Croplan Genetics | 599 | 7 | 3.2 | 61.5 | 6.0 | 2.7 | 52.3 | 2.53 | −0.19 |
| Golden Harvest | H2530 | 7.1 | 3.4 | 61.2 | 6.0 | 2.9 | 52.0 | 2.54 | −0.18 |
| Asgrow | RX632 | 7.3 | 3.3 | 60.8 | 6.2 | 2.8 | 51.7 | 2.56 | −0.16 |
| Pioneer | 3489 | 7.2 | 3.5 | 61.0 | 6.1 | 3.0 | 51.9 | 2.55 | −0.17 |
| Bioseed | 9498 | 7.1 | 3.4 | 61.1 | 6.0 | 2.9 | 51.9 | 2.54 | −0.18 |
| Pfister | 2650 | 7.3 | 3.3 | 60.8 | 6.2 | 2.8 | 51.7 | 2.56 | −0.16 |
| Crows | 445 | 7.1 | 3.4 | 61.1 | 6.0 | 2.9 | 51.9 | 2.54 | −0.18 |
| Terra | TR1091 | 7.6 | 3.5 | 60.6 | 6.5 | 3.0 | 51.5 | 2.57 | −0.15 |
| Payco | 834 | 7.2 | 3.2 | 60.7 | 6.1 | 2.7 | 51.6 | 2.55 | −0.17 |

TABLE 1-continued

Commercial Hybrids*

| | | Moisture Content for Each Composition** | | | | | | Feed | Premium over current price |
|---|---|---|---|---|---|---|---|---|---|
| Company | Hybrid | 0% Protein | 0% Oil | 0% Starch | 15% Protein | 15% Oil | 15% Starch | Feed EPV | $/bu @ $2.72/bu |
| LG Seeds | LG-2583 | 7.3 | 3.3 | 60.8 | 6.2 | 2.8 | 51.7 | 2.56 | −0.16 |
| Renze | 6345 | 7.3 | 3.2 | 61.0 | 6.2 | 2.7 | 51.9 | 2.56 | −0.16 |
| Crows | 494 | 7.9 | 3.1 | 61.1 | 6.7 | 2.6 | 51.9 | 2.60 | −0.12 |
| Kline | KSX350 | 7.2 | 3.2 | 60.8 | 6.1 | 2.7 | 51.7 | 2.55 | −0.17 |
| Epley | EX3608 | 7.2 | 3.2 | 60.9 | 6.1 | 2.7 | 51.8 | 2.55 | −0.17 |
| Kruger | 9513 | 7.1 | 3.1 | 61.2 | 6.0 | 2.6 | 52.0 | 2.54 | −0.18 |
| Rainbow | 3109 | 7.6 | 3.4 | 61.1 | 6.5 | 2.9 | 51.9 | 2.57 | −0.15 |
| Golden Harvest | H2539 | 7.5 | 3.3 | 61.2 | 6.4 | 2.8 | 52.0 | 2.57 | −0.15 |
| Cargill | 7557 | 7.4 | 3.3 | 61.4 | 6.3 | 2.8 | 52.2 | 2.57 | −0.15 |
| Crows | 510 | 7.6 | 3.4 | 60.9 | 6.5 | 2.9 | 51.8 | 2.57 | −0.15 |
| Kline | KSX60A | 7.9 | 3.3 | 61.0 | 6.7 | 2.8 | 51.9 | 2.60 | −0.12 |
| Mark | MRk95117 | 7.6 | 3.2 | 61.0 | 6.5 | 2.7 | 51.9 | 2.57 | −0.15 |
| Cornelius | C642 | 7.0 | 3.3 | 61.7 | 6.0 | 2.8 | 52.4 | 2.53 | −0.19 |
| Moews | 3892 | 7.7 | 3.2 | 61.1 | 6.5 | 2.7 | 51.9 | 2.58 | −0.14 |
| Uthoff | U66 | 6.8 | 3.4 | 61.6 | 5.8 | 2.9 | 52.4 | 2.51 | −0.21 |
| Kruger | 9415A | 7.1 | 3.4 | 61.4 | 6.0 | 2.9 | 52.2 | 2.54 | −0.18 |
| ICI/Garst | 8400 | 7.5 | 3.4 | 60.9 | 6.4 | 2.9 | 51.8 | 2.57 | −0.15 |
| Ottlie | 2466 | 7.0 | 3.3 | 61.4 | 6.0 | 2.8 | 52.2 | 2.53 | −0.19 |
| Cargill | 7777 | 7.6 | 3.3 | 61.0 | 6.5 | 2.8 | 51.9 | 2.57 | −0.15 |
| Bioseed | 9550 | 7.6 | 3.3 | 60.9 | 6.5 | 2.8 | 51.8 | 2.57 | −0.15 |
| Cargill | 7997 | 7.1 | 3.4 | 61.4 | 6.0 | 2.9 | 52.2 | 2.54 | −0.18 |
| Average | | 7.4 | 3.3 | 61.1 | 6.3 | 2.8 | 51.9 | 2.56 | −0.16 |

*Data from "The 1996 Corn Yield Test Report District 5 'A supplement to the December 14, 1996 issue of Iowa Farmer Today'"
**Averages of 1994–96 of Varieties Tested in District 5.

TABLE 2

High Protein Selections

| | | Moisture content for each composition | | | | | | | Feed | Premium over current price |
|---|---|---|---|---|---|---|---|---|---|---|
| Sample | Moisture | 0% Protein | 0% Oil | 0% Starch | 15% Protein | 15% Oil | 15% Starch | 15% Density | Feed EPV | $/bu @ $2.72/bu |
| GC#3892 | 7.4 | 17.4 | 6.7 | 63.1 | 14.8 | 5.7 | 53.6 | 1.340 | 3.33 | 0.61 |
| GC#3805 | 8.5 | 16.4 | 4.2 | 67.1 | 13.9 | 3.6 | 57.0 | 1.348 | 3.26 | 0.54 |
| GC#3978 | 7.8 | 16.2 | 6.2 | 64.0 | 13.8 | 5.3 | 54.4 | 1.340 | 3.24 | 0.52 |
| GC#3728 | 9.0 | 15.8 | 4.2 | 65.1 | 13.4 | 3.6 | 55.3 | 1.291 | 3.21 | 0.49 |
| GC#3963 | 7.7 | 15.6 | 5.4 | 66.9 | 13.3 | 4.6 | 56.9 | 1.336 | 3.19 | 0.47 |
| GC#3642 | 7.8 | 15.2 | 4.7 | 66.9 | 12.9 | 4.0 | 56.9 | 1.319 | 3.16 | 0.44 |
| GC#3781 | 8.4 | 15.2 | 5.9 | 65.5 | 12.9 | 5.0 | 55.7 | 1.317 | 3.16 | 0.44 |
| GC#3663 | 8.1 | 15.1 | 4.1 | 67.4 | 12.8 | 3.5 | 57.3 | 1.340 | 3.16 | 0.44 |
| Average | | 15.9 | 5.2 | 65.8 | 13.5 | 4.4 | 55.9 | 1.3 | 3.21 | 0.49 |

TABLE 3

High Oil Selections

| | | Moisture content for each composition | | | | | | | Feed | Premium over current price |
|---|---|---|---|---|---|---|---|---|---|---|
| Sample | Moisture | 0% Protein | 0% Oil | 0% Starch | 15% Protein | 15% Oil | 15% Starch | 15% Density | Feed EPV | $/bu @ $2.72/bu |
| GC#4066 | 6.7 | 12.1 | 7.7 | 64.3 | 10.3 | 6.5 | 54.7 | 1.287 | 2.92 | 0.20 |
| GC#3886 | 0.2 | 11.4 | 7.7 | 60.7 | 9.7 | 6.5 | 51.6 | 1.332 | 2.87 | 0.15 |
| GC#3831 | 7.2 | 14.8 | 7.6 | 64.8 | 12.6 | 6.5 | 55.1 | 1.334 | 3.13 | 0.41 |
| GC#3833 | 7.2 | 14.6 | 7.5 | 65.2 | 12.4 | 6.4 | 55.4 | 1.317 | 3.11 | 0.39 |
| GC#3641 | 7.4 | 13.2 | 7.5 | 66.3 | 11.2 | 6.4 | 56.4 | 1.322 | 3.01 | 0.29 |
| GC#3839 | 7.7 | 13.9 | 7.4 | 65.2 | 11.8 | 6.3 | 55.4 | 1.323 | 3.06 | 0.34 |
| GC#3822 | 6.9 | 13.6 | 7.2 | 66.7 | 11.6 | 6.1 | 56.7 | 1.313 | 3.04 | 0.32 |
| GC#3930 | 8.7 | 10.7 | 7.2 | 66.9 | 9.1 | 6.1 | 56.9 | 1.287 | 2.81 | 0.09 |
| GC#3969 | 7.4 | 11.7 | 7.1 | 67.8 | 9.9 | 6.0 | 57.6 | 1.316 | 2.89 | 0.17 |
| GC#3696 | 6.9 | 10.1 | 7.1 | 68.7 | 8.6 | 6.0 | 58.4 | 1.270 | 2.77 | 0.05 |

TABLE 3-continued

High Oil Selections

| | | Moisture content for each composition | | | | | | | | Premium over current price |
|---|---|---|---|---|---|---|---|---|---|---|
| Sample | Moisture | 0% Protein | 0% Oil | 0% Starch | 15% Protein | 15% Oil | 15% Starch | 15% Density | Feed EPV | $/bu @ $2.72/bu |
| GC#3829 | 8.1 | 12.8 | 6.9 | 66.5 | 10.9 | 5.9 | 56.5 | 1.320 | 2.97 | 0.25 |
| GC#3713 | 8.8 | 12.3 | 6.9 | 65.7 | 10.5 | 5.9 | 55.8 | 1.311 | 2.94 | 0.22 |
| GC#4037 | 8.0 | 12.0 | 6.9 | 66.8 | 10.2 | 5.9 | 56.8 | 1.311 | 2.91 | 0.19 |
| GC#3700 | 7.8 | 11.9 | 6.9 | 67.8 | 10.1 | 5.9 | 57.6 | 1.319 | 2.91 | 0.19 |
| GC#3901 | 7.9 | 13.3 | 6.8 | 66.0 | 11.3 | 5.8 | 56.1 | 1.334 | 3.01 | 0.29 |
| GC#3809 | 8.2 | 13.0 | 6.8 | 67.1 | 11.1 | 5.8 | 57.0 | 1.331 | 2.99 | 0.27 |
| GC#3689 | 7.5 | 12.6 | 6.8 | 66.8 | 10.7 | 5.8 | 56.8 | 1.326 | 2.96 | 0.24 |
| GC#3640 | 7.3 | 12.1 | 6.8 | 67.8 | 10.3 | 5.8 | 57.6 | 1.320 | 2.92 | 0.20 |
| GC#3723 | 6.9 | 11.8 | 6.8 | 68.4 | 10.0 | 5.8 | 58.1 | 1.296 | 2.90 | 0.18 |
| GC#3821 | 7.4 | 10.1 | 6.8 | 69.1 | 8.6 | 5.8 | 58.7 | 1.268 | 2.77 | 0.05 |
| GC#3892 | 7.4 | 17.4 | 6.7 | 63.1 | 14.8 | 5.7 | 53.6 | 1.340 | 3.33 | 0.61 |
| GC#3697 | 8.0 | 14.7 | 6.7 | 64.7 | 12.5 | 5.7 | 55.0 | 1.321 | 3.12 | 0.40 |
| GC#4053 | 7.4 | 13.9 | 6.7 | 66.8 | 11.8 | 5.7 | 56.8 | 1.319 | 3.06 | 0.34 |
| GC#3711 | 8.3 | 13.5 | 6.7 | 65.9 | 11.5 | 5.7 | 56.0 | 1.313 | 3.03 | 0.31 |
| GC#3712 | 7.5 | 12.6 | 6.7 | 67.0 | 10.7 | 5.7 | 57.0 | 1.314 | 2.96 | 0.24 |
| GC#3823 | 9.0 | 12.1 | 6.7 | 66.5 | 10.3 | 5.7 | 56.5 | 1.285 | 2.92 | 0.20 |
| GC#3694 | 6.6 | 9.1 | 6.7 | 70.6 | 7.7 | 5.7 | 60.0 | 1.305 | 2.69 | −0.03 |
| GC#3838 | 6.8 | 14.8 | 6.6 | 66.0 | 12.6 | 5.6 | 56.1 | 1.323 | 3.13 | 0.41 |
| GC#3717 | 7.3 | 13.1 | 6.6 | 67.6 | 11.1 | 5.6 | 57.5 | 1.324 | 3.00 | 0.28 |
| GC#3687 | 8.6 | 12.8 | 6.6 | 65.7 | 10.9 | 5.6 | 55.8 | 1.317 | 2.97 | 0.25 |
| GC#3968 | 6.6 | 12.0 | 6.6 | 68.3 | 10.2 | 5.6 | 58.1 | 1.303 | 2.91 | 0.19 |
| GC#4151 | 7.0 | 11.6 | 6.6 | 61.0 | 9.9 | 5.6 | 51.9 | 1.299 | 2.88 | 0.16 |
| GC#3941 | 7.5 | 11.1 | 6.6 | 69.0 | 9.4 | 5.6 | 58.7 | 1.334 | 2.85 | 0.13 |
| GC#3695 | 8.1 | 10.6 | 6.6 | 68.2 | 9.0 | 5.6 | 58.0 | 1.295 | 2.81 | 0.09 |
| GC#3806 | 8.0 | 14.4 | 6.5 | 66.3 | 12.2 | 5.5 | 56.4 | 1.336 | 3.10 | 0.38 |
| GC#3926 | 8.6 | 14.4 | 6.5 | 65.3 | 12.2 | 5.5 | 55.5 | 1.317 | 3.10 | 0.38 |
| GC#3896 | 6.7 | 12.2 | 6.5 | 67.3 | 10.4 | 5.5 | 57.2 | 1.316 | 2.93 | 0.21 |
| GC#3808 | 7.5 | 11.8 | 6.5 | 68.5 | 10.0 | 5.5 | 58.2 | 1.325 | 2.90 | 0.18 |
| GC#3927 | 7.4 | 11.5 | 6.5 | 68.4 | 9.8 | 5.5 | 58.1 | 1.308 | 2.87 | 0.15 |
| GC#3719 | 7.0 | 11.1 | 6.5 | 68.8 | 9.4 | 5.5 | 58.5 | 1.307 | 2.85 | 0.13 |
| GC#3810 | 7.9 | 11.1 | 6.5 | 68.6 | 9.4 | 5.5 | 58.3 | 1.331 | 2.85 | 0.13 |
| Average | | 12.5 | 6.9 | 66.6 | 10.7 | 5.8 | 56.6 | 1.3 | 2.95 | 0.23 |
| GC#3847 | 8.7 | 12.7 | 6.4 | 66.8 | 10.8 | 5.4 | 56.8 | 1.306 | 2.97 | 0.25 |
| GC#3763 | 7.7 | 12.4 | 6.4 | 66.4 | 10.5 | 5.4 | 56.4 | 1.294 | 2.95 | 0.23 |
| GC#3913 | 7.1 | 11.3 | 6.4 | 67.6 | 9.6 | 5.4 | 57.5 | 1.276 | 2.86 | 0.14 |
| GC#3753 | 7.4 | 11.1 | 6.4 | 67.9 | 9.4 | 5.4 | 57.7 | 1.296 | 2.85 | 0.13 |
| GC#3820 | 7.9 | 10.5 | 6.4 | 68.2 | 8.9 | 5.4 | 58.0 | 1.289 | 2.80 | 0.08 |
| GC#3905 | 7.3 | 13.9 | 6.3 | 66.5 | 11.8 | 5.4 | 56.5 | 1.323 | 3.06 | 0.34 |
| GC#3815 | 8.1 | 12.5 | 6.3 | 67.7 | 10.6 | 5.4 | 57.5 | 1.326 | 2.96 | 0.24 |
| GC#3911 | 6.8 | 12.3 | 6.3 | 68.0 | 10.5 | 5.4 | 57.8 | 1.321 | 2.94 | 0.22 |
| GC#3646 | 6.5 | 11.5 | 6.3 | 69.1 | 9.8 | 5.4 | 58.7 | 1.297 | 2.97 | 0.25 |
| GC#3951 | 6.3 | 10.9 | 6.3 | 69.7 | 9.3 | 5.4 | 59.2 | 1.335 | 2.83 | 0.11 |
| GC#4026 | 6.1 | 10.4 | 6.3 | 69.7 | 8.8 | 5.4 | 59.2 | 1.306 | 2.79 | 0.07 |
| GC#3692 | 7.4 | 10.3 | 6.3 | 69.1 | 8.8 | 5.4 | 58.7 | 1.302 | 2.78 | 0.06 |
| GC#3929 | 7.5 | 10.0 | 6.3 | 69.8 | 8.5 | 5.4 | 59.3 | 1.296 | 2.77 | 0.05 |
| GC#3978 | 7.8 | 16.2 | 6.2 | 64.0 | 13.8 | 5.3 | 54.4 | 1.340 | 3.24 | 0.52 |
| GC#3807 | 8.2 | 14.8 | 6.2 | 66.3 | 12.6 | 5.3 | 56.4 | 1.340 | 3.13 | 0.41 |
| GC#3643 | 7.8 | 14.2 | 6.2 | 66.8 | 12.1 | 5.3 | 56.8 | 1.314 | 3.08 | 0.36 |
| GC#4090 | 7.6 | 12.8 | 6.2 | 61.1 | 10.9 | 5.3 | 51.9 | 1.252 | 2.97 | 0.25 |
| GC#3961 | 7.7 | 12.6 | 6.2 | 67.3 | 10.7 | 5.3 | 57.2 | 1.292 | 2.96 | 0.24 |
| GC#3922 | 8.3 | 11.9 | 6.2 | 67.5 | 10.1 | 5.3 | 57.4 | 1.319 | 2.91 | 0.19 |
| GC#3631 | 8.1 | 11.5 | 6.2 | 68.7 | 9.8 | 5.3 | 58.4 | 1.303 | 2.87 | 0.15 |
| GC#3812 | 6.6 | 11.3 | 6.2 | 68.9 | 9.6 | 5.3 | 58.6 | 1.313 | 2.86 | 0.14 |
| GC#3716 | 6.3 | 11.2 | 6.2 | 68.9 | 9.5 | 5.3 | 58.6 | 1.262 | 2.86 | 0.14 |
| GC#3691 | 7.7 | 11.1 | 6.2 | 67.8 | 9.4 | 5.3 | 57.6 | 1.302 | 2.85 | 0.13 |
| GC#3674 | 8.0 | 10.5 | 6.2 | 69.0 | 8.9 | 5.3 | 58.7 | 1.280 | 2.80 | 0.08 |
| GC#3714 | 8.5 | 10.4 | 6.2 | 67.5 | 8.8 | 5.3 | 57.4 | 1.240 | 2.79 | 0.07 |
| GC#4020 | 7.2 | 14.8 | 6.1 | 65.7 | 12.6 | 5.2 | 55.8 | 1.307 | 3.10 | 0.38 |
| GC#3636 | 6.4 | 12.2 | 6.1 | 68.5 | 10.4 | 5.2 | 58.2 | 1.311 | 2.93 | 0.21 |
| GC#1330 | 6.9 | 12.1 | 6.1 | 68.4 | 10.3 | 5.2 | 58.1 | 1.295 | 2.92 | 0.20 |
| GC#3747 | 7.9 | 11.2 | 6.1 | 68.3 | 9.5 | 5.2 | 58.1 | 1.309 | 2.86 | 0.14 |
| GC#3933 | 7.4 | 10.9 | 6.1 | 68.7 | 9.3 | 5.2 | 58.4 | 1.294 | 2.83 | 0.11 |
| GC#3932 | 8.1 | 10.6 | 6.1 | 68.7 | 9.0 | 5.2 | 58.4 | 1.308 | 2.81 | 0.09 |
| GC#3924 | 6.9 | 8.9 | 6.1 | 71.4 | 7.6 | 5.2 | 60.7 | 1.303 | 2.67 | −0.05 |
| GC#3762 | 8.1 | 14.8 | 6.0 | 64.2 | 12.6 | 5.1 | 54.6 | 1.293 | 3.13 | 0.41 |
| GC#3971 | 8.1 | 14.4 | 6.0 | 66.6 | 12.2 | 5.1 | 56.6 | 1.332 | 3.10 | 0.38 |
| GC#3904 | 7.2 | 13.7 | 6.0 | 67.7 | 11.6 | 5.1 | 57.5 | 1.358 | 3.05 | 0.33 |
| GC#3956 | 6.6 | 12.7 | 6.0 | 68.0 | 10.8 | 5.1 | 57.8 | 1.347 | 2.97 | 0.25 |
| GC#4158 | 8.4 | 12.2 | 6.0 | 59.7 | 10.4 | 5.1 | 50.7 | 1.320 | 2.93 | 0.21 |
| GC#3964 | 7.3 | 10.8 | 6.0 | 69.6 | 9.2 | 5.1 | 59.2 | 1.301 | 2.87 | 0.15 |

TABLE 3-continued

High Oil Selections

| | | Moisture content for each composition | | | | | | | Premium over current price |
|---|---|---|---|---|---|---|---|---|---|
| Sample | Moisture | 0% Protein | 0% Oil | 0% Starch | 15% Protein | 15% Oil | 15% Starch | 15% Density | Feed EPV | $/bu @ $2.72/bu |
| GC#4030 | 7.1 | 10.8 | 6.0 | 68.9 | 9.2 | 5.1 | 58.6 | 1.325 | 2.82 | 0.10 |
| GC#4054 | 8.1 | 10.7 | 6.0 | 69.3 | 9.1 | 5.1 | 58.9 | 1.288 | 2.81 | 0.09 |
| GC#1324 | 3.6 | 9.6 | 6.0 | 64.5 | 8.2 | 5.1 | 54.8 | 1.274 | 2.73 | 0.01 |
| Average | | 11.9 | 6.2 | 67.5 | 10.1 | 5.3 | 57.4 | 1.3 | 2.91 | 0.19 |

TABLE 4

High Protein/High Oil Selections Crossed to Mo17 for a Controlled Test

| | | Moisture content for each composition | | | | | | | Premium over current price |
|---|---|---|---|---|---|---|---|---|---|
| Sample IuuN: | Moisture | 0% Protein | 0% Oil | 0% Starch | 15% Protein | 15% Oil | 15% Starch | 15% Density | Feed EPV | $/bu @ $2.72/bu |
| 2332 | 9.6 | 18.1 | 5.4 | 63.7 | 15.4 | 4.6 | 54.1 | 1.340 | 3.38 | 0.66 |
| 2328 | 9.3 | 15.9 | 5.4 | 65.2 | 13.5 | 4.6 | 55.4 | 1.334 | 3.21 | 0.49 |
| 2338 | 8.7 | 15.9 | 4.5 | 65.9 | 13.5 | 3.8 | 56.0 | 1.333 | 3.21 | 0.49 |
| 2334 | 8.9 | 15.6 | 5.5 | 65.3 | 13.3 | 4.7 | 55.5 | 1.314 | 3.19 | 0.47 |
| 2314 | 9.0 | 15.4 | 5.6 | 66.0 | 13.1 | 4.8 | 56.1 | 1.331 | 3.17 | 0.45 |
| 2329 | 9.8 | 15.0 | 4.4 | 66.3 | 12.8 | 3.7 | 56.4 | 1.313 | 3.15 | 0.43 |
| 2330 | 9.4 | 14.6 | 5.2 | 66.1 | 12.4 | 4.4 | 56.2 | 1.316 | 3.11 | 0.39 |
| 2331 | 9.5 | 14.4 | 5.8 | 66.0 | 12.2 | 4.9 | 56.1 | 1.313 | 3.10 | 0.38 |
| 2333 | 9.0 | 13.7 | 5.2 | 68.1 | 11.6 | 4.4 | 57.9 | 1.317 | 3.05 | 0.33 |
| 2360 | 9.7 | 12.1 | 5.0 | 67.0 | 10.3 | 4.3 | 57.0 | 1.281 | 2.92 | 0.20 |
| Average | | 15.1 | 5.2 | 66.0 | 12.8 | 4.4 | 56.1 | 1.3 | 3.15 | 0.43 |

Table 5 shows parameters used to calculate economic premium value (EPV) for corn lines according to the present invention.

TABLE 5

EPV is the estimate premium value as calculated from the formula in Nutrient Content and Feeding Value of Iowa Corn and the current statistics from gopher://shelley.cauky.edu/00/.agwx/usr/markets/usda/PAGR210 3/24/97.

Current Statistics.
Terms for end-use calculations for corn:

| | |
|---|---|
| Corn Price $/bu | 2.72 |
| Protein Content of average corn | 8.0 |
| Oil content of average corn | 3.5 |
| Starch content of average corn | 59.5 |
| Corn oil price $/lb | 0.24 |
| Oil refining loss % | 2.5 |
| DDG price $/ton (Distillers Dried Grain) | 145 |
| Moisture content DDG % | 9 |
| Ethanol price $/gal | 1.30 |
| Ethanol Conversion factor | 100 |
| Protein content of meal % | 44 |
| Meal price (soybean) $/ton | 214 |
| Feed additive price $/lb | 0.1 |
| Weight of feed additives % | 60 |
| Protein content of feed % | 16 |

Table 6 shows the pedigrees for the corn lines selected for high protein and high oil content. In Table 6, the progression of pedigrees is from right to left with those to the left being most advanced. The first column, labeled "GC#," is the numeric identifier for a particular line tested using a gas chromatograph (e.g., row 1 is for GC#3631). The second column, labeled "IuuN," is the numeric identifier for that particular line grown in an Iowa Nursery plot in the summer of calendar year U, showing the row number and plant number (e.g., row 1, column 2 shows that GC#3631 is from row 5092, plant 1). (Only the top ear from each plant was bred and harvested for this embodiment.) The third column, labeled "Activity," shows the breeding act performed to obtain the line shown in column 1 (e.g., row 1, column 3 shows that GC#3631 is from S2, or selfed twice generation of the pedigree to its right).

The fourth column, labeled "Temp#," is the numeric identifier for the parent line (e.g., row 1, column 4 shows that parent of GC#3631 is temp# 23). The fifth column, labeled "Source 1," is the alphanumeric identifier for that particular line grown in a Puerto Rico Nursery plot in the winter (for Iowa) growing period starting in calendar year T and ending in calendar year U, showing the row number and plant number (e.g., row 1, column 5 shows that the parent GC#3631 is from Puerto Rico nursery row 596, plant 1 of growing period TU). The sixth column, labeled "Activity," shows the breeding act performed to obtain the parent line shown in column 4 (e.g., row 1, column 6 shows that temp#23 is from S1, or selfed once generation of the pedigree to its right).

The seventh column, labeled "Source 2," is the alphanumeric identifier for that particular line grown in a Iowa Nursery plot in the summer growing period in calendar year T, showing the row number and plant number (e.g., row 1, column 7 shows that the grandparent of GC#3631 is from Iowa nursery row 2400, plant 1 of growing period T). The eighth column, labeled "Activity," shows the breeding act performed to obtain the grandparent line shown in column 7 (e.g., row 1, column 8 shows that source IttN:2400 has itself as the ovule parent and IttN:2399 as the pollen parent). The ninth column, labeled "Analysis ID," shows the measurement acts performed to select the breeding act for the grandparent line shown in column 7 (e.g., row 1, column 9 shows that source IttN:2400 has crossed plants from seeds having gas chromatograph measurements 118 and 11 (GC#118×GC#11)).

The tenth column, labeled "Source 3," is the alphanumeric identifier for that particular line grown in a Iowa Nursery plot in the summer growing period in calendar year S, showing the row number and plant number (e.g., row 1, column 10 shows that the great-grandparents of GC#3631 are from Iowa nursery row 270, plant 3 crossed from Iowa nursery row 250, plant 13 of growing period S (IssN:270-3xIssN:250-13)). The eleventh column, labeled "Pedigree," shows the breeding act performed to obtain the grandparent line shown in column 10 (e.g., row 1, column 11 shows that the source pedigree is a cross of #15S1 from #5S1 as the pollen parent, each of which is a maize-Tripsacum open-pollination introgression from a Harlan-DeWet source). The maize-Tripsacum sources (i.e., #5S1, #13S1, #15S1) were each initially separately measured and selected based on the measured trait(s). Deposits of #5S1, #13S1 and #15S1 were made under the terms of the Budapest Treaty on Apr. 24, 2003, at the American Type Culture Collection (ATCC) in Manassas, Va., and have been assigned ATCC Accession Nos. PTA-5159, PTA-5158, and PTA-5160, respectively. The original maize sources (i.e., Mo17, A632, W153R, H99) are publicly available Corn-Belt maize lines.

TABLE 6

High-Protein-High-Oil Pedigrees
Pedigrees for code name "red" selfing block

| GC# | IuuN: | Activity | Temp# | Source 1 | Activity | Source 2 | Activity | Analysis ID | Source 3 | Pedigree |
|---|---|---|---|---|---|---|---|---|---|---|
| 3631 | 5092-1 | @s(=S2) | 23 | PtuN:854-2 | @s(=S1) | IttN:2400-1 | IttN:2400xIttN:2399 | GC#118xGC#11 | IssN:270-3xIssN:250-13 | #15S1x#5S1 |
| 3636 | 5093-1 | @s(=S2) | 24 | PtuN:854-3 | @s(=S1) | IttN:2400-1 | IttN:2400xIttN:2399 | GC#118xGC#11 | IssN:270-3xIssN:250-13 | #15S1x#5S1 |
| 3640 | 5093-5 | @s(=S2) | 24 | PtuN:854-3 | @s(=S1) | IttN:2400-1 | IttN:2400xIttN:2399 | GC#118xGC#11 | IssN:270-3xIssN:250-13 | #15S1x#5S1 |
| 3641 | 5093-6 | @s(=S2) | 24 | PtuN:854-3 | @s(=S1) | IttN:2400-1 | IttN:2400xIttN:2399 | GC#118xGC#11 | IssN:270-3xIssN:250-13 | #15S1x#5S1 |
| 3642 | 5093-7 | @s(=S2) | 24 | PtuN:854-3 | @s(=S1) | IttN:2400-1 | IttN:2400xIttN:2399 | GC#118xGC#11 | IssN:270-3xIssN:250-13 | #15S1x#5S1 |
| 3643 | 5093-8 | @s(=S2) | 24 | PtuN:854-3 | @s(=S1) | IttN:2400-1 | IttN:2400xIttN:2399 | GC#118xGC#11 | IssN:270-3xIssN:250-13 | #15S1x#5S1 |
| 3646 | 5094-3 | @s(=S2) | 27 | PtuN:855-1 | @s(=S1) | IttN:2401-1 | IttN:2401xIttN:2402 | GC#26xGC#63 | IssN:251-7xIssN:259-2 | #5S1xW153R |
| 3663 | 5096-4 | @s(=S2) | 28 | PtuN:854-3 | @s(=S1) | IttN:2401-1 | IttN:2401xIttN:2402 | GC#26xGC#63 | IssN:251-7xIssN:259-2 | #5S1xW153R |
| 3674 | 5101-3 | @s(=S2) | 48 | PtuN:857-2 | @s(=S1) | IttN:2403-1 | IttN:2403xIttN:2404 | GC#29xMo17 | (IssN:251-8xIssN:257-15)xMo17 | (#5S1xMo17)xMo17 |
| 3687 | 5110-3 | @s(=S2) | 62 | PtuN:860-2 | @s(=S1) | IttN:2406-1 | IttN:2406xIttN:2405 | GC#26xGC#74 | IssN:251-7xIssN:260-16 | #5S1x#13S1 |
| 3689 | 5110-5 | @s(=S2) | 62 | PtuN:860-2 | @s(=S1) | IttN:2406-1 | IttN:2406xIttN:2405 | GC#26xGC#74 | IssN:251-7xIssN:260-16 | #5S1x#13S1 |
| 3691 | 5110-7 | @s(=S2) | 62 | PtuN:860-2 | @s(=S1) | IttN:2406-1 | IttN:2406xIttN:2405 | GC#26xGC#74 | IssN:251-7xIssN:260-16 | #5S1x#13S1 |
| 3692 | 5110-8 | @s(=S2) | 62 | PtuN:860-2 | @s(=S1) | IttN:2406-1 | IttN:2406xIttN:2405 | GC#26xGC#74 | IssN:251-7xIssN:260-16 | #5S1x#13S1 |
| 3694 | 5112-1 | @s(=S2) | 68 | PtuN:861-1 | @s(=S1) | IttN:2407-1 | IttN:2407xIttN:2408 | GC#74xGC#26 | IssN:260-16xIssN:251-7 | #13S1x#5S1 |
| 3695 | 5112-2 | @s(=S2) | 68 | PtuN:861-1 | @s(=S1) | IttN:2407-1 | IttN:2407xIttN:2408 | GC#74xGC#26 | IssN:260-16xIssN:251-7 | #13S1x#5S1 |
| 3697 | 5112-4 | @s(=S2) | 68 | PtuN:861-1 | @s(=S1) | IttN:2407-1 | IttN:2407xIttN:2408 | GC#74xGC#26 | IssN:260-16xIssN:251-7 | #13S1x#5S1 |
| 3700 | 5113-1 | @s(=S2) | 69 | PtuN:861-2 | @s(=S1) | IttN:2407-1 | IttN:2407xIttN:2408 | GC#74xGC#26 | IssN:260-16xIssN:251-7 | #13S1x#5S1 |
| 3711 | 5113-2 | @s(=S2) | 69 | PtuN:861-2 | @s(=S1) | IttN:2407-1 | IttN:2407xIttN:2408 | GC#74xGC#26 | IssN:260-16xIssN:251-7 | #13S1x#5S1 |
| 3712 | 5113-3 | @s(=S2) | 69 | PtuN:861-2 | @s(=S1) | IttN:2407-1 | IttN:2407xIttN:2408 | GC#74xGC#26 | IssN:260-16xIssN:251-7 | #13S1x#5S1 |
| 3713 | 5113-4 | @s(=S2) | 69 | PtuN:861-2 | @s(=S1) | IttN:2407-1 | IttN:2407xIttN:2408 | GC#74xGC#26 | IssN:260-16xIssN:251-7 | #13S1x#5S1 |
| 3714 | 5113-5 | @s(=S2) | 69 | PtuN:861-2 | @s(=S1) | IttN:2407-1 | IttN:2407xIttN:2408 | GC#74xGC#26 | IssN:260-16xIssN:251-7 | #13S1x#5S1 |
| 3716 | 5114-1 | @s(=S2) | 70 | PtuN:861-3 | @s(=S1) | IttN:2407-1 | IttN:2407xIttN:2408 | GC#74xGC#26 | IssN:260-16xIssN:251-7 | #13S1x#5S1 |
| 3717 | 5114-2 | @s(=S2) | 70 | PtuN:861-3 | @s(=S1) | IttN:2407-1 | IttN:2407xIttN:2408 | GC#74xGC#26 | IssN:260-16xIssN:251-7 | #13S1x#5S1 |
| 3719 | 5114-4 | @s(=S2) | 70 | PtuN:861-3 | @s(=S1) | IttN:2407-1 | IttN:2407xIttN:2408 | GC#74xGC#26 | IssN:260-16xIssN:251-7 | #13S1x#5S1 |
| 3723 | 5114-8 | @s(=S2) | 70 | PtuN:861-3 | @s(=S1) | IttN:2407-1 | IttN:2407xIttN:2408 | GC#74xGC#26 | IssN:260-16xIssN:251-7 | #13S1x#5S1 |
| 3728 | 5119-5 | @s(=S2) | 83 | PtuN:863-2 | @s(=S1) | IttN:2409-1 | IttN:2409xIttN:2410 | GC#117xGC#63 | IssN:269-2x(IssN:260-8)xIssN:259-2 | (W153Rx13S1)xW153R |
| 3747 | 5127-1 | @s(=S2) | 103 | PtuN:866-1 | @s(=S1) | IttN:2414-1 | IttN:2414xIttN:2413 | GC#63xGC#129 | IssN:259-2xIssN:271-1 | W153Rx#15S1 |
| 3753 | 5128-1 | @s(=S2) | 104 | PtuN:866-2 | @s(=S1) | IttN:2414-1 | IttN:2414xIttN:2413 | GC#63xGC#129 | IssN:259-2xIssN:271-1 | W153Rx#15S1 |
| 3762 | 5129-7 | @s(=S2) | 105 | PtuN:866-3 | @s(=S1) | IttN:2414-1 | IttN:2414xIttN:2413 | GC#63xGC#129 | IssN:259-2xIssN:271-1 | W153Rx#15S1 |
| 3763 | 5129-8 | @s(=S2) | 105 | PtuN:866-3 | @s(=S1) | IttN:2414-1 | IttN:2414xIttN:2413 | GC#63xGC#129 | IssN:259-2xIssN:271-1 | W153Rx#15S1 |
| 3781 | 5138-6 | @s(=S2) | 129 | PtuN:870-3 | @s(=S1) | IttN:2420-1 | IttN:2420xIttN:2419 | GC#162xGC#66 | IssN:279-2x(IssN:259-12x250-10) | W153Rx(W153Rx#5S1) |
| 3801 | 5149-8 | @s(=S2) | 148 | PtuN:875-2 | @s(=S1) | IttN:2427-1 | IttN:2427xIttN:2428 | GC#68xGC#82 | (IssN:259-14x251-5)xIssN:261-2 | (W153Rx#5S1)x#13S1 |
| 3806 | 5156-5 | @s(=S2) | 160 | PtuN:877-3 | @s(=S1) | IttN:2429-1 | IttN:2429xIttN:2430 | GC#74xGC#82 | IssN:260-16xIssN:261-2 | #13S1x#13S1 |
| 3807 | 5156-6 | @s(=S2) | 160 | PtuN:877-3 | @s(=S1) | IttN:2429-1 | IttN:2429xIttN:2430 | GC#74xGC#82 | IssN:260-16xIssN:261-2 | #13S1x#13S1 |
| 3808 | 5156-7 | @s(=S2) | 160 | PtuN:877-3 | @s(=S1) | IttN:2429-1 | IttN:2429xIttN:2430 | GC#74xGC#82 | IssN:260-16xIssN:261-2 | #13S1x#13S1 |
| 3809 | 5156-8 | @s(=S2) | 160 | PtuN:877-3 | @s(=S1) | IttN:2429-1 | IttN:2429xIttN:2430 | GC#74xGC#82 | IssN:260-16xIssN:261-2 | #13S1x#13S1 |
| 3810 | 5156-9 | @s(=S2) | 160 | PtuN:877-3 | @s(=S1) | IttN:2429-1 | IttN:2429xIttN:2430 | GC#74xGC#82 | IssN:260-16xIssN:261-2 | #13S1x#13S1 |
| 3812 | 5156-11 | @s(=S2) | 160 | PtuN:877-3 | @s(=S1) | IttN:2429-1 | IttN:2429xIttN:2430 | GC#74xGC#82 | IssN:260-16xIssN:261-2 | #13S1x#13S1 |
| 3815 | 5158-2 | @s(=S2) | 164 | PtuN:878-1 | @s(=S1) | IttN:2430-1 | IttN:2430xIttN:2429 | GC#82xGC#74 | IssN:261-2xIssN:260-16 | #13S1x#13S1 |
| 3820 | 5157-1 | @s(=S2) | 163 | PtuN:878-1 | @s(=S1) | IttN:2430-1 | IttN:2430xIttN:2429 | GC#82xGC#74 | IssN:261-2xIssN:260-16 | #13S1x#13S1 |
| 3821 | 5157-2 | @s(=S2) | 163 | PtuN:878-1 | @s(=S1) | IttN:2430-1 | IttN:2430xIttN:2429 | GC#82xGC#74 | IssN:261-2xIssN:260-16 | #13S1x#13S1 |
| 3822 | 5157-3 | @s(=S2) | 163 | PtuN:878-1 | @s(=S1) | IttN:2430-1 | IttN:2430xIttN:2429 | GC#82xGC#74 | IssN:261-2xIssN:260-16 | #13S1x#13S1 |
| 3823 | 5157-5 | @s(=S2) | 163 | PtuN:878-1 | @s(=S1) | IttN:2430-1 | IttN:2430xIttN:2429 | GC#82xGC#74 | IssN:261-2xIssN:260-16 | #13S1x#13S1 |
| 3829 | 5156-1 | @s(=S2) | 160 | PtuN:877-3 | @s(=S1) | IttN:2429-1 | IttN:2429xIttN:2430 | GC#74xGC#82 | IssN:260-16xIssN:261-2 | #13S1x#13S1 |
| 3831 | 5156-3 | @s(=S2) | 160 | PtuN:877-3 | @s(=S1) | IttN:2429-1 | IttN:2429xIttN:2430 | GC#74xGC#82 | IssN:260-16xIssN:261-2 | #13S1x#13S1 |
| 3833 | 5156-5 | @s(=S2) | 160 | PtuN:877-3 | @s(=S1) | IttN:2429-1 | IttN:2429xIttN:2430 | GC#74xGC#82 | IssN:260-16xIssN:261-2 | #13S1x#13S1 |

TABLE 6-continued

High-Protein-High-Oil Pedigrees
Pedigrees for code name "red" selfing block

| GC# | IuuN: | Activity | Temp# | Source 1 | Activity | Source 2 | Activity | Analysis ID | Source 3 | Pedigree |
|---|---|---|---|---|---|---|---|---|---|---|
| 3838 | 5162-5 | @s(=S2) | 169 | PtuN:879-3 | @s(=S1) | IttN:2431-1 | IttN:2431xIttN:2432 | GC#74xGC#82 | IssN:260-16xIssN:261-2 | #13S1x#13S1 |
| 3839 | 5162-6 | @s(=S2) | 169 | PtuN:879-3 | @s(=S1) | IttN:2431-1 | IttN:2431xIttN:2432 | GC#74xGC#82 | IssN:260-16xIssN:261-2 | #13S1x#13S1 |
| 3886 | 5196-5 | @s(=S2) | 232 | PtuN:892-1 | @s(=S1) | IttN:2445-1 | IttN:2445xIttn:2446 | GC#88xA632 | IssN:261-6xA632 | #13S1xA632 |
| 3892 | 5198-4 | @s(=S2) | 234 | PtuN:892-3 | @s(=S1) | IttN:2445-1 | IttN:2445xIttn:2446 | GC#88xA632 | IssN:261-6xA632 | #13S1xA632 |
| 3896 | 5202-3 | @s(=S2) | 240 | PtuN:894-1 | @s(=S1) | IttN:2448-1 | IttN:2448xIttN:2447 | GC#162xGC#82 | IssN:279-2xIssN:261-2 | W153Rx#13S1 |
| 3901 | 5203-1 | @s(=S2) | 241 | PtuN:894-2 | @s(=S1) | IttN:2448-1 | IttN:2448xIttN:2447 | GC#162xGC#82 | IssN:279-2xIssN:261-2 | W153Rx#13S1 |
| 3904 | 5203-4 | @s(=S2) | 241 | PtuN:894-2 | @s(=S1) | IttN:2448-1 | IttN:2448xIttN:2447 | GC#162xGC#82 | IssN:279-2xIssN:261-2 | W153Rx#13S1 |
| 3905 | 5203-5 | @s(=S2) | 241 | PtuN:894-2 | @s(=S1) | IttN:2448-1 | IttN:2448xIttN:2447 | GC#162xGC#82 | IssN:279-2xIssN:261-2 | W153Rx#13S1 |
| 3911 | 5203-11 | @s(=S2) | 241 | PtuN:894-2 | @s(=S1) | IttN:2448-1 | IttN:2448xIttN:2447 | GC#162xGC#82 | IssN:279-2xIssN:261-2 | W153Rx#13S1 |
| 3913 | 5204-2 | @s(=S2) | 242 | PtuN:894-3 | @s(=S1) | IttN:2448-1 | IttN:2448xIttN:2447 | GC#162xGC#82 | IssN:279-2xIssN:261-2 | W153Rx#13S1 |
| 3922 | 5205-1 | @s(=S2) | 248 | PtuN:895-1 | @s(=S1) | IttN:2449-1 | IttN:2449xIttN:2450 | GC#73xGC#83 | IssN:260-14xIssN:261-2 | #13S1x#13S1 |
| 3924 | 5205-3 | @s(=S2) | 248 | PtuN:895-1 | @s(=S1) | IttN:2449-1 | IttN:2449xIttN:2450 | GC#73xGC#83 | IssN:260-14xIssN:261-2 | #13S1x#13S1 |
| 3926 | 5205-5 | @s(=S2) | 248 | PtuN:895-1 | @s(=S1) | IttN:2449-1 | IttN:2449xIttN:2450 | GC#73xGC#83 | IssN:260-14xIssN:261-2 | #13S1x#13S1 |
| 3927 | 5205-6 | @s(=S2) | 248 | PtuN:895-1 | @s(=S1) | IttN:2449-1 | IttN:2449xIttN:2450 | GC#73xGC#83 | IssN:260-14xIssN:261-2 | #13S1x#13S1 |
| 3929 | 5206-2 | @s(=S2) | 249 | PtuN:895-2 | @s(=S1) | IttN:2449-1 | IttN:2449xIttN:2450 | GC#73xGC#83 | IssN:260-14xIssN:261-2 | #13S1x#13S1 |
| 3930 | 5206-3 | @s(=S2) | 249 | PtuN:895-2 | @s(=S1) | IttN:2449-1 | IttN:2449xIttN:2450 | GC#73xGC#83 | IssN:260-14xIssN:261-2 | #13S1x#13S1 |
| 3932 | 5206-5 | @s(=S2) | 249 | PtuN:895-2 | @s(=S1) | IttN:2449-1 | IttN:2449xIttN:2450 | GC#73xGC#83 | IssN:260-14xIssN:261-2 | #13S1x#13S1 |
| 3933 | 5206-6 | @s(=S2) | 249 | PtuN:895-2 | @s(=S1) | IttN:2449-1 | IttN:2449xIttN:2450 | GC#73xGC#83 | IssN:260-14xIssN:261-2 | #13S1x#13S1 |
| 3941 | 5208-4 | @s(=S2) | 252 | PtuN:896-1 | @s(=S1) | IttN:2450-1 | IttN:2450xIttN:2449 | GC#83xGC#73 | IssN:261-2xIssN:260-14 | #13S1x#13S1 |
| 3951 | 5209-5 | @s(=S2) | 253 | PtuN:896-2 | @s(=S1) | IttN:2450-1 | IttN:2450xIttN:2449 | GC#83xGC#73 | IssN:261-2xIssN:260-14 | #13S1x#13S1 |
| 3956 | 5210-2 | @s(=S2) | 254 | PtuN:896-3 | @s(=S1) | IttN:2450-1 | IttN:2450xIttN:2449 | GC#83xGC#73 | IssN:261-2xIssN:260-14 | #13S1x#13S1 |
| 3961 | 5211-2 | @s(=S2) | 257 | PtuN:897-1 | @s(=S1) | IttN:2451-1 | IttN:2451xIttN:2452 | GC#68xGC#83 | (IssN:259-14x251-5)x261-2 | (W153Rx#5S1)x#13S1 |
| 3963 | 5212-2 | @s(=S2) | 258 | PtuN:897-2 | @s(=S1) | IttN:2451-1 | IttN:2451xIttN:2452 | GC#68xGC#83 | (IssN:259-14x251-5)x261-2 | (W153Rx#5S1)x#13S1 |
| 3964 | 5212-3 | @s(=S2) | 258 | PtuN:897-2 | @s(=S1) | IttN:2451-1 | IttN:2451xIttN:2452 | GC#68xGC#83 | (IssN:259-14x251-5)x261-2 | (W153Rx#5S1)x#13S1 |
| 3968 | 5212-7 | @s(=S2) | 258 | PtuN:897-2 | @s(=S1) | IttN:2451-1 | IttN:2451xIttN:2452 | GC#68xGC#83 | (IssN:259-14x251-5)x261-2 | (W153Rx#5S1)x#13S1 |
| 3969 | 5212-8 | @s(=S2) | 258 | PtuN:897-2 | @s(=S1) | IttN:2451-1 | IttN:2451xIttN:2452 | GC#68xGC#83 | (IssN:259-14x251-5)x261-2 | (W153Rx#5S1)x#13S1 |
| 3971 | 5213-2 | @s(=S2) | 260 | PtuN:898-1 | @s(=S1) | IttN:2454-1 | IttN:2454xIttN:2453 | GC#67xGC#88 | (IssN:259-13x251-11)x261-6 | (W153Rx#5S1)x#13S1 |
| 3978 | 5214-4 | @s(=S2) | 261 | PtuN:898-2 | @s(=S1) | IttN:2454-1 | IttN:2454xIttN:2453 | GC#67xGC#88 | (IssN:259-13x251-11)x261-6 | (W153Rx#5S1)x#13S1 |
| 3996 | 5216-7 | @s(=S2) | 269 | PtuN:899-2 | @s(=S1) | IttN:2455-1 | IttN:2455xIttN:2456 | GC#85xMo17 | IssN:261-5xMo17 | #13S1xMo17 |
| 4020 | 5227-5 | @s(=S2) | 303 | PtuN:905-1 | @s(=S1) | IttN:2461-1 | IttN:2461-6xIttN:279-2 | GC#88xGC#162 | IssN:261-6xIssN:279-2 | #13S1xW153R |
| 4026 | 5228-4 | @s(=S2) | 304 | PtuN:905-2 | @s(=S1) | IttN:2461-1 | IttN:2461-6xIttN:2462 | GC#88xGC#162 | IssN:261-6xIssN:279-2 | #13S1xW153R |
| 4030 | 5231-4 | @s(=S2) | 317 | PtuN:908-1 | @s(=S1) | IttN:2465-1 | IttN:2465xIttN:2466 | A632xGC#85 | A632xIssN:261-5 | A632x#13S1 |
| 4037 | 5232-2 | @s(=S2) | 318 | PtuN:908-2 | @s(=S1) | IttN:2465-1 | IttN:2465xIttN:2466 | GC#29xGC#85 | A632xIssN:261-5 | A632x#13S1 |
| 4053 | 5257-5 | @s(=S2) | 380 | PtuN:921-1 | @s(=S1) | IttN:2479-1 | IttN:2479xIttN:2480 | GC#29xGC#59 | (IssN:251-8x257-15)x | (#5S1xMo17)x(#5S1xMo17) |
| 4054 | 5257-6 | @s(=S2) | 380 | PtuN:921-1 | @s(=S1) | IttN:2479-1 | IttN:2479xIttN:2480 | GC#29xGC#59 | (IssN:251-8x257-15)x | (#5S1xMo17)x(#5S1xMo17) |
| 4066 | 5259-9 | @s(=S2) | 385 | PtuN:922-1 | @s(=S1) | IttN:2480-1 | IttN:2480xIttN:2479 | GC#59xGC#29 | (IssN:257-15x251-8)x | (#5S1xMo17)x(#5S1xMo17) |
| 4090 | 5279-3 | @s(=S2) | 420 | PtuN:933-2 | @s(=S1) | | IttN:2494 @ | #8851 | Parental | |
| 4151 | 5299-1 | @s(=S2) | | PtuN:943-2 | @s(=S1) | IttN:2506-1 | IttN:2506 @ | GC#11 | IssN:250-13@ | #5S1 |
| 4158 | 5307-3 | @s(=S2) | 465 | PtuN:948-1 | @s(=S1) | IttN:2511 @ | GC#17 | IssN251-2x256-10 | #5S1xH99 | |

Table 7 shows the pedigrees for high-protein-and-high-oil top-cross lines. A "top cross" is a test process wherein each of a number of inbred lines (in the present case, introgressed lines) is crossed with a well-understood standard inbred corn line such as Mo17, in order to better understand the capabilities of the inbred lines. The top-cross lines were bred to yield-test the lines of the present invention as bred to a standard (Mo17) conventional corn variety.

TABLE 7

High Protein High Oil Top Cross

Pedigrees for Top Cross Block

| IuuN: | IttN: | Analysis ID | Analysis ID | Source | Pedigree |
|---|---|---|---|---|---|
| 2314 | 2495-1 | GC#1396 | | | #90S1@ |
| 2328 | 2790-1 | | GC#412 | IssN: 340-11 | #87S1@ |
| 2329 | 2499-6 | GC#1429 | | | #92S1@ |
| 2330 | 2740-2 | | GC#412 | IssN: 340-11 | #87S1@ |
| 2331 | 2790-3 | | GC#412 | IssN: 340-11 | #87S1@ |
| 2332 | 2790-4 | | GC#412 | IssN: 340-11 | #87S1@ |
| 2333 | 2789-1 | | GC#411 | IssN: 340-10 | #87S1@ |
| 2334 | 2790-5 | | GC#412 | IssN: 340-11 | #87S1@ |
| 2338 | 2908-6 | ts206 | GC#630 | IssN: 380-15 × 383-6 | #92S1 × A632 |
| 2360 | 2479-1 | GC#1321 | | (IssN: 251-8 × 257-15) × Mo17 | (#5S1 × Mo17) × Mo17 |

One aspect of the present invention provides crossing a first parent corn plant with a second parent corn plant and harvesting resultant first-generation (F1) hybrid corn seed, wherein said first or second parent corn plant, (or both) is a corn plant derived from one of the high-protein or high-oil or high-protein-and-oil content lines of the present invention. In the case where one parent is not a corn plant derived from one of the high-protein or high-oil or high-protein-and-oil content lines, one tends to obtain seed that, while not as high in protein or oil as shown above, is still significantly higher in protein than commercial hybrid (e.g., higher than about 8% protein at 0% moisture; for example between 8% and 12% protein content) and/or significantly higher in oil than commercial hybrid (e.g., higher than about 3.5% oil at 0% moisture; for example between 3.6% and 5% oil content). Even though such inbred lines or hybrids have a lower percentage increase in protein and/or oil content than other lines of the present invention, they have significantly higher protein and/or oil than conventional commercial corn, and may have other desirable characteristics as well.

Tables 2, 3, and 4 illustrate some of the best exemplary combinations of protein and oil. In various embodiments, the high-protein and/or high-oil corn lines described above are crossed with conventional corn lines to obtain other corn lines of the present invention. A large number of combinations of high protein and/or high oil content are thus obtained by selection and/or inbreeding of suitable seeds.

Table 8 illustrates some exemplary combinations (each of the exemplary combinations of the present invention that are shown in this Table 8 is labeled "Embodiment") according to the present invention which are achieved. Where particular embodiments of the present invention have been measured (and described above) that meet the specified criteria, these are explicitly shown as examples (e.g., GC#3892 which measured 17.4% protein and 6.7% oil at 0% moisture, is shown in the position where the >17% protein column and >6.5% oil row intersect). In other embodiments of this table, crosses between lines of the present invention as described herein are made, and selections are tested for the desired combination of protein and oil to choose the seeds, and those seeds are inbred. In other embodiments, inbred lines of the introgressed lines of the present invention are inbred, and top crosses made to conventional inbred corn lines, and the F1 hybrids tested for oil and protein content, and are tested, in order to achieve average values for the desired combination of protein and oil.

TABLE 8

Exemplary Inventive Combinations of High-Protein and/or High-Oil Content

| | >3% oil | >3.5% oil | >4% oil | >4.5% oil |
|---|---|---|---|---|
| >7% protein | | >7% & >3.5% Embodiment | >7% & >4% Embodiment | >7% & >4.5% Embodiment |
| >8% protein | >8% & >3% Embodiment | >8% & >3.5% Embodiment | >8% & >4% Embodiment | >8% & >4.5% Embodiment |
| >9% protein | >9% & >3% Embodiment | >9% & >3.5% Embodiment | >9% & >4% Embodiment | >9% & >4.5% Embodiment |
| >10% protein | >10% & >3% Embodiment | >10% & >3.5% Embodiment | >10% & >4% Embodiment | >10% & >4.5% Embodiment |
| >11% protein | >11% & >3% Embodiment | >11% & >3.5% Embodiment | >11% & >4% Embodiment | >11% & >4.5% Embodiment |
| >12% protein | >12% & >3% Embodiment | >12% & >3.5% Embodiment | >12% & >4% Embodiment | 2360 |
| >13% protein | >13% & >3% Embodiment | >13% & >3.5% Embodiment | >13% & >4% Embodiment | >12% & >4.5% Embodiment |
| >14% protein | >14% & >3% Embodiment | >14% & >3.5% Embodiment | >14% & >4% Embodiment | >13% & >4.5% Embodiment |
| >15% protein | >15% & >3% Embodiment | >15% & >3.5% Embodiment | >15% & >4% Embodiment | >15% & >4.5% Embodiment |
| >16% protein | >16% & >3% Embodiment | >16% & >3.5% 2338 | | >16% & >4.5% Embodiment |
| >17% protein | >17% & >3% Embodiment | >17% & >3.5% Embodiment | GC#3805 | >17% & >4.5% Embodiment |
| >18% protein | >18% & >3% Embodiment | >18% & >3.5% Embodiment | >18% & >4% Embodiment | >18% & >4.5% Embodiment |

| | >5% oil | >5.5% oil | >6% oil | >6.5% oil |
|---|---|---|---|---|
| >7% protein | >7% & >5% Embodiment | >7% & >5.5% Embodiment | >7% & >6% Embodiment | >7% & >6.5% Embodiment |
| >8% protein | >8% & >5% Embodiment | >8% & >5.5% Embodiment | >8% & >6% Embodiment | >8% & >6.5% Embodiment |
| >9% protein | >9% & >5% Embodiment | >9% & >5.5% Embodiment | >9% & >6% Embodiment | GC#3694 |
| >10% protein | >10% & >5% Embodiment | >10% & >5.5% Embodiment | >10% & >6% Embodiment | GC#3821 |
| >11% protein | >11% & >5% Embodiment | >11% & >5.5% Embodiment | >11% & >6% Embodiment | GC#3700 |
| >12% protein | >12% & >5% Embodiment | >12% & >5.5% Embodiment | >12% & >6% Embodiment | GC#3829 |
| >13% protein | >13% & >5% Embodiment | >13% & >5.5% Embodiment | >13% & >6% Embodiment | GC#3901 |
| >14% protein | >14% & >5% Embodiment | >14% & >5.5% Embodiment | >14% & >6% Embodiment | >14% & >6.5% Embodiment |

TABLE 8-continued

Exemplary Inventive Combinations of High-Protein and/or High-Oil Content

| | >15% & >5% | >15% & >5.5% | >15% & >6% | >15% & >6.5% |
|---|---|---|---|---|
| >15% protein | Embodiment | Embodiment | Embodiment | Embodiment |
| >16% protein | 2328 | >16% & >5.5% Embodiment | >16% & >6% Embodiment | >16% & >6.5% Embodiment |
| >17% protein | >17% & >5% Embodiment | >17% & >5.5% Embodiment | GC#3978 | >17% & >6.5% Embodiment |
| >18% protein | 2332 | >18% & >5.5% Embodiment | >18% & >6% Embodiment | GC#3892 |

| | >7% oil | >7.5% oil |
|---|---|---|
| >7% protein | >7% & >7% Embodiment | >7% & >7.5% Embodiment |
| >8% protein | >8% & >7% Embodiment | >8% & >7.5% Embodiment |
| >9% protein | >9% & >7% Embodiment | >9% & >7.5% Embodiment |
| >10% protein | GC#3930 | >10% & >7.5% Embodiment |
| >11% protein | >11% & >7% Embodiment | GC#3886 |
| >12% protein | >12% & >7% Embodiment | GC#4066 |
| >13% protein | GC#3841 | >13% & >7.5% Embodiment |
| >14% protein | >14% & >7% Embodiment | GC#3831 |
| >15% protein | >15% & >7% Embodiment | >15% & >7.5% Embodiment |
| >16% protein | >16% & >7% Embodiment | >16% & >7.5% Embodiment |
| >17% protein | >17% & >7% Embodiment | >17% & >7.5% Embodiment |
| >18% protein | >18% & >7% Embodiment | >18% & >7.5% Embodiment |

ALTERED FATTY-ACID CORN LINES

Corn oil from Corn-Belt lines has a very narrow range for fatty-acid composition. Historically, this narrow range resulted from using genetically uniform material to create the modern Corn-Belt hybrids. According one embodiment of the present invention, new genes from a novel source, viz. *Tripsacum dactyloides L.* (also called eastern gamagrass), are introduced into the Corn-Belt genome and thus genetic diversity is increased and germplasm and value-added trait enhancement are allowed through traditional plant-breeding practices.

As used herein "introgression" involves conventional pollination breeding techniques to incorporate foreign genetic material into a line of breeding stock. According to one embodiment of the present invention, a population of corn introgressed with genes from related species, viz. *Tripsacum dactyloides L.*, was screened for unique value-added traits, and in particular, the traits of high oleic fatty acid, low total saturated fatty acid, or high total saturated fatty acid. In other embodiments, breeding stock is selected for having high or low palmitic content, high or low stearic content, high or low oleic content, high or low linoleic content, and/or high or low linolenic content (i.e., any particular combination, as desired). The selected introgressed lines that were found to have useful oil quality traits were crossed to Corn-Belt inbreds in an attempt to alter the fatty-acid composition of the Corn-Belt material, i.e., recovered parental introgressed corn lines with desirable fatty-acid profiles were reciprocally crossed to Corn-Belt inbreds. These breeding crosses were self-pollinated and back-crossed for several generations to create new inbreds of the present invention having enhanced oil quality. In one embodiment, the fatty acids targeted for improvement were oleic acid and total saturated fatty acids (palmitic and stearic acids). The breeding program of one embodiment successfully resulted in markedly higher oleic acid composition and significantly lower total saturated fatty-acid composition.

The altered fatty-acid corn lines of the present invention are corn lines which were created through traditional plant-breeding techniques of cross- and self-pollination methods using as parents (1) Corn-Belt inbred maize lines of public origin and (2) corn lines introgressed with *Tripsacum dactyloides L.* This process resulted in genetic material (i.e., seeds) with altered fatty-acid compositions of the oil. The corn lines of the present invention that were developed had high oleic fatty-acid composition, and/or low total saturated fatty-acid composition or high total saturated fatty-acid compositions.

These corn lines of the present invention can be used to enhance the oil quality of corn in a commercial program to improve the nutritional quality of maize for human and animal consumption. Corn oil in Corn-Belt lines has less than optimum fatty-acid compositions and ranges of compositions, e.g., oleic fatty-acid content is only 20–30% generally, (however, W153R has been measured to have up to 42% oleic) and saturated fatty acids are only 11–13%. Fatty-acid compositions in the high-oil corn lines of the present invention are up to 14.8% total saturated and up to 31.6% oleic. Commercial seed industries, food or feed industries would benefit from such inventions.

Corn is the most important feed grain in the United States. Corn production in 1995 was 10,962 million bushels. Fifty-three percent of this grain was used for feed; 17% for food, seed, and industrial uses; 25% was exported (mainly for feed); and 5% was in ending stocks.

Conventional corn kernels (according to some sources) include approximately 73% starch, 10% protein, and 5% oil, with the remainder as fiber, vitamins, and minerals. Among feed grains, corn is one of the most concentrated sources of energy, containing more metabolized energy or total digestible nutrients because of its high-starch and low-fiber content.

The lipid portion of the grain not only provides energy but essential fatty acids for animal growth. Feeding swine a diet with an elevated level of monounsaturated fatty acid effectively increases the level of this important lipid in the pork. This impacts on human nutrition by increasing the monounsaturated lipids and decreasing the saturated fats consumed in the human diet. Increased unsaturated fatty acids in a poultry diet increases the absorption of oxycarotenoids (pigments responsible for yellow color of skin and egg yolks), which improves the consumer acceptability of poultry products. Additionally, high-oleic oils are nutritionally desirable as they are thought to reduce heart disease.

Further, many people have heard that saturated fats are bad for a human diet, however they are quite desirable for a number of applications. For example, corn oil with high percentages of one or more saturates (e.g., palmitic and/or stearic fatty acids) derived from the corn lines according to the present invention allow the production of margarine products (and other foodstuffs needing solidified oils) without hydrogenation of the corn oil (thus avoiding the "bad" trans-fatty acids), thus providing a benefit to the human diet. High-saturate oils of the present invention are also useful as naturally stable frying oils.

Soybean, canola, and sunflower oils, as well as the corn oil of the present invention, have been targeted for research to alter their fatty acid compositions to meet various consumer demands:

(i) low total saturated fatty acids: with this type of oil, consumers may more readily get less than 10% of their energy from saturated fat and stay within this dietary guideline recommended by the United States Department of Agriculture;

(ii) increased monounsaturated fatty acids: oils with increased monounsaturates (such as the high-oleic varieties of sunflower and safflower) are low in polyunsaturated fatty acids, which are prone to oxidation and polymerization during frying. A high-oleic oil also may help to reduce raised levels of total plasma cholesterol without reducing the high-density lipoprotein (HDL)-cholesterol level; and (iii) decreased trans fatty acids. Trans fatty acids occur in hydrogenated oils used in products such as margarines and shortenings.

Oils are hydrogenated to convert liquid oils into semisolid fats and to improve oxidative stability. Although we do not know their long-term health effects, the consumption of trans isomers may be a nutritional concern. A recent study reported that a diet high in trans fatty acids raised total and low-density lipoprotein (LDL)-cholesterol and lowered HDL-cholesterol levels compared to a diet high in cis fatty acids.

Decreased Genetic Diversity of Conventional Corn Lines

Improvements in crops by plant breeding are usually followed by a decrease in genetic diversity, especially in the materials that ultimately reach commercial production. On a worldwide basis, only 5% of available corn germplasm is used commercially. From biochemical data, United States maize cultivation and breeding appear, to remain heavily dependent upon usage of the inbred lines B73, A632, Oh43, and Mo17, or closely related derivatives. In contrast to many other crops, corn breeders have continued to focus on short-term breeding goals largely because of the predominance of the private sector in corn breeding and its need for short-term results. This pattern has resulted in the development of a very narrow genetic base of corn produced on the farm, with many companies selling closely related hybrids. This outcome makes it difficult to develop hybrids for new market demands.

According to Ertl and Orman, 1994 (Ertl, D. S. and Orman, B. A., 1994, Agronomy Abstracts:198), there is limited variability for feed quality in present-day hybrids, or elite breeding materials, as shown by the composition trait values in 7,399 samples collected from 27 locations in North America from 1987 to 1993 and analyzed for protein, oil, and starch composition. There is also limited variability in hybrids entered in the Iowa Corn Yield Tests since 1988.

One source of genetic material used for one embodiment of the present invention includes a pool of introgressed lines of maize-*Tripsacum dactyloides* seeds generally attributed to Harlan and DeWet (Harlan J. R., De Wet J. M. J., Naik S. M. and Lambert R. J., 1970—Chromosome pairing within genomes in maize x Tripsacum hybrids; Science, 167:1247–1248). The *Zea mays* parent used in the original crosses to *Tripsacum dactyloides* by Harlan and DeWet is said to be a standard purple maize inbred line, viz. UI1974, which has purple aleurone and exhibits purple kernels and purple plants. In one embodiment, this Harlan and DeWet source of genetic material is introgressed with one or more standard Corn-Belt varieties to obtain inbred lines that retain the desirable characteristics of the maize parent lines such as stiff stalks, large ears, pest resistance, and high yield, while also obtaining the desired characteristics of the Tripsacum, e.g., high protein content, high oil content, or a combination of high oil and high protein content. In other embodiments, additional desirable characteristics (such as particular types of fatty acid content in the oil, or pest resistance, or plants that generate seed by apomixis, or color) conferred from the Tripsacum are also selected for. Seeds from individual plants are tested (in one embodiment, by gas chromatography; in another embodiment, selection is based on near-infrared refelctance measurement of protein, oil, and/or starch of seed) for protein and/or oil content and/or starch (and/or other desired characteristic), and seeds are selected for further breeding based on the results of the testing. In this way, corn lines are developed that retain satisfactory characteristics from the maize lines, while also acquiring superior characteristics contributed by the addition of Tripsacum genetic material.

By using selective breeding programs, the present invention also provides improved protein content which is higher in percentage than either the maize parental lines or the original Tripsacumxmaize introgressed population. Further, the present invention provides improved oil content which is higher in percentage than either the maize parental lines or the original Tripsacumxmaize introgressed population. Still further, the present invention provides improved combined protein and oil content which is higher in percentages and in combination than either the maize parental lines or the original Tripsacumxmaize introgressed population. In still other embodiments, the oleic fatty acid content is increased in percentage over either the maize parental lines or the original Tripsacumxmaize introgressed population. In yet other embodiments, the saturated fatty acid content is increased (or in other embodiments, decreased) in percentage relative to either the maize parental lines or the original Tripsacumxmaize introgressed population.

Further, the present invention provides corn lines having the above-listed improved characteristics by careful application of traditional plant breeding procedures, without resort to gene splicing recombinant-DNA techniques which many people are wary of, in corn-growing regions of Europe, for example.

Grain Quality of Corn-belt Lines

TABLE 11

Composition of Corn-Belt lines

| Item | Protein[1] | Oil[1] | Starch[1] | Density[1] |
|---|---|---|---|---|
| B73 | 11.9 | 3.4 | 71.8 | 1.278 |
| Mo17 | 11.9 | 3.3 | 71.6 | 1.294 |
| B73 × Mo17 | 12.9 | 3.8 | 70.4 | 1.291 |
| Mo17 × B73 | 12.9 | 3.5 | 69.0 | 1.307 |
| Pioneer 3394 | 11.4 | 3.3 | 71.5 | 1.302 |
| Pioneer 3489 | 9.1 | 4.0 | 71.9 | 1.263 |

[1]NIT prediction on a dry matter (0% moisture) basis.

TABLE 12

Premium Grain Value

| Item | EPV[2] (S) | Premium[3] (S) |
|---|---|---|
| Pioneer 3394 | 2.57 | −.015 |
| Pioneer 3489 | 2.55 | −0.17 |

[2]Estimated Premium value as calculated from the formula in Nutrient content and Feeding value of Iowa Corn Current Statistics with corn priced at $2.72/Bu, 8.0% protein, 3.5% oil, 59.5% starch, oil refining loss at 2.5%. Distillers dried grain priced at $145/ton, 9% moisture, 44% protein content of soymeal, soybean meal prices at $214/ton, feed additive priced at $0.1/LB, weight of feed additives 60%, and 16% protein content of feed.
[3]Premium paid per bushel over the $2.72/Bu value.

Grain Quality Traits of Introgressed Corn

Over 6,000 introgressed corn lines were evaluated for fatty-acid composition. Lines with unique profiles were selected for advancement and incorporated into a plant breeding scheme to enhance the oil quality of Corn-Belt lines (A619, A632, B14A, B73, H99, Oh43, Mo17, and WI53R) and improve the agronomic characteristics of the introgressed lines.

TABLE 13

Compositions of Introgressed Lines with Most Extreme Values

| Item | Protein[1] | Oil[1] | Starch[1] | Density[1] |
|---|---|---|---|---|
| High Protein | 18.1 | 5.4 | 63.7 | 1.340 |
| High Oil | 13.2 | 7.5 | 64.8 | 1.334 |
| High Protein and High Oil | 17.4 | 6.7 | 63.1 | 1.340 |

[1]NIT prediction on a dry matter (0% moisture) basis.
The impact on the premium value of grain from the introgressed lines (Table 13) is shown in Table 14.

TABLE 14

Premium Grain Value

| Item | EPV[2] (S) | Premium[3] (S) |
|---|---|---|
| High Protein | 3.38 | 0.66 |
| High Oil | 3.13 | 0.41 |
| High Protein and High Oil | 3.33 | 0.61 |

[2]Estimated Premium value as calculated from the formula in Nutrient content and Feeding value of Iowa Corn Current Statistics with corn priced at $2.72/Bu, 8.0% protein, 3.5% oil, 59.5% starch, oil refining loss at 2.5%. Distillers dried grain priced at $145/ton, 9% moisture, 44% protein content of soymeal, soybean meal priced at $214/ton, feed additive priced at $0.1/LB, weight of feed additives 60%, and 16% protein content of feed.
[3]Premium paid per bushel over the $2.72/Bu value. In addition to the lines listed in Table 14, there are 8 high-protein selections with value ranges of 15.1% to 17.4% protein, 82 high oil lines with value ranges of 6.0 to 7.7% oil, 10 high protein and high oil lines crossed to Mo17 and currently in yield trials at six locations with value ranges of 12.1% protein with 5.0% oil to 18.1% protein with 5.4% oil.

Oil Quality Traits for Corn-belt Lines

TABLE 15

Fatty-Acid Compositions for Corn-Belt lines

| Corn-Belt Variety | Palmitic | Stearic | Oleic | Linoleic | Linolenic | Total Saturates |
|---|---|---|---|---|---|---|
| B73 | 10.0 | 2.1 | 30.0 | 56.7 | 1.2 | 12.1 |
| A632 | 9.9 | 1.4 | 18.8 | 68.5 | 1.4 | 11.3 |
| Oh43 | 12.0 | 1.7 | 18.8 | 65.6 | 1.7 | 13.7 |
| Mo17 | 9.9 | 2.0 | 20.0 | 66.7 | 0.7 | 11.9 |
| Pioneer 3394 | 10.4 | 1.8 | 22.9 | 60.1 | 1.1 | 11.1 |
| Pioneer 3489 | 8.6 | 2.5 | 26.8 | 60.1 | 1.1 | 12.1 |

Oil Quality Traits for Introgressed Lines

TABLE 16A

Fatty-Acid Compositions of Introgressed Lines with Most Extreme Values

| Item | Palmitic | Stearic | Oleic | Linoleic | Linolenic | Total Saturates |
|---|---|---|---|---|---|---|
| High Oleic | 5.9 | 3.2 | 70.1 | 20.1 | 0.7 | 9.1 |
| High Total Saturates | 22.3 | 1.9 | 18.3 | 54.9 | 2.6 | 24.3 |
| Low Total Saturates | 4.9 | 1.8 | 45.0 | 47.3 | 1.0 | 6.7 |

In addition to the lines listed in Table 16A, there are seven high oleic recovered introgressed lines with value ranges of 53% to 68% oleic, thirty-five high oleic lines from crosses of introgressed lines with Corn-Belt lines, A619, A632, B73, Mo17, or W153R, with value ranges of 59% to 70% oleic, and nine lines from crosses of introgressed lines with Corn-Belt lines were backcrossed and selfed several generations resulting in material with value ranges of 52% to 60% oleic.

In one embodiment, the present invention is embodied as GC#5687 (which is also called PuvN 360-4) which is S3 (i.e., a line selfed three generations) of (W153R×#5S1)× #13S1. Embodiment GC#5687 exhibits markedly higher oleic fatty acid content than Corn Belt varieties. A deposit of GC#5687 was made under the terms of the Budapest Treaty on Apr. 3, 1998, with the American Type Culture Collection (ATCC), and has been assigned ATCC Accession No. 209733. Table 16B shows measured fatty acid content for ten samples of GC#5687 showing a high of 70.1% oleic (as a percentage of all fatty acids) and a mean of 62.4% oleic. Table 16C shows measured weights for a sample of 100 individual kernels of GC#5687, showing a minimum kernel weight of 0.167 grams, a maximum kernel weight of 0.302 grams, a median kernel, weight of 0.227 grams.

TABLE 16B

Fatty Acid Percentages data for High Oleic Sample GC#5687 which is PuvN 360-4 which is S3 of (W153R x #5S1) x #13S1.

| GC# | Sample | Palmitic | Stearic | Oleic | Linoeic | Linolenic | Saturates |
|---|---|---|---|---|---|---|---|
| 5687 | 1 | 6.1 | 3.9 | 65.4 | 23.8 | 0.8 | 10.0 |
| 5687 | 2 | 7.0 | 3.7 | 53.4 | 35.0 | 0.9 | 10.8 |
| 5687 | 3 | 6.0 | 3.5 | 66.7 | 23.1 | 0.8 | 9.4 |
| 5687 | 4 | 7.0 | 3.5 | 56.4 | 32.2 | 0.9 | 10.5 |
| 5687 | 5 | 6.2 | 3.8 | 63.4 | 26.3 | 0.3 | 10.0 |
| 5687 | 6 | 6.5 | 3.6 | 61.2 | 27.8 | 0.9 | 10.2 |
| 5687 | 7 | 6.0 | 3.5 | 62.0 | 27.6 | 0.8 | 9.5 |
| 5687 | 8 | 6.5 | 3.6 | 62.6 | 26.5 | 0.8 | 10.0 |
| 5687 | 9 | 6.6 | 3.7 | 63.3 | 25.6 | 0.8 | 10.2 |
| 5687 | 10 | 5.9 | 3.2 | 70.1 | 20.1 | 0.7 | 9.1 |
| 5687 | Means | 6.4 | 3.6 | 62.4 | 26.8 | 0.8 | 10.0 |

TABLE 16C

Weight samples for seeds for High Oleic material GC#5687 which is PuvN 360-4 which is S3 of (W153R x #5S1) x #13S1.

| Seed # | g | Seed # | g | Seed # | g | Seed # | g |
|---|---|---|---|---|---|---|---|
| 1 | 0.262 | 26 | 0.222 | 51 | 0.26 | 76 | 0.204 |
| 2 | 0.167 | 27 | 0.226 | 52 | 0.241 | 77 | 0.247 |
| 3 | 0.230 | 28 | 0.227 | 53 | 0.284 | 78 | 0.182 |
| 4 | 0.277 | 29 | 0.216 | 54 | 0.176 | 79 | 0.257 |
| 5 | 0.216 | 30 | 0.249 | 55 | 0.209 | 80 | 0.223 |
| 6 | 0.218 | 31 | 0.274 | 56 | 0.286 | 81 | 0.207 |
| 7 | 0.247 | 32 | 0.239 | 57 | 0.251 | 82 | 0.234 |
| 8 | 0.197 | 33 | 0.279 | 58 | 0.205 | 83 | 0.268 |
| 9 | 0.247 | 34 | 0.211 | 59 | 0.237 | 84 | 0.276 |
| 10 | 0.205 | 35 | 0.212 | 60 | 0.233 | 85 | 0.193 |
| 11 | 0.258 | 36 | 0.209 | 61 | 0.265 | 86 | 0.268 |
| 12 | 0.246 | 37 | 0.223 | 62 | 0.209 | 87 | 0.228 |
| 13 | 0.197 | 38 | 0.175 | 63 | 0.249 | 88 | 0.185 |
| 14 | 0.227 | 39 | 0.283 | 64 | 0.232 | 89 | 0.242 |
| 15 | 0.211 | 40 | 0.234 | 65 | 0.251 | 90 | 0.261 |
| 16 | 0.219 | 41 | 0.238 | 66 | 0.333 | 91 | 0.264 |
| 17 | 0.271 | 42 | 0.191 | 67 | 0.219 | 92 | 0.246 |
| 18 | 0.302 | 43 | 0.215 | 68 | 0.208 | 93 | 0.261 |
| 19 | 0.234 | 44 | 0.220 | 69 | 0.271 | 94 | 0.220 |
| 20 | 0.194 | 45 | 0.186 | 70 | 0.244 | 95 | 0.262 |
| 21 | 0.211 | 46 | 0.239 | 71 | 0.254 | 96 | 0.223 |
| 22 | 0.225 | 47 | 0.264 | 72 | 0.278 | 97 | 0.246 |
| 23 | 0.193 | 48 | 0.277 | 73 | 0.204 | 98 | 0.203 |
| 24 | 0.253 | 49 | 0.231 | 74 | 0.235 | 99 | 0.222 |
| 25 | 0.262 | 50 | 0.249 | 75 | 0.275 | 100 | 0.228 |
| | | | | | | Min | 0.167 |
| | | | | | | Max | 0.302 |
| | | | | | | Median | 0.227 |

High total saturated fatty-acid lines not listed in Table 16A include twenty-eight recovered introgressed lines with value ranges of 19% to 22% total saturates, twenty-three introgressed lines crossed to Corn-Belt lines either B73, Mo17, or W153R with value ranges of 19% to 24% total saturates, and four introgressed lines backcrossed and selfed several generations with value ranges of 16% to 18% total saturates.

In one embodiment, the present invention is embodied as GC#6175 (which is also called PuvN426-4) which is an S3 of B73x#88S1. Embodiment GC#6175 exhibits markedly higher total saturated fatty acid (the sum of Palmitic and Stearic) content than Corn Belt varieties. A deposit of GC#6175 was made under the terms of the Budapest Treaty on Apr. 3, 1998, with the American Type Culture Collection (ATCC), and has been assigned ATCC Accession No. 209734. Table 16D shows measured fatty acid content for five samples having a high of 23.0% total saturates (as a percentage of all fatty acids) and a mean of 19.5% total saturates. Table 16E shows measured weights for a sample of 100 individual kernels of GC#6175, showing a minimum kernel weight of 0.142 grams, a maximum kernel weight of 0.253 grams, a median kernel weight of 0.213 grams.

TABLE 16D

Fatty Acid Percentages Data for High Total Saturates Sample GC#6175 which is PuvN426-4 which is S3 of B73 x #88S1 which came from IuuN4958-2 (GC# 4473)

| GC# | Sample | Palmitic | Stearic | Oleic | Linoeic | Linolenic | Saturates |
|---|---|---|---|---|---|---|---|
| 6175 | 1 | 15.6 | 3.1 | 32.4 | 48.3 | 0.6 | 18.7 |
| 6175 | 2 | 20.2 | 2.7 | 24.5 | 51.0 | 1.6 | 23.0 |
| 6175 | 3 | 14.7 | 3.8 | 37.7 | 43.0 | 0.8 | 18.5 |
| 6175 | 4 | 15.7 | 3.4 | 34.8 | 45.4 | 0.7 | 19.1 |
| 6175 | 5 | 14.9 | 3.4 | 38.8 | 42.2 | 0.7 | 18.3 |
| 6175 | Means | 16.2 | 3.3 | 33.6 | 46.0 | 0.9 | 19.5 |

TABLE 16E

Weight samples for seeds High Total Saturates Sample GC#6175 which is PuvN426-4 which is S3 of B73 x #88S1

| Seed | g | Seed | g | Seed | g | Seed | g |
|---|---|---|---|---|---|---|---|
| 1 | 0.232 | 26 | 0.152 | 51 | 0.135 | 76 | 0.255 |
| 2 | 0.245 | 27 | 0.159 | 52 | 0.223 | 77 | 0.231 |
| 3 | 0.191 | 28 | 0.186 | 53 | 0.146 | 78 | 0.231 |
| 4 | 0.172 | 29 | 0.160 | 54 | 0.165 | 79 | 0.204 |
| 5 | 0.253 | 30 | 0.267 | 55 | 0.225 | 80 | 0.158 |
| 6 | 0.229 | 31 | 0.241 | 56 | 0.198 | 81 | 0.149 |
| 7 | 0.174 | 32 | 0.148 | 57 | 0.227 | 82 | 0.253 |
| 8 | 0.241 | 33 | 0.138 | 58 | 0.233 | 83 | 0.232 |
| 9 | 0.224 | 34 | 0.133 | 59 | 0.140 | 84 | 0.188 |
| 10 | 0.198 | 35 | 0.194 | 60 | 0.279 | 85 | 0.186 |
| 11 | 0.238 | 36 | 0.173 | 61 | 0.246 | 86 | 0.260 |
| 12 | 0.142 | 37 | 0.176 | 62 | 0.155 | 87 | 0.156 |
| 13 | 0.143 | 38 | 0.180 | 63 | 0.256 | 88 | 0.265 |
| 14 | 0.181 | 39 | 0.236 | 64 | 0.167 | 89 | 0.204 |
| 15 | 0.148 | 40 | 0.225 | 65 | 0.173 | 90 | 0.287 |
| 16 | 0.170 | 41 | 0.252 | 66 | 0.236 | 91 | 0.231 |
| 17 | 0.173 | 42 | 0.213 | 67 | 0.250 | 92 | 0.248 |
| 18 | 0.213 | 43 | 0.309 | 68 | 0.238 | 93 | 0.287 |
| 19 | 0.233 | 44 | 0.176 | 69 | 0.211 | 94 | 0.145 |
| 20 | 0.248 | 45 | 0.205 | 70 | 0.217 | 95 | 0.258 |
| 21 | 0.170 | 46 | 0.272 | 71 | 0.137 | 96 | 0.246 |
| 22 | 0.191 | 47 | 0.238 | 72 | 0.227 | 97 | 0.247 |
| 23 | 0.251 | 48 | 0.318 | 73 | 0.261 | 98 | 0.228 |
| 24 | 0.249 | 49 | 0.220 | 74 | 0.210 | 99 | 0.239 |
| 25 | 0.228 | 50 | 0.268 | 75 | 0.211 | 100 | 0.159 |
| | | | | | | Min | 0.142 |
| | | | | | | Max | 0.253 |
| | | | | | | Median | 0.213 |

Low total saturated fatty-acid lines not listed in Table 16A include three recovered lines with value ranges of 8.2% to 8.4% total saturates, fourteen lines from crosses to Corn-Belt lines and selfed several generations with value ranges of 7.4% to 8.1% total saturates, and two crossed lines backcrossed to Corn-Belt lines and selfed several generations with value ranges of 7.4% to 8.1% total saturated fatty-acid compositions.

Conclusion

Introgressing genes from Tripsacum into Corn-Belt material greatly enhances both the grain and oil quality making it possible to develop new products from corn.

Method

Selfed ears of a population of recovered maize from interspecific crosses between *Zea mays L.* and *Tripsacum dactyloides L.* by Harlan and DeWet (Harlan J. R., De Wet J. M. J., Naik S. M. and Lambert R. J., 1970—Chromosome pairing within genomes in maize x Tripsacum hybrids; *Science*, 167:1247–1248) were evaluated for fatty-acid composition using gas chromatography. Thirteen ears were selected for further research based on their unusual compositions as compared to Corn-Belt lines. Kernels from these ears were grown in the nursery. The individual plants were self-pollinated and reciprocally crossed to conventional Corn-Belt inbred lines of public origin. The crossed seeds were evaluated for fatty-acid compositions. Those with altered fatty-acid compositions were selected and either selfed or backcrossed to one of the conventional Corn-Belt inbred parents. The same pattern was repeated for several generations resulting in several lines with enhanced oil for altered fatty-acid compositions.

In one embodiment, two sequential generations of corn are bred and selected every 12 months: one planted in Iowa in approximately May and harvested in approximately October, followed by a generation planted and harvested in Puerto Rico.

Results:

TABLE 17

Oil Fatty-Acid Compositions

| Corn-Belt Variety | Palmitic | Stearic | Oleic | Linoleic | Linolenic | Total Saturates |
|---|---|---|---|---|---|---|
| Mo17 | 9.9 | 2.0 | 20.0 | 66.7 | 0.7 | 11.9 |
| B73 | 10.0 | 2.1 | 30.0 | 56.7 | 1.2 | 12.1 |
| Pioneer 3394 | 10.4 | 1.8 | 22.9 | 60.1 | 1.1 | 11.1 |
| Pioneer 3489 | 8.6 | 2.5 | 26.8 | 60.1 | 1.1 | 12.1 |

TABLE 17a

High Oleic Group

| Recovered Lines* | Palmitic | Stearic | Oleic | Linoleic | Linolenic | Total Saturates |
|---|---|---|---|---|---|---|
| 4214 | 7.2 | 2.1 | 50.3 | 39.3 | 1.0 | 9.4 |
| 4221 | 7.0 | 3.4 | 55.3 | 33.4 | 0.9 | 10.4 |
| 4660 | 8.6 | 4.4 | 53.1 | 33.4 | 0.4 | 13.1 |
| 4674 | 7.1 | 7.6 | 67.8 | 17.0 | 0.6 | 14.7 |
| 4679 | 8.3 | 8.4 | 55.0 | 27.9 | 0.4 | 16.7 |
| 4692 | 7.6 | 5.3 | 64.3 | 21.8 | 0.9 | 13.0 |
| 4701 | 8.6 | 5.4 | 56.8 | 28.2 | 1.0 | 14.0 |
| 4708 | 7.9 | 5.6 | 54.8 | 31.4 | 0.3 | 13.6 |
| 4717 | 8.1 | 5.5 | 51.9 | 33.8 | 0.7 | 13.6 |
| 4745 | 6.6 | 3.5 | 51.2 | 37.7 | 1.1 | 10.1 |
| 4751 | 6.6 | 2.7 | 51.1 | 38.7 | 0.9 | 9.3 |

TABLE 17b

High Oleic Group

| Lines from Crosses** | Palmitic | Stearic | Oleic | Linoleic | Linolenic | Total Saturates |
|---|---|---|---|---|---|---|
| Temp 324 | 5.4 | 3.3 | 69.5 | 21.1 | 0.8 | 8.7 |
| Temp 160 | 9.7 | 2.8 | 54.3 | 32.5 | 0.7 | 12.5 |
| 3721 | 5.4 | 3.3 | 59.7 | 30.5 | 1.1 | 8.7 |
| 3816 | 6.3 | 2.9 | 59.7 | 30.4 | 0.8 | 9.2 |
| 3828 | 7.0 | 3.6 | 58.0 | 30.5 | 0.9 | 10.6 |
| 3902 | 7.1 | 2.3 | 58.5 | 31.3 | 0.8 | 9.4 |

TABLE 17b-continued

High Oleic Group

| Lines from Crosses** | Palmitic | Stearic | Oleic | Linoleic | Linolenic | Total Saturates |
|---|---|---|---|---|---|---|
| 3916 | 7.3 | 1.9 | 59.5 | 30.4 | 0.9 | 9.2 |
| 3962 | 7.0 | 3.1 | 60.5 | 28.9 | 0.6 | 10.0 |
| 4014 | 6.1 | 3.1 | 57.1 | 32.6 | 1.2 | 9.2 |
| 4023 | 7.9 | 2.1 | 58.3 | 30.9 | 1.0 | 9.9 |
| 3634 | 8.4 | 3.6 | 50.4 | 36.9 | 0.6 | 12.0 |
| 3664 | 9.2 | 2.6 | 54.4 | 33.0 | 0.8 | 11.8 |
| 3652 | 8.6 | 3.9 | 54.2 | 32.7 | 0.7 | 12.4 |
| 3660 | 8.4 | 2.9 | 52.1 | 35.8 | 0.8 | 11.3 |
| 3700 | 7.0 | 3.7 | 55.4 | 33.1 | 0.9 | 10.7 |
| 3745 | 8.5 | 3.2 | 54.9 | 32.6 | 0.9 | 11.7 |
| 3757 | 9.9 | 3.5 | 50.1 | 35.8 | 0.7 | 13.4 |
| 3765 | 9.2 | 2.2 | 54.1 | 33.8 | 0.7 | 11.4 |
| 3806 | 6.9 | 2.4 | 51.2 | 38.7 | 0.8 | 9.3 |
| 3839 | 6.5 | 3.6 | 56.4 | 32.7 | 0.8 | 10.1 |
| 3843 | 8.4 | 3.5 | 51.5 | 35.2 | 1.4 | 11.9 |
| 3862 | 7.4 | 2.8 | 51.7 | 37.0 | 1.1 | 10.2 |
| 3867 | 6.9 | 2.3 | 56.9 | 33.0 | 0.9 | 9.2 |
| 3880 | 8.1 | 5.4 | 55.7 | 30.1 | 0.8 | 13.5 |
| 3894 | 8.3 | 2.2 | 54.3 | 34.4 | 0.9 | 10.5 |
| 3920 | 7.0 | 2.7 | 55.7 | 33.8 | 0.8 | 9.8 |
| 3928 | 6.4 | 3.0 | 55.0 | 34.5 | 1.1 | 9.4 |
| 3937 | 6.4 | 2.5 | 56.7 | 33.5 | 1.0 | 8.9 |
| 3980 | 7.0 | 2.8 | 52.7 | 36.6 | 0.9 | 9.8 |
| 4656 | 8.5 | 4.2 | 55.9 | 30.9 | 0.6 | 12.7 |
| 4659 | 8.5 | 3.8 | 50.1 | 37.1 | 0.6 | 12.3 |
| 4726 | 7.9 | 3.3 | 53.7 | 34.2 | 0.9 | 11.2 |
| 4738 | 6.4 | 2.8 | 61.5 | 28.3 | 1.1 | 9.2 |
| 4736 | 7.0 | 2.4 | 55.3 | 34.4 | 0.9 | 9.4 |

TABLE 17c

| Lines from Back-crosses* | Palmitic | Stearic | Oleic | Linoleic | Linolenic | Total Saturates |
|---|---|---|---|---|---|---|
| 3617 | 8.0 | 2.5 | 54.2 | 34.4 | 0.8 | 10.5 |
| 3620 | 8.8 | 2.4 | 52.5 | 35.7 | 0.6 | 11.2 |
| 3674 | 10.2 | 2.6 | 59.6 | 27.0 | 0.5 | 12.8 |
| 3730 | 6.5 | 3.7 | 51.6 | 37.5 | 0.8 | 10.1 |
| 3742 | 8.3 | 2.6 | 55.0 | 33.2 | 0.9 | 11.0 |
| 3767 | 9.5 | 3.2 | 56.7 | 29.8 | 0.9 | 12.7 |
| 3775 | 9.0 | 3.4 | 52.7 | 34.0 | 1.0 | 12.4 |
| 3785 | 8.3 | 3.6 | 53.1 | 34.5 | 0.6 | 11.9 |
| 3797 | 7.7 | 2.4 | 54.8 | 34.1 | 1.1 | 10.1 |

TABLE 18

Low Total Saturates Group

| Recovered Lines* | Palmitic | Stearic | Oleic | Linoleic | Linolenic | Total Saturates |
|---|---|---|---|---|---|---|
| 4083 | 6.4 | 2.0 | 46.7 | 44.1 | 0.8 | 8.4 |
| 4758 | 6.6 | 1.6 | 36.3 | 54.4 | 1.1 | 8.2 |

TABLE 18a

| Lines from Crosses** | Palmitic | Stearic | Oleic | Linoleic | Linolenic | Total Saturates |
|---|---|---|---|---|---|---|
| 3687 | 6.9 | 1.7 | 39.6 | 51.3 | 1.0 | 8.6 |
| 3698 | 6.3 | 1.6 | 42.7 | 48.3 | 1.2 | 7.9 |
| 3720 | 6.6 | 1.3 | 39.3 | 51.7 | 1.1 | 7.9 |
| 3851 | 6.1 | 1.9 | 26.8 | 63.8 | 1.4 | 7.9 |
| 3895 | 5.5 | 1.4 | 43.5 | 48.5 | 1.2 | 6.8 |
| 3905 | 4.9 | 1.8 | 45.0 | 47.3 | 1.0 | 6.7 |

TABLE 18a-continued

| Lines from Crosses** | Palmitic | Stearic | Oleic | Linoleic | Linolenic | Total Saturates |
|---|---|---|---|---|---|---|
| 3908 | 5.1 | 1.6 | 42.6 | 49.7 | 1.0 | 6.8 |
| 3921 | 5.8 | i.5 | 32.4 | 59.2 | 1.1 | 7.3 |

TABLE 18b

| Lines from Crosses** | Palmitic | Stearic | Oleic | Linoleic | Linolenic | Total Saturates |
|---|---|---|---|---|---|---|
| 3960 | 5.5 | 1.3 | 36.6 | 55.6 | 1.0 | 6.8 |
| 3989 | 6.1 | 1.4 | 34.2 | 57.5 | 0.8 | 7.5 |
| 4018 | 5.2 | 1.62 | 37.8 | 53.8 | 1.4 | 6.8 |
| 4032 | 6.3 | 1.2 | 25.6 | 65.7 | 1.3 | 7.5 |
| 4039 | 5.2 | 1.6 | 32.2 | 59.9 | 1.1 | 6.7 |
| 4727 | 6.3 | 2.2 | 52.9 | 37.5 | 1.1 | 8.5 |

TABLE 18c

| Lines from Backcrosses+ | Palmitic | Stearic | Oleic | Linoleic | Linolenic | Total Saturates |
|---|---|---|---|---|---|---|
| 3731 | 6.0 | 1.5 | 30.8 | 60.4 | 1.4 | 7.4 |
| 3798 | 6.5 | 1.6 | 42.9 | 47.1 | 1.0 | 8.1 |

TABLE 19

High Total Saturates Group

| Recovered Lines* | Palmitic | Stearic | Oleic | Linoleic | Linolenic | Total Saturates |
|---|---|---|---|---|---|---|
| Temp 421 | 16.5 | 4.7 | 30.2 | 47.9 | 0.7 | 21.2 |
| Temp 420 | 16.9 | 4.1 | 33.1 | 45.5 | 0.4 | 21.0 |
| 4086 | 16.0 | 3.6 | 31.0 | 48.5 | 0.9 | 19.6 |
| 4090 | 16.0 | 5.5 | 31.7 | 46.2 | 0.6 | 21.5 |
| 4102 | 16.1 | 3.2 | 27.6 | 51.8 | 1.3 | 19.2 |
| 4107 | 15.0 | 4.1 | 41.1 | 39.0 | 0.8 | 19.1 |
| 4119 | 15.5 | 3.3 | 29.9 | 50.1 | 1.2 | 18.8 |
| 4129 | 10.6 | 3.5 | 42.1 | 42.7 | 1.1 | 14.1 |
| 4146 | 11.5 | 3.8 | 41.9 | 41.5 | 1.3 | 15.3 |
| 4152 | 12.0 | 4.2 | 37.5 | 45.4 | 1.0 | 16.2 |
| 4159 | 15.0 | 2.7 | 35.1 | 46.3 | 0.9 | 17.7 |
| 4193 | 12.6 | 4.4 | 37.6 | 44.8 | 0.7 | 17.0 |
| 4292 | 16.4 | 4.9 | 27.6 | 50.4 | 0.7 | 21.4 |
| 4234 | 14.8 | 2.7 | 27.1 | 54.3 | 1.0 | 17.5 |
| 4243 | 14.7 | 2.7 | 28.6 | 53.0 | 1.0 | 17.4 |
| 4255 | 13.3 | 3.8 | 27.0 | 54.9 | 1.0 | 17.1 |
| 4300 | 15.2 | 5.5 | 31.6 | 47.1 | 0.6 | 20.7 |
| 4309 | 15.5 | 4.8 | 31.4 | 47.5 | 0.8 | 20.3 |
| 4335 | 15.4 | 2.8 | 29.8 | 51.0 | 1.0 | 18.2 |
| 4338 | 15.3 | 3.4 | 27.0 | 53.2 | 1.0 | 18.8 |
| 4356 | 15.7 | 2.8 | 28.1 | 52.4 | 1.0 | 18.5 |
| 4359 | 15.4 | 3.6 | 34.3 | 46.0 | 0.7 | 19.0 |
| 4372 | 15.4 | 4.3 | 31.6 | 48.2 | 0.6 | 19.6 |
| 4379 | 16.8 | 3.2 | 30.9 | 48.4 | 0.7 | 20.0 |
| 4395 | 15.7 | 2.6 | 20.6 | 60.7 | 0.5 | 18.3 |
| 4408 | 15.5 | 3.5 | 36.9 | 43.7 | 0.4 | 19.0 |
| 4417 | 14.9 | 3.2 | 34.0 | 47.2 | 0.7 | 18.1 |
| 4674 | 12.0 | 5.0 | 40.5 | 40.5 | 2.0 | 17.0 |
| 4770 | 16.8 | 4.9 | 28.9 | 48.8 | 0.6 | 21.7 |
| 4830 | 17.6 | 2.9 | 32.9 | 46.0 | 0.6 | 20.5 |

TABLE 19-continued

High Total Saturates Group

| Recovered Lines* | Palmitic | Stearic | Oleic | Linoleic | Linolenic | Total Saturates |
|---|---|---|---|---|---|---|
| 4838 | 17.8 | 3.4 | 28.1 | 50.2 | 0.5 | 21.2 |
| 4854 | 16.7 | 3.1 | 31.3 | 48.4 | 0.6 | 19.7 |
| 4862 | 14.6 | 5.5 | 33.8 | 45.4 | 0.7 | 20.1 |
| 4874 | 14.5 | 5.1 | 32.7 | 46.7 | 1.1 | 19.5 |
| 4880 | 14.7 | 4.8 | 30.9 | 48.9 | 0.6 | 19.5 |
| 4893 | 14.9 | 4.3 | 32.6 | 46.3 | 2.0 | 19.1 |
| 4897 | 15.8 | 3.5 | 32.4 | 47.6 | 0.7 | 19.3 |

TABLE 19a

| Recovered Lines* | Palmitic | Stearic | Oleic | Linoleic | Linolenic | Total Saturates |
|---|---|---|---|---|---|---|
| 4932 | 17.2 | 4.5 | 30.7 | 47.1 | 0.5 | 21.7 |
| 4936 | 16.5 | 3.7 | 31.0 | 48.2 | 0.6 | 20.2 |
| 4957 | 16.1 | 4.5 | 31.9 | 46.8 | 0.6 | 20.6 |
| 4948 | 15.2 | 4.7 | 31.6 | 48.0 | 0.5 | 19.8 |

TABLE 19b

| Lines from Crosses** | Palmitic | Stearic | Oleic | Linoleic | Linolenic | Total Saturates |
|---|---|---|---|---|---|---|
| 3641 | 12.2 | 4.5 | 42.6 | 40.1 | 0.6 | 16.7 |
| 3752 | 12.5 | 4.4 | 41.9 | 40.4 | 0.9 | 16.9 |
| 4050 | 13.3 | 3.5 | 31.1 | 49.7 | 2.3 | 16.8 |
| 4075 | 13.3 | 3.4 | 35.9 | 46.9 | 0.4 | 16.8 |
| 4077 | 13.8 | 3.0 | 35.6 | 46.9 | 0.7 | 16.9 |
| 4407 | 14.6 | 3.7 | 33.6 | 47.8 | 0.4 | 18.3 |
| 4423 | 16.3 | 2.3 | 29.9 | 50.7 | 0.7 | 18.6 |
| 4428 | 15.6 | 3.1 | 26.2 | 54.6 | 0.5 | 18.7 |
| 4442 | 15.3 | 4.3 | 37.0 | 42.9 | 0.5 | 19.6 |
| 4456 | 15.0 | 3.8 | 20.9 | 59.4 | 0.9 | 18.8 |
| 4458 | 14.9 | 3.6 | 29.3 | 51.5 | 0.7 | 18.5 |
| 4473 | 22.3 | 1.9 | 18.3 | 54.9 | 2.6 | 24.3 |
| 4485 | 21.8 | 2.4 | 19.4 | 54.3 | 2.1 | 24.1 |
| 4489 | 20.3 | 1.8 | 18.8 | 56.7 | 2.4 | 22.1 |
| 4499 | 14.8 | 3.2 | 20.0 | 61.0 | 1.1 | 18.0 |
| 4512 | 14.4 | 3.2 | 23.1 | 58.3 | 1.0 | 17.6 |
| 4524 | 15.3 | 3.5 | 25.3 | 55.0 | 0.9 | 18.8 |
| 4534 | 15.3 | 2.7 | 23.5 | 57.5 | 1.1 | 18.0 |
| 4545 | 15.0 | 3.5 | 24.6 | 55.9 | 1.1 | 18.4 |
| 4549 | 14.2 | 4.1 | 32.4 | 48.7 | 0.6 | 18.2 |
| 4565 | 17.0 | 4.3 | 27.8 | 50.2 | 0.7 | 21.3 |
| 4573 | 17.2 | 3.1 | 26.4 | 52.6 | 0.8 | 20.2 |
| 4578 | 16.0 | 3.7 | 25.4 | 54.0 | 0.9 | 19.7 |
| 4655 | 12.4 | 2.8 | 42.4 | 41.9 | 0.5 | 15.2 |
| 4657 | 12.9 | 2.3 | 38.9 | 45.5 | 0.5 | 15.2 |
| 4782 | 16.3 | 2.7 | 36.5 | 43.8 | 0.7 | 19.0 |
| 4790 | 11.5 | 8.6 | 31.8 | 46.2 | 1.9 | 20.1 |
| 4805 | 15.8 | 4.3 | 28.6 | 50.4 | 1.1 | 20.1 |
| 4813 | 18.3 | 1.8 | 18.3 | 60.6 | 1.0 | 20.1 |
| 4822 | 18.5 | 3.1 | 29.3 | 48.3 | 0.8 | 21.6 |
| 4828 | 14.7 | 3.3 | 30.4 | 50.8 | 0.8 | 18.0 |

TABLE 19c

| Lines from Backcrosses[+] | Palmitic | Stearic | Oleic | Linoleic | Linolenic | Total Saturates |
|---|---|---|---|---|---|---|
| 3672 | 12.8 | 2.9 | 33.2 | 50.5 | 0.6 | 15.8 |
| 3676 | 12.9 | 3.2 | 37.0 | 46.5 | 0.4 | 16.1 |
| 3768 | 10.8 | 4.1 | 51.0 | 33.3 | 0.8 | 14.9 |
| 3777 | 14.7 | 2.8 | 28.5 | 47.5 | 6.5 | 17.5 |

*Recovered Lines are ears that were selected from the recovered maize and selfed for several additional generations
**Lines from Crosses are selfs (either 1, 2 or 3 generations, see the individual data set for specifics) of the crosses between the Corn-Belt inbred parents and the introgressed parents.
[+]Lines from Backcross are crosses (Tripsacum x Corn-Belt inbred) that were backcrossed once to the Corn-Belt parent and then selfed 1 or 2 generations.

TABLE 20

Intro 1 selfs
Parental Corn-Belt Public Inbred Lines
Values are average from multiple ears

| Sample | Palmitic | Stearic | Oleic | Linoleic | Linolenic | Total Saturates |
|---|---|---|---|---|---|---|
| A619 | 10.8 | 1.3 | 19.1 | 67.1 | 1.7 | 12.1 |
| A619 | 10.6 | 1.4 | 18.2 | 68.6 | 1.2 | 12.0 |
| A632 | 10.1 | 1.7 | 22.2 | 64.5 | 1.5 | 11.8 |
| A632 | 9.9 | 1.4 | 18.8 | 68.5 | 1.4 | 11.3 |
| B14A | 9.3 | 1.8 | 23.2 | 64.7 | 1.0 | 11.1 |
| B14A | 9.3 | 1.6 | 20.8 | 67.2 | 1.1 | 10.9 |
| B73 | 9.8 | 2.1 | 31.5 | 55.2 | 1.4 | 11.9 |
| B73 | 10.2 | 2.1 | 28.5 | 58.1 | 1.0 | 12.3 |
| H99 | 7.8 | 2.1 | 29.8 | 59.4 | 0.9 | 9.9 |
| H99 | 8.3 | 1.9 | 31.8 | 57.3 | 0.8 | 10.2 |
| MO17 | 9.6 | 2.0 | 19.9 | 67.8 | 0.6 | 11.6 |
| MO17 | 10.2 | 2.0 | 21.6 | 65.5 | 0.7 | 12.2 |
| OH43 | 12.2 | 2.6 | 18.8 | 65.2 | 1.2 | 14.8 |
| OH43 | 12.0 | 1.7 | 18.9 | 65.6 | 1.7 | 13.7 |
| WI53R | 8.4 | 2.7 | 42.7 | 44.8 | 1.4 | 11.1 |
| WI53R | 8.2 | 2.7 | 42.1 | 45.7 | 1.3 | 10.9 |

TABLE 21

Temp Selection

| Temp GC # | Palmitic | Stearic | Oleic | Linoleic | Linolenic | Total Saturates |
|---|---|---|---|---|---|---|
| Temp-160 | 6.9 | 2.0 | 49.0 | 41.4 | 0.7 | 8.9 |
| 160 | 13.5 | 2.3 | 35.0 | 48.3 | 0.8 | 15.9 |
| 160 | 10.9 | 2.6 | 38.8 | 46.9 | 0.8 | 13.5 |
| 160 | 10.6 | 2.6 | 48.5 | 37.6 | 0.8 | 13.2 |
| 160 | 8.3 | 2.8 | 40.6 | 47.5 | 0.8 | 11.1 |
| 160 | 9.7 | 2.6 | 45.4 | 41.5 | 0.8 | 12.3 |
| 160 | 12.3 | 1.9 | 28.0 | 56.8 | 1.1 | 14.1 |
| 160 | 8.2 | 2.1 | 48.5 | 40.4 | 0.8 | 10.3 |
| 160 | 10.2 | 2.4 | 46.6 | 39.9 | 0.9 | 12.6 |
| 160 | 9.7 | 2.8 | 54.3 | 32.5 | 0.7 | 12.5 |
| Means | 10.0 | 2.4 | 43.5 | 43.3 | 0.8 | 12.4 |
| Temp-324 | 6.4 | 3.7 | 63.8 | 25.3 | 0.9 | 10.1 |
| 324 | 6.0 | 3.2 | 63.5 | 26.5 | 0.9 | 9.2 |
| 324 | 7.7 | 3.3 | 46.1 | 41.7 | 1.2 | 11.0 |
| 324 | 6.9 | 3.0 | 50.3 | 38.5 | 1.4 | 9.9 |
| 324 | 5.4 | 3.3 | 69.5 | 21.1 | 0.8 | 8.7 |
| 324 | 6.2 | 3.9 | 60.8 | 28.3 | 0.8 | 10.1 |
| 324 | 6.4 | 3.4 | 51.7 | 37.4 | 1.1 | 9.7 |
| 324 | 6.7 | 3.1 | 51.4 | 37.8 | 1.0 | 9.8 |
| 324 | 6.0 | 3.1 | 66.1 | 24.0 | 0.8 | 9.1 |
| Means | 6.4 | 3.3 | 58.1 | 31.2 | 1.0 | 9.7 |
| Tem-420 | 16.9 | 4.1 | 33.1 | 45.5 | 0.4 | 21.0 |
| 420 | 15.4 | 4.1 | 37.9 | 42.1 | 0.5 | 19.5 |
| 420 | 15.7 | 4.5 | 35.6 | 43.1 | 1.1 | 20.2 |
| 420 | 15.3 | 5.1 | 36.2 | 42.8 | 0.7 | 20.4 |
| 420 | 15.4 | 4.8 | 38.4 | 41.0 | 0.5 | 20.2 |
| 420 | 14.3 | 3.5 | 37.0 | 43.9 | 1.4 | 17.8 |
| 420 | 16.1 | 4.5 | 38.2 | 40.6 | 0.7 | 20.5 |
| 420 | 15.3 | 5.2 | 34.8 | 44.3 | 0.4 | 20.5 |
| 420 | 15.7 | 3.6 | 36.7 | 43.3 | 0.7 | 19.3 |
| 420 | 15.2 | 5.2 | 36.7 | 42.2 | 0.7 | 20.5 |
| Means | 15.5 | 4.5 | 36.5 | 42.9 | 0.7 | 20.0 |
| Temp-421 | 16.1 | 3.7 | 34.2 | 45.2 | 0.8 | 19.8 |
| 421 | 15.7 | 4.0 | 35.6 | 44.4 | 0.4 | 19.6 |
| 421 | 15.5 | 3.8 | 35.1 | 45.2 | 0.5 | 19.2 |
| 421 | 14.5 | 4.1 | 29.8 | 51.1 | 0.6 | 18.6 |
| 421 | 15.9 | 3.9 | 33.7 | 46.4 | 0.2 | 19.8 |
| 421 | 15.2 | 4.3 | 31.9 | 48.3 | 0.3 | 19.5 |
| 421 | 15.3 | 3.5 | 34.0 | 46.7 | 0.6 | 18.7 |
| 421 | 15.2 | 3.8 | 33.8 | 46.5 | 0.8 | 18.9 |
| 421 | 16.5 | 4.7 | 30.2 | 47.9 | 0.7 | 21.2 |
| 421 | 15.8 | 5.1 | 35.3 | 43.2 | 0.7 | 20.9 |
| Means | 15.6 | 4.1 | 33.3 | 46.5 | 0.6 | 19.6 |

TABLE 21a

| GC#s | PR# | Activity | SOURCE | Activity | Pedigree | Pedigree | Comments |
|---|---|---|---|---|---|---|---|
| 160 | 877-3 | @ s(=S1) | IttN: 2429-1 | IttN: 2429 × IttN: 2430 | GC#74 x GC#82 | IssN: 260-16 × IssN: 261-2 | #13S1 x #13S1 |
| 324 | 909-4 | @ s(=S1) | IttN: 2467-1 | IttN: 2467 × IttN: 2468 | GC#73 x GC#85 | IssN: 260-14 × 261-5 | #13S1 x #13S1 |
| 420 | 933-2 | @ s(=S1) | IttN: 2494-1 | | IttN: 2494 @ | #88S1 | Parental |
| 421 | 933-3 | @ s(=S1) | IttN: 2494-1 | | IttN: 2494 @ | #88S1 | Parental |

TABLE 22

Selected Pedigrees Yellow Block

| GC# | IuuN | Source | Pedigree | Prev ID | Source | Pedigree |
|---|---|---|---|---|---|---|
| 4193 | 4896-4 | IttN: 2483-5 | GC#1346 | | Parental | #5S1 @ |
| 4214 | 4901-1 | IttN: 2484-1 | GC#1347 | | Parental | #13S1 @ |
| 4221 | 4903-1 | IttN: 2484-5 | GC#1351 | | Parental | #13S1 @ |
| 4234 | 4906-1 | IttN: 2486-5 | GC#1359 | | Parental | #17S1 @ |
| 4243 | 4907-5 | IttN: 2486-5 | GC#1359 | | Parental | #17S1 @ |
| 4255 | 4911-1 | IttN: 2492-1 | GC#1367 | | Parental | #85S1 @ |
| 4292 | 4918-3 | IttN: 351-10@ | GC#460 | | Parental | #88S1 @ |
| 4300 | 4920-2 | IttN: 2494-1 | GC#1386 | | Parental | #88S1 @ |
| 4309 | 4921-4 | IttN: 2494-1 | GC#1386 | | Parental | #88S1 @ |
| 4326 | 4925-2 | IttN: 2495-1 | GC#1396 | | Parental | #90S1 @ |
| 4335 | 4926-6 | IttN: 2495-2 | GC#1397 | | Parental | #90S1 @ |
| 4338 | 4927-1 | IttN: 2495-2 | GC#1397 | | Parental | #90S1 @ |
| 4356 | 4934-2 | IttN: 2499-1 | GC#1424 | | Parental | #92S1 @ |
| 4359 | 4934-5 | IttN: 2499-1 | GC#1424 | | Parental | #92S1 @ |
| 4372 | 4939-5 | IttN: 2499-6 | GC#1429 | | Parental | #92S1 @ |
| 4379 | 4940-2 | IttN: 2789-1 | GC#2707 | from GC#411 | IssN: 340-10@ | #87S1 @ |
| 4395 | 4943-2 | IttN: 2789-2 | GC#2708 | from GC#411 | IssN: 340-10@ | #87S1 @ |
| 4407 | 4945-5 | IttN: 2872-2 | ts166 = GC#2947 | from GC#488 | IssN: 357-6 × 350-4 | Mo17 × #88S1 |
| 4408 | 4946-1 | IttN: 2783-1 | GC#2702 | from GC#409 | IssN: 340-3 | #87S1 @ |
| 4417 | 4947-5 | IttN: 2783-1 | GC#2702 | from GC#409 | IssN: 340-3 | #87S1 @ |
| 4423 | 4949-1 | IttN: 2908-6 | ts206 = GC#3045 | from GC#630 | IssN: 380-15 × 383-6 | #92S1 × A632 |
| 4428 | 4949-6 | IttN: 2908-6 | ts206 = GC#3045 | from GC#630 | IssN: 380-15 × 383-6 | #92S1 × A632 |
| 4442 | 4952-3 | IttN: 2855-1 | ts86 = ?GC# | from GC#471 | IssN: 352-1 × 350-5 | A619 × #88S1 |
| 4456 | 4954-6 | IttN: 2837-1 | ts42 = ?GC# | from GC#459 | IssN: 350-10 × 353-9 | #88S1 × A632 |
| 4458 | 4955-1 | IttN: 2837-1 | ts42 = ?GC# | from GC#459 | IssN: 350-10 × 353-9 | #88S1 × A632 |
| 4473 | 4958-2 | IttN: 2866-2 | | from GC#482 | IssN: 355-1 × 351-3 | B73 × #88S1 |
| 4485 | 4960-4 | IttN: 2866-2 | | from GC#482 | IssN: 355-1 × 351-3 | B73 × #88S1 |
| 4489 | 4961-3 | IttN: 2866-2 | | from GC#482 | IssN: 355-1 × 351-3 | B73 × #88S1 |
| 4499 | 4963-2 | IttN: 2874-4 | ts174 = GC#2955 | from GC#490 | IssN: 358-9 × 350-16 | OH43 × #88S1 |
| 4512 | 4965-1 | IttN: 2874-4 | ts174 = GC#2955 | from GC#490 | IssN: 358-9 × 350-16 | OH43 × #88S1 |
| 4524 | 4966-5 | IttN: 2874-4 | ts174 = GC#2955 | from GC#490 | IssN: 358-9 × 350-16 | OH43 × #88S1 |
| 4534 | 4968-1 | IttN: 2874-2 | ts172 = GC#2953 | from GC#490 | IssN: 358-9 × 350-16 | OH43 × #88S1 |
| 4545 | 4969-6 | IttN: 2874-2 | ts172 = GC#2953 | from GC#490 | IssN: 358-9 × 350-16 | OH43 × #88S1 |
| 4549 | 4970-3 | IttN: 2874-2 | ts172 = GC#2953 | from GC#490 | IssN: 358-9 × 350-16 | OH43 × #88S1 |
| 4565 | 4973-5 | IttN: 2874-7 | ts177 = GC#2958 | from GC#490 | IssN: 358-9 × 350-16 | OH43 × #88S1 |
| 4573 | 4975-3 | IttN: 2874-7 | ts177 = GC#2958 | from GC#490 | IssN: 358-9 × 350-16 | OH43 × #88S1 |
| 4578 | 4976-3 | IttN: 2874-7 | ts177 = GC#2958 | from GC#490 | IssN: 358-9 × 350-16 | OH43 × #88S1 |
| 4655 | 4997-1 | IttN: 2480-16 | GC#1337 | GC#59 × GC#29 | (IssN: 257-15 × 251-8) × IssN: 251-8 × 257-15) | (Mo17 × #5S1) (#5S1 × Mo17) |
| 4656 | 4997-2 | IttN: 2480-16 | GC#1337 | GC#59 × GC#29 | (IssN: 257-15 × 251-8) × IssN: 251-8 × 257-15) | (Mo17 × #5S1) (#5S1 × Mo17) |
| 4657 | 4997-3 | IttN: 2480-16 | GC#1337 | GC#59 × GC#29 | (IssN: 257-15 × 251-8) × IssN: 251-8 × 257-15) | (Mo17 × #5S1) (#5S1 × Mo17) |
| 4659 | 4997-5 | IttN: 2480-16 | GC#1337 | GC#59 × GC#29 | (IssN: 257-15 × 251-8) × IssN: 251-8 × 257-15) | (Mo17 × #5S1) (#5S1 × Mo17) |
| 4660 | 4999-1 | IttN: 2519-1 | GC#1534 | from GC#33 | IssN: 251-12 | #5S1 @ |
| 4674 | 5004-3 | IttN: 2519-2 | GC#1535 | from GC#33 | IssN: 251-12 | #5S1 @ |
| 4679 | 5005-4 | IttN: 2519-2 | GC#1535 | From GC#33 | IssN: 251-12 | #5S1 @ |
| 4692 | 5007-5 | IttN: 2519-2 | GC#1535 | From GC#33 | IssN: 251-12 | #5S1 @ |
| 4701 | 5010-1 | IttN: 2519-3 | GC#1536 | From GC#33 | IssN: 251-12 | #5S1 @ |
| 4708 | 5013-2 | IttN: 2520-1 | GC#1537 | from GC#34 | IssN: 251-13 | #5S1 @ |
| 4717 | 5015-2 | IttN: 2520-1 | GC#1537 | from GC#34 | IssN: 251-13 | #5S1 @ |
| 4726 | 5019-1 | IttN: 2522-6 | GC#1659 | from GC#58 | IssN: 257-12 × 251-1 | MO17 × #5S1 |
| 4727 | 5019-2 | IttN: 2522-6 | GC#1659 | from GC#58 | IssN: 257-12 × 251-1 | MO17 × #5S1 |
| 4736 | 5022-1 | IttN: 2522-6 | GC#1659 | from GC#58 | IssN: 257-12 × 251-1 | MO17 × #5S1 |
| 4738 | 5022-3 | IttN: 2522-6 | GC#1659 | from GC#58 | IssN: 257-12 × 251-1 | MO17 × #5S1 |
| 4745 | 5025-2 | IttN: 2532-2 | GC#1660 | from GC#70 | IssN: 260-3 | #13S1 @ |
| 4751 | 5028-4 | IttN: 2549-1 | GC#1708 | from GC#83 | IssN: 261-2 | #13S1 @ |
| 4758 | 5030-2 | IttN: 2549-1 | GC#1708 | from GC#83 | IssN: 261-2 | #13S1 @ |
| 4770 | 5039-1 | IssN: 351-10@ | GC#460 | | | #88S1 @ |

TABLE 22-continued

Selected Pedigrees Yellow Block

| GC# | IuuN | Source | Pedigree | Prev ID | Source | Pedigree |
|---|---|---|---|---|---|---|
| 4776 | 5041-1 | ts41 | IttN: 2837-4 | GC#459 | IssN: 350-10 × 353-9 | #88S1 × A632 |
| 4782 | 5042-1 | ts41 | IttN: 2837-4 | GC#459 | IssN: 350-10 × 353-9 | #88S1 × A632 |
| 4790 | 5043-1 | ts41 | IttN: 2837-4 | GC#459 | IssN: 350-10 × 353-9 | #88S1 × A632 |
| 4805 | 5046-3 | ts41 | IttN: 2837-4 | GC#459 | IssN: 350-10 × 353-9 | #88S1 × A632 |
| 4813 | 5047-4 | ts41 | IttN: 2837-4 | GC#459 | IssN: 350-10 × 353-9 | #88S1 × A632 |
| 4822 | 5049-2 | ts41 | IttN: 2837-4 | GC#459 | IssN: 350-10 × 353-9 | #88S1 × A632 |
| 4828 | 5050-4 | ts41 | IttN: 2837-4 | GC#459 | IssN: 350-10 × 353-9 | #88S1 × A632 |
| 4830 | 5051-1 | ts2 | IttN: 2792-1 | GC#414 | IssN: 340-15 @ til | #88S1 @ |
| 4838 | 5053-2 | ts2 | IttN: 2792-1 | GC#414 | IssN: 340-15 @ til | #87S1 @ |
| 4854 | 5056-4 | ts3 | IttN: 2792-2 | GC#414 | IssN: 340-15 @ til | #87S1 @ |
| 4862 | 5058-3 | IttN: 2790-1 | GC#412 | IssN: 340-11 @ | #87S1 @ | |
| 4874 | 5060-3 | IttN: 2790-1 | GC#412 | IssN: 340-11 @ | #87S1 @ | |
| 4880 | 5061-4 | IttN: 2790-1 | GC#412 | IssN: 340-11 @ | #87S1 @ | |
| 4893 | 5064-4 | IttN: 2790-2 | GC#412 | IssN: 340-11 @ | #87S1 @ | |
| 4897 | 5065-4 | IttN: 2790-2 | GC#412 | IssN: 340-11 @ | #87S1 @ | |
| 4907 | 5067-1 | IttN: 2790-3 | GC#412 | IssN: 340-11 @ | #87S1 @ | |
| 4923 | 5070-6 | IttN: 2790-3 | GC#412 | IssN: 340-11 @ | #87S1 @ | |
| 4932 | 5072-4 | IttN: 2790-3 | GC#412 | IssN: 340-11 @ | #87S1 @ | |
| 4936 | 5073-2 | IttN: 2790-3 | GC#412 | IssN: 340-11 @ | #87S1 @ | |
| 4948 | 5074-5 | IttN: 2790-3 | GC#412 | IssN: 340-11 @ | #87S1 @ | |
| 4957 | 5075-9 | IttN: 2790-3 | GC#412 | IssN: 340-11 @ | #87S1 @ | |

TABLE 23

Selected Yellow Best for invention.

| GC # | Category | Palmitic | Stearic | Oleic | Linoleic | Linolenic | Saturates |
|---|---|---|---|---|---|---|---|
| 4193 | S3 | 12.6 | 4.0 | 38.8 | 43.9 | 0.7 | 16.6 |
| 4193 | S3 | 12.4 | 3.9 | 37.7 | 45.4 | 0.7 | 16.3 |
| 4193 | S3 | 12.5 | 3.7 | 36.8 | 46.0 | 1.0 | 16.2 |
| 4193 | S3 | 12.2 | 4.0 | 35.6 | 47.5 | 0.7 | 16.2 |
| 4193 | S3 | 12.6 | 4.4 | 37.6 | 44.8 | 0.7 | 17.0 |
| 4193 | S3 | 11.7 | 3.6 | 56.6 | 27.0 | 1.1 | 15.3 |
| 4193 | S3 | 12.3 | 4.1 | 38.4 | 44.4 | 0.8 | 16.4 |
| 4193 | S3 | 12.3 | 4.7 | 37.2 | 45.2 | 0.7 | 17.0 |
| 4193 | S3 | 12.6 | 3.4 | 35.8 | 47.4 | 0.8 | 16.0 |
| 4193 | S3 | 12.3 | 4.0 | 37.9 | 45.2 | 0.7 | 16.2 |
| 4193 | Mean S3 | 12.3 | 4.0 | 39.2 | 43.7 | 0.8 | 16.3 |
| 4214 | S3 | 7.1 | 2.0 | 45.1 | 44.8 | 1.0 | 9.1 |
| 4214 | S3 | 7.3 | 1.9 | 45.9 | 43.8 | 1.1 | 9.2 |
| 4214 | S3 | 7.5 | 1.8 | 44.6 | 45.0 | 1.0 | 9.3 |
| 4214 | S3 | 7.3 | 2.0 | 48.6 | 41.2 | 0.9 | 9.3 |
| 4214 | S3 | 7.2 | 1.9 | 44.8 | 45.1 | 1.1 | 9.0 |
| 4214 | S3 | 10.0 | 2.1 | 28.7 | 56.0 | 3.2 | 12.1 |
| 4214 | S3 | 7.2 | 2.1 | 50.3 | 39.3 | 1.0 | 9.4 |
| 4214 | S3 | 7.2 | 2.0 | 46.0 | 44.0 | 1.0 | 9.1 |
| 4214 | S3 | 7.2 | 1.8 | 43.5 | 46.4 | 1.1 | 9.0 |
| 4214 | S3 | 7.7 | 1.7 | 40.8 | 48.7 | 1.2 | 9.4 |
| 4214 | Mean | 7.6 | 1.9 | 43.8 | 45.4 | 1.3 | 9.5 |
| 4221 | S3 | 7.8 | 3.5 | 52.9 | 34.9 | 0.9 | 11.2 |
| 4221 | S3 | 7.7 | 2.3 | 49.3 | 39.9 | 0.9 | 10.0 |
| 4221 | S3 | 7.0 | 3.4 | 55.3 | 33.4 | 0.9 | 10.4 |
| 4221 | S3 | 7.2 | 3.4 | 54.9 | 33.7 | 0.8 | 10.6 |
| 4221 | S3 | 7.3 | 2.9 | 47.2 | 41.6 | 1.0 | 10.2 |
| 4221 | S3 | 7.5 | 3.1 | 53.1 | 35.4 | 0.9 | 10.6 |
| 4221 | S3 | 7.7 | 2.8 | 48.2 | 40.3 | 1.0 | 10.5 |
| 4221 | S3 | 6.9 | 3.3 | 52.3 | 36.5 | 1.0 | 10.3 |
| 4221 | S3 | 7.1 | 3.1 | 50.0 | 39.0 | 0.9 | 10.2 |
| 4221 | S3 | 7.5 | 2.8 | 50.2 | 38.5 | 1.0 | 10.3 |
| 4221 | Mean | 7.4 | 3.1 | 51.3 | 37.3 | 0.9 | 10.4 |
| 4234 | S3 | 14.3 | 2.7 | 29.6 | 52.2 | 1.2 | 17.0 |
| 4234 | S3 | 14.1 | 2.5 | 27.9 | 54.2 | 1.2 | 16.7 |
| 4234 | S3 | 13.8 | 2.0 | 21.3 | 61.6 | 1.3 | 15.8 |
| 4234 | S3 | 14.8 | 2.7 | 27.1 | 54.3 | 1.0 | 17.5 |
| 4234 | S3 | 14.7 | 2.3 | 27.3 | 54.6 | 1.1 | 17.0 |
| 4234 | S3 | 14.2 | 2.4 | 28.6 | 53.5 | 1.2 | 16.6 |
| 4234 | S3 | 15.0 | 2.4 | 27.0 | 54.5 | 1.1 | 17.4 |
| 4234 | S3 | 13.8 | 1.9 | 20.9 | 62.0 | 1.3 | 15.7 |
| 4234 | S3 | 14.9 | 2.2 | 26.2 | 55.9 | 0.8 | 17.1 |
| 4234 | S3 | 14.8 | 2.4 | 27.1 | 54.6 | 1.2 | 17.2 |

TABLE 23-continued

Selected Yellow Best for invention.

| GC # | Category | Palmitic | Stearic | Oleic | Linoleic | Linolenic | Saturates |
|---|---|---|---|---|---|---|---|
| 4234 | Mean | 14.5 | 2.3 | 26.3 | 55.8 | 1.1 | 16.8 |
| 4243 | S3 | 14.7 | 2.7 | 28.6 | 53.0 | 1.0 | 17.4 |
| 4243 | S3 | 14.6 | 2.2 | 24.9 | 57.4 | 0.9 | 16.8 |
| 4243 | S3 | 14.8 | 2.5 | 27.9 | 53.7 | 1.1 | 17.3 |
| 4243 | S3 | 14.8 | 2.0 | 24.4 | 57.8 | 1.0 | 16.8 |
| 4243 | S3 | 12.5 | 2.0 | 18.9 | 65.1 | 1.5 | 14.5 |
| 4243 | S3 | 13.6 | 1.9 | 19.2 | 64.1 | 1.3 | 15.5 |
| 4243 | S3 | 14.3 | 2.3 | 25.1 | 57.2 | 1.2 | 16.6 |
| 4243 | S3 | 14.0 | 1.5 | 18.9 | 64.5 | 1.1 | 15.5 |
| 4243 | S3 | 14.0 | 2.6 | 28.3 | 54.2 | 0.9 | 16.6 |
| 4243 | S3 | 13.5 | 1.4 | 19.0 | 64.9 | 1.1 | 14.9 |
| 4243 | S3 | 14.1 | 2.1 | 23.5 | 59.2 | 1.1 | 16.2 |
| 4255 | S3 | 13.3 | 3.8 | 27.0 | 54.9 | 1.0 | 17.1 |
| 4255 | S3 | 14.2 | 2.7 | 24.3 | 56.4 | 2.4 | 16.9 |
| 4255 | S3 | 14.1 | 2.7 | 24.9 | 57.2 | 1.2 | 16.7 |
| 4255 | S3 | 14.2 | 2.2 | 25.1 | 57.5 | 1.0 | 16.4 |
| 4255 | S3 | 13.5 | 2.1 | 24.8 | 58.5 | 1.2 | 15.5 |
| 4255 | S3 | 13.9 | 2.9 | 24.6 | 57.5 | 1.2 | 16.8 |
| 4255 | S3 | 14.0 | 3.1 | 25.4 | 56.5 | 1.1 | 17.1 |
| 4255 | S3 | 14.4 | 2.4 | 22.5 | 59.4 | 1.3 | 16.8 |
| 4255 | S3 | 13.7 | 3.2 | 24.9 | 57.2 | 1.1 | 16.8 |
| 4255 | S3 | 13.9 | 2.8 | 24.8 | 57.2 | 1.3 | 16.7 |
| 4292 | S3 | 16.0 | 3.3 | 29.9 | 50.1 | 0.6 | 19.3 |
| 4292 | S3 | 16.5 | 4.2 | 28.7 | 50.0 | 0.6 | 20.7 |
| 4292 | S3 | 16.0 | 4.2 | 28.2 | 50.9 | 0.6 | 20.2 |
| 4292 | S3 | 15.9 | 4.1 | 29.9 | 49.7 | 0.5 | 20.0 |
| 4292 | S3 | 16.1 | 4.2 | 29.6 | 49.6 | 0.5 | 20.2 |
| 4292 | S3 | 16.4 | 4.9 | 27.6 | 50.4 | 0.7 | 21.4 |
| 4292 | S3 | 16.2 | 4.4 | 28.1 | 50.6 | 0.7 | 20.6 |
| 4292 | S3 | 16.0 | 3.9 | 28.7 | 50.7 | 0.7 | 19.9 |
| 4292 | S3 | 15.9 | 4.9 | 29.1 | 49.5 | 0.5 | 20.9 |
| 4292 | S3 | 16.1 | 4.2 | 28.9 | 50.2 | 0.6 | 20.4 |
| 4300 | S3 | 15.1 | 5.3 | 31.7 | 47.4 | 0.5 | 20.4 |
| 4300 | S3 | 15.5 | 4.9 | 30.8 | 48.3 | 0.6 | 20.4 |
| 4300 | S3 | 14.6 | 4.2 | 34.0 | 46.8 | 0.5 | 18.7 |
| 4300 | S3 | 15.7 | 3.8 | 30.0 | 49.8 | 0.7 | 19.5 |
| 4300 | S3 | 14.9 | 5.3 | 30.8 | 48.5 | 0.5 | 20.3 |
| 4300 | S3 | 14.7 | 4.4 | 33.4 | 47.0 | 0.6 | 19.1 |
| 4300 | S3 | 15.5 | 4.2 | 29.9 | 49.8 | 0.6 | 19.7 |
| 4300 | S3 | 14.8 | 4.4 | 33.0 | 47.2 | 0.6 | 19.2 |
| 4300 | S3 | 15.0 | 4.2 | 32.2 | 48.1 | 0.5 | 19.2 |
| 4300 | S3 | 15.2 | 5.5 | 31.6 | 47.1 | 0.6 | 20.7 |
| 4300 | S3 | 15.1 | 4.6 | 31.7 | 48.0 | 0.6 | 19.7 |
| 4309 | S3 | 16.4 | 3.4 | 28.6 | 50.6 | 1.0 | 19.8 |
| 4309 | S3 | 15.7 | 3.3 | 30.1 | 50.1 | 0.8 | 19.0 |
| 4309 | S3 | 15.2 | 3.8 | 30.9 | 49.3 | 0.8 | 19.0 |
| 4309 | S3 | 16.1 | 2.8 | 29.9 | 50.4 | 0.8 | 18.9 |
| 4309 | S3 | 16.0 | 3.8 | 31.3 | 48.3 | 0.7 | 19.8 |
| 4309 | S3 | 16.1 | 3.4 | 28.5 | 51.3 | 0.8 | 19.4 |
| 4309 | S3 | 15.7 | 3.2 | 28.5 | 51.7 | 0.8 | 19.0 |
| 4309 | S3 | 15.9 | 4.0 | 30.3 | 48.9 | 0.8 | 20.0 |
| 4309 | S3 | 15.8 | 4.0 | 29.1 | 50.3 | 0.8 | 19.8 |
| 4309 | S3 | 15.5 | 4.8 | 31.4 | 47.5 | 0.8 | 20.3 |
| 4309 | Mean | 15.8 | 3.7 | 29.9 | 49.8 | 0.8 | 19.5 |
| 4326 | S3 | 14.2 | 3.2 | 28.3 | 53.3 | 1.1 | 17.4 |
| 4326 | S3 | 13.0 | 3.8 | 37.7 | 44.6 | 1.0 | 16.8 |
| 4326 | S3 | 12.7 | 3.1 | 35.3 | 47.8 | 1.1 | 15.8 |
| 4326 | S3 | 13.1 | 3.0 | 35.1 | 47.8 | 1.1 | 16.1 |
| 4326 | S3 | 13.1 | 3.2 | 33.6 | 49.3 | 1.0 | 16.2 |
| 4326 | S3 | 13.3 | 3.0 | 30.1 | 52.6 | 1.0 | 16.3 |
| 4326 | S3 | 13.3 | 3.3 | 31.9 | 50.6 | 0.9 | 16.6 |
| 4326 | S3 | 13.2 | 3.1 | 30.3 | 52.3 | 1.1 | 16.4 |
| 4326 | S3 | 13.4 | 2.8 | 29.6 | 53.1 | 1.1 | 16.2 |
| 4326 | S3 | 12.9 | 3.3 | 31.9 | 50.8 | 1.0 | 16.3 |
| 4326 | Mean | 13.2 | 3.2 | 32.4 | 50.2 | 1.0 | 16.4 |
| 4335 | S3 | 14.3 | 3.2 | 36.5 | 44.9 | 1.1 | 17.4 |
| 4335 | S3 | 13.5 | 2.8 | 32.1 | 50.4 | 1.3 | 16.3 |
| 4335 | S3 | 14.4 | 3.2 | 30.9 | 50.6 | 1.0 | 17.6 |
| 4335 | S3 | 13.7 | 3.5 | 33.6 | 48.1 | 1.1 | 17.2 |
| 4335 | S3 | 14.4 | 3.0 | 34.7 | 47.0 | 0.9 | 17.4 |
| 4335 | S3 | 14.1 | 2.7 | 35.3 | 46.5 | 1.4 | 16.8 |
| 4335 | S3 | 14.4 | 3.7 | 34.5 | 46.5 | 0.9 | 18.1 |
| 4335 | S3 | 13.6 | 2.9 | 29.2 | 52.9 | 1.4 | 16.5 |
| 4335 | S3 | 15.4 | 2.8 | 29.8 | 51.0 | 1.0 | 18.2 |
| 4335 | S3 | 14.3 | 2.6 | 31.4 | 50.7 | 1.1 | 16.8 |

TABLE 23-continued

Selected Yellow Best for invention.

| GC # | Category | Palmitic | Stearic | Oleic | Linoleic | Linolenic | Saturates |
|---|---|---|---|---|---|---|---|
| 4335 | Mean | 14.2 | 3.0 | 32.8 | 48.8 | 1.1 | 17.2 |
| 4338 | S3 | 15.3 | 3.4 | 28.2 | 52.2 | 0.9 | 18.7 |
| 4338 | S3 | 15.1 | 3.4 | 29.4 | 51.3 | 1.0 | 18.4 |
| 4338 | S3 | 15.1 | 3.4 | 28.2 | 52.1 | 1.2 | 18.6 |
| 4338 | S3 | 15.1 | 3.4 | 28.0 | 52.2 | 1.4 | 18.4 |
| 4338 | S3 | 15.1 | 3.0 | 28.1 | 52.7 | 1.2 | 18.1 |
| 4338 | S3 | 15.0 | 2.9 | 27.5 | 53.6 | 1.0 | 17.8 |
| 4338 | S3 | 15.3 | 3.4 | 27.0 | 53.2 | 1.0 | 18.8 |
| 4338 | S3 | 14.7 | 3.9 | 28.8 | 51.6 | 1.0 | 18.6 |
| 4338 | S3 | 14.8 | 3.4 | 29.2 | 51.6 | 1.0 | 18.2 |
| 4338 | S3 | 15.2 | 3.3 | 28.1 | 52.3 | 1.1 | 18.5 |
| 4338 | Mean | 15.1 | 3.3 | 28.2 | 52.3 | 1.1 | 18.4 |
| 4356 | S3 | 14.9 | 2.8 | 28.6 | 52.7 | 1.0 | 17.7 |
| 4356 | S3 | 15.5 | 2.9 | 28.4 | 52.2 | 1.0 | 18.4 |
| 4356 | S3 | 14.9 | 3.1 | 28.4 | 52.6 | 1.0 | 18.0 |
| 4356 | S3 | 15.4 | 3.0 | 29.0 | 51.6 | 1.0 | 18.4 |
| 4356 | S3 | 15.2 | 2.8 | 27.6 | 53.3 | 1.2 | 18.0 |
| 4356 | S3 | 15.7 | 2.8 | 28.1 | 52.4 | 1.0 | 18.5 |
| 4356 | S3 | 14.8 | 3.3 | 28.7 | 52.4 | 1.0 | 18.0 |
| 4356 | S3 | 14.9 | 2.7 | 27.3 | 53.9 | 1.2 | 17.6 |
| 4356 | S3 | 15.4 | 2.9 | 29.2 | 51.5 | 1.1 | 18.3 |
| 4356 | S3 | 14.5 | 2.9 | 27.8 | 53.6 | 1.1 | 17.4 |
| 4356 | Mean | 15.1 | 2.9 | 28.3 | 52.6 | 1.1 | 18.0 |
| 4359 | S3 | 14.3 | 3.9 | 37.7 | 43.3 | 0.8 | 18.2 |
| 4359 | S3 | 14.2 | 3.9 | 37.8 | 43.3 | 0.8 | 18.1 |
| 4359 | S3 | 14.5 | 4.4 | 35.7 | 44.5 | 0.9 | 18.9 |
| 4359 | S3 | 14.8 | 3.9 | 34.0 | 46.6 | 0.7 | 18.7 |
| 4359 | S3 | 15.4 | 3.6 | 34.3 | 46.0 | 0.7 | 19.0 |
| 4359 | S3 | 14.4 | 3.5 | 36.2 | 45.2 | 0.8 | 17.9 |
| 4359 | S3 | 14.5 | 4.3 | 34.5 | 45.8 | 0.9 | 18.8 |
| 4359 | S3 | 14.4 | 4.3 | 36.2 | 44.3 | 0.8 | 18.7 |
| 4359 | S3 | 14.3 | 4.0 | 39.2 | 41.5 | 0.9 | 18.3 |
| 4359 | S3 | 15.2 | 3.7 | 35.7 | 44.6 | 0.8 | 18.9 |
| 4359 | Mean | 14.6 | 3.9 | 36.1 | 44.5 | 0.8 | 18.5 |
| 4372 | S3 | 15.1 | 2.5 | 31.3 | 50.6 | 0.6 | 17.6 |
| 4372 | S3 | 15.4 | 4.3 | 31.6 | 48.2 | 0.6 | 19.6 |
| 4372 | S3 | 14.3 | 4.3 | 34.2 | 46.5 | 0.8 | 18.6 |
| 4372 | S3 | 11.5 | 2.4 | 39.6 | 45.8 | 0.8 | 13.9 |
| 4372 | S3 | 14.9 | 3.1 | 31.3 | 49.9 | 0.8 | 18.0 |
| 4372 | S3 | 15.0 | 3.6 | 34.5 | 46.4 | 0.6 | 18.6 |
| 4372 | S3 | 14.9 | 3.2 | 29.8 | 51.4 | 0.7 | 18.1 |
| 4372 | S3 | 15.4 | 4.0 | 30.7 | 49.4 | 0.7 | 19.3 |
| 4372 | S3 | 14.7 | 3.9 | 33.6 | 47.0 | 0.8 | 18.6 |
| 4372 | S3 | 15.5 | 2.8 | 31.1 | 49.8 | 0.8 | 18.3 |
| 4372 | Mean | 14.7 | 3.4 | 32.8 | 48.5 | 0.7 | 18.1 |
| 4379 | S3 | 16.2 | 3.5 | 31.0 | 48.6 | 0.7 | 19.7 |
| 4379 | S3 | 16.6 | 3.2 | 31.2 | 48.4 | 0.6 | 19.8 |
| 4379 | S3 | 16.4 | 3.0 | 30.8 | 49.1 | 0.6 | 19.4 |
| 4379 | S3 | 16.6 | 3.1 | 30.4 | 49.2 | 0.7 | 19.7 |
| 4379 | S3 | 16.6 | 3.2 | 30.1 | 49.5 | 0.7 | 19.7 |
| 4379 | S3 | 16.4 | 3.1 | 31.2 | 48.7 | 0.6 | 19.5 |
| 4379 | S3 | 16.6 | 3.0 | 30.4 | 49.3 | 0.7 | 19.6 |
| 4379 | S3 | 16.3 | 3.1 | 30.9 | 49.0 | 0.7 | 19.5 |
| 4379 | S3 | 16.5 | 3.3 | 31.4 | 48.3 | 0.6 | 19.7 |
| 4379 | S3 | 16.8 | 3.2 | 30.9 | 48.4 | 0.7 | 20.0 |
| 4379 | Mean | 16.5 | 3.2 | 30.8 | 48.9 | 0.7 | 19.7 |
| 4395 | S3 | 15.3 | 2.6 | 21.0 | 60.6 | 0.6 | 17.9 |
| 4395 | S3 | 15.3 | 2.4 | 21.5 | 60.2 | 0.6 | 17.7 |
| 4395 | S3 | 15.3 | 2.0 | 21.0 | 61.1 | 0.7 | 17.2 |
| 4395 | S3 | 15.6 | 1.8 | 21.0 | 61.1 | 0.6 | 17.3 |
| 4395 | S3 | 16.1 | 1.7 | 19.0 | 62.4 | 0.7 | 17.9 |
| 4395 | S3 | 15.1 | 2.0 | 22.6 | 59.8 | 0.6 | 17.0 |
| 4395 | S3 | 15.7 | 2.6 | 20.6 | 60.7 | 0.5 | 18.3 |
| 4395 | S3 | 15.5 | 2.0 | 20.3 | 61.5 | 0.8 | 17.5 |
| 4395 | S3 | 15.7 | 2.1 | 20.2 | 61.2 | 0.8 | 17.8 |
| 4395 | S3 | 15.2 | 1.8 | 20.7 | 61.6 | 0.7 | 17.0 |
| 4395 | Mean | 15.5 | 2.1 | 20.8 | 61.0 | 0.7 | 17.6 |
| 4407 | CS2 | 14.8 | 3.3 | 32.3 | 49.0 | 0.6 | 18.1 |
| 4407 | CS2 | 14.7 | 3.5 | 32.2 | 49.2 | 0.5 | 18.2 |
| 4407 | CS2 | 14.5 | 3.5 | 37.9 | 43.6 | 0.6 | 18.0 |
| 4407 | CS2 | 14.6 | 3.7 | 33.6 | 47.8 | 0.4 | 18.3 |
| 4407 | CS2 | 14.3 | 3.2 | 32.2 | 49.9 | 0.5 | 17.5 |
| 4407 | CS2 | 14.2 | 3.9 | 39.2 | 42.2 | 0.5 | 18.1 |
| 4407 | CS2 | 14.2 | 3.7 | 32.1 | 49.5 | 0.5 | 17.9 |
| 4407 | CS2 | 14.4 | 3.7 | 29.2 | 52.3 | 0.5 | 18.1 |

TABLE 23-continued

Selected Yellow Best for invention.

| GC # | Category | Palmitic | Stearic | Oleic | Linoleic | Linolenic | Saturates |
|---|---|---|---|---|---|---|---|
| 4407 | CS2 | 13.9 | 3.3 | 38.1 | 44.2 | 0.5 | 17.2 |
| 4407 | CS2 | 14.2 | 3.7 | 34.3 | 47.3 | 0.5 | 17.9 |
| 4407 | Mean | 14.4 | 3.6 | 34.1 | 47.5 | 0.5 | 17.9 |
| 4408 | S3 | 14.6 | 3.5 | 35.1 | 46.4 | 0.5 | 18.1 |
| 4408 | S3 | 14.3 | 3.7 | 36.8 | 44.8 | 0.4 | 18.0 |
| 4408 | S3 | 15.5 | 3.5 | 36.9 | 43.7 | 0.4 | 19.0 |
| 4408 | S3 | 14.6 | 3.7 | 32.4 | 48.9 | 0.5 | 18.3 |
| 4408 | S3 | 14.6 | 4.1 | 35.7 | 45.2 | 0.4 | 18.7 |
| 4408 | S3 | 15.1 | 3.7 | 31.8 | 49.1 | 0.4 | 18.7 |
| 4408 | S3 | 14.9 | 3.4 | 31.2 | 50.0 | 0.5 | 18.3 |
| 4408 | S3 | 14.4 | 3.6 | 38.3 | 43.3 | 0.5 | 18.0 |
| 4408 | S3 | 14.6 | 3.9 | 36.3 | 44.8 | 0.5 | 18.5 |
| 4408 | S3 | 14.9 | 3.7 | 32.5 | 48.4 | 0.5 | 18.6 |
| 4408 | Mean | 14.7 | 3.7 | 34.7 | 46.4 | 0.5 | 18.4 |
| 4417 | S3 | 11.7 | 4.1 | 33.8 | 49.6 | 0.8 | 15.8 |
| 4417 | S3 | 14.9 | 3.2 | 34.0 | 47.2 | 0.7 | 18.1 |
| 4417 | S3 | 14.7 | 3.7 | 33.8 | 46.9 | 1.0 | 18.4 |
| 4417 | S3 | 12.5 | 4.2 | 43.6 | 38.9 | 0.8 | 16.7 |
| 4417 | S3 | 13.3 | 3.4 | 33.8 | 48.6 | 1.0 | 16.7 |
| 4417 | S3 | 13.4 | 4.2 | 37.6 | 44.1 | 0.7 | 17.6 |
| 4417 | S3 | 12.9 | 4.0 | 34.2 | 48.7 | 0.3 | 16.8 |
| 4417 | S3 | 13.5 | 3.7 | 37.2 | 44.8 | 0.8 | 17.2 |
| 4417 | S3 | 14.1 | 3.7 | 36.0 | 45.4 | 0.7 | 17.9 |
| 4417 | S3 | 11.5 | 3.7 | 36.4 | 47.5 | 0.9 | 15.2 |
| 4417 | Mean | 13.2 | 3.8 | 36.0 | 46.2 | 0.8 | 17.0 |
| 4423 | CS2 | 15.7 | 2.4 | 35.2 | 45.9 | 0.8 | 18.1 |
| 4423 | CS2 | 15.8 | 2.5 | 30.5 | 50.5 | 0.8 | 18.3 |
| 4423 | CS2 | 15.7 | 2.1 | 33.6 | 47.7 | 0.8 | 17.8 |
| 4423 | CS2 | 16.3 | 2.3 | 29.9 | 50.7 | 0.7 | 18.6 |
| 4423 | CS2 | 15.5 | 2.1 | 29.7 | 51.9 | 0.8 | 17.6 |
| 4423 | CS2 | 15.4 | 2.5 | 33.9 | 47.5 | 0.7 | 17.8 |
| 4423 | CS2 | 14.9 | 2.9 | 33.9 | 47.6 | 0.8 | 17.8 |
| 4423 | CS2 | 15.0 | 2.2 | 33.2 | 48.8 | 0.7 | 17.3 |
| 4423 | CS2 | 15.6 | 2.3 | 32.3 | 48.9 | 0.8 | 17.9 |
| 4423 | CS2 | 15.3 | 2.7 | 33.4 | 47.9 | 0.8 | 18.0 |
| 4423 | Mean | 15.5 | 2.4 | 32.6 | 48.7 | 0.8 | 17.9 |
| 4428 | CS2 | 14.2 | 3.3 | 29.0 | 52.8 | 0.7 | 17.6 |
| 4428 | CS2 | 14.7 | 3.3 | 26.0 | 55.2 | 0.9 | 18.0 |
| 4428 | CS2 | 15.4 | 3.0 | 28.5 | 52.6 | 0.5 | 18.4 |
| 4428 | CS2 | 15.5 | 2.9 | 24.2 | 56.5 | 0.9 | 18.4 |
| 4428 | CS2 | 13.9 | 3.0 | 19.1 | 62.9 | 1.2 | 16.9 |
| 4428 | CS2 | 15.6 | 3.1 | 26.2 | 54.6 | 0.5 | 18.7 |
| 4428 | CS2 | 14.2 | 2.6 | 20.0 | 62.3 | 0.9 | 16.8 |
| 4428 | CS2 | 15.6 | 2.8 | 26.0 | 54.8 | 0.8 | 18.4 |
| 4428 | CS2 | 14.2 | 3.6 | 29.5 | 52.1 | 0.6 | 17.8 |
| 4428 | CS2 | 15.0 | 3.0 | 29.3 | 52.0 | 0.7 | 18.0 |
| 4428 | Mean | 14.8 | 3.1 | 25.8 | 55.6 | 0.8 | 17.9 |
| 4442 | CS2 | 14.1 | 4.1 | 32.6 | 48.6 | 0.6 | 18.2 |
| 4442 | CS2 | 14.0 | 4.1 | 30.7 | 50.5 | 0.7 | 18.1 |
| 4442 | CS2 | 14.6 | 3.9 | 34.1 | 46.6 | 0.8 | 18.5 |
| 4442 | CS2 | 13.6 | 3.4 | 31.7 | 50.7 | 0.6 | 16.9 |
| 4442 | CS2 | 15.4 | 3.9 | 31.3 | 48.7 | 0.7 | 19.3 |
| 4442 | CS2 | 14.6 | 3.8 | 30.1 | 50.9 | 0.6 | 18.4 |
| 4442 | CS2 | 15.0 | 4.3 | 32.0 | 48.1 | 0.6 | 19.3 |
| 4442 | CS2 | 15.1 | 3.8 | 30.6 | 49.9 | 0.6 | 18.9 |
| 4442 | CS2 | 14.4 | 4.2 | 35.9 | 44.9 | 0.6 | 18.6 |
| 4442 | CS2 | 15.3 | 4.3 | 37.0 | 42.9 | 0.5 | 19.6 |
| 4442 | Mean | 14.6 | 4.0 | 32.6 | 48.2 | 0.6 | 18.6 |
| 4456 | CS2 | 15.0 | 2.8 | 21.4 | 60.0 | 0.8 | 17.8 |
| 4456 | CS2 | 14.9 | 2.8 | 18.7 | 62.4 | 1.3 | 17.7 |
| 4456 | CS2 | 14.8 | 3.0 | 20.2 | 61.1 | 0.9 | 17.8 |
| 4456 | CS2 | 13.9 | 3.3 | 18.9 | 62.9 | 1.1 | 17.2 |
| 4456 | CS2 | 14.6 | 3.2 | 20.4 | 61.0 | 0.8 | 17.8 |
| 4456 | CS2 | 15.0 | 3.8 | 20.9 | 59.4 | 0.9 | 18.8 |
| 4456 | CS2 | 14.8 | 3.2 | 20.8 | 60.5 | 0.9 | 17.9 |
| 4456 | CS2 | 13.8 | 3.3 | 19.5 | 62.2 | 1.1 | 17.2 |
| 4456 | CS2 | 14.3 | 3.8 | 20.8 | 60.3 | 0.8 | 18.1 |
| 4456 | CS2 | 14.4 | 3.2 | 20.6 | 61.0 | 0.9 | 17.6 |
| 4456 | Mean | 14.6 | 3.2 | 20.2 | 61.1 | 0.9 | 17.8 |
| 4458 | CS2 | 14.3 | 3.6 | 29.3 | 52.2 | 0.7 | 17.8 |
| 4458 | CS2 | 14.9 | 3.6 | 29.3 | 51.5 | 0.7 | 18.5 |
| 4458 | CS2 | 14.6 | 3.9 | 27.1 | 53.8 | 0.6 | 18.5 |
| 4458 | CS2 | 14.3 | 3.3 | 28.2 | 53.5 | 0.6 | 17.7 |
| 4458 | CS2 | 13.6 | 3.6 | 30.2 | 52.0 | 0.6 | 17.2 |
| 4458 | CS2 | 12.9 | 2.4 | 19.3 | 64.8 | 0.7 | 15.3 |

TABLE 23-continued

Selected Yellow Best for invention.

| GC # | Category | Palmitic | Stearic | Oleic | Linoleic | Linolenic | Saturates |
|------|----------|----------|---------|-------|----------|-----------|-----------|
| 4458 | CS2 | 13.8 | 3.4 | 28.6 | 53.5 | 0.7 | 17.2 |
| 4458 | CS2 | 14.3 | 3.7 | 30.3 | 51.1 | 0.7 | 18.0 |
| 4458 | CS2 | 14.4 | 3.2 | 26.6 | 55.1 | 0.8 | 17.6 |
| 4458 | CS2 | 13.5 | 3.8 | 28.6 | 53.3 | 0.7 | 17.4 |
| 4458 | Mean | 14.1 | 3.5 | 27.8 | 54.1 | 0.7 | 17.5 |
| 4473 | CS2 | 12.8 | 2.4 | 38.7 | 45.0 | 1.1 | 15.2 |
| 4473 | CS2 | 19.7 | 2.0 | 21.9 | 54.2 | 2.3 | 21.6 |
| 4473 | CS2 | 11.2 | 2.8 | 37.4 | 47.7 | 0.9 | 13.9 |
| 4473 | CS2 | 13.3 | 2.4 | 35.2 | 48.2 | 1.0 | 15.7 |
| 4473 | CS2 | 18.6 | 1.7 | 18.0 | 59.0 | 2.7 | 20.3 |
| 4473 | CS2 | 18.4 | 1.8 | 17.6 | 59.9 | 2.2 | 20.2 |
| 4473 | CS2 | 20.1 | 1.9 | 19.5 | 57.0 | 1.5 | 21.9 |
| 4473 | CS2 | 22.3 | 1.9 | 18.3 | 54.9 | 2.6 | 24.3 |
| 4473 | CS2 | 19.0 | 1.9 | 19.1 | 56.8 | 3.2 | 20.9 |
| 4473 | CS2 | 13.3 | 2.5 | 35.0 | 48.2 | 1.1 | 15.8 |
| 4473 | Mean | 16.9 | 2.1 | 26.1 | 53.1 | 1.9 | 19.0 |
| 4485 | CS2 | 13.4 | 2.7 | 29.7 | 53.3 | 0.9 | 16.1 |
| 4485 | CS2 | 21.8 | 2.4 | 19.4 | 54.3 | 2.1 | 24.1 |
| 4485 | CS2 | 14.6 | 2.8 | 26.2 | 55.7 | 0.8 | 17.4 |
| 4485 | CS2 | 12.3 | 2.7 | 28.6 | 55.6 | 0.9 | 14.9 |
| 4485 | CS2 | 13.2 | 2.7 | 34.9 | 48.4 | 0.8 | 15.9 |
| 4485 | CS2 | 14.8 | 2.7 | 33.3 | 48.7 | 0.6 | 17.4 |
| 4485 | CS2 | 13.5 | 3.0 | 33.2 | 49.4 | 1.0 | 16.5 |
| 4485 | CS2 | 13.1 | 3.3 | 30.7 | 52.0 | 0.9 | 16.4 |
| 4485 | CS2 | 13.6 | 3.3 | 33.0 | 49.2 | 0.8 | 16.9 |
| 4485 | CS2 | 12.0 | 2.9 | 31.8 | 52.8 | 0.5 | 14.9 |
| 4485 | Mean | 14.2 | 2.8 | 30.1 | 51.9 | 0.9 | 17.1 |
| 4489 | CS2 | 13.5 | 1.9 | 23.9 | 59.6 | 1.2 | 15.4 |
| 4489 | CS2 | 20.3 | 1.8 | 18.8 | 56.7 | 2.4 | 22.1 |
| 4489 | CS2 | 13.5 | 2.3 | 23.9 | 59.7 | 0.6 | 15.8 |
| 4489 | CS2 | 15.4 | 3.6 | 29.9 | 50.5 | 0.6 | 19.0 |
| 4489 | CS2 | 18.4 | 2.1 | 22.9 | 54.6 | 1.9 | 20.5 |
| 4489 | CS2 | 13.7 | 2.3 | 29.9 | 53.1 | 1.0 | 16.0 |
| 4489 | CS2 | 11.6 | 2.5 | 31.0 | 53.6 | 1.3 | 14.2 |
| 4489 | CS2 | 12.5 | 2.3 | 28.8 | 55.6 | 0.8 | 14.7 |
| 4489 | CS2 | 11.5 | 2.7 | 27.0 | 57.6 | 1.3 | 14.1 |
| 4489 | CS2 | 15.7 | 2.9 | 36.1 | 44.5 | 0.8 | 18.6 |
| 4489 | Mean | 14.6 | 2.4 | 27.2 | 54.6 | 1.2 | 17.1 |
| 4499 | CS2 | 13.1 | 3.9 | 20.0 | 61.9 | 1.2 | 17.0 |
| 4499 | CS2 | 14.8 | 3.2 | 20.0 | 61.0 | 1.1 | 18.0 |
| 4499 | CS2 | 14.0 | 3.8 | 21.9 | 59.3 | 1.2 | 17.7 |
| 4499 | CS2 | 14.1 | 3.9 | 22.0 | 59.0 | 1.0 | 18.0 |
| 4499 | CS2 | 12.9 | 4.3 | 20.3 | 61.5 | 1.0 | 17.2 |
| 4499 | CS2 | 13.7 | 3.7 | 20.4 | 61.3 | 1.0 | 17.3 |
| 4499 | CS2 | 14.2 | 3.4 | 19.3 | 62.1 | 1.0 | 17.6 |
| 4499 | CS2 | 14.7 | 3.2 | 21.5 | 59.5 | 1.2 | 17.9 |
| 4499 | CS2 | 14.0 | 3.8 | 20.2 | 60.7 | 1.2 | 17.8 |
| 4499 | CS2 | 14.1 | 3.9 | 22.7 | 58.4 | 1.0 | 18.0 |
| 4499 | Mean | 14.0 | 3.7 | 20.8 | 60.5 | 1.1 | 17.6 |
| 4512 | CS2 | 13.3 | 2.8 | 22.9 | 60.1 | 0.9 | 16.2 |
| 4512 | CS2 | 13.5 | 2.6 | 21.9 | 60.9 | 1.1 | 16.1 |
| 4512 | CS2 | 13.6 | 2.2 | 23.4 | 59.7 | 1.1 | 15.8 |
| 4512 | CS2 | 13.6 | 2.5 | 26.4 | 56.8 | 0.8 | 16.1 |
| 4512 | CS2 | 13.2 | 2.6 | 25.1 | 58.1 | 1.0 | 15.8 |
| 4512 | CS2 | 14.2 | 2.5 | 24.0 | 58.4 | 1.0 | 16.7 |
| 4512 | CS2 | 14.4 | 3.2 | 23.1 | 58.3 | 1.0 | 17.6 |
| 4512 | CS2 | 14.1 | 3.4 | 21.4 | 60.0 | 1.1 | 17.5 |
| 4512 | CS2 | 13.4 | 2.6 | 22.7 | 60.4 | 1.0 | 15.9 |
| 4512 | CS2 | 14.7 | 2.5 | 21.6 | 60.1 | 1.1 | 17.2 |
| 4512 | Mean | 13.8 | 2.7 | 23.2 | 59.3 | 1.0 | 16.5 |
| 4524 | CS2 | 13.8 | 2.4 | 20.0 | 62.8 | 1.0 | 16.1 |
| 4524 | CS2 | 14.2 | 2.7 | 22.1 | 60.0 | 1.0 | 17.0 |
| 4524 | CS2 | 14.6 | 2.4 | 23.2 | 59.0 | 0.8 | 17.0 |
| 4524 | CS2 | 15.3 | 3.5 | 25.3 | 55.0 | 0.9 | 18.8 |
| 4524 | CS2 | 14.0 | 3.4 | 20.8 | 60.9 | 0.9 | 17.4 |
| 4524 | CS2 | 13.8 | 3.1 | 23.1 | 59.2 | 0.8 | 16.9 |
| 4524 | CS2 | 13.9 | 3.2 | 23.6 | 58.5 | 0.8 | 17.1 |
| 4524 | CS2 | 14.2 | 3.3 | 21.5 | 60.1 | 0.9 | 17.5 |
| 4524 | CS2 | 14.8 | 3.1 | 22.4 | 58.9 | 0.8 | 17.9 |
| 4524 | CS2 | 14.2 | 3.0 | 23.4 | 58.5 | 0.9 | 17.2 |
| 4524 | Mean | 14.3 | 3.0 | 22.5 | 59.3 | 0.9 | 17.3 |
| 4534 | CS2 | 14.8 | 2.8 | 24.3 | 57.0 | 1.1 | 17.6 |
| 4534 | CS2 | 14.1 | 2.7 | 23.6 | 58.6 | 1.0 | 16.7 |
| 4534 | CS2 | 15.0 | 2.5 | 22.5 | 58.9 | 1.1 | 17.5 |
| 4534 | CS2 | 14.3 | 2.9 | 22.0 | 59.8 | 1.0 | 17.2 |

TABLE 23-continued

Selected Yellow Best for invention.

| GC # | Category | Palmitic | Stearic | Oleic | Linoleic | Linolenic | Saturates |
|---|---|---|---|---|---|---|---|
| 4534 | CS2 | 14.7 | 2.5 | 22.8 | 58.9 | 1.0 | 17.2 |
| 4534 | CS2 | 14.1 | 2.4 | 22.4 | 60.2 | 1.0 | 16.5 |
| 4534 | CS2 | 13.3 | 2.8 | 23.8 | 59.3 | 0.8 | 16.1 |
| 4534 | CS2 | 14.2 | 2.4 | 22.3 | 60.0 | 1.2 | 16.5 |
| 4534 | CS2 | 14.5 | 2.9 | 22.9 | 58.7 | 1.0 | 17.4 |
| 4534 | CS2 | 15.3 | 2.7 | 23.5 | 57.5 | 1.1 | 18.0 |
| 4534 | Mean | 14.4 | 2.6 | 23.0 | 58.9 | 1.0 | 17.1 |
| 4545 | CS2 | 13.6 | 2.3 | 23.1 | 59.6 | 1.4 | 15.9 |
| 4545 | CS2 | 14.6 | 3.2 | 23.6 | 57.5 | 1.1 | 17.8 |
| 4545 | CS2 | 14.8 | 3.0 | 24.4 | 57.0 | 0.9 | 17.8 |
| 4545 | CS2 | 14.7 | 3.6 | 23.5 | 57.2 | 1.0 | 18.3 |
| 4545 | CS2 | 14.7 | 2.9 | 24.3 | 57.1 | 1.1 | 17.5 |
| 4545 | CS2 | 15.0 | 3.5 | 24.6 | 55.9 | 1.1 | 18.4 |
| 4545 | CS2 | 13.9 | 3.1 | 24.6 | 57.6 | 0.9 | 17.0 |
| 4545 | CS2 | 14.7 | 2.9 | 24.6 | 56.9 | 1.0 | 17.6 |
| 4545 | CS2 | 14.7 | 3.4 | 24.2 | 56.7 | 0.9 | 18.1 |
| 4545 | CS2 | 14.6 | 3.2 | 26.8 | 54.5 | 1.0 | 17.8 |
| 4545 | Mean | 14.5 | 3.1 | 24.4 | 57.0 | 1.0 | 17.6 |
| 4549 | CS2 | 12.4 | 4.2 | 36.4 | 46.6 | 0.6 | 16.5 |
| 4549 | CS2 | 14.2 | 4.1 | 32.4 | 48.7 | 0.6 | 18.2 |
| 4549 | CS2 | 13.3 | 3.3 | 40.3 | 42.4 | 0.6 | 16.6 |
| 4549 | CS2 | 12.7 | 4.5 | 36.0 | 46.1 | 0.7 | 17.2 |
| 4549 | CS2 | 13.2 | 4.2 | 35.0 | 47.0 | 0.6 | 17.4 |
| 4549 | CS2 | 12.4 | 3.6 | 35.7 | 47.5 | 0.7 | 16.1 |
| 4549 | CS2 | 12.7 | 3.8 | 36.5 | 46.3 | 0.7 | 16.5 |
| 4549 | CS2 | 12.8 | 3.3 | 35.5 | 47.7 | 0.7 | 16.2 |
| 4549 | CS2 | 12.9 | 3.5 | 36.0 | 47.0 | 0.7 | 16.4 |
| 4549 | CS2 | 13.8 | 3.5 | 32.2 | 49.8 | 0.7 | 17.3 |
| 4549 | Mean | 13.0 | 3.8 | 35.6 | 46.9 | 0.7 | 16.8 |
| 4565 | CS2 | 15.7 | 3.7 | 26.5 | 53.3 | 0.8 | 19.4 |
| 4565 | CS2 | 15.0 | 4.0 | 30.3 | 50.0 | 0.7 | 19.0 |
| 4565 | CS2 | 14.9 | 2.8 | 25.9 | 55.6 | 0.8 | 17.8 |
| 4565 | CS2 | 14.5 | 2.0 | 20.5 | 62.1 | 0.9 | 16.5 |
| 4565 | CS2 | 14.6 | 2.3 | 21.3 | 60.9 | 0.9 | 16.9 |
| 4565 | CS2 | 15.6 | 2.5 | 21.4 | 59.6 | 0.9 | 18.1 |
| 4565 | CS2 | 16.4 | 3.2 | 28.1 | 51.5 | 0.7 | 19.6 |
| 4565 | CS2 | 17.0 | 4.3 | 27.8 | 50.2 | 0.7 | 21.3 |
| 4565 | CS2 | 15.0 | 2.4 | 21.6 | 60.2 | 0.8 | 17.4 |
| 4565 | CS2 | 14.6 | 3.0 | 27.1 | 54.7 | 0.7 | 17.5 |
| 4565 | Mean | 15.3 | 3.0 | 25.1 | 55.8 | 0.8 | 18.3 |
| 4573 | CS2 | 16.0 | 1.9 | 27.6 | 53.8 | 0.7 | 17.9 |
| 4573 | CS2 | 16.1 | 2.6 | 27.4 | 53.2 | 0.8 | 18.6 |
| 4573 | CS2 | 15.1 | 2.6 | 29.5 | 52.0 | 0.8 | 17.7 |
| 4573 | CS2 | 16.7 | 2.0 | 24.6 | 55.9 | 0.9 | 18.7 |
| 4573 | CS2 | 17.2 | 3.1 | 26.4 | 52.6 | 0.8 | 20.2 |
| 4573 | CS2 | 15.7 | 2.6 | 27.1 | 54.0 | 0.7 | 18.2 |
| 4573 | CS2 | 15.5 | 2.2 | 19.8 | 61.4 | 1.1 | 17.7 |
| 4573 | CS2 | 16.0 | 2.2 | 29.0 | 52.1 | 0.8 | 18.2 |
| 4573 | CS2 | 15.2 | 2.3 | 25.8 | 55.8 | 0.9 | 17.5 |
| 4573 | CS2 | 15.6 | 2.2 | 26.4 | 54.9 | 0.9 | 17.8 |
| 4573 | Mean | 15.9 | 2.4 | 26.3 | 54.6 | 0.8 | 18.2 |
| 4578 | CS2 | 14.1 | 3.1 | 19.8 | 61.9 | 1.1 | 17.2 |
| 4578 | CS2 | 16.0 | 3.7 | 25.4 | 54.0 | 0.9 | 19.7 |
| 4578 | CS2 | 14.8 | 3.8 | 30.3 | 50.3 | 0.8 | 18.6 |
| 4578 | CS2 | 13.7 | 3.4 | 20.8 | 61.3 | 0.8 | 17.2 |
| 4578 | CS2 | 14.2 | 3.6 | 26.7 | 54.6 | 0.9 | 17.8 |
| 4578 | CS2 | 14.3 | 4.3 | 30.6 | 50.1 | 0.7 | 18.6 |
| 4578 | CS2 | 15.1 | 4.6 | 29.6 | 49.9 | 0.8 | 19.7 |
| 4578 | CS2 | 14.3 | 3.7 | 26.3 | 54.8 | 0.9 | 18.0 |
| 4578 | CS2 | 14.4 | 3.7 | 26.5 | 54.5 | 0.8 | 18.1 |
| 4578 | CS2 | 15.1 | 3.4 | 21.0 | 59.6 | 1.0 | 18.5 |
| 4578 | Mean | 14.6 | 3.7 | 25.7 | 55.1 | 0.9 | 18.3 |
| 4655 | CS2 | 12.5 | 2.2 | 39.8 | 45.0 | 0.5 | 14.7 |
| 4655 | CS2 | 11.1 | 2.8 | 39.0 | 46.5 | 0.5 | 13.9 |
| 4655 | CS2 | 12.4 | 2.8 | 42.4 | 41.9 | 0.5 | 15.2 |
| 4655 | CS2 | 11.7 | 2.6 | 43.4 | 41.9 | 0.5 | 14.3 |
| 4655 | CS2 | 10.0 | 3.0 | 37.4 | 49.0 | 0.5 | 13.1 |
| 4655 | CS2 | 10.8 | 2.1 | 33.3 | 53.1 | 0.6 | 12.9 |
| 4655 | CS2 | 12.0 | 2.6 | 43.3 | 41.5 | 0.6 | 14.5 |
| 4655 | CS2 | 9.7 | 2.3 | 31.0 | 56.4 | 0.6 | 12.0 |
| 4655 | CS2 | 11.5 | 3.1 | 37.5 | 47.3 | 0.6 | 14.6 |
| 4655 | CS2 | 11.7 | 2.5 | 32.5 | 52.8 | 0.5 | 14.3 |
| 4655 | Mean | 11.3 | 2.6 | 38.0 | 47.5 | 0.5 | 14.0 |
| 4656 | CS2 | 9.4 | 3.6 | 46.6 | 39.8 | 0.6 | 13.0 |
| 4656 | CS2 | 9.3 | 3.4 | 42.1 | 44.7 | 0.5 | 12.7 |

TABLE 23-continued

Selected Yellow Best for invention.

| GC # | Category | Palmitic | Stearic | Oleic | Linoleic | Linolenic | Saturates |
|---|---|---|---|---|---|---|---|
| 4656 | CS2 | 8.5 | 3.8 | 46.0 | 41.3 | 0.4 | 12.3 |
| 4656 | CS2 | 8.5 | 4.3 | 54.8 | 31.8 | 0.7 | 12.8 |
| 4656 | CS2 | 8.8 | 4.0 | 48.5 | 38.2 | 0.6 | 12.8 |
| 4656 | CS2 | 8.5 | 4.2 | 55.9 | 30.9 | 0.6 | 12.7 |
| 4656 | CS2 | 9.3 | 3.7 | 44.8 | 41.9 | 0.4 | 12.9 |
| 4656 | CS2 | 8.3 | 3.7 | 49.0 | 38.5 | 0.5 | 12.0 |
| 4656 | CS2 | 9.9 | 3.7 | 52.7 | 32.9 | 0.9 | 13.5 |
| 4656 | CS2 | 8.5 | 4.0 | 54.4 | 32.4 | 0.6 | 12.6 |
| 4656 | Mean | 8.9 | 3.8 | 49.5 | 37.2 | 0.6 | 12.7 |
| 4657 | CS2 | 11.0 | 2.3 | 35.4 | 50.8 | 0.5 | 13.3 |
| 4657 | CS2 | 11.1 | 2.2 | 38.1 | 48.2 | 0.5 | 13.2 |
| 4657 | CS2 | 11.4 | 2.0 | 28.2 | 57.9 | 0.5 | 13.4 |
| 4657 | CS2 | 12.9 | 2.3 | 38.9 | 45.5 | 0.5 | 15.2 |
| 4657 | CS2 | 10.6 | 1.9 | 30.0 | 56.8 | 0.7 | 12.5 |
| 4657 | CS2 | 10.7 | 1.9 | 38.1 | 48.9 | 0.5 | 12.6 |
| 4657 | CS2 | 11.2 | 2.1 | 31.9 | 54.3 | 0.4 | 13.3 |
| 4657 | CS2 | 12.3 | 2.3 | 36.5 | 48.3 | 0.5 | 14.6 |
| 4657 | CS2 | 11.7 | 2.3 | 34.0 | 51.3 | 0.7 | 14.0 |
| 4657 | CS2 | 10.6 | 2.1 | 36.2 | 50.6 | 0.5 | 12.7 |
| 4657 | Mean | 11.4 | 2.1 | 34.7 | 51.3 | 0.5 | 13.5 |
| 4659 | CS2 | 8.1 | 2.8 | 45.1 | 43.5 | 0.4 | 10.9 |
| 4659 | CS2 | 10.7 | 2.5 | 46.3 | 40.0 | 0.5 | 13.2 |
| 4659 | CS2 | 8.5 | 3.8 | 50.1 | 37.1 | 0.6 | 12.3 |
| 4659 | CS2 | 11.0 | 3.1 | 42.2 | 43.3 | 0.4 | 14.1 |
| 4659 | CS2 | 10.8 | 3.0 | 42.1 | 43.7 | 0.5 | 13.8 |
| 4659 | CS2 | 12.0 | 2.7 | 37.8 | 47.1 | 0.5 | 14.7 |
| 4659 | CS2 | 10.9 | 2.6 | 46.8 | 39.3 | 0.4 | 13.5 |
| 4659 | CS2 | 12.1 | 2.2 | 47.2 | 37.9 | 0.6 | 14.4 |
| 4659 | CS2 | 10.4 | 3.1 | 40.0 | 45.7 | 0.8 | 13.5 |
| 4659 | CS2 | 10.9 | 3.0 | 42.9 | 42.8 | 0.4 | 13.9 |
| 4659 | Mean | 10.5 | 2.9 | 44.0 | 42.0 | 0.5 | 13.4 |
| 4660 | S3 | 9.7 | 4.7 | 46.9 | 38.2 | 0.4 | 14.5 |
| 4660 | S3 | 9.1 | 4.8 | 45.7 | 39.9 | 0.5 | 13.9 |
| 4660 | S3 | 9.5 | 4.6 | 45.5 | 39.9 | 0.5 | 14.1 |
| 4660 | S3 | 9.3 | 4.7 | 45.9 | 39.6 | 0.5 | 14.0 |
| 4660 | S3 | 8.7 | 4.7 | 47.6 | 38.5 | 0.5 | 13.4 |
| 4660 | S3 | 8.6 | 4.4 | 53.1 | 33.4 | 0.4 | 13.1 |
| 4660 | S3 | 9.0 | 4.9 | 48.0 | 37.8 | 0.4 | 13.8 |
| 4660 | S3 | 13.7 | 8.0 | 41.0 | 34.9 | 2.4 | 21.7 |
| 4660 | S3 | 9.0 | 4.5 | 46.4 | 39.6 | 0.5 | 13.5 |
| 4660 | S3 | 9.4 | 4.9 | 46.0 | 39.2 | 0.6 | 14.3 |
| 4660 | Mean | 9.6 | 5.0 | 46.6 | 38.1 | 0.7 | 14.6 |
| 4674 | S3 | 8.3 | 7.1 | 60.3 | 23.6 | 0.7 | 15.4 |
| 4674 | S3 | 8.4 | 7.1 | 59.5 | 24.5 | 0.6 | 15.4 |
| 4674 | S3 | 8.7 | 7.1 | 56.1 | 27.6 | 0.6 | 15.8 |
| 4674 | S3 | 7.4 | 8.3 | 64.4 | 19.1 | 0.8 | 15.7 |
| 4674 | S3 | 9.7 | 4.8 | 49.5 | 35.5 | 0.5 | 14.5 |
| 4674 | S3 | 7.1 | 7.6 | 67.8 | 17.0 | 0.6 | 14.7 |
| 4674 | S3 | 9.5 | 4.5 | 50.0 | 35.6 | 0.5 | 14.0 |
| 4674 | S3 | 12.0 | 5.0 | 40.5 | 40.5 | 2.0 | 17.0 |
| 4674 | S3 | 8.3 | 8.1 | 58.6 | 24.6 | 0.6 | 16.3 |
| 4674 | S3 | 8.9 | 6.9 | 55.3 | 28.3 | 0.6 | 15.8 |
| 4674 | Mean | 8.8 | 6.6 | 56.2 | 27.6 | 0.7 | 15.4 |
| 4679 | S3 | 8.7 | 6.7 | 54.4 | 29.7 | 0.4 | 15.4 |
| 4679 | S3 | 8.9 | 5.5 | 51.1 | 34.2 | 0.4 | 14.3 |
| 4679 | S3 | 9.0 | 5.6 | 53.7 | 31.3 | 0.5 | 14.6 |
| 4679 | S3 | 8.9 | 6.3 | 53.5 | 30.8 | 0.4 | 15.2 |
| 4679 | S3 | 9.1 | 5.7 | 51.9 | 33.0 | 0.4 | 14.8 |
| 4679 | S3 | 9.0 | 4.7 | 52.2 | 33.6 | 0.5 | 13.7 |
| 4679 | S3 | 8.3 | 8.4 | 55.0 | 27.9 | 0.4 | 16.7 |
| 4679 | S3 | 9.0 | 5.3 | 52.0 | 33.2 | 0.5 | 14.4 |
| 4679 | S3 | 8.8 | 6.4 | 52.1 | 32.3 | 0.4 | 15.2 |
| 4679 | S3 | 8.8 | 6.5 | 52.7 | 31.5 | 0.4 | 15.3 |
| 4679 | Mean | 8.8 | 6.1 | 52.9 | 31.8 | 0.4 | 15.0 |
| 4692 | S3 | 7.6 | 5.3 | 64.3 | 21.8 | 0.9 | 13.0 |
| 4692 | S3 | 9.3 | 4.3 | 47.7 | 38.3 | 0.4 | 13.6 |
| 4692 | S3 | 9.2 | 4.1 | 48.4 | 37.9 | 0.5 | 13.3 |
| 4692 | S3 | 9.1 | 4.4 | 50.7 | 35.4 | 0.5 | 13.5 |
| 4692 | S3 | 9.5 | 4.1 | 45.9 | 40.0 | 0.5 | 13.6 |
| 4692 | S3 | 9.0 | 4.1 | 46.0 | 40.4 | 0.5 | 13.1 |
| 4692 | S3 | 9.1 | 4.2 | 47.8 | 38.5 | 0.4 | 13.4 |
| 4692 | S3 | 9.1 | 4.0 | 45.3 | 41.3 | 0.4 | 13.0 |
| 4692 | S3 | 9.0 | 4.1 | 46.9 | 39.6 | 0.4 | 13.1 |
| 4692 | S3 | 9.0 | 4.8 | 47.3 | 38.5 | 0.5 | 13.8 |

TABLE 23-continued

Selected Yellow Best for invention.

| GC # | Category | Palmitic | Stearic | Oleic | Linoleic | Linolenic | Saturates |
|---|---|---|---|---|---|---|---|
| 4692 | Mean | 9.0 | 4.3 | 49.0 | 37.2 | 0.5 | 13.3 |
| 4701 | S3 | 9.1 | 4.3 | 49.6 | 36.5 | 0.5 | 13.5 |
| 4701 | S3 | 9.2 | 4.0 | 46.1 | 40.1 | 0.6 | 13.2 |
| 4701 | S3 | 9.3 | 4.1 | 46.8 | 39.2 | 0.6 | 13.4 |
| 4701 | S3 | 9.8 | 4.3 | 42.2 | 42.9 | 0.7 | 14.1 |
| 4701 | S3 | 11.3 | 3.4 | 39.1 | 44.6 | 1.7 | 14.6 |
| 4701 | S3 | 9.6 | 4.2 | 41.3 | 44.3 | 0.6 | 13.8 |
| 4701 | S3 | 8.6 | 5.4 | 56.8 | 28.2 | 1.0 | 14.0 |
| 4701 | S3 | 10.8 | 4.2 | 36.7 | 46.2 | 2.1 | 15.0 |
| 4701 | S3 | 9.3 | 4.0 | 43.5 | 42.7 | 0.6 | 13.3 |
| 4701 | S3 | 9.5 | 4.1 | 42.8 | 43.1 | 0.6 | 13.6 |
| 4701 | Mean | 9.6 | 4.2 | 44.5 | 40.8 | 0.9 | 13.8 |
| 4708 | S3 | 8.2 | 4.7 | 49.5 | 37.3 | 0.4 | 12.8 |
| 4708 | S3 | 7.9 | 5.1 | 53.1 | 33.5 | 0.4 | 13.0 |
| 4708 | S3 | 8.4 | 5.0 | 49.4 | 36.8 | 0.4 | 13.5 |
| 4708 | S3 | 8.0 | 4.7 | 50.8 | 36.2 | 0.4 | 12.7 |
| 4708 | S3 | 7.9 | 5.6 | 54.8 | 31.4 | 0.3 | 13.6 |
| 4708 | S3 | 8.5 | 5.0 | 47.3 | 38.8 | 0.4 | 13.5 |
| 4708 | S3 | 8.0 | 4.2 | 45.8 | 41.8 | 0.3 | 12.1 |
| 4708 | S3 | 8.1 | 4.3 | 45.6 | 41.6 | 0.4 | 12.4 |
| 4708 | S3 | 8.1 | 5.1 | 50.9 | 35.5 | 0.4 | 13.1 |
| 4708 | S3 | 8.3 | 5.2 | 50.7 | 35.5 | 0.4 | 13.4 |
| 4708 | Mean | 8.1 | 4.9 | 49.8 | 36.8 | 0.4 | 13.0 |
| 4717 | S3 | 9.4 | 4.8 | 34.3 | 51.0 | 0.5 | 14.2 |
| 4717 | S3 | 10.6 | 4.3 | 41.5 | 43.2 | 0.5 | 14.9 |
| 4717 | S3 | 9.7 | 3.7 | 44.0 | 42.1 | 0.5 | 13.4 |
| 4717 | S3 | 8.2 | 5.1 | 47.3 | 39.0 | 0.4 | 13.3 |
| 4717 | S3 | 8.1 | 5.5 | 51.9 | 33.8 | 0.7 | 13.6 |
| 4717 | S3 | 8.4 | 3.7 | 39.3 | 48.0 | 0.6 | 12.1 |
| 4717 | S3 | 8.9 | 3.9 | 44.9 | 41.8 | 0.4 | 12.8 |
| 4717 | S3 | 9.0 | 3.9 | 44.4 | 42.2 | 0.5 | 13.0 |
| 4717 | S3 | 10.2 | 3.7 | 39.8 | 45.9 | 0.5 | 13.9 |
| 4717 | S3 | 8.6 | 4.7 | 44.2 | 41.9 | 0.6 | 13.3 |
| 4717 | Mean | 9.1 | 4.3 | 43.2 | 42.9 | 0.5 | 13.5 |
| 4726 | CS23 | 7.7 | 3.5 | 52.6 | 35.4 | 0.9 | 11.2 |
| 4726 | CS23 | 7.7 | 3.3 | 53.0 | 35.2 | 0.8 | 11.0 |
| 4726 | CS23 | 8.5 | 3.3 | 51.5 | 35.8 | 0.9 | 11.8 |
| 4726 | CS23 | 8.3 | 3.3 | 51.9 | 35.7 | 0.9 | 11.5 |
| 4726 | CS23 | 8.2 | 3.3 | 51.3 | 36.4 | 0.9 | 11.4 |
| 4726 | CS23 | 7.8 | 2.9 | 50.3 | 38.1 | 1.0 | 10.7 |
| 4726 | CS23 | 7.9 | 3.3 | 51.8 | 36.1 | 0.9 | 11.2 |
| 4726 | CS23 | 7.9 | 3.5 | 53.4 | 34.3 | 1.0 | 11.3 |
| 4726 | CS23 | 7.9 | 3.2 | 52.4 | 35.6 | 0.9 | 11.1 |
| 4726 | CS23 | 7.9 | 3.3 | 51.7 | 34.2 | 0.9 | 11.2 |
| 4726 | Mean | 8.0 | 3.3 | 52.2 | 35.7 | 0.9 | 11.2 |
| 4727 | CS23 | 11.2 | 2.0 | 29.2 | 56.7 | 1.0 | 13.2 |
| 4727 | CS23 | 6.8 | 1.9 | 44.8 | 45.4 | 1.0 | 8.8 |
| 4727 | CS23 | 6.9 | 2.0 | 48.7 | 41.4 | 1.1 | 8.9 |
| 4727 | CS23 | 7.3 | 2.5 | 48.5 | 40.7 | 1.0 | 9.8 |
| 4727 | CS23 | 7.0 | 2.0 | 47.8 | 42.3 | 1.0 | 8.9 |
| 4727 | CS23 | 9.9 | 2.6 | 47.8 | 38.4 | 1.2 | 12.5 |
| 4727 | CS23 | 6.3 | 2.2 | 52.9 | 37.5 | 1.1 | 8.5 |
| 4727 | CS23 | 7.0 | 2.7 | 50.8 | 38.6 | 0.9 | 9.7 |
| 4727 | CS23 | 7.2 | 2.4 | 47.4 | 42.0 | 1.0 | 9.6 |
| 4727 | CS23 | 7.5 | 2.5 | 44.7 | 44.4 | 1.0 | 10.0 |
| 4727 | Mean | 7.7 | 2.3 | 46.3 | 42.7 | 1.0 | 10.0 |
| 4736 | CS23 | 7.2 | 2.7 | 51.8 | 37.4 | 0.9 | 9.9 |
| 4736 | CS23 | 7.5 | 2.3 | 49.5 | 39.6 | 1.0 | 9.9 |
| 4736 | CS23 | 7.0 | 2.4 | 55.3 | 34.4 | 0.9 | 9.4 |
| 4736 | CS23 | 7.1 | 2.2 | 54.2 | 35.6 | 1.0 | 9.2 |
| 4736 | CS23 | 7.6 | 2.5 | 52.7 | 36.3 | 0.9 | 10.1 |
| 4736 | CS23 | 7.3 | 2.4 | 53.6 | 35.9 | 0.9 | 9.7 |
| 4736 | CS23 | 7.1 | 2.3 | 53.3 | 36.4 | 0.9 | 9.4 |
| 4736 | CS23 | 7.3 | 2.4 | 54.0 | 35.4 | 0.9 | 9.7 |
| 4736 | CS23 | 7.2 | 2.5 | 53.3 | 36.2 | 0.9 | 9.7 |
| 4736 | CS23 | 7.1 | 2.3 | 53.8 | 36.0 | 0.9 | 9.3 |
| 4736 | Mean | 7.2 | 2.4 | 53.1 | 36.3 | 0.9 | 9.6 |
| 4738 | CS23 | 6.6 | 2.6 | 56.4 | 33.6 | 0.8 | 9.2 |
| 4738 | CS23 | 6.4 | 2.8 | 61.5 | 28.3 | 1.1 | 9.2 |
| 4738 | CS23 | 6.9 | 2.1 | 51.6 | 38.4 | 1.0 | 9.0 |
| 4738 | CS23 | 6.6 | 2.4 | 57.2 | 32.8 | 1.0 | 9.0 |
| 4738 | CS23 | 7.0 | 2.3 | 50.8 | 38.8 | 1.1 | 9.3 |
| 4738 | CS23 | 7.2 | 2.3 | 46.5 | 42.6 | 1.4 | 9.5 |
| 4738 | CS23 | 7.4 | 2.5 | 47.7 | 41.3 | 1.2 | 9.9 |
| 4738 | CS23 | 6.9 | 2.5 | 49.2 | 40.4 | 1.0 | 9.4 |

TABLE 23-continued

Selected Yellow Best for invention.

| GC # | Category | Palmitic | Stearic | Oleic | Linoleic | Linolenic | Saturates |
|---|---|---|---|---|---|---|---|
| 4738 | CS23 | 7.1 | 2.8 | 53.9 | 35.2 | 1.0 | 9.9 |
| 4738 | CS23 | 7.5 | 2.9 | 51.7 | 37.0 | 0.9 | 10.4 |
| 4738 | Mean | 6.9 | 2.5 | 52.7 | 36.8 | 1.0 | 9.5 |
| 4745 | S3 | 7.6 | 3.3 | 43.0 | 45.3 | 0.8 | 10.9 |
| 4745 | S3 | 7.5 | 3.2 | 44.3 | 44.0 | 1.0 | 10.7 |
| 4745 | S3 | 7.6 | 2.9 | 42.5 | 46.1 | 1.0 | 10.4 |
| 4745 | S3 | 7.1 | 3.2 | 48.3 | 40.6 | 0.8 | 10.3 |
| 4745 | S3 | 7.5 | 3.1 | 43.8 | 44.6 | 1.0 | 10.7 |
| 4745 | S3 | 7.4 | 3.0 | 43.1 | 45.6 | 1.0 | 10.4 |
| 4745 | S3 | 6.6 | 3.5 | 51.2 | 37.7 | 1.1 | 10.1 |
| 4745 | S3 | 7.2 | 3.2 | 44.2 | 44.5 | 1.0 | 10.4 |
| 4745 | S3 | 7.3 | 3.1 | 44.0 | 44.7 | 0.9 | 10.4 |
| 4745 | S3 | 7.5 | 3.0 | 43.8 | 44.7 | 1.0 | 10.5 |
| 4745 | Mean | 7.3 | 3.1 | 44.8 | 43.8 | 0.9 | 10.5 |
| 4751 | S3 | 6.6 | 2.7 | 51.1 | 38.7 | 0.9 | 9.3 |
| 4751 | S3 | 7.7 | 2.3 | 46.7 | 42.4 | 0.9 | 10.0 |
| 4751 | S3 | 7.0 | 2.1 | 44.6 | 45.3 | 0.9 | 9.1 |
| 4751 | S3 | 6.8 | 2.1 | 45.3 | 44.8 | 1.0 | 8.9 |
| 4751 | S3 | 7.0 | 2.2 | 44.3 | 45.7 | 0.9 | 9.1 |
| 4751 | S3 | 6.9 | 2.1 | 41.9 | 48.2 | 1.0 | 9.0 |
| 4751 | S3 | 7.0 | 2.4 | 47.1 | 42.6 | 0.9 | 9.4 |
| 4751 | S3 | 6.6 | 2.6 | 49.5 | 40.5 | 0.8 | 9.2 |
| 4751 | S3 | 9.6 | 3.0 | 43.2 | 43.0 | 1.2 | 12.6 |
| 4751 | S3 | 7.1 | 2.0 | 41.5 | 48.5 | 0.9 | 9.1 |
| 4751 | Mean | 7.2 | 2.4 | 45.5 | 44.0 | 0.9 | 9.6 |
| 4758 | S3 | 6.9 | 1.6 | 36.0 | 54.2 | 1.2 | 8.6 |
| 4758 | S3 | 10.8 | 1.9 | 30.8 | 55.4 | 1.2 | 12.7 |
| 4758 | S3 | 7.1 | 1.7 | 36.1 | 53.8 | 1.4 | 8.8 |
| 4758 | S3 | 12.3 | 1.9 | 33.6 | 51.2 | 1.1 | 14.1 |
| 4758 | S3 | 11.2 | 1.7 | 29.9 | 56.1 | 1.2 | 12.8 |
| 4758 | S3 | 6.6 | 1.6 | 36.3 | 54.4 | 1.1 | 8.2 |
| 4758 | S3 | 12.0 | 1.8 | 32.5 | 52.5 | 1.2 | 13.8 |
| 4758 | S3 | 7.0 | 1.8 | 39.2 | 50.8 | 1.2 | 8.7 |
| 4758 | S3 | 11.7 | 1.9 | 32.1 | 53.1 | 1.2 | 13.6 |
| 4758 | S3 | 7.0 | 1.7 | 36.9 | 53.1 | 1.3 | 8.8 |
| 4758 | Mean | 9.3 | 1.8 | 34.3 | 53.5 | 1.2 | 11.0 |
| 4770 | S3 | 15.9 | 3.9 | 33.7 | 46.0 | 0.5 | 19.8 |
| 4770 | S3 | 16.0 | 3.7 | 34.0 | 45.8 | 0.5 | 19.7 |
| 4770 | S3 | 16.3 | 4.3 | 30.5 | 48.4 | 0.5 | 20.6 |
| 4770 | S3 | 16.1 | 3.8 | 29.9 | 49.7 | 0.5 | 19.9 |
| 4770 | S3 | 16.4 | 4.0 | 28.7 | 50.4 | 0.6 | 20.4 |
| 4770 | S3 | 15.6 | 3.8 | 31.6 | 48.5 | 0.5 | 19.4 |
| 4770 | S3 | 15.6 | 3.8 | 31.2 | 48.8 | 0.7 | 19.4 |
| 4770 | S3 | 16.8 | 4.9 | 28.9 | 48.8 | 0.6 | 21.7 |
| 4770 | S3 | 16.7 | 3.7 | 29.8 | 49.3 | 0.6 | 20.3 |
| 4770 | S3 | 15.8 | 4.3 | 32.3 | 47.1 | 0.5 | 20.1 |
| 4770 | Mean | 16.1 | 4.0 | 31.1 | 48.3 | 0.6 | 20.1 |
| 4776 | CS23 | 13.5 | 2.2 | 30.3 | 53.3 | 0.7 | 15.7 |
| 4775 | CS23 | 11.3 | 3.2 | 32.6 | 52.3 | 0.6 | 14.5 |
| 4776 | CS23 | 12.8 | 1.7 | 22.8 | 61.8 | 0.8 | 14.5 |
| 4776 | CS23 | 11.4 | 2.7 | 29.7 | 55.5 | 0.8 | 14.1 |
| 4776 | CS23 | 11.4 | 2.6 | 26.0 | 59.6 | 0.5 | 13.9 |
| 4776 | CS23 | 12.6 | 2.5 | 29.4 | 54.9 | 0.6 | 15.1 |
| 4776 | CS23 | 14.2 | 2.1 | 26.0 | 57.0 | 0.8 | 16.3 |
| 4776 | CS23 | 12.2 | 3.5 | 24.5 | 59.1 | 0.7 | 15.8 |
| 4776 | CS23 | 10.9 | 3.7 | 30.1 | 54.6 | 0.7 | 14.6 |
| 4776 | CS23 | 11.1 | 2.4 | 21.0 | 64.8 | 0.8 | 13.5 |
| 4776 | Mean | 12.1 | 2.7 | 27.2 | 57.3 | 0.7 | 14.8 |
| 4782 | CS23 | 16.6 | 2.1 | 32.6 | 47.9 | 0.8 | 18.7 |
| 4782 | CS23 | 15.7 | 2.1 | 30.9 | 50.6 | 0.7 | 17.8 |
| 4782 | CS23 | 14.8 | 2.6 | 28.8 | 53.0 | 0.8 | 17.4 |
| 4782 | CS23 | 15.0 | 2.0 | 31.2 | 51.0 | 0.8 | 17.0 |
| 4782 | CS23 | 16.3 | 2.1 | 33.3 | 47.5 | 0.8 | 18.4 |
| 4782 | CS23 | 15.5 | 3.3 | 27.6 | 52.6 | 1.0 | 18.7 |
| 4782 | CS23 | 16.3 | 2.2 | 33.4 | 47.3 | 0.8 | 18.5 |
| 4782 | CS23 | 13.5 | 2.1 | 25.6 | 57.9 | 0.9 | 15.6 |
| 4782 | CS23 | 16.3 | 2.7 | 36.5 | 43.8 | 0.7 | 19.0 |
| 4782 | CS23 | 15.7 | 2.6 | 35.7 | 45.3 | 0.7 | 18.4 |
| 4782 | Mean | 15.6 | 2.4 | 31.6 | 49.7 | 0.8 | 17.9 |
| 4790 | CS23 | 14.2 | 3.2 | 31.9 | 50.6 | 0.1 | 17.4 |
| 4790 | CS23 | 14.2 | 3.0 | 32.3 | 49.6 | 0.9 | 17.3 |
| 4790 | CS23 | 13.4 | 3.5 | 30.0 | 52.2 | 1.0 | 16.9 |
| 4790 | CS23 | 13.0 | 3.5 | 28.7 | 53.9 | 0.9 | 16.5 |
| 4790 | CS23 | 13.9 | 3.3 | 29.2 | 52.8 | 0.9 | 17.2 |
| 4790 | CS23 | 11.5 | 8.6 | 31.8 | 46.2 | 1.9 | 20.1 |

TABLE 23-continued

Selected Yellow Best for invention.

| GC # | Category | Palmitic | Stearic | Oleic | Linoleic | Linolenic | Saturates |
|---|---|---|---|---|---|---|---|
| 4790 | CS23 | 12.0 | 3.1 | 31.7 | 52.2 | 1.0 | 15.1 |
| 4790 | CS23 | 13.6 | 2.9 | 28.9 | 53.7 | 1.0 | 16.5 |
| 4790 | CS23 | 12.9 | 3.9 | 30.4 | 52.0 | 0.9 | 16.8 |
| 4790 | CS23 | 14.0 | 3.1 | 28.0 | 53.8 | 1.1 | 17.1 |
| 4790 | Mean | 13.3 | 3.8 | 30.3 | 51.7 | 1.0 | 17.1 |
| 4805 | CS23 | 13.9 | 4.4 | 26.5 | 54.2 | 1.1 | 18.3 |
| 4805 | CS23 | 14.1 | 4.0 | 23.5 | 57.6 | 0.9 | 18.1 |
| 4805 | CS23 | 15.3 | 3.4 | 22.5 | 57.8 | 1.2 | 18.7 |
| 4805 | CS23 | 13.9 | 3.7 | 28.1 | 53.3 | 1.1 | 17.6 |
| 4805 | CS23 | 15.9 | 3.3 | 24.8 | 55.3 | 0.8 | 19.2 |
| 4805 | CS23 | 13.0 | 3.3 | 19.0 | 63.7 | 1.1 | 16.3 |
| 4805 | CS23 | 15.8 | 4.3 | 28.6 | 50.4 | 1.1 | 20.1 |
| 4805 | CS23 | 13.8 | 3.4 | 29.2 | 52.8 | 0.9 | 17.2 |
| 4805 | CS23 | 13.8 | 3.6 | 24.5 | 57.3 | 0.9 | 17.4 |
| 4805 | CS23 | 13.8 | 2.9 | 18.2 | 64.0 | 1.2 | 16.7 |
| 4805 | Mean | 14.3 | 3.6 | 24.5 | 56.6 | 1.0 | 18.0 |
| 4813 | CS23 | 14.6 | 2.3 | 27.9 | 54.6 | 0.7 | 16.9 |
| 4813 | CS23 | 14.4 | 2.2 | 30.8 | 52.1 | 0.7 | 16.6 |
| 4813 | CS23 | 14.2 | 2.1 | 28.1 | 54.9 | 0.8 | 16.4 |
| 4813 | CS23 | 14.3 | 2.5 | 31.5 | 51.2 | 0.8 | 16.8 |
| 4813 | CS23 | 18.3 | 1.8 | 18.3 | 60.6 | 1.0 | 20.1 |
| 4813 | CS23 | 14.5 | 2.4 | 30.9 | 51.5 | 0.8 | 16.8 |
| 4813 | CS23 | 15.5 | 2.3 | 32.0 | 49.7 | 0.7 | 17.8 |
| 4813 | CS23 | 14.8 | 2.1 | 24.5 | 57.8 | 1.0 | 16.8 |
| 4813 | CS23 | 15.6 | 2.3 | 32.4 | 49.2 | 0.6 | 18.0 |
| 4813 | CS23 | 14.5 | 2.3 | 28.3 | 54.3 | 0.8 | 16.8 |
| 4813 | Mean | 15.0 | 2.2 | 28.5 | 53.6 | 0.8 | 17.3 |
| 4822 | CS23 | 16.7 | 3.4 | 31.7 | 47.5 | 0.6 | 20.1 |
| 4822 | CS23 | 17.2 | 3.5 | 30.7 | 47.8 | 0.8 | 20.7 |
| 4822 | CS23 | 17.0 | 3.1 | 32.5 | 46.6 | 0.8 | 20.1 |
| 4822 | CS23 | 16.7 | 3.5 | 33.5 | 45.7 | 0.7 | 20.2 |
| 4822 | CS23 | 17.2 | 2.9 | 33.5 | 45.7 | 0.7 | 20.2 |
| 4822 | CS23 | 18.5 | 3.1 | 29.3 | 48.3 | 0.8 | 21.6 |
| 4822 | CS23 | 16.6 | 3.8 | 33.6 | 45.1 | 1.0 | 20.4 |
| 4822 | CS23 | 17.4 | 3.3 | 35.6 | 43.0 | 0.7 | 20.7 |
| 4822 | CS23 | 16.1 | 3.5 | 30.3 | 49.3 | 0.8 | 19.6 |
| 4822 | CS23 | 17.4 | 3.9 | 34.3 | 43.8 | 0.7 | 21.2 |
| 4822 | Mean | 17.1 | 3.4 | 32.5 | 46.3 | 0.7 | 20.5 |
| 4828 | CS23 | 13.9 | 3.7 | 33.8 | 47.8 | 0.8 | 17.6 |
| 4828 | CS23 | 14.7 | 3.3 | 30.4 | 50.8 | 0.8 | 18.0 |
| 4828 | CS23 | 13.9 | 3.3 | 32.0 | 50.0 | 0.8 | 17.2 |
| 4828 | CS23 | 12.7 | 4.0 | 32.9 | 49.9 | 0.6 | 16.6 |
| 4828 | CS23 | 14.2 | 3.5 | 30.0 | 51.5 | 0.8 | 17.7 |
| 4828 | CS23 | 13.6 | 3.3 | 31.9 | 50.4 | 0.9 | 16.9 |
| 4828 | CS23 | 13.6 | 3.4 | 31.6 | 50.6 | 0.8 | 17.1 |
| 4828 | CS23 | 14.6 | 3.1 | 32.2 | 49.4 | 0.8 | 17.7 |
| 4828 | CS23 | 13.2 | 3.8 | 32.9 | 49.4 | 0.7 | 17.0 |
| 4828 | CS23 | 13.7 | 3.5 | 31.7 | 50.3 | 0.8 | 17.2 |
| 4828 | Mean | 13.8 | 3.5 | 31.9 | 50.0 | 0.8 | 17.3 |
| 4830 | S3 | 16.6 | 3.1 | 34.3 | 45.5 | 0.5 | 19.7 |
| 4830 | S3 | 16.4 | 3.1 | 33.5 | 46.5 | 0.6 | 19.4 |
| 4830 | S3 | 16.5 | 2.8 | 32.5 | 47.6 | 0.6 | 19.3 |
| 4830 | S3 | 16.8 | 3.0 | 35.0 | 44.7 | 0.6 | 19.7 |
| 4830 | S3 | 16.5 | 2.9 | 33.1 | 46.5 | 1.1 | 19.4 |
| 4830 | S3 | 17.6 | 2.9 | 32.9 | 46.0 | 0.6 | 20.5 |
| 4830 | S3 | 16.8 | 3.1 | 34.3 | 45.2 | 0.6 | 19.9 |
| 4830 | S3 | 16.4 | 3.1 | 34.4 | 45.6 | 0.6 | 19.5 |
| 4830 | S3 | 16.4 | 2.9 | 33.1 | 47.0 | 0.7 | 19.3 |
| 4830 | S3 | 17.0 | 2.9 | 33.9 | 45.7 | 0.6 | 19.9 |
| 4830 | Mean | 16.7 | 3.0 | 33.7 | 46.0 | 0.6 | 19.7 |
| 4838 | S3 | 17.4 | 3.5 | 30.7 | 47.6 | 0.8 | 20.9 |
| 4838 | S3 | 16.7 | 3.5 | 35.9 | 43.3 | 0.5 | 20.2 |
| 4838 | S3 | 17.1 | 3.6 | 34.3 | 44.5 | 0.6 | 20.7 |
| 4838 | S3 | 16.8 | 3.5 | 30.0 | 49.2 | 0.6 | 20.2 |
| 4838 | S3 | 16.7 | 3.8 | 32.6 | 46.4 | 0.6 | 20.4 |
| 4838 | S3 | 17.1 | 3.5 | 34.1 | 44.8 | 0.5 | 20.6 |
| 4838 | S3 | 17.8 | 3.4 | 28.1 | 50.2 | 0.5 | 21.2 |
| 4838 | S3 | 17.5 | 3.2 | 28.0 | 50.7 | 0.7 | 20.7 |
| 4838 | S3 | 16.9 | 3.5 | 29.5 | 49.6 | 0.6 | 20.3 |
| 4838 | S3 | 17.8 | 3.1 | 26.4 | 52.1 | 0.7 | 20.9 |
| 4838 | Mean | 17.2 | 3.4 | 30.9 | 47.8 | 0.6 | 20.6 |
| 4854 | S3 | 15.7 | 2.8 | 29.8 | 51.1 | 0.7 | 18.5 |
| 4854 | S3 | 15.7 | 2.9 | 30.4 | 50.3 | 0.7 | 18.7 |
| 4854 | S3 | 16.0 | 3.1 | 32.9 | 47.6 | 0.6 | 19.1 |
| 4854 | S3 | 16.7 | 3.1 | 31.3 | 48.4 | 0.6 | 19.7 |

TABLE 23-continued

Selected Yellow Best for invention.

| GC # | Category | Palmitic | Stearic | Oleic | Linoleic | Linolenic | Saturates |
|---|---|---|---|---|---|---|---|
| 4854 | S3 | 15.3 | 2.9 | 32.1 | 49.2 | 0.6 | 18.1 |
| 4854 | S3 | 16.6 | 2.6 | 31.6 | 48.7 | 0.6 | 19.2 |
| 4854 | S3 | 16.1 | 3.0 | 31.8 | 48.6 | 0.6 | 19.1 |
| 4854 | S3 | 16.7 | 2.6 | 31.0 | 49.1 | 0.6 | 19.3 |
| 4854 | S3 | 16.2 | 2.9 | 29.2 | 51.1 | 0.5 | 19.1 |
| 4854 | S3 | 15.8 | 2.8 | 31.2 | 49.7 | 0.6 | 18.5 |
| 4854 | Mean | 16.1 | 2.9 | 31.1 | 49.4 | 0.6 | 18.9 |
| 4862 | S3 | 13.8 | 3.5 | 35.0 | 46.9 | 0.9 | 17.2 |
| 4862 | S3 | 14.6 | 5.5 | 33.8 | 45.4 | 0.7 | 20.1 |
| 4862 | S3 | 14.3 | 3.9 | 35.4 | 45.7 | 0.7 | 18.2 |
| 4862 | S3 | 13.1 | 3.6 | 38.7 | 43.9 | 0.7 | 16.7 |
| 4862 | S3 | 13.3 | 4.8 | 35.8 | 45.5 | 0.7 | 18.0 |
| 4862 | S3 | 13.4 | 3.7 | 37.9 | 44.3 | 0.8 | 17.1 |
| 4862 | S3 | 14.3 | 4.9 | 33.6 | 46.3 | 0.8 | 19.2 |
| 4862 | S3 | 13.1 | 4.8 | 37.8 | 43.7 | 0.7 | 17.8 |
| 4862 | S3 | 14.0 | 5.0 | 35.1 | 45.3 | 0.6 | 19.0 |
| 4862 | S3 | 14.2 | 4.8 | 35.4 | 44.8 | 0.8 | 19.0 |
| 4862 | Mean | 13.8 | 4.4 | 35.8 | 45.2 | 0.7 | 18.2 |
| 4874 | S3 | 14.4 | 4.5 | 31.6 | 48.7 | 0.8 | 18.9 |
| 4874 | S3 | 13.0 | 4.5 | 34.8 | 47.1 | 0.6 | 17.6 |
| 4874 | S3 | 13.9 | 4.8 | 33.9 | 46.9 | 0.5 | 18.7 |
| 4874 | S3 | 14.5 | 5.1 | 32.7 | 46.7 | 1.1 | 19.5 |
| 4874 | S3 | 14.9 | 4.5 | 30.9 | 49.0 | 0.7 | 19.4 |
| 4874 | S3 | 14.0 | 4.0 | 33.3 | 47.9 | 0.7 | 18.1 |
| 4874 | S3 | 14.0 | 4.7 | 33.2 | 47.6 | 0.6 | 18.6 |
| 4874 | S3 | 14.1 | 3.6 | 36.1 | 45.5 | 0.7 | 17.7 |
| 4874 | S3 | 14.8 | 3.8 | 32.5 | 48.4 | 0.6 | 18.6 |
| 4874 | S3 | 13.0 | 3.7 | 33.6 | 49.1 | 0.6 | 16.7 |
| 4874 | Mean | 14.1 | 4.3 | 33.2 | 47.7 | 0.7 | 18.4 |
| 4880 | S3 | 14.5 | 4.6 | 30.7 | 49.4 | 0.8 | 19.1 |
| 4880 | S3 | 14.5 | 4.5 | 30.8 | 49.5 | 0.7 | 19.0 |
| 4880 | S3 | 14.8 | 4.3 | 32.6 | 47.7 | 0.7 | 19.1 |
| 4880 | S3 | 14.7 | 4.8 | 30.9 | 48.9 | 0.6 | 19.5 |
| 4880 | S3 | 14.4 | 4.2 | 31.4 | 49.3 | 0.7 | 18.6 |
| 4880 | S3 | 14.3 | 4.6 | 30.8 | 49.6 | 0.7 | 18.9 |
| 4880 | S3 | 14.9 | 4.5 | 30.1 | 49.8 | 0.7 | 19.4 |
| 4880 | S3 | 14.8 | 4.2 | 30.4 | 49.9 | 0.7 | 19.1 |
| 4880 | S3 | 14.8 | 4.2 | 30.0 | 50.2 | 0.8 | 19.1 |
| 4880 | S3 | 14.7 | 3.6 | 30.6 | 50.3 | 0.8 | 18.3 |
| 4880 | Mean | 14.6 | 4.4 | 30.8 | 49.5 | 0.7 | 19.0 |
| 4893 | S3 | 14.5 | 2.6 | 33.1 | 49.1 | 0.7 | 17.1 |
| 4893 | S3 | 14.9 | 4.3 | 32.6 | 46.3 | 2.0 | 19.1 |
| 4893 | S3 | 13.3 | 2.8 | 33.6 | 49.8 | 0.6 | 16.0 |
| 4893 | S3 | 13.6 | 2.7 | 33.8 | 49.2 | 0.6 | 16.3 |
| 4893 | S3 | 14.2 | 2.6 | 35.0 | 47.7 | 0.5 | 16.8 |
| 4893 | S3 | 15.4 | 2.6 | 32.5 | 49.0 | 0.6 | 17.9 |
| 4893 | S3 | 13.2 | 2.8 | 33.8 | 49.7 | 0.6 | 16.0 |
| 4893 | S3 | 13.7 | 2.9 | 35.3 | 47.3 | 0.7 | 16.6 |
| 4893 | S3 | 15.2 | 2.5 | 31.7 | 50.1 | 0.5 | 17.7 |
| 4893 | S3 | 13.3 | 2.6 | 33.2 | 50.3 | 0.5 | 16.0 |
| 4893 | Mean | 14.1 | 2.8 | 33.5 | 48.9 | 0.7 | 16.9 |
| 4897 | S3 | 15.8 | 3.5 | 32.4 | 47.6 | 0.7 | 19.3 |
| 4897 | S3 | 15.1 | 3.2 | 33.8 | 47.3 | 0.6 | 18.3 |
| 4897 | S3 | 13.5 | 3.2 | 34.3 | 48.4 | 0.6 | 16.7 |
| 4897 | S3 | 14.0 | 3.3 | 32.7 | 49.5 | 0.5 | 17.2 |
| 4897 | S3 | 14.5 | 3.2 | 33.4 | 48.4 | 0.6 | 17.6 |
| 4897 | S3 | 13.5 | 3.8 | 35.0 | 47.3 | 0.4 | 17.3 |
| 4897 | S3 | 15.2 | 3.3 | 34.0 | 47.0 | 0.5 | 18.5 |
| 4897 | S3 | 14.6 | 3.1 | 32.2 | 49.5 | 0.6 | 17.7 |
| 4897 | S3 | 15.8 | 3.5 | 31.7 | 48.3 | 0.8 | 19.3 |
| 4897 | S3 | 15.3 | 2.9 | 32.6 | 48.7 | 0.5 | 18.3 |
| 4897 | Mean | 14.7 | 3.3 | 33.2 | 48.2 | 0.6 | 18.0 |
| 4907 | S3 | 13.2 | 3.3 | 34.4 | 48.5 | 0.6 | 16.5 |
| 4907 | S3 | 13.3 | 3.9 | 36.6 | 45.7 | 0.6 | 17.1 |
| 4907 | S3 | 13.5 | 3.4 | 33.9 | 48.6 | 0.6 | 16.9 |
| 4907 | S3 | 15.2 | 4.0 | 33.0 | 47.8 | 0.0 | 19.2 |
| 4907 | S3 | 13.3 | 3.3 | 34.2 | 48.6 | 0.6 | 16.6 |
| 4907 | S3 | 13.4 | 3.7 | 35.1 | 47.1 | 0.6 | 17.1 |
| 4907 | S3 | 13.2 | 3.3 | 35.7 | 47.2 | 0.6 | 16.5 |
| 4907 | S3 | 13.5 | 3.5 | 34.2 | 48.1 | 0.6 | 17.1 |
| 4907 | S3 | 13.2 | 3.3 | 34.7 | 48.2 | 0.6 | 16.6 |
| 4907 | S3 | 12.7 | 3.5 | 34.1 | 49.1 | 0.6 | 16.1 |
| 4907 | Mean | 13.5 | 3.5 | 34.6 | 47.9 | 0.5 | 17.0 |
| 4923 | S3 | 14.3 | 3.4 | 31.1 | 50.5 | 0.7 | 17.6 |
| 4923 | S3 | 13.9 | 2.7 | 34.8 | 48.0 | 0.6 | 16.6 |

TABLE 23-continued

Selected Yellow Best for invention.

| GC # | Category | Palmitic | Stearic | Oleic | Linoleic | Linolenic | Saturates |
|---|---|---|---|---|---|---|---|
| 4923 | S3 | 13.8 | 3.0 | 32.7 | 49.9 | 0.6 | 16.8 |
| 4923 | S3 | 14.0 | 3.0 | 32.9 | 49.6 | 0.6 | 17.0 |
| 4923 | S3 | 13.9 | 3.5 | 29.8 | 52.2 | 0.6 | 17.4 |
| 4923 | S3 | 14.2 | 2.8 | 33.0 | 49.3 | 0.7 | 17.0 |
| 4923 | S3 | 13.2 | 3.7 | 36.2 | 46.4 | 0.5 | 16.9 |
| 4923 | S3 | 14.6 | 3.6 | 32.1 | 49.1 | 0.6 | 18.2 |
| 4923 | S3 | 14.0 | 3.1 | 32.5 | 49.8 | 0.6 | 17.1 |
| 4923 | S3 | 14.0 | 3.3 | 32.9 | 49.2 | 0.6 | 17.3 |
| 4923 | Mean | 14.0 | 3.2 | 32.8 | 49.4 | 0.6 | 17.2 |
| 4932 | S3 | 16.7 | 4.1 | 30.2 | 48.3 | 0.7 | 20.8 |
| 4932 | S3 | 16.9 | 4.3 | 29.8 | 48.4 | 0.6 | 21.2 |
| 4932 | S3 | 16.4 | 4.4 | 31.3 | 47.3 | 0.6 | 20.9 |
| 4932 | S3 | 16.6 | 4.0 | 30.4 | 48.4 | 0.6 | 20.6 |
| 4932 | S3 | 16.9 | 4.7 | 31.6 | 46.2 | 0.6 | 21.6 |
| 4932 | S3 | 15.7 | 3.6 | 30.4 | 49.7 | 0.6 | 19.3 |
| 4932 | S3 | 17.2 | 4.5 | 30.7 | 47.1 | 0.5 | 21.7 |
| 4932 | S3 | 16.5 | 4.0 | 29.5 | 49.2 | 0.7 | 20.5 |
| 4932 | S3 | 16.6 | 4.6 | 29.7 | 48.5 | 0.6 | 21.2 |
| 4932 | S3 | 16.6 | 3.9 | 29.3 | 49.5 | 0.7 | 20.5 |
| 4932 | Mean | 16.6 | 4.2 | 30.3 | 48.3 | 0.6 | 20.8 |
| 4936 | S3 | 16.3 | 2.5 | 30.4 | 50.2 | 0.6 | 18.8 |
| 4936 | S3 | 15.6 | 3.4 | 30.1 | 50.3 | 0.6 | 19.0 |
| 4936 | S3 | 15.9 | 2.4 | 31.7 | 49.3 | 0.7 | 18.3 |
| 4936 | S3 | 15.7 | 3.2 | 31.3 | 49.3 | 0.5 | 18.8 |
| 4936 | S3 | 16.0 | 3.2 | 31.1 | 49.0 | 0.7 | 19.2 |
| 4936 | S3 | 16.5 | 3.7 | 31.0 | 48.2 | 0.6 | 20.2 |
| 4936 | S3 | 16.7 | 3.1 | 30.2 | 49.4 | 0.6 | 19.8 |
| 4936 | S3 | 16.2 | 2.9 | 30.0 | 50.1 | 0.8 | 19.1 |
| 4936 | S3 | 16.0 | 2.7 | 31.4 | 49.4 | 0.6 | 18.7 |
| 4936 | S3 | 15.9 | 2.7 | 29.4 | 51.5 | 0.6 | 18.6 |
| 4936 | Mean | 16.1 | 3.0 | 30.6 | 49.7 | 0.6 | 19.1 |
| 4948 | S3 | 15.3 | 4.3 | 31.5 | 48.4 | 0.5 | 19.5 |
| 4948 | S3 | 14.9 | 4.0 | 30.9 | 49.7 | 0.6 | 18.9 |
| 4948 | S3 | 15.3 | 4.2 | 31.2 | 48.8 | 0.6 | 19.4 |
| 4948 | S3 | 15.6 | 3.7 | 31.8 | 48.3 | 0.7 | 19.3 |
| 4948 | S3 | 15.3 | 3.7 | 32.2 | 48.3 | 0.5 | 19.0 |
| 4948 | S3 | 14.7 | 4.2 | 31.7 | 48.8 | 0.6 | 18.9 |
| 4948 | S3 | 14.8 | 4.2 | 31.6 | 48.9 | 0.5 | 19.0 |
| 4948 | S3 | 15.9 | 3.8 | 31.2 | 48.6 | 0.5 | 19.6 |
| 4948 | S3 | 15.1 | 4.4 | 31.6 | 48.3 | 0.6 | 19.5 |
| 4948 | S3 | 15.2 | 4.7 | 31.6 | 48.0 | 0.5 | 19.8 |
| 4948 | Mean | 15.2 | 4.1 | 31.5 | 48.6 | 0.5 | 19.3 |
| 4957 | S3 | 15.9 | 4.4 | 32.1 | 47.0 | 0.6 | 20.3 |
| 4957 | S3 | 16.0 | 3.2 | 31.5 | 48.7 | 0.7 | 19.2 |
| 4957 | S3 | 15.7 | 3.5 | 31.8 | 48.3 | 0.6 | 19.2 |
| 4957 | S3 | 15.5 | 3.7 | 32.6 | 47.5 | 0.7 | 19.2 |
| 4957 | S3 | 16.2 | 3.0 | 32.1 | 47.9 | 0.7 | 19.3 |
| 4957 | S3 | 15.2 | 4.5 | 32.0 | 47.6 | 0.6 | 19.7 |
| 4957 | S3 | 15.5 | 3.4 | 31.3 | 49.0 | 0.7 | 19.0 |
| 4957 | S3 | 16.1 | 4.5 | 31.9 | 46.8 | 0.6 | 20.6 |
| 4957 | S3 | 15.2 | 3.4 | 32.2 | 48.6 | 0.6 | 18.6 |
| 4957 | S3 | 15.6 | 3.4 | 32.0 | 48.2 | 0.7 | 19.0 |
| 4957 | Mean | 15.7 | 3.7 | 32.0 | 48.0 | 0.6 | 19.4 |

Category Symbols:
S3 = Lines from recovered introgressed materials selfed three or more generations.
CS = Lines from crosses of recovered introgressed material and Corn-Belt inbred parents, the progeny were selfed twice.

TABLE 24

GC Data for lines selected for the invention disclosure.

| GC # | Category | Palmitic | Stearic | Oleic | Linoleic | Linolenic | Saturates |
|---|---|---|---|---|---|---|---|
| 3617 | BC1S2 | 7.7 | 1.8 | 48.6 | 41.0 | 0.9 | 9.5 |
| 3617 | BC1S2 | 7.8 | 1.9 | 42.8 | 46.5 | 1.0 | 9.7 |
| 3617 | BC1S2 | 7.6 | 1.8 | 42.3 | 47.3 | 1.0 | 9.5 |
| 3617 | BC1S2 | 8.4 | 2.9 | 44.3 | 43.5 | 0.9 | 11.3 |
| 3617 | BC1S2 | 8.0 | 2.5 | 54.2 | 34.4 | 0.8 | 10.5 |
| 3617 | BC1S2 | 7.7 | 2.1 | 50.2 | 39.1 | 0.9 | 9.8 |
| 3617 | BC1S2 | 8.0 | 2.5 | 48.7 | 40.0 | 0.9 | 10.4 |
| 3617 | BC1S2 | 7.3 | 1.9 | 36.7 | 52.8 | 1.3 | 9.2 |

TABLE 24-continued

GC Data for lines selected for the invention disclosure.

| GC # | Category | Palmitic | Stearic | Oleic | Linoleic | Linolenic | Saturates |
|------|----------|----------|---------|-------|----------|-----------|-----------|
| 3617 | BC1S2 | 8.2 | 2.8 | 48.0 | 40.2 | 0.8 | 11.0 |
| 3617 | BC1S2 | 7.9 | 2.9 | 46.0 | 42.5 | 0.8 | 10.7 |
| 3617 | Mean | 7.9 | 2.3 | 46.2 | 42.7 | 0.9 | 10.2 |
| 3620 | BC1S2 | 9.1 | 2.3 | 48.3 | 39.7 | 0.6 | 11.4 |
| 3620 | BC1S2 | 8.4 | 2.1 | 46.4 | 42.6 | 0.4 | 10.6 |
| 3620 | BC1S2 | 9.0 | 2.5 | 42.5 | 45.6 | 0.5 | 11.5 |
| 3620 | BC1S2 | 8.6 | 2.8 | 48.2 | 39.9 | 0.5 | 11.4 |
| 3620 | BC1S2 | 8.8 | 2.4 | 52.5 | 35.7 | 0.6 | 11.2 |
| 3620 | BC1S2 | 8.7 | 2.9 | 48.1 | 39.8 | 0.5 | 11.6 |
| 3620 | BC1S2 | 9.1 | 2.9 | 49.8 | 37.8 | 0.5 | 11.9 |
| 3620 | BC1S2 | 8.7 | 2.6 | 45.4 | 42.8 | 0.5 | 11.3 |
| 3620 | BC1S2 | 9.0 | 2.7 | 49.9 | 37.9 | 0.5 | 11.7 |
| 3620 | BC1S2 | 9.0 | 3.3 | 50.5 | 36.7 | 0.5 | 12.3 |
| 3620 | Mean | 8.8 | 2.6 | 48.2 | 39.8 | 0.5 | 11.5 |
| 3634 | CS2 | 9.3 | 3.3 | 46.4 | 40.4 | 0.7 | 12.5 |
| 3634 | CS2 | 9.4 | 3.0 | 40.1 | 46.5 | 1.0 | 12.4 |
| 3634 | CS2 | 10.0 | 3.2 | 43.8 | 42.3 | 0.7 | 13.2 |
| 3634 | CS2 | 8.4 | 3.6 | 50.4 | 36.9 | 0.6 | 12.0 |
| 3634 | CS2 | 9.8 | 3.1 | 42.4 | 44.1 | 0.7 | 12.9 |
| 3634 | CS2 | 8.8 | 3.1 | 45.4 | 42.0 | 0.7 | 12.0 |
| 3634 | CS2 | 9.3 | 2.6 | 43.7 | 43.8 | 0.7 | 11.8 |
| 3634 | CS2 | 11.6 | 3.6 | 45.5 | 38.8 | 0.6 | 15.1 |
| 3634 | Mean | 9.6 | 3.2 | 44.7 | 41.8 | 0.7 | 12.7 |
| 3641 | CS2 | 12.4 | 3.9 | 45.3 | 37.8 | 0.7 | 16.2 |
| 3641 | CS2 | 12.4 | 3.8 | 45.1 | 38.1 | 0.7 | 16.2 |
| 3641 | CS2 | 12.2 | 3.5 | 47.3 | 36.3 | 0.7 | 15.7 |
| 3641 | CS2 | 12.2 | 4.5 | 42.6 | 40.1 | 0.6 | 16.7 |
| 3641 | CS2 | 12.0 | 3.6 | 40.9 | 42.9 | 0.7 | 15.6 |
| 3641 | CS2 | 11.8 | 4.0 | 42.1 | 41.5 | 0.7 | 15.8 |
| 3641 | CS2 | 12.1 | 4.0 | 41.5 | 41.7 | 0.8 | 16.1 |
| 3641 | CS2 | 11.7 | 3.1 | 40.4 | 44.1 | 0.7 | 14.8 |
| 3641 | CS2 | 12.0 | 3.5 | 44.4 | 39.4 | 0.7 | 15.5 |
| 3641 | CS2 | 8.3 | 2.4 | 44.0 | 44.4 | 0.9 | 10.8 |
| 3641 | Mean | 11.7 | 3.6 | 43.3 | 40.6 | 0.7 | 15.3 |
| 3652 | CS2 | 8.3 | 2.5 | 48.5 | 40.0 | 0.8 | 10.8 |
| 3652 | CS2 | 8.5 | 2.9 | 49.1 | 38.9 | 0.7 | 11.3 |
| 3652 | CS2 | 8.7 | 2.8 | 51.9 | 35.8 | 0.8 | 11.5 |
| 3652 | CS2 | 8.2 | 2.6 | 48.5 | 40.0 | 0.8 | 10.8 |
| 3652 | CS2 | 8.5 | 3.0 | 45.7 | 42.1 | 0.8 | 11.5 |
| 3652 | CS2 | 8.6 | 3.9 | 54.2 | 32.7 | 0.7 | 12.4 |
| 3652 | CS2 | 8.3 | 3.0 | 51.5 | 36.5 | 0.8 | 11.2 |
| 3652 | CS2 | 8.4 | 2.7 | 46.5 | 41.6 | 0.8 | 11.0 |
| 3652 | CS2 | 8.8 | 2.6 | 52.1 | 35.6 | 0.9 | 11.4 |
| 3652 | CS2 | 9.0 | 2.7 | 47.5 | 39.9 | 0.9 | 11.7 |
| 3652 | Mean | 8.5 | 2.9 | 49.5 | 38.3 | 0.8 | 11.4 |
| 3660 | CS2 | 9.0 | 2.8 | 47.5 | 39.8 | 0.9 | 11.8 |
| 3660 | CS2 | 8.4 | 3.2 | 49.7 | 38.0 | 0.8 | 11.5 |
| 3660 | CS2 | 8.7 | 2.4 | 42.3 | 45.4 | 1.1 | 11.2 |
| 3660 | CS2 | 8.1 | 2.1 | 42.7 | 46.1 | 1.0 | 10.2 |
| 3660 | CS2 | 8.4 | 2.9 | 52.1 | 35.8 | 0.8 | 11.3 |
| 3660 | CS2 | 9.3 | 2.1 | 38.8 | 48.7 | 1.1 | 11.4 |
| 3660 | CS2 | 8.3 | 2.8 | 51.5 | 36.7 | 0.8 | 11.0 |
| 3660 | CS2 | 8.3 | 2.3 | 35.8 | 52.7 | 0.9 | 10.6 |
| 3660 | CS2 | 8.7 | 2.7 | 44.4 | 43.3 | 0.9 | 11.4 |
| 3660 | CS2 | 8.4 | 2.7 | 47.0 | 41.3 | 0.7 | 11.1 |
| 3660 | Mean | 8.5 | 2.6 | 45.2 | 42.8 | 0.9 | 11.1 |
| 3664 | CS2 | 8.7 | 2.6 | 37.7 | 49.7 | 1.4 | 11.2 |
| 3664 | CS2 | 9.8 | 2.5 | 44.0 | 43.1 | 0.7 | 12.3 |
| 3664 | CS2 | 9.2 | 2.6 | 54.4 | 33.0 | 0.8 | 11.8 |
| 3664 | CS2 | 11.2 | 2.2 | 44.0 | 42.0 | 0.6 | 13.4 |
| 3664 | CS2 | 9.2 | 2.3 | 41.1 | 46.6 | 0.9 | 11/4 |
| 3664 | CS2 | 11.4 | 1.8 | 39.5 | 46.7 | 0.6 | 13.2 |
| 3664 | CS2 | 10.6 | 2.5 | 41.7 | 44.7 | 0.5 | 13.0 |
| 3664 | CS2 | 10.3 | 2.5 | 48.0 | 38.5 | 0.8 | 12.8 |
| 3664 | CS2 | 11.3 | 3.0 | 36.9 | 48.3 | 0.5 | 14.3 |
| 3664 | Mean | 10.2 | 2.4 | 43.0 | 43.6 | 0.7 | 12.6 |
| 3672 | BC1S2 | 10.6 | 2.7 | 32.9 | 53.1 | 0.6 | 13.4 |
| 3672 | BC1S2 | 8.9 | 2.9 | 37.0 | 50.9 | 0.4 | 11.8 |
| 3672 | BC1S2 | 10.5 | 2.4 | 42.5 | 44.1 | 0.4 | 12.9 |
| 3672 | BC1S2 | 11.1 | 3.0 | 38.7 | 46.8 | 0.4 | 14.1 |
| 3672 | BC1S2 | 12.8 | 2.9 | 33.2 | 50.5 | 0.6 | 15.8 |
| 3672 | BC1S2 | 11.3 | 2.6 | 41.0 | 44.6 | 0.4 | 13.9 |
| 3672 | BC1S2 | 10.4 | 2.5 | 39.5 | 47.1 | 0.4 | 12.9 |
| 3672 | BC1S2 | 10.3 | 2.8 | 36.2 | 50.1 | 0.6 | 13.1 |
| 3672 | BC1S2 | 8.4 | 2.5 | 41.4 | 47.3 | 0.4 | 10.9 |

TABLE 24-continued

GC Data for lines selected for the invention disclosure.

| GC # | Category | Palmitic | Stearic | Oleic | Linoleic | Linolenic | Saturates |
|---|---|---|---|---|---|---|---|
| 3672 | BC1S2 | 11.4 | 2.5 | 36.7 | 48.6 | 0.8 | 13.9 |
| 3672 | Mean | 10.6 | 2.7 | 37.9 | 48.3 | 0.5 | 13.3 |
| 3674 | BC1S2 | 10.9 | 2.3 | 39.3 | 46.7 | 0.7 | 13.2 |
| 3674 | BC1S2 | 11.1 | 2.7 | 42.8 | 42.8 | 0.7 | 13.7 |
| 3674 | BC1S2 | 11.8 | 3.2 | 47.4 | 37.0 | 0.6 | 15.0 |
| 3674 | BC1S2 | 11.1 | 2.4 | 42.2 | 43.6 | 0.7 | 13.5 |
| 3674 | BC1S2 | 12.2 | 2.0 | 43.4 | 41.7 | 0.6 | 14.3 |
| 3674 | BC1S2 | 11.3 | 2.3 | 40.7 | 44.9 | 0.8 | 13.6 |
| 3674 | BC1S2 | 10.2 | 2.6 | 59.6 | 27.0 | 0.5 | 21.8 |
| 3674 | BC1S2 | 10.1 | 2.2 | 41.3 | 45.9 | 0.5 | 12.3 |
| 3674 | BC1S2 | 9.5 | 2.5 | 49.1 | 38.4 | 0.5 | 11.9 |
| 3674 | BC1S2 | 12.4 | 2.5 | 26.1 | 58.2 | 0.8 | 15.0 |
| 3674 | Mean | 11.1 | 2.5 | 43.2 | 42.6 | 0.6 | 13.5 |
| 3676 | BC1S2 | 12.7 | 2.4 | 35.5 | 48.9 | 0.5 | 15.1 |
| 3676 | BC1S2 | 12.8 | 2.7 | 42.2 | 41.9 | 0.4 | 15.5 |
| 3676 | BC1S2 | 12.3 | 3.2 | 37.9 | 46.1 | 0.5 | 15.5 |
| 3676 | BC1S2 | 12.9 | 1.9 | 25.5 | 59.2 | 0.5 | 14.8 |
| 3676 | BC1S2 | 13.0 | 1.9 | 24.1 | 60.5 | 0.6 | 14.9 |
| 3676 | BC1S2 | 12.3 | 2.7 | 35.7 | 48.8 | 0.5 | 15.0 |
| 3676 | BC1S2 | 12.0 | 1.8 | 25.6 | 60.1 | 0.5 | 13.8 |
| 3676 | BC1S2 | 12.7 | 2.3 | 32.1 | 52.5 | 0.5 | 15.0 |
| 3676 | BC1S2 | 12.9 | 3.2 | 37.0 | 46.5 | 0.4 | 16.1 |
| 3676 | BC1S2 | 6.9 | 1.7 | 39.2 | 51.3 | 1.0 | 8.6 |
| 3676 | Mean | 12.0 | 2.4 | 33.5 | 51.6 | 0.5 | 14.4 |
| 3687 | CS2 | 7.4 | 2.3 | 42.5 | 46.9 | 0.9 | 9.7 |
| 3687 | CS2 | 7.2 | 1.8 | 37.5 | 52.5 | 1.1 | 9.0 |
| 3687 | CS2 | 7.3 | 1.7 | 39.4 | 50.5 | 1.1 | 9.0 |
| 3687 | CS2 | 7.6 | 2.2 | 38.8 | 50.4 | 1.0 | 9.8 |
| 3687 | CS2 | 7.0 | 2.0 | 37.8 | 52.3 | 0.9 | 8.9 |
| 3687 | CS2 | 7.6 | 2.6 | 43.8 | 45.2 | 0.9 | 10.1 |
| 3687 | CS2 | 7.5 | 2.9 | 43.6 | 45.2 | 0.8 | 10.4 |
| 3687 | CS2 | 7.2 | 2.2 | 43.4 | 46.3 | 0.9 | 9.4 |
| 3687 | CS2 | 7.0 | 1.8 | 40.4 | 49.7 | 1.0 | 8.9 |
| 3687 | CS2 | 8.4 | 1.9 | 43.9 | 45.0 | 0.9 | 10.3 |
| 3687 | Mean | 7.4 | 2.1 | 41.1 | 48.4 | 1.0 | 9.5 |
| 3698 | CS2 | 8.7 | 1.8 | 42.0 | 46.5 | 1.0 | 10.5 |
| 3698 | CS2 | 6.3 | 1.6 | 42.7 | 48.3 | 1.2 | 7.9 |
| 3698 | CS2 | 8.4 | 1.5 | 41.4 | 47.7 | 1.0 | 9.9 |
| 3698 | CS2 | 9.4 | 1.8 | 39.6 | 48.1 | 1.1 | 11.2 |
| 3698 | CS2 | 6.4 | 1.7 | 41.9 | 49.0 | 1.0 | 8.1 |
| 3698 | CS2 | 9.1 | 2.2 | 44.2 | 43.4 | 1.1 | 11.3 |
| 3698 | CS2 | 8.6 | 1.9 | 45.2 | 43.3 | 1.0 | 10.5 |
| 3698 | CS2 | 8.5 | 1.5 | 42.1 | 46.9 | 1.0 | 10.0 |
| 3698 | CS2 | 8.7 | 1.9 | 43.5 | 45.0 | 1.0 | 10.6 |
| 3698 | CS2 | 6.4 | 2.1 | 53.5 | 37.0 | 1.0 | 8.5 |
| 3698 | Mean | 8.0 | 1.8 | 43.6 | 45.5 | 1.0 | 9.8 |
| 3700 | CS2 | 8.6 | 2.5 | 52.9 | 34.9 | 1.1 | 11.2 |
| 3700 | CS2 | 6.6 | 2.7 | 44.3 | 45.5 | 0.9 | 9.3 |
| 3700 | CS2 | 9.3 | 2.3 | 47.5 | 40.1 | 0.9 | 11.5 |
| 3700 | CS2 | 8.1 | 2.2 | 50.4 | 38.3 | 1.0 | 10.3 |
| 3700 | CS2 | 7.0 | 3.7 | 55.4 | 33.1 | 0.9 | 10.7 |
| 3700 | CS2 | 6.2 | 2.7 | 50.7 | 39.4 | 1.0 | 8.8 |
| 3700 | CS2 | 7.4 | 3.0 | 49.9 | 38.8 | 0.9 | 10.5 |
| 3700 | CS2 | 8.1 | 2.5 | 44.1 | 44.3 | 0.9 | 10.6 |
| 3700 | CS2 | 7.8 | 2.6 | 47.5 | 41.3 | 0.8 | 10.4 |
| 3700 | CS2 | 6.8 | 1.4 | 36.1 | 54.3 | 1.3 | 8.2 |
| 3700 | Mean | 7.6 | 2.6 | 47.9 | 41.0 | 1.0 | 10.1 |
| 3720 | CS2 | 6.8 | 1.3 | 37.7 | 53.0 | 1.3 | 8.1 |
| 3720 | CS2 | 6.9 | 1.4 | 36.2 | 54.3 | 1.2 | 8.3 |
| 3720 | CS2 | 6.6 | 1.5 | 39.2 | 51.6 | 1.1 | 8.1 |
| 3720 | CS2 | 6.7 | 1.3 | 37.8 | 53.0 | 1.2 | 8.0 |
| 3720 | CS2 | 7.3 | 1.2 | 37.1 | 53.2 | 1.2 | 8.5 |
| 3720 | CS2 | 7.0 | 1.5 | 35.9 | 54.4 | 1/2 | 8.5 |
| 3720 | CS2 | 7.0 | 1.3 | 35.2 | 55.0 | 1.5 | 8.3 |
| 3720 | CS2 | 6.9 | 1.3 | 35.1 | 55.6 | 1.2 | 8.2 |
| 3720 | CS2 | 6.6 | 1.3 | 39.3 | 51.7 | 1.1 | 7.9 |
| 3720 | CS2 | 5.4 | 3.3 | 59.7 | 30.5 | 1.1 | 8.7 |
| 3720 | Mean | 6.9 | 1.4 | 37.0 | 53.6 | 1.2 | 8.2 |
| 3721 | CS2 | 6.2 | 3.9 | 52.1 | 36.6 | 1.2 | 10.1 |
| 3721 | CS2 | 5.9 | 2.9 | 54.9 | 35.4 | 0.9 | 8.8 |
| 3721 | CS2 | 6.0 | 2.8 | 54.0 | 36.3 | 0.9 | 8.8 |
| 3721 | CS2 | 5.9 | 3.2 | 55.0 | 35.0 | 1.0 | 9.1 |
| 3721 | CS2 | 5.5 | 2.7 | 52.7 | 38.1 | 1.0 | 8.2 |
| 3721 | CS2 | 5.9 | 3.8 | 52.9 | 36.3 | 1.1 | 9.7 |
| 3721 | CS2 | 5.9 | 2.5 | 50.4 | 40.4 | 0.9 | 8.3 |

TABLE 24-continued

GC Data for lines selected for the invention disclosure.

| GC # | Category | Palmitic | Stearic | Oleic | Linoleic | Linolenic | Saturates |
|---|---|---|---|---|---|---|---|
| 3721 | CS2 | 5.9 | 3.3 | 54.1 | 35.6 | 1.0 | 9.2 |
| 3721 | CS2 | 6.2 | 3.6 | 53.8 | 35.2 | 1.2 | 9.8 |
| 3721 | BC1S2 | 8.4 | 3.1 | 45.8 | 41.7 | 1.0 | 11.6 |
| 3721 | Mean | 5.9 | 3.2 | 54.0 | 35.9 | 1.0 | 9.1 |
| 3730 | BC1S2 | 7.4 | 3.1 | 50.4 | 38.1 | 0.9 | 10.5 |
| 3730 | BC1S2 | 7.1 | 2.8 | 44.8 | 44.3 | 0.9 | 10.0 |
| 3730 | BC1S2 | 7.7 | 3.7 | 47.3 | 40.3 | 0.9 | 11.4 |
| 3730 | BC1S2 | 8.8 | 2.9 | 40.9 | 46.2 | 1.2 | 11.6 |
| 3730 | BC1S2 | 7.5 | 2.1 | 38.1 | 51.1 | 1.2 | 9.6 |
| 3730 | BC1S2 | 7.3 | 2.5 | 49.5 | 39.7 | 1.0 | 9.8 |
| 3730 | BC1S2 | 6.5 | 3.7 | 51.6 | 37.5 | 0.8 | 10.1 |
| 3730 | BC1S2 | 6.1 | 2.7 | 39.9 | 50.2 | 1.0 | 8.8 |
| 3730 | BC1S2 | 7.6 | 2.9 | 44.0 | 44.5 | 1.0 | 10.5 |
| 3730 | BC1S2 | 6.3 | 2.0 | 43.1 | 47.5 | 1.0 | 8.4 |
| 3730 | Mean | 7.4 | 3.0 | 45.2 | 43.4 | 1.0 | 10.4 |
| 3731 | BC1S2 | 6.1 | 1.8 | 37.7 | 53.3 | 1.1 | 8.0 |
| 3731 | BC1S2 | 6.0 | 1.9 | 45.4 | 45.8 | 0.9 | 7.9 |
| 3731 | BC1S2 | 6.1 | 2.0 | 40.4 | 50.4 | 1.1 | 8.1 |
| 3731 | BC1S2 | 6.0 | 1.5 | 30.8 | 60.4 | 1.4 | 7.4 |
| 3731 | BC1S2 | 6.2 | 1.9 | 42.7 | 48.2 | 1.0 | 8.1 |
| 3731 | BC1S2 | 6.6 | 2.9 | 48.0 | 41.7 | 0.8 | 9.5 |
| 3731 | BC1S2 | 6.4 | 2.0 | 40.1 | 50.3 | 1.2 | 8.5 |
| 3731 | BC1S2 | 6.7 | 2.0 | 39.5 | 50.5 | 1.2 | 8.8 |
| 3731 | BC1S2 | 5.9 | 1.9 | 40.4 | 50.7 | 1.0 | 7.8 |
| 3731 | BC1S2 | 7.9 | 2.9 | 53.0 | 35.3 | 0.9 | 10.8 |
| 3731 | Mean | 6.2 | 2.0 | 40.8 | 49.9 | 1.1 | 8.2 |
| 3742 | BC1S2 | 8.1 | 2.5 | 53.6 | 34.9 | 0.9 | 10.6 |
| 3742 | BC1S2 | 8.4 | 2.7 | 51.7 | 36.4 | 0.9 | 11.0 |
| 3742 | BC1S2 | 8.0 | 2.0 | 44.9 | 44.1 | 1.0 | 10.1 |
| 3742 | BC1S2 | 8.3 | 2.6 | 55.0 | 33.2 | 0.9 | 11.0 |
| 3742 | BC1S2 | 8.5 | 3.7 | 52.6 | 34.3 | 0.8 | 12.3 |
| 3742 | BC1S2 | 8.3 | 2.4 | 49.7 | 38.8 | 0.9 | 10.6 |
| 3742 | BC1S2 | 7.9 | 2.1 | 44.6 | 44.5 | 1.1 | 9.9 |
| 3742 | BC1S2 | 8.5 | 2.3 | 49.6 | 38.7 | 1.0 | 10.9 |
| 3742 | BC1S2 | 8.4 | 2.6 | 54.2 | 33.9 | 0.9 | 11.0 |
| 3742 | CS2 | 9.3 | 2.7 | 42.6 | 44.5 | 0.9 | 12.0 |
| 3742 | Mean | 8.2 | 2.6 | 50.9 | 37.4 | 0.9 | 10.8 |
| 3745 | CS2 | 9.1 | 2.9 | 44.5 | 42.8 | 0.8 | 12.0 |
| 3745 | CS2 | 9.7 | 2.4 | 35.1 | 51.8 | 1.1 | 12.1 |
| 3745 | CS2 | 10.5 | 3.6 | 48.4 | 37.0 | 0.5 | 14.1 |
| 3745 | CS2 | 9.8 | 2.8 | 45.6 | 41.3 | 0.5 | 12.6 |
| 3745 | CS2 | 9.0 | 3.0 | 54.2 | 33.1 | 0.8 | 12.0 |
| 3745 | CS2 | 8.5 | 3.2 | 54.9 | 32.6 | 0.9 | 11.7 |
| 3745 | CS2 | 9.4 | 2.7 | 49.0 | 38.3 | 0.6 | 12.1 |
| 3745 | CS2 | 10.2 | 2.8 | 47.2 | 39.1 | 0.7 | 13.0 |
| 3745 | CS2 | 8.9 | 2.9 | 54.7 | 32.7 | 0.8 | 11.9 |
| 3745 | CS2 | 9.5 | 3.7 | 47.4 | 38.6 | 0.8 | 13.2 |
| 3745 | Mean | 9.4 | 2.9 | 47.6 | 39.3 | 0.8 | 12.3 |
| 3752 | CS2 | 10.5 | 4.3 | 43.8 | 40.5 | 0.8 | 14.8 |
| 3752 | CS2 | 12.5 | 3.6 | 44.2 | 38.7 | 1.0 | 16.1 |
| 3752 | CS2 | 12.5 | 4.4 | 41.9 | 40.4 | 0.9 | 16.9 |
| 3752 | CS2 | 9.4 | 4.2 | 50.1 | 35.4 | 0.8 | 13.6 |
| 3752 | CS2 | 10.7 | 4.8 | 41.8 | 42.0 | 0.8 | 15.4 |
| 3752 | CS2 | 11.0 | 4.1 | 41.7 | 42.2 | 1.1 | 15.1 |
| 3752 | CS2 | 9.9 | 4.2 | 45.2 | 39.9 | 0.8 | 14.1 |
| 3752 | CS2 | 10.0 | 4.7 | 39.5 | 44.8 | 1.0 | 14.7 |
| 3752 | CS2 | 11.8 | 4.5 | 41.5 | 41.5 | 0.8 | 16.3 |
| 3752 | CS2 | 12.3 | 3.0 | 43.2 | 40.7 | 0.8 | 15.3 |
| 3752 | Mean | 10.8 | 4.2 | 43.7 | 40.4 | 0.9 | 15.0 |
| 3757 | CS2 | 11.6 | 4.2 | 47.0 | 36.5 | 0.7 | 15.8 |
| 3757 | CS2 | 10.9 | 3.7 | 49.2 | 35.5 | 0.7 | 14.6 |
| 3757 | CS2 | 10.7 | 3.4 | 48.9 | 36.1 | 1.0 | 14.0 |
| 3757 | CS2 | 10.5 | 3.9 | 48.1 | 36.9 | 0.7 | 14.4 |
| 3757 | CS2 | 9.9 | 3.5 | 50.1 | 35.8 | 0.7 | 13.4 |
| 3757 | CS2 | 11.0 | 3.4 | 47.8 | 37.1 | 0.8 | 14.3 |
| 3757 | CS2 | 10.1 | 3.9 | 48.0 | 37.2 | 0.8 | 14.0 |
| 3757 | CS2 | 11.4 | 3.0 | 48.6 | 36.2 | 0.8 | 14.5 |
| 3757 | CS2 | 10.4 | 4.0 | 46.7 | 38.1 | 0.8 | 14.4 |
| 3757 | CS2 | 10.3 | 2.1 | 48.8 | 38.0 | 0.8 | 12.4 |
| 3757 | Mean | 10.9 | 3.6 | 47.8 | 37.0 | 0.8 | 14.5 |
| 3765 | CS2 | 9.0 | 2.2 | 51.7 | 36.5 | 0.7 | 11.2 |
| 3765 | CS2 | 9.4 | 2.4 | 47.3 | 40.3 | 0.7 | 11.7 |
| 3765 | CS2 | 10.0 | 2.1 | 50.1 | 37.0 | 0.8 | 12.1 |
| 3765 | CS2 | 9.6 | 2.4 | 48.5 | 38.8 | 0.8 | 12.0 |
| 3765 | CS2 | 9.2 | 2.2 | 54.1 | 33.8 | 0.7 | 11.4 |

TABLE 24-continued

GC Data for lines selected for the invention disclosure.

| GC # | Category | Palmitic | Stearic | Oleic | Linoleic | Linolenic | Saturates |
|---|---|---|---|---|---|---|---|
| 3765 | CS2 | 9.3 | 2.5 | 48.2 | 39.2 | 0.8 | 11.8 |
| 3765 | CS2 | 9.3 | 2.1 | 49.4 | 38.5 | 0.7 | 11.4 |
| 3765 | CS2 | 9.9 | 2.2 | 49.5 | 37.7 | 0.8 | 12.1 |
| 3765 | CS2 | 9.6 | 2.8 | 48.9 | 38.1 | 0.6 | 12.4 |
| 3765 | BC1S2 | 9.1 | 3.9 | 56.3 | 29.8 | 0.8 | 13.1 |
| 3765 | Mean | 9.6 | 2.3 | 49.7 | 37.8 | 0.7 | 11.8 |
| 3767 | BC1S2 | 9.6 | 3.8 | 54.2 | 31.5 | 0.9 | 13.4 |
| 3767 | BC1S2 | 9.5 | 3.2 | 56.7 | 29.8 | 0.9 | 12.7 |
| 3767 | BC1S2 | 9.5 | 4.0 | 56.4 | 29.3 | 0.9 | 13.5 |
| 3767 | BC1S2 | 9.5 | 3.6 | 53.9 | 32.3 | 0.8 | 13.1 |
| 3767 | BC1S2 | 9.6 | 4.0 | 56.2 | 29.4 | 0.8 | 13.6 |
| 3767 | BC1S2 | 9.2 | 3.4 | 50.8 | 35.5 | 1.1 | 12.6 |
| 3767 | BC1S2 | 9.5 | 3.4 | 52.4 | 33.8 | 0.9 | 12.9 |
| 3767 | BC1S2 | 9.4 | 4.1 | 55.5 | 30.2 | 0.8 | 13.5 |
| 3767 | BC1S2 | 10.8 | 4.1 | 51.0 | 33.3 | 0.8 | 14.9 |
| 3767 | Mean | 9.4 | 3.7 | 54.7 | 31.3 | 0.9 | 13.1 |
| 3768 | BC1S2 | 10.4 | 3.7 | 50.5 | 34.6 | 0.8 | 14.1 |
| 3768 | BC1S2 | 10.3 | 3.5 | 51.2 | 34.1 | 0.9 | 13.8 |
| 3768 | BC1S2 | 10.7 | 3.6 | 48.7 | 36.2 | 0.9 | 14.3 |
| 3768 | BC1S2 | 9.7 | 4.0 | 54.3 | 31.4 | 0.8 | 13.7 |
| 3768 | BC1S2 | 10.1 | 3.7 | 51.7 | 33.9 | 0.6 | 13.8 |
| 3768 | BC1S2 | 8.8 | 3.9 | 53.4 | 33.1 | 0.8 | 12.7 |
| 3768 | BC1S2 | 10.1 | 4.0 | 52.1 | 33.1 | 0.7 | 14.2 |
| 3768 | BC1S2 | 10.5 | 4.3 | 47.2 | 37.2 | 0.9 | 14.8 |
| 3768 | BC1S2 | 9.9 | 3.8 | 52.8 | 32.7 | 0.8 | 13.7 |
| 3768 | BC1S2 | 8.9 | 3.0 | 48.2 | 39.0 | 1.0 | 11.8 |
| 3768 | Mean | 10.1 | 3.8 | 51.3 | 33.9 | 0.8 | 14.0 |
| 3775 | BC1S2 | 9.0 | 3.4 | 52.7 | 34.0 | 1.0 | 12.4 |
| 3775 | BC1S2 | 8.7 | 2.8 | 50.6 | 36.8 | 1.1 | 11.6 |
| 3775 | BC1S2 | 8.9 | 3.3 | 48.8 | 38.0 | 1.0 | 12.2 |
| 3775 | BC1S2 | 8.9 | 2.8 | 49.8 | 37.5 | 1.1 | 11.7 |
| 3775 | BC1S2 | 9.0 | 2.9 | 51.8 | 35.3 | 1.0 | 12.0 |
| 3775 | BC1S2 | 9.0 | 3.0 | 48.1 | 39.0 | 1.0 | 12.0 |
| 3775 | BC1S2 | 10.6 | 2.6 | 48.9 | 36.9 | 1.0 | 13.3 |
| 3775 | BC1S2 | 8.8 | 2.6 | 48.6 | 38.9 | 1.1 | 11.4 |
| 3775 | BC1S2 | 8.6 | 3.0 | 49.2 | 38.3 | 1.0 | 11.6 |
| 3775 | BC1S2 | 10.2 | 2.0 | 37.3 | 50.0 | 0.5 | 12.2 |
| 3775 | Mean | 9.0 | 2.9 | 49.7 | 37.3 | 1.0 | 12.0 |
| 3777 | BC1S2 | 10.0 | 2.0 | 41.4 | 46.1 | 0.5 | 12.0 |
| 3777 | BC1S2 | 11.2 | 1.8 | 39.2 | 47.2 | 0.6 | 13.0 |
| 3777 | BC1S2 | 12.1 | 2.4 | 33.8 | 47.1 | 4.7 | 14.5 |
| 3777 | BC1S2 | 10.2 | 2.3 | 41.5 | 45.4 | 0.7 | 12.4 |
| 3777 | BC1S2 | 11.6 | 2.3 | 47.1 | 38.3 | 0.8 | 13.9 |
| 3777 | BC1S2 | 10.4 | 1.7 | 37.3 | 49.9 | 0.6 | 12.1 |
| 3777 | BC1S2 | 12.5 | 2.9 | 33.4 | 47.2 | 4.0 | 15.4 |
| 3777 | BC1S2 | 14.7 | 2.8 | 28.5 | 47.5 | 6.5 | 17.5 |
| 3777 | BC1S2 | 11.9 | 2.8 | 35.0 | 45.8 | 4.5 | 14.6 |
| 3777 | BC1S2 | 8.2 | 3.9 | 49.0 | 38.1 | 0.9 | 12.1 |
| 3777 | Mean | 11.5 | 2.3 | 37.5 | 46.4 | 2.4 | 13.8 |
| 3785 | BC1S2 | 8.2 | 4.0 | 50.9 | 36.3 | 0.6 | 12.2 |
| 3785 | BC1S2 | 8.4 | 3.8 | 47.3 | 39.8 | 0.6 | 12.2 |
| 3785 | BC1S2 | 10.0 | 3.8 | 40.5 | 44.9 | 0.8 | 13.8 |
| 3785 | BC1S2 | 9.3 | 4.0 | 43.1 | 42.7 | 0.9 | 13.3 |
| 3785 | BC1S2 | 8.5 | 4.5 | 44.0 | 42.2 | 0.9 | 13.0 |
| 3785 | BC1S2 | 8.3 | 4.4 | 46.0 | 40.5 | 0.9 | 12.7 |
| 3785 | BC1S2 | 8.9 | 4.7 | 42.4 | 43.2 | 0.9 | 13.6 |
| 3785 | BC1S2 | 9.0 | 4.3 | 40.8 | 45.2 | 0.8 | 13.2 |
| 3785 | BC1S2 | 8.3 | 3.6 | 53.1 | 34.5 | 0.6 | 11.9 |
| 3785 | BC1S2 | 9.7 | 2.5 | 41.6 | 44.7 | 1.6 | 12.2 |
| 3785 | Mean | 8.7 | 4.1 | 45.7 | 40.7 | 0.8 | 12.8 |
| 3797 | BC1S2 | 9.7 | 3.0 | 48.9 | 37.3 | 1.1 | 12.7 |
| 3797 | BC1S2 | 10.9 | 2.8 | 43.1 | 41.9 | 1.3 | 13.7 |
| 3797 | BC1S2 | 9.5 | 1.9 | 44.1 | 43.5 | 1.1 | 11.4 |
| 3797 | BC1S2 | 9.8 | 3.2 | 52.2 | 33.9 | 1.0 | 12.9 |
| 3797 | BC1S2 | 7.7 | 2.4 | 54.8 | 34.1 | 1.1 | 10.1 |
| 3797 | BC1S2 | 10.0 | 2.4 | 46.9 | 39.6 | 1.1 | 12.4 |
| 3797 | BC1S2 | 9.9 | 3.4 | 47.5 | 38.2 | 1.1 | 13.2 |
| 3797 | BC1S2 | 10.7 | 2.7 | 38.5 | 46.7 | 1.5 | 13.3 |
| 3797 | BC1S2 | 9.6 | 3.2 | 51.6 | 34.6 | 1.0 | 12.8 |
| 3797 | BC1S2 | 8.0 | 1.9 | 44.6 | 44.0 | 1.4 | 9.9 |
| 3797 | Mean | 9.7 | 2.7 | 46.9 | 39.4 | 1.2 | 12.5 |
| 3798 | BC1S2 | 7.3 | 1.8 | 40.5 | 49.4 | 1.0 | 9.0 |
| 3798 | BC1S2 | 6.5 | 1.6 | 36.0 | 54.6 | 1.4 | 8.1 |
| 3798 | BC1S2 | 7.3 | 1.7 | 42.9 | 47.1 | 1.0 | 9.0 |
| 3798 | BC1S2 | 7.6 | 1.8 | 40.2 | 49.5 | 0.9 | 9.4 |

TABLE 24-continued

GC Data for lines selected for the invention disclosure.

| GC # | Category | Palmitic | Stearic | Oleic | Linoleic | Linolenic | Saturates |
|---|---|---|---|---|---|---|---|
| 3798 | BC1S2 | 7.8 | 1.5 | 30.0 | 59.5 | 1.3 | 9.3 |
| 3798 | BC1S2 | 7.4 | 1.9 | 41.4 | 48.4 | 0.9 | 9.3 |
| 3798 | BC1S2 | 7.3 | 1.9 | 46.4 | 43.5 | 0.9 | 9.3 |
| 3798 | BC1S2 | 7.9 | 1.9 | 38.4 | 50.8 | 1.0 | 9.8 |
| 3798 | BC1S2 | 8.3 | 1.7 | 40.3 | 48.5 | 1.2 | 10.0 |
| 3798 | CS2 | 7.2 | 2.3 | 36.9 | 52.9 | 0.9 | 9.5 |
| 3798 | Mean | 7.5 | 1.8 | 40.1 | 49.5 | 1.1 | 9.3 |
| 3806 | CS2 | 6.9 | 2.4 | 51.2 | 38.7 | 0.8 | 9.3 |
| 3806 | CS2 | 12.7 | 2.3 | 43.5 | 40.8 | 0.9 | 15.0 |
| 3806 | CS2 | 12.3 | 2.3 | 43.3 | 41.5 | 0.8 | 14.6 |
| 3806 | CS2 | 10.0 | 2.2 | 37.2 | 49.9 | 0.9 | 12.1 |
| 3806 | CS2 | 12.4 | 2.3 | 34.1 | 50.5 | 0.9 | 14.6 |
| 3806 | CS2 | 10.6 | 2.0 | 33.9 | 52.6 | 1.0 | 12.6 |
| 3806 | CS2 | 10.3 | 2.0 | 32.8 | 54.2 | 0.9 | 12.2 |
| 3806 | CS2 | 10.4 | 1.8 | 29.0 | 57.9 | 1.1 | 12.2 |
| 3806 | CS2 | 10.2 | 2.3 | 38.7 | 47.9 | 1.0 | 12.5 |
| 3806 | CS2 | 6.5 | 3.1 | 54.5 | 35.1 | 0.9 | 9.5 |
| 3806 | Mean | 10.3 | 2.2 | 38.1 | 48.7 | 0.9 | 12.5 |
| 3816 | CS2 | 7.4 | 3.5 | 45.4 | 42.8 | 1.0 | 10.9 |
| 3816 | CS2 | 7.9 | 2.3 | 44.2 | 44.7 | 1.1 | 10.2 |
| 3816 | CS2 | 8.5 | 3.0 | 43.3 | 44.2 | 1.1 | 11.5 |
| 3816 | CS2 | 7.5 | 2.8 | 47.1 | 41.7 | 1.1 | 10.3 |
| 3816 | CS2 | 6.8 | 2.9 | 51.4 | 38.0 | 0.9 | 9.8 |
| 3816 | CS2 | 6.3 | 2.9 | 59.7 | 30.4 | 0.8 | 9.2 |
| 3816 | CS2 | 7.0 | 2.7 | 48.2 | 41.0 | 1.1 | 9.8 |
| 3816 | CS2 | 7.0 | 2.9 | 50.0 | 39.1 | 1.1 | 9.9 |
| 3816 | CS2 | 8.0 | 2.4 | 39.4 | 49.0 | 1.2 | 10.4 |
| 3816 | CS2 | 7.4 | 3.4 | 55.9 | 32.4 | 0.9 | 10.8 |
| 3816 | Mean | 7.3 | 2.9 | 48.3 | 40.6 | 1.0 | 10.1 |
| 3828 | CS2 | 6.9 | 4.3 | 57.0 | 30.9 | 0.9 | 11.2 |
| 3828 | CS2 | 7.2 | 3.5 | 55.7 | 32.7 | 0.9 | 10.7 |
| 3828 | CS2 | 7.5 | 3.5 | 55.0 | 33.1 | 0.9 | 11.0 |
| 3828 | CS2 | 7.2 | 3.7 | 53.1 | 35.0 | 1.0 | 10.9 |
| 3828 | CS2 | 7.0 | 3.6 | 58.0 | 30.5 | 0.9 | 10.6 |
| 3828 | CS2 | 7.4 | 3.6 | 56.9 | 31.2 | 1.0 | 10.9 |
| 3828 | CS2 | 8.0 | 2.5 | 45.9 | 42.4 | 1.2 | 10.5 |
| 3828 | CS2 | 7.1 | 3.0 | 54.8 | 34.1 | 0.9 | 10.1 |
| 3828 | CS2 | 6.8 | 3.6 | 57.6 | 31.1 | 0.9 | 10.4 |
| 3828 | CS2 | 6.8 | 4.3 | 53.4 | 34.7 | 0.9 | 11.0 |
| 3828 | Mean | 7.3 | 3.5 | 55.0 | 33.3 | 1.0 | 10.7 |
| 3839 | CS2 | 7.2 | 3.1 | 49.8 | 39.0 | 0.9 | 10.3 |
| 3839 | CS2 | 7.3 | 3.0 | 52.8 | 36.1 | 0.8 | 10.3 |
| 3839 | CS2 | 6.7 | 4.0 | 54.7 | 33.7 | 0.8 | 10.7 |
| 3839 | CS2 | 7.4 | 3.2 | 52.8 | 35.7 | 0.9 | 10.6 |
| 3839 | CS2 | 7.1 | 3.2 | 50.4 | 38.5 | 0.9 | 10.3 |
| 3839 | CS2 | 11.4 | 3.2 | 38.4 | 43.8 | 3.1 | 14.6 |
| 3839 | CS2 | 6.5 | 3.6 | 56.4 | 32.7 | 0.8 | 10.1 |
| 3839 | CS2 | 7.4 | 3.1 | 49.0 | 39.6 | 0.9 | 10.5 |
| 3839 | CS2 | 7.2 | 3.4 | 52.6 | 36.0 | 0.9 | 10.5 |
| 3839 | CS2 | 9.8 | 3.2 | 50.8 | 35.4 | 0.8 | 13.0 |
| 3839 | Mean | 7.5 | 3.4 | 51.0 | 37.0 | 1.1 | 10.9 |
| 3843 | CS2 | 10.2 | 2.9 | 45.7 | 40.3 | 1.0 | 13.1 |
| 3843 | CS2 | 9.3 | 3.0 | 44.9 | 41.7 | 1.1 | 12.2 |
| 3843 | CS2 | 10.9 | 3.0 | 40.2 | 44.8 | 1.2 | 13.9 |
| 3843 | CS2 | 7.9 | 2.4 | 45.6 | 43.0 | 1.0 | 10.4 |
| 3843 | CS2 | 10.3 | 2.4 | 45.0 | 41.4 | 1.0 | 12.7 |
| 3843 | CS2 | 9.3 | 2.9 | 46.8 | 39.9 | 1.1 | 12.2 |
| 3843 | CS2 | 9.1 | 2.5 | 46.3 | 40.8 | 1.2 | 11.6 |
| 3843 | CS2 | 10.4 | 2.9 | 49.1 | 36.7 | 1.1 | 13.2 |
| 3843 | CS2 | 8.4 | 3.5 | 51.5 | 35.2 | 1.4 | 11.9 |
| 3843 | CS2 | 7.1 | 2.7 | 40.1 | 48.8 | 1.3 | 9.8 |
| 3843 | Mean | 9.5 | 2.9 | 46.6 | 39.9 | 1.1 | 12.4 |
| 3851 | CS2 | 7.2 | 2.8 | 35.7 | 53.0 | 1.2 | 10.0 |
| 3851 | CS2 | 7.6 | 2.4 | 33.9 | 54.8 | 1.3 | 10.0 |
| 3851 | CS2 | 7.6 | 2.9 | 38.2 | 50.2 | 1.2 | 10.5 |
| 3851 | CS2 | 6.4 | 2.5 | 32.0 | 57.9 | 1.2 | 8.9 |
| 3851 | CS2 | 6.4 | 2.4 | 29.3 | 60.3 | 1.6 | 8.8 |
| 3851 | CS2 | 6.9 | 2.3 | 35.8 | 53.6 | 1.4 | 9.2 |
| 3851 | CS2 | 7.2 | 2.6 | 37.5 | 51.5 | 1.2 | 9.7 |
| 3851 | CS2 | 7.2 | 2.7 | 33.8 | 55.2 | 1.1 | 9.9 |
| 3851 | CS2 | 6.1 | 1.9 | 26.8 | 63.8 | 1.4 | 7.9 |
| 3851 | CS2 | 7.4 | 2.8 | 51.7 | 37.0 | 1.1 | 10.2 |
| 3851 | Mean | 7.0 | 2.5 | 34.3 | 54.9 | 1.3 | 9.5 |
| 3862 | CS2 | 7.6 | 2.5 | 49.2 | 39.8 | 0.9 | 10.1 |
| 3862 | CS2 | 7.4 | 1.9 | 48.1 | 41.6 | 1.0 | 9.3 |

TABLE 24-continued

GC Data for lines selected for the invention disclosure.

| GC # | Category | Palmitic | Stearic | Oleic | Linoleic | Linolenic | Saturates |
|---|---|---|---|---|---|---|---|
| 3862 | CS2 | 7.4 | 1.9 | 48.3 | 41.3 | 1.0 | 9.4 |
| 3862 | CS2 | 8.4 | 2.8 | 50.9 | 36.8 | 1.2 | 11.1 |
| 3862 | CS2 | 7.7 | 2.6 | 49.1 | 39.8 | 0.9 | 10.2 |
| 3862 | CS2 | 7.5 | 2.4 | 49.5 | 39.7 | 1.0 | 9.8 |
| 3862 | CS2 | 8.5 | 2.7 | 48.2 | 39.4 | 1.2 | 11.2 |
| 3862 | CS2 | 8.3 | 3.3 | 48.5 | 38.7 | 1.2 | 11.6 |
| 3862 | CS2 | 7.8 | 3.0 | 49.4 | 38.8 | 0.9 | 10.9 |
| 3862 | CS2 | 7.2 | 2.9 | 53.6 | 35.0 | 1.2 | 10.1 |
| 3862 | Mean | 7.8 | 2.6 | 49.3 | 39.3 | 1.0 | 10.4 |
| 3867 | CS2 | 7.8 | 3.3 | 51.3 | 36.4 | 1.3 | 11.1 |
| 3867 | CS2 | 6.8 | 2.3 | 54.7 | 35.4 | 0.9 | 9.1 |
| 3867 | CS2 | 6.6 | 2.1 | 50.3 | 40.0 | 0.9 | 8.7 |
| 3867 | CS2 | 6.9 | 2.3 | 56.9 | 33.0 | 0.9 | 9.2 |
| 3867 | CS2 | 6.4 | 2.2 | 54.6 | 35.9 | 1.0 | 8.6 |
| 3867 | CS2 | 6.5 | 2.5 | 52.6 | 37.5 | 1.0 | 9.0 |
| 3867 | CS2 | 6.9 | 2.7 | 51.4 | 38.1 | 0.9 | 9.6 |
| 3867 | CS2 | 7.1 | 2.3 | 50.7 | 38.8 | 1.1 | 9.4 |
| 3867 | CS2 | 10.7 | 3.2 | 39.5 | 43.6 | 3.0 | 13.9 |
| 3867 | CS2 | 8.7 | 4.7 | 48.0 | 37.6 | 1.0 | 13.4 |
| 3867 | Mean | 7.3 | 2.6 | 51.6 | 37.4 | 1.2 | 9.9 |
| 3880 | CS2 | 8.4 | 5.1 | 51.8 | 33.9 | 0.7 | 13.5 |
| 3880 | CS2 | 8.8 | 4.2 | 50.5 | 35.8 | 0.8 | 13.0 |
| 3880 | CS2 | 8.4 | 4.3 | 51.5 | 35.0 | 0.9 | 12.6 |
| 3880 | CS2 | 8.1 | 5.4 | 55.7 | 30.1 | 0.8 | 13.5 |
| 3880 | CS2 | 8.0 | 4.1 | 50.3 | 36.7 | 0.9 | 12.1 |
| 3880 | CS2 | 8.7 | 4.0 | 51.9 | 34.5 | 0.9 | 12.7 |
| 3880 | CS2 | 8.0 | 4.7 | 50.9 | 35.5 | 0.9 | 12.7 |
| 3880 | CS2 | 7.8 | 3.6 | 53.8 | 34.1 | 0.7 | 11.4 |
| 3880 | CS2 | 9.0 | 3.8 | 49.3 | 37.1 | 0.8 | 12.8 |
| 3880 | CS2 | 8.3 | 2.2 | 54.3 | 34.4 | 0.9 | 10.5 |
| 3880 | Mean | 8.4 | 4.4 | 51.4 | 35.0 | 0.8 | 12.8 |
| 3894 | CS2 | 8.9 | 1.8 | 38.1 | 50.1 | 1.1 | 10.7 |
| 3894 | CS2 | 8.8 | 2.0 | 44.4 | 43.9 | 1.0 | 10.8 |
| 3894 | CS2 | 9.3 | 2.5 | 51.1 | 35.9 | 1.1 | 11.9 |
| 3894 | CS2 | 8.8 | 2.5 | 50.4 | 37.4 | 0.9 | 11.3 |
| 3894 | CS2 | 9.1 | 1.7 | 48.7 | 39.5 | 1.1 | 10.8 |
| 3894 | CS2 | 9.0 | 2.7 | 49.4 | 38.1 | 0.9 | 11.7 |
| 3894 | CS2 | 8.6 | 1.7 | 37.1 | 51.6 | 1.1 | 10.3 |
| 3894 | CS2 | 8.2 | 2.4 | 45.3 | 43.2 | 0.9 | 10.6 |
| 3894 | CS2 | 9.5 | 2.5 | 49.1 | 38.1 | 0.9 | 11.9 |
| 3894 | CS2 | 7.4 | 2.1 | 49.2 | 40.3 | 1.0 | 9.5 |
| 3894 | Mean | 8.8 | 2.2 | 46.8 | 41.2 | 1.0 | 11.0 |
| 3895 | CS2 | 7.6 | 1.6 | 43.6 | 46.1 | 1.0 | 9.2 |
| 3895 | CS2 | 6.3 | 2.0 | 44.4 | 46.2 | 1.1 | 8.3 |
| 3895 | CS2 | 7.1 | 2.2 | 42.8 | 46.8 | 1.2 | 9.2 |
| 3895 | CS2 | 7.1 | 1.7 | 47.0 | 43.1 | 1.0 | 8.8 |
| 3895 | CS2 | 5.5 | 1.4 | 43.5 | 48.5 | 1.2 | 6.8 |
| 3895 | CS2 | 6.9 | 1.6 | 37.1 | 53.2 | 1.1 | 8.5 |
| 3895 | CS2 | 8.0 | 1.8 | 38.8 | 50.4 | 1.1 | 9.8 |
| 3895 | CS2 | 7.6 | 1.9 | 36.1 | 53.5 | 1.0 | 9.5 |
| 3895 | CS2 | 6.4 | 2.4 | 39.8 | 50.3 | 1.1 | 8.8 |
| 3895 | CS2 | 5.5 | 1.9 | 48.4 | 43.3 | 0.9 | 7.4 |
| 3895 | Mean | 7.0 | 1.9 | 42.2 | 47.9 | 1.1 | 8.8 |
| 3902 | CS2 | 6.0 | 2.0 | 41.2 | 50.0 | 0.9 | 7.9 |
| 3902 | CS2 | 7.0 | 2.6 | 47.1 | 42.4 | 0.8 | 9.6 |
| 3902 | CS2 | 7.8 | 2.4 | 49.0 | 40.0 | 0.9 | 10.2 |
| 3902 | CS2 | 6.9 | 2.1 | 50.9 | 39.2 | 0.9 | 9.0 |
| 3902 | CS2 | 8.0 | 2.4 | 45.3 | 43.5 | 0.8 | 10.5 |
| 3902 | CS2 | 7.4 | 2.1 | 39.8 | 49.7 | 1.0 | 9.5 |
| 3902 | CS2 | 7.1 | 2.3 | 58.5 | 31.3 | 0.8 | 9.4 |
| 3902 | CS2 | 5.8 | 1.4 | 38.4 | 53.3 | 1.1 | 7.2 |
| 3902 | CS2 | 6.1 | 1.9 | 39.6 | 51.2 | 1.1 | 8.1 |
| 3902 | CS2 | 5.5 | 1.7 | 41.7 | 50.1 | 1.0 | 7.2 |
| 3902 | Mean | 6.8 | 2.1 | 45.8 | 44.4 | 0.9 | 8.9 |
| 3905 | CS2 | 4.9 | 1.8 | 45.0 | 47.3 | 1.0 | 6.7 |
| 3905 | CS2 | 6.4 | 3.1 | 44.6 | 45.1 | 0.9 | 9.5 |
| 3905 | CS2 | 6.4 | 2.8 | 52.9 | 37.0 | 0.8 | 9.2 |
| 3905 | CS2 | 6.4 | 2.8 | 37.5 | 52.3 | 1.1 | 9.2 |
| 3905 | CS2 | 6.0 | 2.5 | 41.8 | 48.6 | 1.1 | 8.5 |
| 3905 | CS2 | 6.0 | 2.7 | 46.8 | 43.6 | 0.9 | 8.7 |
| 3905 | CS2 | 5.8 | 2.2 | 47.7 | 43.4 | 0.9 | 8.0 |
| 3905 | CS2 | 5.4 | 2.3 | 45.2 | 46.0 | 1.1 | 7.7 |
| 3905 | CS2 | 5.8 | 2.7 | 40.9 | 49.6 | 1.0 | 8.5 |
| 3905 | CS2 | 8.3 | 2.2 | 31.0 | 57.3 | 1.1 | 10.5 |

TABLE 24-continued

GC Data for lines selected for the invention disclosure.

| GC # | Category | Palmitic | Stearic | Oleic | Linoleic | Linolenic | Saturates |
|---|---|---|---|---|---|---|---|
| 3905 | Mean | 5.9 | 2.5 | 44.4 | 46.3 | 1.0 | 8.3 |
| 3908 | CS2 | 6.9 | 2.1 | 39.2 | 50.8 | 1.0 | 9.1 |
| 3908 | CS2 | 5.9 | 1.6 | 31.4 | 60.0 | 1.2 | 7.5 |
| 3908 | CS2 | 8.3 | 3.0 | 34.0 | 51.5 | 3.3 | 11.3 |
| 3908 | CS2 | 7.6 | 1.9 | 34.9 | 54.5 | 1.2 | 9.4 |
| 3908 | CS2 | 6.7 | 1.3 | 36.9 | 54.1 | 1.0 | 8.0 |
| 3908 | CS2 | 7.7 | 3.0 | 37.9 | 48.6 | 2.8 | 10.7 |
| 3908 | CS2 | 5.8 | 1.8 | 33.4 | 57.9 | 1.1 | 7.6 |
| 3908 | CS2 | 8.1 | 1.6 | 29.5 | 59.7 | 1.2 | 9.7 |
| 3908 | CS2 | 5.1 | 1.6 | 42.6 | 49.7 | 1.0 | 6.8 |
| 3908 | CS2 | 5.8 | 1.9 | 44.0 | 47.3 | 0.9 | 7.8 |
| 3908 | Mean | 7.0 | 2.0 | 35.1 | 54.4 | 1.5 | 9.0 |
| 3916 | CS2 | 7.4 | 2.4 | 56.0 | 33.4 | 0.8 | 9.8 |
| 3916 | CS2 | 7.3 | 1.9 | 59.5 | 30.4 | 0.9 | 9.2 |
| 3916 | CS2 | 6.0 | 2.5 | 56.2 | 34.5 | 0.8 | 8.6 |
| 3916 | CS2 | 7.1 | 1.9 | 44.3 | 45.7 | 1.0 | 9.0 |
| 3916 | CS2 | 7.3 | 2.6 | 57.4 | 31.9 | 0.8 | 9.9 |
| 3916 | CS2 | 7.5 | 3.3 | 56.7 | 31.8 | 0.8 | 10.8 |
| 3916 | CS2 | 5.8 | 2.5 | 51.8 | 39.1 | 0.9 | 8.3 |
| 3916 | CS2 | 7.3 | 2.8 | 53.2 | 36.0 | 0.7 | 10.1 |
| 3916 | CS2 | 7.7 | 2.4 | 51.4 | 37.7 | 0.8 | 10.2 |
| 3916 | CS2 | 7.4 | 2.8 | 52.4 | 36.5 | 0.9 | 10.2 |
| 3916 | Mean | 6.9 | 2.4 | 53.0 | 36.8 | 0.8 | 9.3 |
| 3920 | CS2 | 6.5 | 2.0 | 42.2 | 48.1 | 1.2 | 8.5 |
| 3920 | CS2 | 7.0 | 2.7 | 55.7 | 33.8 | 0.8 | 9.8 |
| 3920 | CS2 | 7.4 | 2.7 | 53.6 | 35.4 | 1.0 | 10.1 |
| 3920 | CS2 | 7.8 | 2.8 | 44.6 | 43.8 | 1.1 | 10.6 |
| 3920 | CS2 | 7.4 | 3.0 | 49.0 | 39.7 | 0.9 | 10.4 |
| 3920 | CS2 | 8.1 | 2.9 | 51.0 | 37.1 | 0.9 | 11.0 |
| 3920 | CS2 | 8.1 | 2.4 | 47.6 | 40.9 | 1.0 | 10.5 |
| 3920 | CS2 | 7.6 | 2.2 | 51.6 | 37.8 | 0.9 | 9.8 |
| 3920 | CS2 | 7.7 | 2.5 | 51.7 | 37.2 | 0.9 | 10.3 |
| 3920 | CS2 | 5.9 | 1.6 | 34.4 | 56.8 | 1.3 | 7.5 |
| 3920 | Mean | 7.5 | 2.6 | 49.9 | 39.0 | 1.0 | 10.1 |
| 3921 | CS2 | 6.1 | 1.5 | 30.2 | 61.1 | 1.1 | 7.6 |
| 3921 | CS2 | 6.1 | 1.8 | 31.4 | 59.7 | 1.0 | 7.9 |
| 3921 | CS2 | 6.6 | 2.1 | 27.5 | 62.6 | 1.2 | 8.7 |
| 3921 | CS2 | 6.6 | 2.0 | 24.1 | 66.0 | 1.2 | 8.6 |
| 3921 | CS2 | 8.7 | 2.3 | 30.2 | 57.9 | 1.0 | 11.0 |
| 3921 | CS2 | 6.7 | 2.1 | 31.1 | 59.0 | 1.1 | 8.8 |
| 3921 | CS2 | 5.8 | 1.5 | 32.4 | 59.2 | 1.1 | 7.3 |
| 3921 | CS2 | 6.0 | 1.7 | 25.0 | 66.0 | 1.4 | 7.7 |
| 3921 | CS2 | 6.0 | 1.8 | 33.3 | 57.9 | 1.1 | 7.8 |
| 3921 | CS2 | 7.1 | 2.6 | 50.8 | 38.4 | 1.1 | 9.7 |
| 3921 | Mean | 6.5 | 1.8 | 30.0 | 60.6 | 1.2 | 8.3 |
| 3928 | CS2 | 7.1 | 2.2 | 47.5 | 42.1 | 1.0 | 9.4 |
| 3928 | CS2 | 7.0 | 2.7 | 49.5 | 39.5 | 1.3 | 9.7 |
| 3928 | CS2 | 6.8 | 2.5 | 49.2 | 40.5 | 1.1 | 9.2 |
| 3928 | CS2 | 6.4 | 3.0 | 55.0 | 34.5 | 1.1 | 9.4 |
| 3928 | CS2 | 7.0 | 2.9 | 49.7 | 39.2 | 1.3 | 9.8 |
| 3928 | CS2 | 6.6 | 2.6 | 51.3 | 38.3 | 1.2 | 9.3 |
| 3928 | CS2 | 6.7 | 2.6 | 53.2 | 36.3 | 1.2 | 9.3 |
| 3928 | CS2 | 6.8 | 2.7 | 53.3 | 36.0 | 1.1 | 9.6 |
| 3928 | CS2 | 6.7 | 3.0 | 52.3 | 36.8 | 1.2 | 9.8 |
| 3928 | CS2 | 6.9 | 2.9 | 51.7 | 37.5 | 1.0 | 9.8 |
| 3928 | Mean | 6.8 | 2.7 | 51.2 | 38.2 | 1.2 | 9.5 |
| 3937 | CS2 | 6.4 | 2.5 | 56.7 | 33.5 | 1.0 | 8.9 |
| 3937 | CS2 | 7.1 | 2.2 | 51.6 | 38.0 | 1.1 | 9.2 |
| 3937 | CS2 | 7.8 | 2.8 | 47.6 | 40.6 | 1.2 | 10.6 |
| 3937 | CS2 | 7.5 | 2.4 | 47.2 | 41.7 | 1.2 | 9.9 |
| 3937 | CS2 | 7.6 | 2.4 | 47.3 | 41.6 | 1.2 | 10.0 |
| 3937 | CS2 | 7.4 | 2.8 | 47.6 | 41.0 | 1.2 | 10.2 |
| 3937 | CS2 | 6.4 | 2.3 | 55.8 | 34.5 | 1.1 | 8.7 |
| 3937 | CS2 | 7.7 | 2.8 | 46.4 | 41.9 | 1.2 | 10.5 |
| 3937 | CS2 | 7.2 | 2.9 | 49.2 | 39.6 | 1.2 | 10.1 |
| 3937 | CS2 | 7.2 | 2.9 | 49.2 | 39.6 | 1.2 | 10.1 |
| 3973 | CS2 | 5.5 | 1.3 | 36.6 | 55.6 | 1.0 | 6.8 |
| 3937 | Mean | 7.2 | 2.6 | 50.1 | 39.0 | 1.1 | 9.8 |
| 3960 | CS2 | 7.8 | 1.2 | 30.7 | 59.2 | 1.2 | 8.9 |
| 3960 | CS2 | 5.8 | 1.1 | 34.4 | 57.7 | 1.1 | 6.9 |
| 3960 | CS2 | 8.4 | 1.2 | 29.9 | 59.0 | 1.5 | 9.6 |
| 3960 | CS2 | 5.8 | 1.2 | 35.4 | 56.6 | 1.0 | 7.1 |
| 3960 | CS2 | 5.8 | 1.1 | 33.8 | 58.1 | 1.1 | 6.9 |
| 3960 | CS2 | 8.1 | 1.1 | 30.7 | 58.7 | 1.4 | 9.2 |
| 3960 | CS2 | 9.2 | 1.2 | 32.5 | 55.6 | 1.5 | 10.4 |

TABLE 24-continued

GC Data for lines selected for the invention disclosure.

| GC # | Category | Palmitic | Stearic | Oleic | Linoleic | Linolenic | Saturates |
|---|---|---|---|---|---|---|---|
| 3960 | CS2 | 7.9 | 1.3 | 32.0 | 57.3 | 1.5 | 9.2 |
| 3960 | CS2 | 9.6 | 1.1 | 28.4 | 59.3 | 1.6 | 10.7 |
| 3960 | CS2 | 8.7 | 3.0 | 58.5 | 28.9 | 0.9 | 11.7 |
| 3960 | Mean | 7.4 | 1.2 | 32.4 | 57.7 | 1.3 | 8.6 |
| 3962 | CS2 | 8.7 | 2.4 | 58.0 | 30.3 | 0.6 | 11.1 |
| 3962 | CS2 | 10.5 | 2.7 | 56.3 | 29.4 | 1.1 | 13.2 |
| 3962 | CS2 | 9.2 | 2.8 | 59.5 | 27.8 | 0.8 | 12.0 |
| 3962 | CS2 | 7.7 | 2.3 | 54.2 | 35.2 | 0.7 | 10.0 |
| 3962 | CS2 | 7.0 | 3.1 | 60.5 | 28.9 | 0.6 | 10.0 |
| 3962 | CS2 | 7.5 | 2.7 | 58.5 | 30.6 | 0.7 | 10.2 |
| 3962 | CS2 | 8.9 | 3.0 | 57.6 | 29.7 | 0.9 | 11.8 |
| 3962 | CS2 | 9.4 | 3.6 | 58.9 | 27.3 | 0.8 | 13.1 |
| 3962 | CS2 | 9.3 | 2.5 | 54.8 | 32.4 | 1.0 | 11.7 |
| 3962 | CS2 | 8.8 | 3.5 | 46.1 | 40.8 | 0.8 | 12.3 |
| 3962 | Mean | 8.7 | 2.8 | 57.7 | 30.0 | 0.8 | 11.5 |
| 3980 | CS2 | 8.0 | 2.2 | 39.7 | 49.3 | 1.0 | 10.1 |
| 3980 | CS2 | 8.1 | 2.5 | 42.9 | 45.6 | 0.9 | 10.7 |
| 3980 | CS2 | 9.5 | 2.9 | 44.8 | 42.0 | 0.8 | 12.4 |
| 3980 | CS2 | 6.6 | 2.8 | 46.8 | 43.0 | 0.8 | 9.4 |
| 3980 | CS2 | 8.6 | 2.6 | 39.2 | 48.6 | 1.0 | 11.2 |
| 3980 | CS2 | 7.0 | 2.8 | 52.7 | 36.6 | 0.9 | 9.8 |
| 3980 | CS2 | 8.6 | 3.3 | 40.6 | 46.8 | 0.8 | 12.0 |
| 3980 | CS2 | 6.9 | 2.8 | 42.6 | 47.0 | 0.8 | 9.7 |
| 3980 | CS2 | 8.7 | 3.3 | 44.1 | 43.0 | 0.9 | 12.1 |
| 3980 | CS2 | 6.1 | 1.6 | 33.6 | 57.9 | 0.8 | 7.7 |
| 3980 | Mean | 8.1 | 2.9 | 43.9 | 44.3 | 0.9 | 11.0 |
| 3989 | CS2 | 6.0 | 2.1 | 36.3 | 54.7 | 0.9 | 8.1 |
| 3989 | CS2 | 9.2 | 1.7 | 30.1 | 58.5 | 0.6 | 10.8 |
| 3989 | CS2 | 7.9 | 1.5 | 37.2 | 52.5 | 0.9 | 9.4 |
| 3989 | CS2 | 7.5 | 1.5 | 31.7 | 58.5 | 0.8 | 9.0 |
| 3989 | CS2 | 6.1 | 1.4 | 34.2 | 57.5 | 0.8 | 7.5 |
| 3989 | CS2 | 8.6 | 1.4 | 35.2 | 53.7 | 1.1 | 10.0 |
| 3989 | CS2 | 8.8 | 1.5 | 30.1 | 59.1 | 0.6 | 10.3 |
| 3989 | CS2 | 6.4 | 1.6 | 38.0 | 53.1 | 1.0 | 8.0 |
| 3989 | CS2 | 7.8 | 1.3 | 32.8 | 57.2 | 0.9 | 9.1 |
| 3989 | CS2 | 6.2 | 3.0 | 57.0 | 32.7 | 1.1 | 9.2 |
| 3989 | Mean | 7.4 | 1.4 | 33.9 | 56.3 | 0.8 | 9.0 |
| 4014 | CS2 | 7.3 | 2.5 | 46.5 | 42.8 | 1.0 | 9.7 |
| 4014 | CS2 | 6.3 | 2.6 | 55.5 | 34.5 | 1.1 | 8.9 |
| 4014 | CS2 | 6.3 | 2.9 | 54.2 | 35.5 | 1.1 | 9.2 |
| 4014 | CS2 | 6.1 | 3.0 | 55.2 | 34.6 | 1.1 | 9.1 |
| 4014 | CS2 | 6.1 | 2.7 | 55.4 | 34.7 | 1.1 | 8.8 |
| 4014 | CS2 | 6.8 | 3.1 | 52.0 | 37.0 | 1.1 | 9.9 |
| 4014 | CS2 | 6.7 | 2.8 | 50.6 | 38.9 | 1.0 | 9.5 |
| 4014 | CS2 | 6.2 | 3.8 | 54.7 | 34.3 | 1.0 | 10.0 |
| 4014 | CS2 | 6.1 | 3.1 | 57.1 | 32.6 | 1.2 | 9.2 |
| 4014 | CS2 | 5.9 | 2.8 | 39.1 | 50.8 | 1.5 | 8.7 |
| 4014 | Mean | 6.4 | 3.0 | 53.8 | 35.7 | 1.1 | 9.4 |
| 4018 | CS2 | 7.6 | 1.6 | 32.3 | 57.1 | 1.4 | 9.2 |
| 4018 | CS2 | 5.2 | 1.6 | 34.4 | 56.7 | 2.1 | 6.8 |
| 4018 | CS2 | 5.5 | 1.6 | 37.8 | 53.8 | 1.4 | 7.1 |
| 4018 | CS2 | 11.5 | 2.9 | 26.1 | 53.3 | 6.2 | 14.4 |
| 4018 | CS2 | 5.6 | 2.3 | 35.8 | 54.9 | 1.3 | 8.0 |
| 4018 | CS2 | 11.6 | 0.0 | 32.1 | 51.3 | 5.0 | 11.6 |
| 4018 | CS2 | 6.6 | 1.6 | 40.8 | 49.7 | 1.4 | 8.2 |
| 4018 | CS2 | 8.4 | 1.9 | 31.2 | 57.0 | 1.5 | 10.2 |
| 4018 | CS2 | 7.6 | 1.7 | 30.2 | 59.1 | 1.4 | 9.3 |
| 4018 | CS2 | 8.5 | 1.7 | 44.4 | 44.2 | 1.2 | 10.2 |
| 4018 | Mean | 7.5 | 1.8 | 34.0 | 54.4 | 2.3 | 9.3 |
| 4023 | CS2 | 7.7 | 2.0 | 50.3 | 39.0 | 1.1 | 9.7 |
| 4023 | CS2 | 6.7 | 1.7 | 46.1 | 44.6 | 0.9 | 8.4 |
| 4023 | CS2 | 5.9 | 1.7 | 52.4 | 39.0 | 1.0 | 7.6 |
| 4023 | CS2 | 6.9 | 1.4 | 37.4 | 45.1 | 9.2 | 8.3 |
| 4023 | CS2 | 9.1 | 2.2 | 47.4 | 40.1 | 1.3 | 11.3 |
| 4023 | CS2 | 7.6 | 1.5 | 37.6 | 51.9 | 1.5 | 9.1 |
| 4023 | CS2 | 7.3 | 1.9 | 41.5 | 48.0 | 1.4 | 9.2 |
| 4023 | CS2 | 7.7 | 1.9 | 50.6 | 38.8 | 1.1 | 9.5 |
| 4023 | CS2 | 7.9 | 2.1 | 58.3 | 30.9 | 1.0 | 9.9 |
| 4023 | CS2 | 8.4 | 1.1 | 27.4 | 61.9 | 1.3 | 9.5 |
| 4023 | Mean | 7.5 | 1.8 | 46.6 | 42.2 | 2.0 | 9.3 |
| 4032 | CS2 | 9.2 | 1.4 | 28.6 | 59.3 | 1.5 | 10.6 |
| 4032 | CS2 | 6.3 | 1.2 | 25.6 | 65.7 | 1.3 | 7.5 |
| 4032 | CS2 | 8.2 | 1.5 | 25.9 | 62.8 | 1.6 | 9.7 |
| 4032 | CS2 | 8.6 | 1.3 | 26.7 | 62.2 | 1.3 | 9.9 |
| 4032 | CS2 | 8.2 | 1.2 | 24.2 | 65.0 | 1.4 | 9.4 |

TABLE 24-continued

GC Data for lines selected for the invention disclosure.

| GC # | Category | Palmitic | Stearic | Oleic | Linoleic | Linolenic | Saturates |
|---|---|---|---|---|---|---|---|
| 4032 | CS2 | 7.9 | 1.0 | 28.7 | 61.2 | 1.2 | 8.9 |
| 4032 | CS2 | 8.1 | 1.3 | 24.8 | 64.0 | 1.9 | 9.3 |
| 4032 | CS2 | 5.2 | 1.6 | 32.2 | 59.9 | 1.1 | 6.7 |
| 4032 | Mean | 8.1 | 1.2 | 26.5 | 62.8 | 1.4 | 9.3 |
| 4039 | CS2 | 7.4 | 2.1 | 33.0 | 56.5 | 1.1 | 9.4 |
| 4039 | CS2 | 8.2 | 1.8 | 28.4 | 60.4 | 1.2 | 10.0 |
| 4039 | CS2 | 8.6 | 1.8 | 32.2 | 56.3 | 1.2 | 10.4 |
| 4039 | CS2 | 7.6 | 2.1 | 31.0 | 58.0 | 1.3 | 9.7 |
| 4039 | CS2 | 7.8 | 1.6 | 24.9 | 64.5 | 1.2 | 9.4 |
| 4039 | CS2 | 9.2 | 1.7 | 31.0 | 56.7 | 1.3 | 11.0 |
| 4039 | CS2 | 6.1 | 1.8 | 31.6 | 59.4 | 1.2 | 7.9 |
| 4039 | CS2 | 8.0 | 1.7 | 26.4 | 62.4 | 1.5 | 9.7 |
| 4039 | CS2 | 8.2 | 2.1 | 30.2 | 58.6 | 1.0 | 10.2 |
| 4039 | CS2 | 12.2 | 2.5 | 38.7 | 46.0 | 0.6 | 14.7 |
| 4039 | Mean | 7.6 | 1.8 | 30.1 | 59.3 | 1.2 | 9.4 |
| 4050 | CS2 | 12.1 | 2.7 | 40.1 | 44.6 | 0.6 | 14.8 |
| 4050 | CS2 | 11.7 | 2.5 | 38.8 | 46.6 | 0.5 | 14.2 |
| 4050 | CS2 | 11.9 | 2.7 | 42.9 | 42.1 | 0.5 | 14.6 |
| 4050 | CS2 | 12.1 | 2.3 | 42.2 | 42.8 | 0.6 | 14.4 |
| 4050 | CS2 | 11.3 | 2.1 | 43.8 | 42.2 | 0.6 | 13.4 |
| 4050 | CS2 | 12.7 | 2.1 | 38.0 | 46.3 | 0.9 | 14.8 |
| 4050 | CS2 | 13.3 | 3.5 | 31.1 | 49.7 | 2.3 | 16.8 |
| 4050 | CS2 | 12.8 | 3.4 | 33.0 | 47.6 | 3.3 | 16.1 |
| 4050 | CS2 | 12.4 | 2.3 | 40.8 | 43.9 | 0.6 | 14.7 |
| 4050 | CS2 | 12.9 | 3.0 | 37.4 | 46.2 | 0.6 | 15.8 |
| 4050 | Mean | 12.2 | 2.6 | 38.9 | 45.2 | 1.0 | 14.8 |
| 4075 | CS2 | 13.4 | 3.4 | 35.9 | 46.9 | 0.4 | 16.8 |
| 4075 | CS2 | 13.1 | 3.0 | 34.5 | 48.8 | 0.5 | 16.2 |
| 4075 | CS2 | 12.6 | 3.7 | 36.6 | 46.5 | 0.6 | 16.2 |
| 4075 | CS2 | 12.5 | 3.4 | 35.5 | 48.2 | 0.5 | 15.9 |
| 4075 | CS2 | 13.3 | 2.5 | 36.7 | 46.9 | 0.6 | 15.8 |
| 4075 | CS2 | 13.1 | 3.2 | 33.5 | 49.6 | 0.7 | 16.3 |
| 4075 | CS2 | 13.5 | 3.0 | 36.2 | 46.9 | 0.5 | 16.5 |
| 4075 | CS2 | 12.8 | 3.3 | 37.5 | 45.9 | 0.6 | 16.0 |
| 4075 | CS2 | 12.7 | 3.4 | 35.8 | 47.6 | 0.6 | 16.0 |
| 4075 | CS2 | 13.0 | 2.6 | 39.1 | 44.8 | 0.6 | 15.6 |
| 4075 | Mean | 13.0 | 3.2 | 35.9 | 47.4 | 0.6 | 16.1 |
| 4077 | CS2 | 13.1 | 3.3 | 33.3 | 49.7 | 0.6 | 16.5 |
| 4077 | CS2 | 13.8 | 1.8 | 37.6 | 46.1 | 0.6 | 15.7 |
| 4077 | CS2 | 13.6 | 2.6 | 36.8 | 46.6 | 0.5 | 16.1 |
| 4077 | CS2 | 13.8 | 3.0 | 35.6 | 46.9 | 0.7 | 16.9 |
| 4077 | CS2 | 13.3 | 2.9 | 35.9 | 47.4 | 0.5 | 16.2 |
| 4077 | CS2 | 14.3 | 2.0 | 34.3 | 48.7 | 0.7 | 16.3 |
| 4077 | CS2 | 13.0 | 2.8 | 38.7 | 45.1 | 0.5 | 15.8 |
| 4077 | CS2 | 12.6 | 2.6 | 37.2 | 47.2 | 0.4 | 15.2 |
| 4077 | CS2 | 12.4 | 2.9 | 42.6 | 41.7 | 0.5 | 15.2 |
| 4077 | S3 | 12.4 | 1.9 | 28.3 | 56.8 | 0.7 | 14.3 |
| 4077 | Mean | 13.3 | 2.6 | 37.1 | 46.4 | 0.6 | 15.9 |
| 4078 | S3 | 12.3 | 2.0 | 38.1 | 47.1 | 0.5 | 14.3 |
| 4078 | S3 | 11.4 | 2.7 | 45.9 | 39.2 | 0.8 | 14.1 |
| 4078 | S3 | 11.4 | 3.1 | 48.8 | 36.2 | 0.6 | 14.5 |
| 4078 | S3 | 11.3 | 2.3 | 49.2 | 36.4 | 0.8 | 13.7 |
| 4078 | S3 | 12.0 | 2.6 | 35.0 | 49.6 | 0.9 | 14.5 |
| 4078 | S3 | 12.0 | 2.3 | 41.7 | 43.2 | 0.8 | 14.3 |
| 4078 | S3 | 10.7 | 3.0 | 53.1 | 32.4 | 0.8 | 13.7 |
| 4078 | S3 | 11.4 | 2.1 | 41.3 | 44.3 | 0.8 | 13.6 |
| 4078 | S3 | 11.5 | 2.9 | 49.5 | 35.4 | 0.7 | 14.4 |
| 4078 | S3 | 6.4 | 2.0 | 46.7 | 44.1 | 0.8 | 8.4 |
| 4078 | Mean | 11.7 | 2.5 | 43.1 | 42.0 | 0.7 | 14.1 |
| 4083 | S3 | 6.4 | 2.6 | 42.1 | 48.0 | 1.0 | 9.0 |
| 4083 | S3 | 11.6 | 2.2 | 43.9 | 41.4 | 0.9 | 13.8 |
| 4083 | S3 | 8.5 | 2.4 | 46.8 | 41.6 | 0.8 | 10.9 |
| 4083 | S3 | 7.1 | 1.6 | 44.0 | 46.5 | 0.9 | 8.6 |
| 4083 | S3 | 6.6 | 2.5 | 46.8 | 43.3 | 0.8 | 9.1 |
| 4083 | S3 | 12.0 | 1.7 | 41.1 | 44.5 | 0.7 | 13.8 |
| 4083 | S3 | 9.3 | 2.7 | 40.1 | 47.2 | 0.8 | 12.0 |
| 4083 | S3 | 12.0 | 2.0 | 39.1 | 46.2 | 0.7 | 14.0 |
| 4083 | S3 | 12.3 | 1.9 | 38.8 | 46.1 | 0.8 | 14.2 |
| 4083 | S3 | 15.1 | 3.5 | 32.2 | 48.5 | 0.7 | 18.6 |
| 4083 | Mean | 9.2 | 2.2 | 42.9 | 44.9 | 0.8 | 11.4 |
| 4086 | S3 | 15.7 | 2.8 | 32.7 | 48.3 | 0.6 | 18.5 |
| 4086 | S3 | 16.0 | 3.6 | 31.0 | 48.5 | 0.9 | 19.6 |
| 4086 | S3 | 15.5 | 2.6 | 32.5 | 48.5 | 0.8 | 18.2 |
| 4086 | S3 | 15.4 | 2.7 | 32.0 | 49.0 | 0.8 | 18.1 |
| 4086 | S3 | 15.1 | 2.1 | 32.2 | 49.7 | 0.9 | 17.1 |

TABLE 24-continued

GC Data for lines selected for the invention disclosure.

| GC # | Category | Palmitic | Stearic | Oleic | Linoleic | Linolenic | Saturates |
|------|----------|----------|---------|-------|----------|-----------|-----------|
| 4086 | S3 | 15.6 | 2.8 | 31.6 | 49.2 | 0.8 | 18.5 |
| 4086 | S3 | 14.9 | 2.4 | 33.7 | 48.3 | 0.8 | 17.3 |
| 4086 | S3 | 15.2 | 2.2 | 33.4 | 48.5 | 0.7 | 17.5 |
| 4086 | S3 | 14.9 | 2.5 | 33.5 | 48.2 | 0.9 | 17.5 |
| 4086 | S3 | 15.2 | 4.9 | 33.2 | 46.1 | 0.6 | 20.2 |
| 4086 | Mean | 15.3 | 2.7 | 32.5 | 48.7 | 0.8 | 18.1 |
| 4090 | S3 | 16.0 | 5.5 | 31.7 | 46.2 | 0.6 | 21.5 |
| 4090 | S3 | 15.1 | 5.2 | 33.1 | 46.0 | 0.6 | 20.3 |
| 4090 | S3 | 15.4 | 5.5 | 32.1 | 46.4 | 0.6 | 20.9 |
| 4090 | S3 | 15.8 | 4.9 | 29.6 | 49.0 | 0.7 | 20.7 |
| 4090 | S3 | 15.8 | 5.4 | 33.0 | 45.2 | 0.6 | 21.2 |
| 4090 | S3 | 14.9 | 4.7 | 32.9 | 47.0 | 0.5 | 19.6 |
| 4090 | S3 | 14.6 | 4.6 | 33.2 | 46.6 | 0.9 | 19.2 |
| 4090 | S3 | 15.4 | 5.3 | 31.7 | 46.9 | 0.7 | 20.7 |
| 4090 | S3 | 15.9 | 5.4 | 30.3 | 47.7 | 0.6 | 21.3 |
| 4090 | S3 | 14.6 | 3.7 | 31.5 | 49.2 | 1.0 | 18.3 |
| 4090 | Mean | 15.4 | 5.1 | 32.1 | 46.7 | 0.6 | 20.6 |
| 4102 | S3 | 15.2 | 2.4 | 27.4 | 53.0 | 1.9 | 17.6 |
| 4102 | S3 | 14.7 | 2.8 | 29.3 | 51.6 | 1.7 | 17.4 |
| 4102 | S3 | 14.8 | 3.6 | 32.2 | 47.9 | 1.5 | 18.5 |
| 4102 | S3 | 14.8 | 2.5 | 29.9 | 50.9 | 1.8 | 17.3 |
| 4102 | S3 | 15.5 | 3.2 | 28.5 | 51.4 | 1.4 | 18.7 |
| 4102 | S3 | 14.3 | 3.2 | 29.8 | 51.4 | 1.2 | 17.5 |
| 4102 | S3 | 15.4 | 3.3 | 29.3 | 50.8 | 1.1 | 18.7 |
| 4102 | S3 | 16.1 | 3.2 | 27.6 | 51.8 | 1.3 | 19.2 |
| 4102 | S3 | 14.1 | 2.7 | 30.2 | 51.7 | 1.3 | 16.7 |
| 4102 | S3 | 13.7 | 2.5 | 32.5 | 50.6 | 0.8 | 16.2 |
| 4102 | Mean | 14.9 | 3.1 | 29.6 | 51.0 | 1.4 | 18.0 |
| 4107 | S3 | 15.0 | 4.1 | 41.1 | 39.0 | 0.8 | 19.1 |
| 4107 | S3 | 12.4 | 2.5 | 32.2 | 51.7 | 1.1 | 15.0 |
| 4107 | S3 | 11.2 | 2.9 | 34.2 | 51.1 | 0.6 | 14.1 |
| 4107 | S3 | 14.1 | 3.7 | 36.6 | 45.1 | 0.6 | 17.8 |
| 4107 | S3 | 14.3 | 2.6 | 35.0 | 47.3 | 0.9 | 16.8 |
| 4107 | S3 | 14.7 | 2.4 | 30.5 | 51.7 | 0.7 | 17.1 |
| 4107 | S3 | 11.5 | 2.2 | 32.2 | 53.3 | 0.9 | 13.7 |
| 4107 | S3 | 15.2 | 3.3 | 34.7 | 46.2 | 0.7 | 18.4 |
| 4107 | S3 | 12.9 | 2.1 | 33.9 | 50.1 | 1.1 | 14.9 |
| 4107 | S3 | 15.4 | 3.0 | 30.5 | 50.0 | 1.1 | 18.4 |
| 4107 | Mean | 13.5 | 2.8 | 34.3 | 48.6 | 0.8 | 16.3 |
| 4119 | S3 | 14.7 | 3.3 | 33.2 | 47.8 | 1.1 | 18.0 |
| 4119 | S3 | 15.1 | 3.0 | 29.1 | 51.8 | 1.0 | 18.1 |
| 4119 | S3 | 15.0 | 3.2 | 30.4 | 50.2 | 1.2 | 18.2 |
| 4119 | S3 | 14.2 | 2.9 | 38.2 | 44.1 | 0.7 | 17.1 |
| 4119 | S3 | 15.5 | 3.3 | 29.9 | 50.1 | 1.2 | 18.8 |
| 4119 | S3 | 13.1 | 2.3 | 39.9 | 43.3 | 1.5 | 15.4 |
| 4119 | S3 | 14.5 | 3.0 | 34.6 | 46.9 | 1.0 | 17.5 |
| 4119 | S3 | 13.2 | 3.2 | 41.1 | 41.5 | 1.0 | 16.4 |
| 4119 | S3 | 14.2 | 3.1 | 29.7 | 52.0 | 1.1 | 17.3 |
| 4119 | S3 | 10.0 | 3.2 | 41.9 | 44.0 | 1.0 | 13.2 |
| 4119 | Mean | 14.5 | 3.0 | 33.6 | 47.8 | 1.1 | 17.5 |
| 4129 | S3 | 9.4 | 3.8 | 44.6 | 41.3 | 0.9 | 13.3 |
| 4129 | S3 | 9.6 | 3.2 | 40.0 | 46.2 | 1.1 | 12.8 |
| 4129 | S3 | 9.7 | 3.5 | 42.6 | 43.2 | 0.9 | 13.2 |
| 4129 | S3 | 10.6 | 3.5 | 42.1 | 42.7 | 1.1 | 14.1 |
| 4129 | S3 | 9.6 | 3.6 | 43.2 | 42.6 | 0.9 | 13.3 |
| 4129 | S3 | 9.4 | 3.5 | 43.0 | 43.1 | 1.0 | 13.0 |
| 4129 | S3 | 9.5 | 3.4 | 41.4 | 44.8 | 0.9 | 12.9 |
| 4129 | S3 | 10.1 | 3.2 | 38.1 | 47.5 | 1.1 | 13.3 |
| 4129 | S3 | 9.5 | 3.7 | 44.0 | 41.8 | 1.0 | 13.2 |
| 4129 | S3 | 9.9 | 3.7 | 39.4 | 46.1 | 0.9 | 13.6 |
| 4129 | Mean | 9.8 | 3.5 | 42.1 | 43.7 | 1.0 | 13.2 |
| 4146 | S3 | 10.1 | 3.6 | 39.9 | 45.6 | 0.8 | 13.7 |
| 4146 | S3 | 10.0 | 3.6 | 38.7 | 46.8 | 0.9 | 13.5 |
| 4146 | S3 | 10.2 | 3.4 | 39.4 | 46.2 | 0.9 | 13.6 |
| 4146 | S3 | 10.1 | 3.6 | 38.6 | 46.8 | 0.9 | 13.7 |
| 4146 | S3 | 10.2 | 3.6 | 39.1 | 46.3 | 0.8 | 13.8 |
| 4146 | S3 | 10.1 | 4.0 | 40.6 | 44.5 | 0.8 | 14.1 |
| 4146 | S3 | 11.5 | 3.8 | 41.9 | 41.5 | 1.3 | 15.3 |
| 4146 | S3 | 10.0 | 3.6 | 39.1 | 46.5 | 0.9 | 13.6 |
| 4146 | S3 | 10.0 | 3.8 | 39.3 | 45.9 | 0.9 | 13.9 |
| 4146 | S3 | 11.6 | 4.1 | 38.5 | 45.0 | 0.9 | 15.6 |
| 4146 | Mean | 10.2 | 3.7 | 39.6 | 45.6 | 0.9 | 13.9 |
| 4152 | S3 | 11.8 | 4.0 | 38.2 | 45.1 | 0.9 | 15.8 |
| 4152 | S3 | 11.8 | 4.2 | 39.5 | 43.7 | 0.9 | 16.0 |
| 4152 | S3 | 12.0 | 4.2 | 37.5 | 45.4 | 1.0 | 16.2 |

TABLE 24-continued

GC Data for lines selected for the invention disclosure.

| GC # | Category | Palmitic | Stearic | Oleic | Linoleic | Linolenic | Saturates |
|---|---|---|---|---|---|---|---|
| 4152 | S3 | 11.4 | 3.8 | 37.9 | 46.0 | 1.0 | 15.2 |
| 4152 | S3 | 11.7 | 4.2 | 37.8 | 45.3 | 1.0 | 15.9 |
| 4152 | S3 | 11.7 | 3.9 | 38.6 | 45.0 | 0.9 | 15.5 |
| 4152 | S3 | 11.9 | 4.0 | 36.2 | 47.1 | 0.9 | 15.8 |
| 4152 | S3 | 11.5 | 3.9 | 37.2 | 46.5 | 0.9 | 15.4 |
| 4152 | S3 | 11.3 | 3.8 | 37.2 | 46.8 | 0.9 | 15.1 |
| 4152 | S3 | 12.1 | 3.3 | 37.1 | 46.6 | 0.9 | 15.4 |
| 4152 | Mean | 11.6 | 4.0 | 37.8 | 45.6 | 0.9 | 15.7 |
| 4159 | S3 | 10.2 | 3.1 | 36.0 | 49.9 | 0.9 | 13.3 |
| 4159 | S3 | 10.8 | 3.0 | 36.0 | 49.3 | 0.9 | 13.8 |
| 4159 | S3 | 13.0 | 2.8 | 36.0 | 47.3 | 0.8 | 15.8 |
| 4159 | S3 | 10.7 | 3.5 | 37.3 | 47.6 | 0.9 | 14.2 |
| 4159 | S3 | 10.5 | 3.5 | 38.0 | 47.2 | 0.9 | 13.9 |
| 4159 | S3 | 13.0 | 2.9 | 38.0 | 45.3 | 0.9 | 15.9 |
| 4159 | S3 | 15.0 | 2.7 | 35.1 | 46.3 | 0.9 | 17.7 |
| 4159 | S3 | 12.9 | 2.9 | 35.7 | 47.7 | 0.8 | 15.8 |
| 4159 | S3 | 12.7 | 3.0 | 36.4 | 47.2 | 0.8 | 15.6 |
| 4159 | S3 | 12.7 | 3.0 | 36.4 | 47.2 | 0.8 | 15.6 |
| 4159 | Mean | 12.1 | 3.0 | 36.5 | 47.5 | 0.9 | 15.2 |

Key to Category Symbols:
BC1S2 = Lines from recovered introgressed material backcrossed to the Corn-Belt inbred parents, the progeny were selfed twice.
CS2 = Lines from crosses of recovered introgressed material and Corn-Belt inbred parents, the progeny were selfed twice.
S3 = Recovered introgressed lines selfed three generations.

ALTERED STARCH CORN LINES

As used herein, Corn Belt lines are typically inbred lines whose F1 hybrids are used to produce "dent" corn seeds (also commonly called "field corn"), which have an indentation in the top of the kernel at maturity. Commercial, agricultural or industrial production of Corn Belt corn is typically grown from F1 hybrids of two distinct inbred lines, each of which can trace its pedigree to open-pollinated varieties which resulted from an intentional or an accidental cross between varieties of the Southern Dent and the Northern Flint races. Such corn is commonly used in industrial applications such as production of corn starch. In other embodiments, other corn lines, such as popcorn and sweet corn lines, are introgressed with Tripsacum genetic material, and the resulting seeds are selected for selected compositions of starch content and, in some embodiments, for other characteristics (such as yield, stalk strength, and pest resistance).

Measurement of Starch Function With Differential Scanning Calorimetry

Starch represents up to approximately 70% or more of the dry weight of the mature corn kernel and is the most economically important component for many varieties. Therefore, it is essential to determine the endosperm variation and starch function of the seeds for some embodiments of the present invention. The process used in one embodiment of the present invention has two steps. The first step is the extraction of the starch from the endosperm using a modified mini wet mill procedure. In one such embodiment, the kernels are steeped in a solution of sodium metabisulfite in water for 48 hours in a 50° C. water bath. The kernels are manually de-germed, and the pericarp removed and discarded. The kernels are ground using a Tekmar tissuemiser (or tissue tearer/grinder) with water. The slurry is filtered through a 32-micron nylon mesh. The filtrate is allowed to settle for 2 hours at 4° C., the upper phase is decanted and discarded. The remaining starch is washed with water, settled, and decanted for a total of four times. The starch is then air dried.

The second step evaluates the starch function by measuring the starch gelatinization properties with the differential scanning calorimeter (DSC). The DSC allows direct measurement of the energy required to cook or gelatinize starch. The gelatinized samples are held for a week in a refrigerator and re-scanned to determine the amount of retrogradation or recrystallization and hence the stability of the starch gel.

Differential scanning calorimetry (DSC) is used to determine starch thermal properties. Numerous studies have demonstrated the strong influence on starch properties of the corn genetic background, and the relationships between starch structure and function.

The DSC data can be directly related to the starch thermal characteristics desired by the industry. The most important values obtained by DSC gelatinization include peak onset temperature, enthalpy, range of gelatinization, and peak height index. A second set of DSC values is obtained by re-scanning an original gelatinized sample after storage for seven days at 4° C. These re-scans give values for DSC retrogradation, the most important ones being enthalpy and, more importantly, percentage of retrogradation. Several studies have examined how thermal properties, as measured by DSC, relate to structural and functional characteristics of the starch. Each of the DSC parameters reveals an important function, as noted in Table ST-1. These criteria have been formulated from many years of evaluating DSC data and from conversations with industry scientists.

Figure 2:
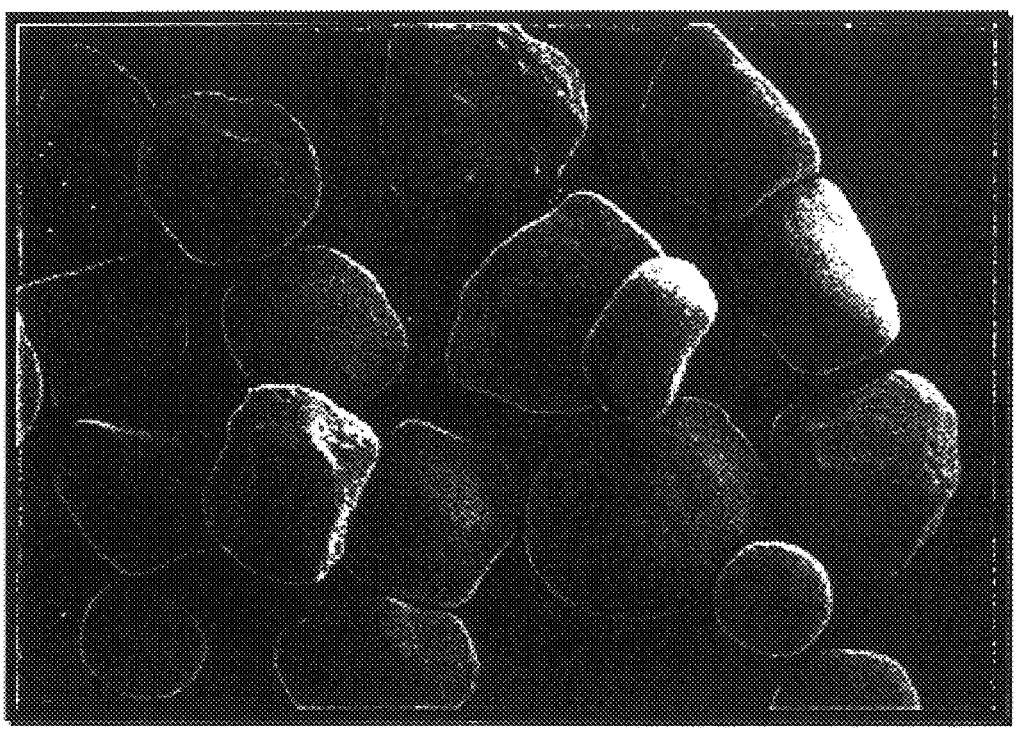
FIG. 2 is a electron microphotograph of normal corn starch granules (corn starch from Sigma).

FIG. 2 is a electron microphotograph of normal corn starch granules (corn starch from Sigma). Note that the granules are moderately angular, and rounded. The population is heterogeneous for shape and size.

Figure 3:
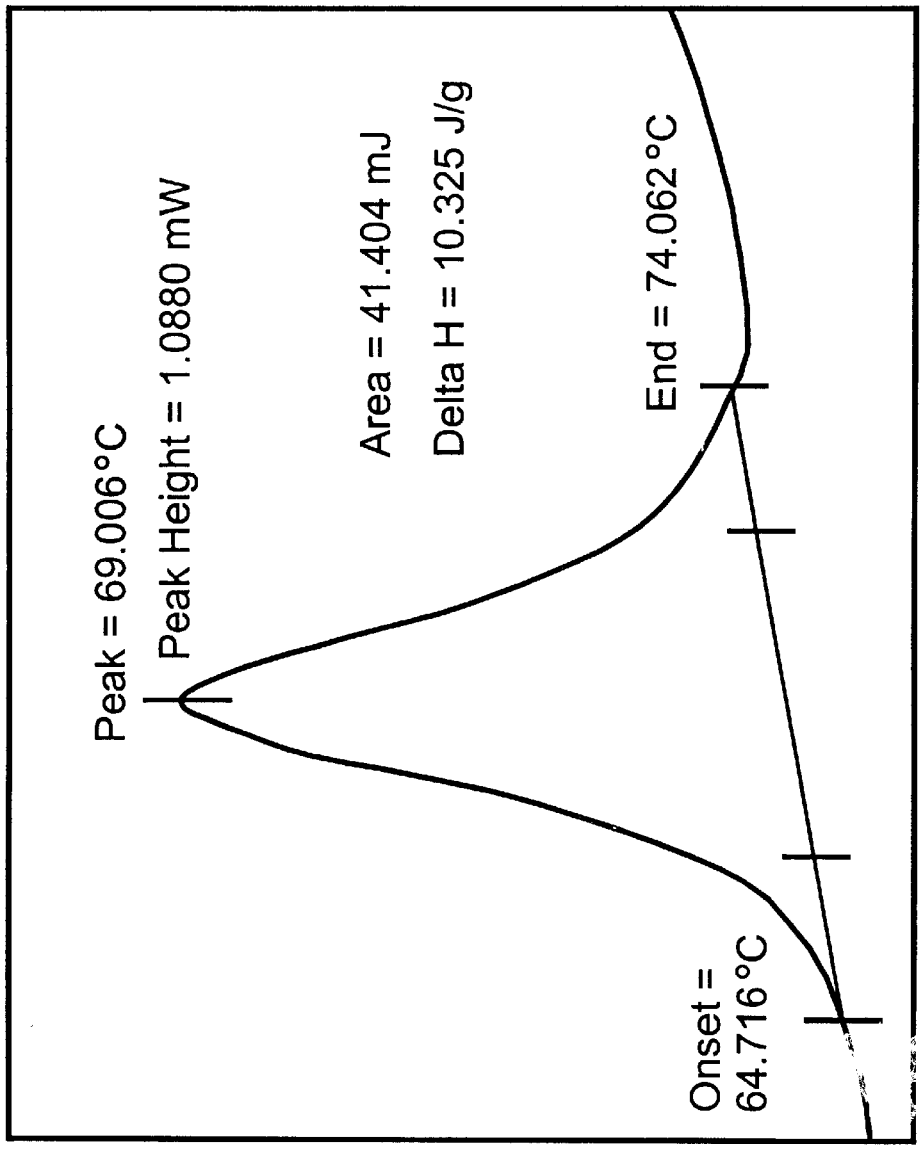
FIG. 3 is a DSC thermograph of normal corn starch granules (starch from Sigma).
Figure 4:
FIG. 4 is a electron microphotograph of corn starch granules from introgressed corn of the present invention (GC#1322 variety).

FIG. 3 is a DSC thermograph of normal corn starch granules (starch from Sigma). The peak is moderately rounded, and broader than the narrow peaks of the FIG. 4 is a electron microphotograph of corn starch granules from introgressed corn of the present invention (GC#1322 variety). The population is very heterogeneous for size and shape, with angular granules.

Figure 5:
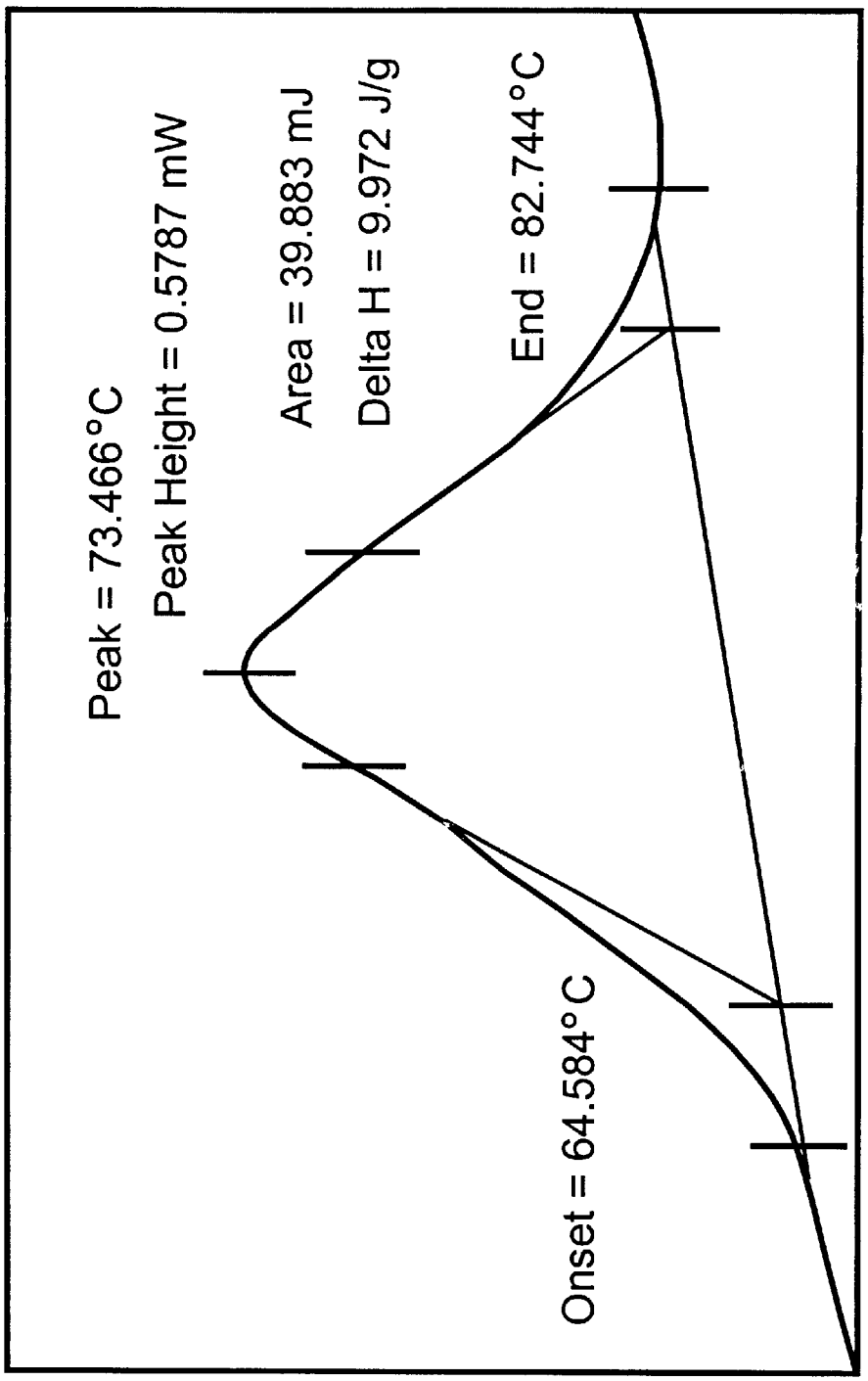
FIG. 5 is a DSC thermograph of corn starch granules from introgressed corn of the present invention (GC#1322 variety).

FIG. 5 is a DSC thermograph of corn starch granules from introgressed corn of the present invention (GC#1322 variety). The peak is quite broad and rounded, and broader than the normal corn starch of FIG. 3.

Figure 6:
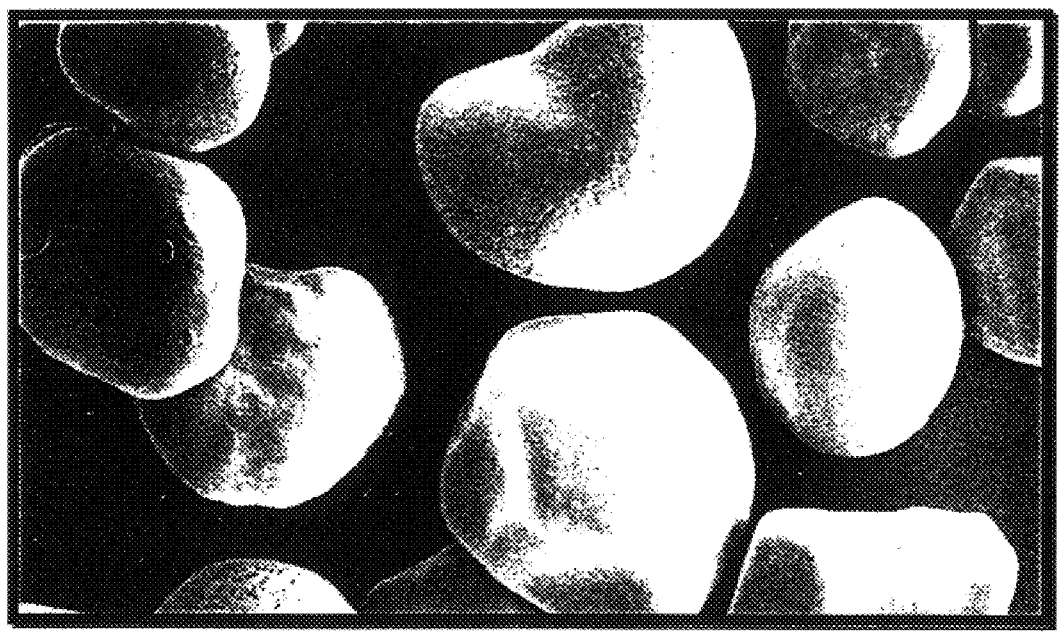
FIG. 6 is a electron microphotograph of corn starch granules from introgressed corn of the present invention (GC#1292 variety).

FIG. 6 is a electron microphotograph of corn starch granules from introgressed corn of the present invention (GC#1292 variety). The population is homogeneous for size and shape.

Figure 7:
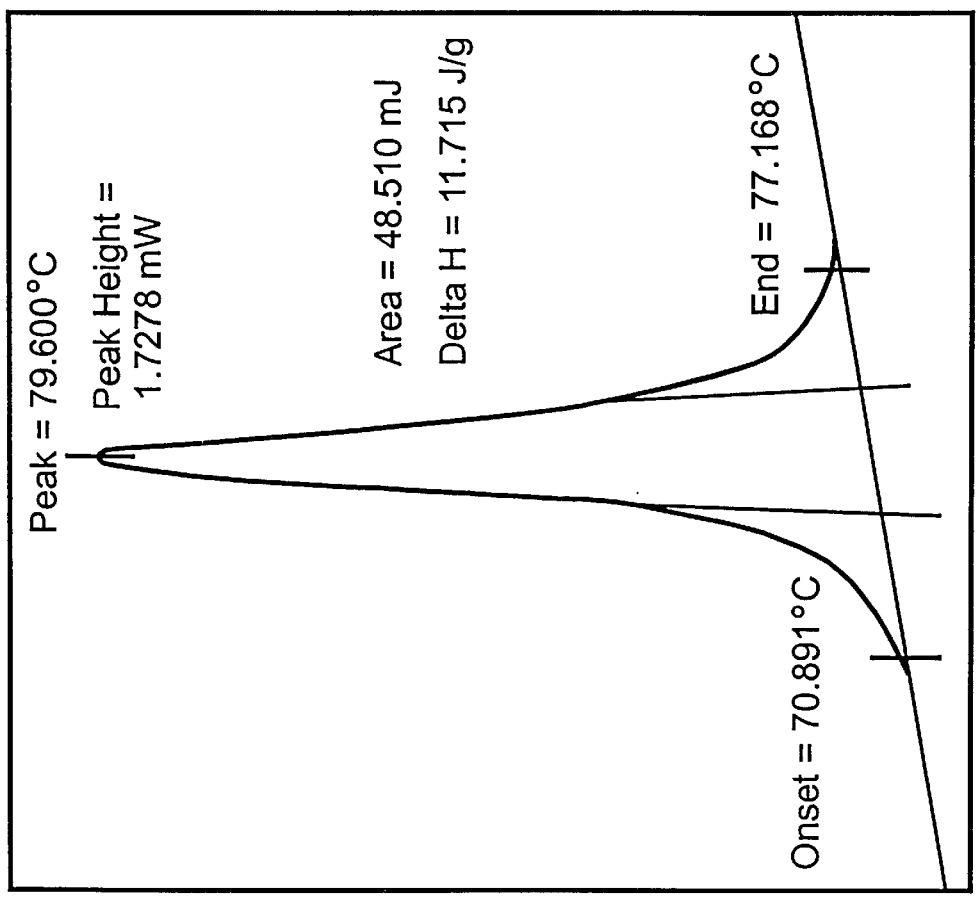
FIG. 7 is a DSC thermograph of corn starch granules from introgressed corn of the present invention (GC#1292 variety).

FIG. 7 is a DSC thermograph of corn starch granules from introgressed corn of the present invention (GC#1292 variety). The peak is quite narrow and defined, and a sharper peak than the normal corn starch of FIG. 3.

Figure 8:
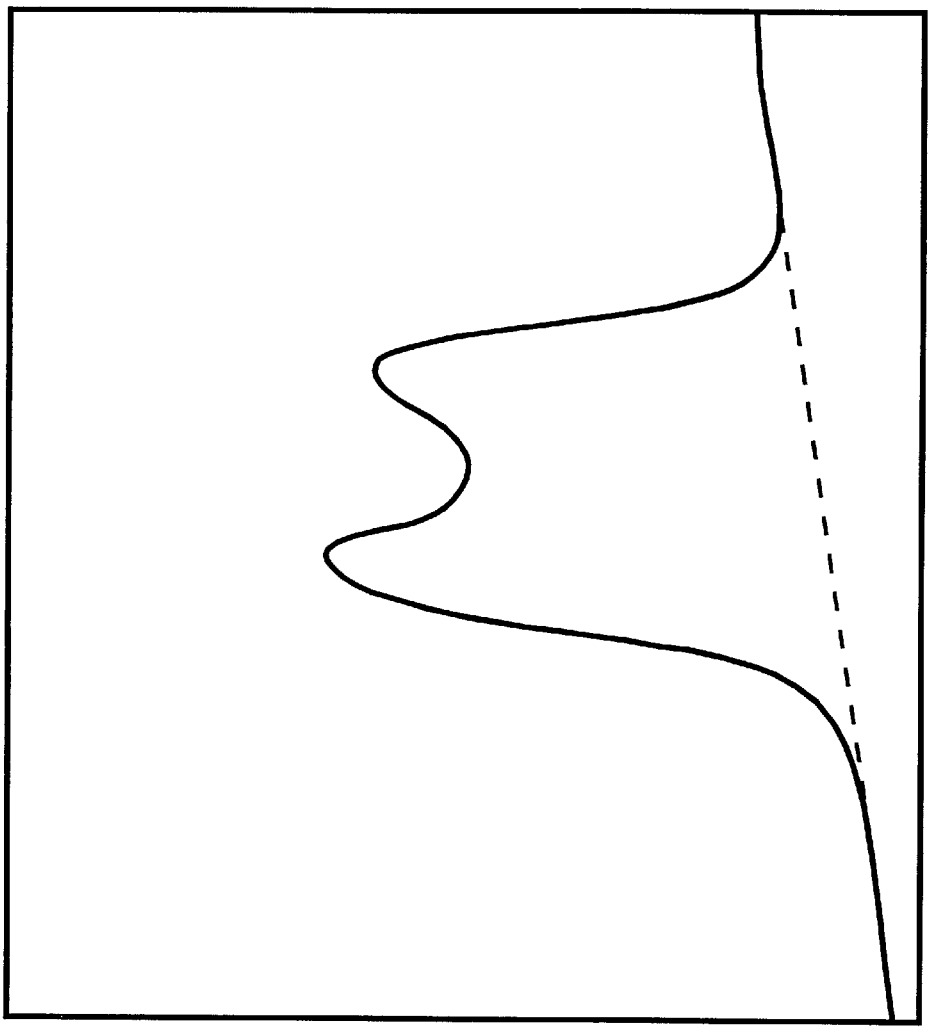
FIG. 8 is a representation of a DSC thermograph of corn starch granules of the present invention and having multiple peaks.

FIG. 8 is a representation of a DSC thermograph of corn starch granules of the present invention and having multiple peaks. This starch would gel at two different temperatures, allowing setting of fruit into place at the lower temperature, and then additional cooking at the higher temperature.

TABLE ST-1

| DSC Parameter | Desired Characteristic[a] | Products |
|---|---|---|
| Peak Onset of gelatinization | Low value means less energy required in a starch cooking process. Target value is <60° C. | Puddings, sauces, gravies, pie fillings |
| Enthalpy of gelatinization | Low value means less energy required in a starch cooking process. Target low value is <2.5 cal/g | products where high carbohydrate is desired but without much viscosity, e.g., baby foods, high-carb drinks, athletic foods |
| | High value means extensive thickening power. Target high value is >4.0 g/cal | Less total starch is needed for thickening. Good for low carbohydrate products needing thickening, or just lower cost of ingredients |
| Range of gelatinization | Low value means starch granules are likely from a homogeneous population. Starch cooking can occur quickly within a brief range. Target low value is <5° C. | thickening occurs quickly so that solids, such as fruit pieces can be held in place |
| | High value means starch granules are likely from a heterogeneous population. Starch cooking occurs over a wide temperature range. Target high value is >15°C. | thickening occurs slowly so that adequate mixing of ingredients and cooking of other components can take place |
| Peak height index (Enthalpy/ 0.5 × range) | High value means the thermogram has a tall narrow peak, which suggests high thickening power within a narrow temperature range. Target value is >1.2 | Less total starch is needed for thickening. Good for low carbohydrate products needing thickening, or just lower cost of ingredients |
| Enthalpy of retrogradation | Low value means the starch is not subject to aligning and recrystallizing. Starch is likely stable in frozen and refrigerated products. Target value <1 cal/g | Canned, fresh or frozen puddings, gravies, sauces, frozen desserts, and specialty frozen products using starch |
| Percentage of retrogradation | Low value gives similar meaning as previous parameter. More information about the relation to the original Enthalpy is obtained. Target low value is <20% | Canned, fresh or frozen puddings, gravies, sauces, frozen desserts, and specialty frozen products using starch |
| | High value may indicate presence of resistant starch. Target high value is >80% | Starch can be added to or used in any starch-containing product to add fiber to the diet |
| Shape of the thermogram | Double or triple peaks suggest two or more different populations of starch granules. Starch cooking occurs over a wide temperature and may have multiple functions. Target: detection of more than one peak | thickening occurs slowly so that adequate mixing of ingredients and cooking of other components can take place |

[a]Under the following DSC operating conditions: Starch dry weight:water = 1:2.
Samples are gelatinized from 30° C. to 120° C. at 10° C./min, and re-scanned for retrogradation from 30° C. to 110° C. at 10° C./min after storage at 4° C. for 7 days.

Conventional Corn Belt lines of corn have a narrow range of starch composition. By introgressing Tripsacum genetic material, the starch composition can be altered. By then measuring various starch parameters, lines of corn of various embodiments are selected that have various starch compositions, having increased or decreased percentages of various starch components, and/or altered structures.

Table ST-2 identifies the lines of some embodiments of the present invention and their unique properties, which are not only significantly different from those found in starch from normal Corn Belt corn, but also are of significant potential interest to industry, for use as described in Table ST-1.

In various embodiments, the present invention provides seed, starch from such seed, and products made using such starch, wherein said starch has a peak onset temperature of gelatinization that is substantially lower than that of conventional Corn Belt lines. For instance, GC#187 and GC#109 listed in Table ST-2, in one embodiment are used in the production of novel microwave products, because of their low gelatinization enthalpies and they also have the added benefit of low (temperature) peak onsets. The present invention includes various different embodiments having peak onset temperature of gelatinization of approximately 65° C. or less, approximately 64° C. or less, approximately 63° C. or less, approximately 62° C. or less, approximately 61° C. or less, and approximately 60° C. or less.

In various embodiments, the present invention provides seed, starch from such seed, and products made using such starch, wherein said starch has a narrow temperature range of gelatinization. For instance, starch from GC#163 and GC#164, in one embodiment are used in the production of novel foods requiring rapid cooking within a narrow range, such as whole fruit sauces, to keep the fruit pieces intact during the heating process. The present invention includes various different embodiments having temperature range of gelatinization of approximately 10° C. or less, approximately 9° C. or less, approximately 8° C. or less, approximately 7° C. or less, approximately 6° C. or less, approximately 5° C. or less, and approximately 4° C. or less. The present invention also includes various different embodiments having temperature range of gelatinization of approximately 14° C. or more, approximately 15° C. or more, and approximately 16° C. or more.

In various embodiments, the present invention provides seed, starch from such seed, and products made using such starch, wherein said starch has a high enthalpy value. For instance, the high enthalpy value of gelatinization of starch from GC#163 and GC#164, in one embodiment are used in the production of novel products having high viscosity, with only a small amount of added starch. The benefits of this starch would be less cost for the thickener, plus reduced carbohydrate (and calorie) amounts, useful in some special dietary products, e.g., puddings, sauces, gravies, etc., and for such products for diabetic diets. The present invention includes various different embodiments having enthalpy of gelatinization of approximately 3.1 cal/g or more, approximately 3.2 cal/g or more, approximately 3.2 cal/g or more, approximately 3.4 cal/g or more, approximately 3.5 cal/g or more, and approximately 3.6 cal/g or more.

In various embodiments, the present invention provides seed, starch from such seed, and products made using such starch, wherein said starch has a low enthalpy value. For instance, the low enthalpy value of gelatinization of starch from GC#187 and GC#109, in one embodiment are used in the production of novel products having low viscosity, even with a large amount of added starch. The benefits of this starch would be increased carbohydrate (and calorie) amounts, useful in some special athletic products, e.g., sport drinks. The present invention includes various different embodiments having enthalpy of gelatinization of approximately 2.7 cal/g or less, approximately 2.6 cal/g or less, and approximately 2.5 cal/g or more.

In various embodiments, the present invention provides seed, starch from such seed, and products made using such starch, wherein said starch has a low percentage retrogradation. For example, the low % retrogradation of GC#182 indicates a starch that, once gelatinized, is stable in frozen or refrigerated products such as gravies, sauces, soups, puddings or frozen desserts. One embodiment of the present invention includes such starch. Other embodiments of the present invention include puddings, pie fillings, sauces, gravies, baby foods, soups, refrigerated deserts, toppings, or frozen desserts made using such starch. Such products also benefit from reduced retrogradation. The present invention includes various different embodiments having percentages of retrogradation of approximately 48% or less, approximately 47% or less, approximately 46% or less, approximately 45% or less, approximately 44% or less, approximately 43% or less, and approximately 42% or less.

One embodiment of the present invention provides a method of food preparation that includes preparing a food product by adding corn starch according to the present invention having a lower peak onset of gelatinization, and a cooking step performed at a temperature significantly lower than the temperature at which conventional starch requires.

In various embodiments, the present invention provides seed, starch from such seed, and products made using such starch, wherein said starch has a high percentage retrogradation. For example, the high % retrogradation of GC#109 indicates a resistant starch that, in some embodiments is used as a dry lubricant or dietary fiber for humans. High-retrograded starches are also used according to the present invention in preparing gelled candies such as formed shapes (e.g., similar to gummi bears, jujubes, and dots, etc.) The present invention includes embodiments having percentages of retrogradation of approximately 55% or greater, approximately 60% or greater, approximately 65% or greater, approximately 70% or greater, and approximately 72% or greater.

TABLE ST-2

Novel thermal characteristics in starch from corn introgressed with Tripsacum[a]

| | | DSC Parameter | | | | |
|---|---|---|---|---|---|---|
| Corn line | Peak onset (° C.) | Enthalpy of gelatinization (cal/g) | Range of gelatinization (° C.) | Peak Height Index | Enthalpy of retrogradation (cal/g) | % Retrogradation |
| Normal Corn Belt[b] | 66.4 | 2.9 | 12.0 | 0.5 | 1.5 | 50.7 |
| GC#187 | 60.0[c] | 2.6 | 16.0 | 0.3 | 1.7 | 65.0 |
| GC#109 | 63.6 | 2.5 | 13.2 | 0.4 | 1.8 | 72.2 |
| GC#163 | 67.6 | 3.5 | 7.4 | 1.0 | 2.0 | 57.8 |
| GC#164 | 68.7 | 3.6 | 4.9 | 1.5 | 2.1 | 57.6 |
| GC#182 | 64.1 | 3.1 | 10.8 | 0.6 | 1.3 | 42.7 |

[a]All corn was grown near Ames, IA. Thermal characteristics are parameters obtained from differential scanning calorimetry (DSC) under the conditions described in Table ST-1.
[b]Values are the average of starch from nine Corn Belt lines chosen to represent a wide range of variability of Corn Belt germplasm based on their pedigrees.
[c]Novel values are in bold italic.

Table W-1 shows average weights for a number of the starting genetic material (the recovered introgressed lines of Harlan DeWet Tripsacumxmaize material are #5S1, #20S1, #34S1 #69S1, #76S1, #91S1 and #92S1; the Corn Belt varieties measured are A632, B73, and Mo17). For each measurement, 100 seeds having a moisture content of 9.4% were weighed. From these measurements, an average weight (in grams per kernel) for a dry kernel of each type is calculated.

TABLE W-1

Seed Weight Table

| Seed Variety | g/100 Kernels | g/One Kernel | Dry weight Basis |
|---|---|---|---|
| #5S1 (recovered introgressed line) | 11.13 | 0.11 | 0.10 |
| #20S1 (recovered introgressed line) | 12.5 | 0.13 | 0.12 |
| #34S1 (recovered introgressed line) | 10.9 | 0.11 | 0.10 |
| #69S1 (recovered introgressed line) | 13.4 | 0.13 | 0.12 |
| #76S1 (recovered introgressed line) | 5.76 (tiny seed) | 0.058 | 0.05 |
| #91S1 (recovered introgressed line) | 9.86 | 0.10 | 0.09 |
| #92S1 (recovered introgressed line) | 14.41 | 0.14 | 0.13 |
| A632 Corn Belt inbred | 24.9 | 0.25 | 0.23 |

TABLE W-1-continued

Seed Weight Table

| Seed Variety | g/100 Kernels | g/One Kernel | Dry weight Basis |
|---|---|---|---|
| B73 Corn Belt inbred | 23.4 | 0.23 | 0.21 |
| Mo17 Corn Belt inbred | 29.2 | 0.29 | 0.26 |

The moisture content of the corn in the Seed Weight Table above was 9.4%. That portion of the kernels is water, so it should be reported that the weight of #5S1 was 0.11 g/kernel on a 9.4% moisture basis, or as 0.10 grams per kernel as the actual dry-matter basis weight.

Additional Enhancement of Value-added Traits
Summer of Year vv Yield Trials

The 41 selected recovered parental and introgressed Corn Belt lines that were test crossed to Mo17 in the Iowa summer of year uu nursery were tested in yield trials at 6 locations. One was discarded. The yield for the introgressed test crosses averaged 61 bu/acre but one cross exceeded yield of a check at 90.4 bu/acre. The Corn belt checks ranged between 85.3 to 122.9 Bu/acre with an average of 100 Bu/acre. The introgressed lines of the present invention will have greater yield potential when it included in a commercial hybrid breeding program with improved inbreds.

Compositional Analysis:

Near infrared spectroscopy (NIR) of whole grain identified lines with high protein (i.e., 18.1%), low protein (i.e., 4.8%); high oil (i.e., 7.7%), low oil (i.e., 1.2%), high starch content (i.e., 74.5%), and a broad density range, 1.1 to 1.4. See Table LAB-1.

TABLE LAB-1

Whole Grain Composition (NIR analysis)[1]

| | Protein | Oil | Starch | Density |
|---|---|---|---|---|
| Summer uu[2] | | | | |
| Min | 5.1 | 1.2 | 59.0 | 1.1 |
| Max | 18.1 | 7.7 | 74.5 | 1.4 |
| Winter uv[3] | | | | |
| Min | 4.8 | 2.8 | 62.5 | 1.2 |
| Max | 15.9 | 7.7 | 72.8 | 1.3 |
| Corn Belt Checks | | | | |
| Mo17 | 11.9 | 3.4 | 70.2 | 1.3 |
| Pioneer 3394 | 11.0 | 3.3 | 70.7 | 1.3 |
| Pioneer 3489 | 8.6 | 4.6 | 70.3 | 1.3 |

[1]Values are on a 0% moisture (dry matter) basis except for density which is based on 15% moisture.
[2]Material grown in Iowa uu nursery near Ames, Iowa
[3]Material grown in Puerto Rico winter uv Oil Quality:

Gas chromatography (GC) analysis for fatty acid composition revealed lines with individual kernels with low palmitic acid 3.8%, high palmitic acid 20.2%, low stearic acid 0.8% and high stearic acid 9%, Low oleic acid, 18%, high oleic acid, 70.1%, low total saturated fatty acids, 6.5% and high total saturated fatty acids, 23%. See Table LAB-2. Corn oil with high and low values for the fatty acids listed in the table have direct commercial application as improved co-products of processed corn.

TABLE LAB-2

Fatty Acid Composition (GC analysis)

| | Palmitic | Stearic | Oleic | Sats |
|---|---|---|---|---|
| Summer uu[1] | | | | |
| Min | 3.8 | 0.8 | 18.0 | 6.5 |
| Max | 17.8 | 9.0 | 69.5 | 23.0 |
| Winter uv[2] | | | | |
| Min | 5.2 | 1.5 | 22.9 | 7.9 |
| Max | 20.2 | 4.9 | 70.1 | 23.0 |
| Corn Belt Checks[2] | | | | |
| Mo17 | 10.1 | 2.0 | 24.2 | 12.1 |
| Pioneer 3394 | 10.9 | 2.0 | 27.9 | 12.9 |
| Pioneer 3489 | 10.0 | 2.1 | 23.4 | 12.1 |

[1]Material grown in Iowa uu nursery near Ames, Iowa
[2]Material grown in Puerto Rico winter uv Summary Corn oil with high and low values for the fatty acids listed in the Table LAB-2 have direct commercial application as improved co-products of processed corn.

Corn oil with increased oxidative stability resulting from superior fatty acid composition will have an increased shelf-life and more consumer acceptability.

Corn lines with enhanced protein and oil composition have an impact on the feed industry by reducing the amount of feed additives needed in feed rations for optimum animal performance.

Corn starch with altered starch types allows the development of new products and increase the premium value of corn.

Thus, the present invention provides corn that produces corn oil having superior nutritive content, not available from conventional corn-belt corn lines.

One aspect of the present invention provides popcorn or a popcorn food product having enhanced nutritive content. One definition of "popcorn" is an assemblage of corn seeds that when heated (e.g. fried in oil or heated in a microwave oven) will pop, and more particularly, will produce a popped volume of at least 10 cubic centimeters (cc) of popped product for each gram of raw kernels. One embodiment of the present invention provides breeding corn plants having Tripsacum germplasm (e.g., those lines identified above as having high protein, high oil, high protein and oil, low oil, or low oil and high protein) with corn plants conventionally used for popcorn. Another embodiment provides selecting among the resulting seed of the above breeding for desired nutritive content, for example, high protein, and further selfing and selecting to further enhance the desired nutritive content, as well as selecting for flavor and/or popped volume.

In one exemplary embodiment, the invention provides popcorn of lines derived from corn described in the following popcorn table of popping data for popcorn grown in year IvvN:

TABLE Pop-1

| IvvN: | Source | Ear # | GC# | Expansion | Hull | Flake |
|---|---|---|---|---|---|---|
| 1 | IuuN: 4853-8 | 1 | Popcorn | 360 | 1 | 3 |
| 1 | IuuN: 4853-8 | 2 | Popcorn | 320 | 1 | 3 |

TABLE Pop-1-continued

| IvvN: | Source | Ear # | GC# | Expansion | Hull | Flake |
|---|---|---|---|---|---|---|
| 1 | IuuN: 4853-8 | 3 | Popcorn | 260 | 1 | 3 |
| 1 | IuuN: 4853-8 | 4 | Popcorn | 280 | 1 | 3 |
| 1 | IuuN: 4853-8 | 5 | Popcorn | 460 | 1 | 3 |
| 1 | IuuN: 4853-8 | 6 | Popcorn | 600 | 1 | 3 |
| 1 | IuuN: 4853-8 | 7 | Popcorn | 240 | 1 | 3 |
| 1 | IuuN: 4853-8 | 8 | Popcorn | 360 | 1 | 3 |
| 1 | IuuN: 4853-8 | 9 | Popcorn | 340 | 1 | 3 |
| 1 | IuuN: 4853-8 | 10 | Popcorn | 3 | | |
| 1 | IuuN: 4853-8 | 11 | Popcorn | 260 | 1 | 3 |
| 2 | IuuN: 4853-10 | 1 | Popcorn | 3 | | |
| 2 | IuuN: 4853-10 | 2 | Popcorn | 200 | 1 | 3 |
| 2 | IuuN: 4853-10 | 3 | Popcorn | 4 | | |
| 2 | IuuN: 4853-10 | 4 | Popcorn | 2 | | |
| 2 | IuuN: 4853-10 | 5 | Popcorn | 3 | | |
| 2 | IuuN: 4853-10 | 6 | Popcorn | 4 | | |
| 3 | IuuN: 4853-12 | 1 | Popcorn | 280 | 1 | 3 |
| 3 | IuuN: 4853-12 | 2 | Popcorn | 2 | | |
| 3 | IuuN: 4853-12 | 3 | Popcorn | 3 | | |
| 3 | IuuN: 4853-12 | 4 | Popcorn | 400 | 1 | 3 |
| 3 | IuuN: 4853-12 | 5 | Popcorn | 240 | 1 | 3 |
| 4 | IuuN: 4863-4 | 1 | Popcorn | 5 | | |
| 4 | IuuN: 4863-4 | 2 | Popcorn | 460 | 1 | 3 |
| 4 | IuuN: 4863-4 | 3 | Popcorn | 400 | 1 | 3 |
| 4 | IuuN: 4863-4 | 4 | Popcorn | 280 | 1 | 3 |
| 5 | IuuN: 4863-11 | 1 | Popcorn | 3 | | |
| 5 | IuuN: 4863-11 | 2 | Popcorn | 3 | | |
| 5 | IuuN: 4863-11 | 3 | Popcorn | 460 | 1 | 3 |
| 5 | IuuN: 4863-11 | 4 | Popcorn | 260 | 1 | 3 |
| 5 | IuuN: 4863-11 | 5 | Popcorn | 460 | 1 | 3 |
| 5 | IuuN: 4863-11 | 6 | Popcorn | 2 | | |
| 5 | IuuN: 4863-11 | 7 | Popcorn | 280 | 1 | 3 |
| 6 | IuuN: 4871-3 | 1 | Popcorn | 220 | 1 | 3 |
| 6 | IuuN: 4871-3 | 2 | Popcorn | 1 | | |
| 6 | IuuN: 4871-3 | 3 | Popcorn | 420 | 1 | 3 |
| 6 | IuuN: 4871-3 | 4 | Popcorn | 4 | | |
| 6 | IuuN: 4871-3 | 5 | Popcorn | 280 | 1 | 3 |
| 6 | IuuN: 4871-3 | 6 | Popcorn | | | |
| 6 | IuuN: 4871-3 | 7 | Popcorn | 2 | | |
| 6 | IuuN: 4871-3 | 8 | Popcorn | 2 | | |
| 6 | IuuN: 4871-3 | 9 | Popcorn | 560 | 1 | 3 |
| 6 | IuuN: 4871-3 | 10 | Popcorn | 4 | | |
| 6 | IuuN: 4871-3 | 11 | Popcorn | 360 | 1 | 3 |
| 6 | IuuN: 4871-3 | 12 | Popcorn | 260 | 1 | 3 |
| 7 | IuuN: 4871-7 | 1 | Popcorn | 280 | 1 | 3 |
| 7 | IuuN: 4871-7 | 2 | Popcorn | 260 | 1 | 3 |
| 7 | IuuN: 4871-7 | 3 | Popcorn | 4 | | |
| 7 | IuuN: 4871-7 | 4 | Popcorn | 2 | | |
| 7 | IuuN: 4871-7 | 5 | Popcorn | 280 | 1 | 3 |
| 7 | IuuN: 4871-7 | 6 | Popcorn | 1 | | |
| 7 | IuuN: 4871-7 | 7 | Popcorn | 3 | | |
| 7 | IuuN: 4871-7 | 8 | Popcorn | 240 | 1 | 3 |
| 7 | IuuN: 4871-7 | 9 | Popcorn | 3 | | |
| 7 | IuuN: 4871-7 | 10 | Popcorn | 3 | | |
| 8 | IuuN: 4873-6 | 1 | Popcorn | 1 | | |
| 8 | IuuN: 4873-6 | 2 | Popcorn | 3 | | |
| 8 | IuuN: 4873-6 | 3 | Popcorn | 4 | | |
| 8 | IuuN: 4873-6 | 4 | Popcorn | 4 | | |
| 8 | IuuN: 4873-6 | 5 | Popcorn | 300 | 1 | 3 |
| 8 | IuuN: 4873-6 | 6 | Popcorn | 2 | | |
| 8 | IuuN: 4873-6 | 7 | Popcorn | 4 | | |
| 8 | IuuN: 4873-6 | 8 | Popcorn | 4 | | |
| 8 | IuuN: 4873-6 | 9 | Popcorn | 360 | 1 | 3 |
| 9 | IuuN: 4877-7 | 1 | Popcorn | 220 | 1 | 3 |
| 9 | IuuN: 4877-7 | 2 | Popcorn | 340 | 1 | 3 |
| 9 | IuuN: 4877-7 | 3 | Popcorn | 3 | | |
| 9 | IuuN: 4877-7 | 4 | Popcorn | 2 | | |
| 9 | IuuN: 4877-7 | 5 | Popcorn | 3 | | |
| 9 | IuuN: 4877-7 | 6 | Popcorn | 4 | | |
| 9 | IuuN: 4877-7 | 7 | Popcorn | 3 | | |
| 10 | IuuN: 4885-2 | 1 | Popcorn | 280 | 1 | 3 |
| 10 | IuuN: 4885-2 | 2 | Popcorn | 3 | | |
| 10 | IuuN: 4885-2 | 3 | Popcorn | 460 | 1 | 3 |
| 10 | IuuN: 4885-2 | 4 | Popcorn | 3 | | |
| 10 | IuuN: 4885-2 | 5 | Popcorn | 300 | 1 | 4 |
| 10 | IuuN: 4885-2 | 6 | Popcorn | 1 | | |
| 10 | IuuN: 4885-2 | 7 | Popcorn | 3 | | |
| 11 | IuuN: 4885-3 | 1 | Popcorn | 420 | 1 | 3 |
| 11 | IuuN: 4885-3 | 2 | Popcorn | 900 | 1 | 4 |
| 11 | IuuN: 4885-3 | 3 | Popcorn | 630 | 1 | 4 |
| 11 | IuuN: 4885-3 | 4 | Popcorn | 460 | 1 | 3 |
| 11 | IuuN: 4885-3 | 5 | Popcorn | 660 | 1 | 3 |
| 12 | IuuN: 4885-4 | 1 | Popcorn | 510 | 1 | 4 |
| 12 | IuuN: 4885-4 | 2 | Popcorn | 200 | 1 | 3 |
| 12 | IuuN: 4885-4 | 3 | Popcorn | 200 | 1 | 3 |
| 12 | IuuN: 4885-4 | 4 | Popcorn | 280 | 1 | 3 |
| 12 | IuuN: 4885-4 | 5 | Popcorn | 4 | | |
| 12 | IuuN: 4885-4 | 6 | Popcorn | 3 | | |
| 13 | IuuN: 4885-6 | 1 | Popcorn | 5 | | |
| 13 | IuuN: 4885-6 | 2 | Popcorn | 300 | 1 | 3 |
| 13 | IuuN: 4885-6 | 3 | Popcorn | 3 | | |
| 13 | IuuN: 4885-6 | 4 | Popcorn | 360 | 1 | 3 |
| 13 | IuuN: 4885-6 | 5 | Popcorn | 4 | | |
| 13 | IuuN: 4885-6 | 6 | Popcorn | 280 | 1 | 3 |
| 13 | IuuN: 4885-6 | 7 | Popcorn | 220 | 1 | 3 |
| 13 | IuuN: 4885-6 | 8 | Popcorn | 420 | 1 | 3 |
| 13 | IuuN: 4885-6 | 9 | Popcorn | 300 | 1 | 3 |
| 13 | IuuN: 4885-6 | 10 | Popcorn | 280 | 1 | 3 |
| 14 | IuuN: 4885-7 | 1 | Popcorn | 480 | 1 | 3 |
| 14 | IuuN: 4885-7 | 2 | Popcorn | 5 | | |
| 14 | IuuN: 4885-7 | 3 | Popcorn | 580 | 1 | 3 |
| 15 | IuuN: 4885-8 | 1 | Popcorn | 3 | | |
| 15 | IuuN: 4885-8 | 2 | Popcorn | 3 | | |
| 15 | IuuN: 4885-8 | 3 | Popcorn | 4 | | |
| 15 | IuuN: 4885-8 | 4 | Popcorn | 340 | 1 | 3 |
| 15 | IuuN: 4885-8 | 5 | Popcorn | 260 | 1 | 3 |
| 16 | IuuN: 4885-9 | 1 | Popcorn | 4 | | |
| 16 | IuuN: 4885-9 | 2 | Popcorn | 380 | 1 | 4 |
| 16 | IuuN: 4885-9 | 3 | Popcorn | 400 | 1 | 3 |
| 16 | IuuN: 4885-9 | 4 | Popcorn | 460 | 1 | 2 |
| 17 | IuuN: 4885-11 | 1 | Popcorn | 600 | 1 | 3 |
| 17 | IuuN: 4885-11 | 2 | Popcorn | 520 | 1 | 4 |
| 17 | IuuN: 4885-11 | 3 | Popcorn | 700 | 1 | 3 |
| 17 | IuuN: 4885-11 | 4 | Popcorn | 600 | 1 | 3 |
| 17 | IuuN: 4885-11 | 5 | Popcorn | 580 | 1 | 3 |
| 18 | IuuN: 4881-2 | 1 | Popcorn | Not Enough | | |
| 19 | IuuN: 4881-3 | 1 | Popcorn | 660 | 2 | 4 |
| 19 | IuuN: 4881-3 | 2 | Popcorn | 4 | | |
| 20 | IuuN: 4879-6 | 1 | Popcorn | 2 | | |
| 20 | IuuN: 4879-6 | 2 | Popcorn | 2 | | |
| 20 | IuuN: 4879-6 | 3 | Popcorn | 4 | | |
| 20 | IuuN: 4879-6 | 4 | Popcorn | 4 | | |
| 20 | IuuN: 4879-6 | 5 | Popcorn | 2 | | |
| 20 | IuuN: 4879-6 | 6 | Popcorn | 2 | | |
| 20 | IuuN: 4879-6 | 7 | Popcorn | 200 | 1 | 3 |
| 21 | IuuN: 4875-3 | 1 | Popcorn | 1 | | |
| 21 | IuuN: 4875-3 | 2 | Popcorn | 3 | | |
| 21 | IuuN: 4875-3 | 3 | Popcorn | 4 | | |
| 21 | IuuN: 4875-3 | 4 | Popcorn | 5 | | |
| 22 | IuuN: 4875-4 | 1 | Popcorn | 200 | 1 | 3 |
| 23 | IuuN: 4875-5 | 1 | Popcorn | 5 | | |
| 23 | IuuN: 4875-5 | 2 | Popcorn | 330 | 1 | 3 |
| 24 | IuuN: 4859-1 | 1 | Popcorn | Not Enough | | |
| 24 | IuuN: 4859-1 | 2 | Popcorn | Not Enough | | |
| 24 | IuuN: 4859-1 | 3 | Popcorn | 900 | 2 | 4 |

In other embodiments, the invention provides popcorn from lines bred from (i.e., derived from breeding with) these lines.

Yield Trials 41 selected recovered parental and introgressed Corn Belt lines that were test crossed to Mo17 in the summer 1996 nursery were tested in yield trials in the summer of 1997 at 6 locations. One was discarded. The yield for the introgressed test crosses averaged 61 bu/acre but one cross exceeded yield of a check at 90.4 bu/acre. The Corn belt checks ranged between 85.3 to 122.9 Bu/acre with an average of 100 Bu/acre. The introgressed lines have greater yield potential when included in a commercial hybrid breeding program with improved conventional Corn Belt inbreds.

The following table provides a background reference for the weights of kernels of Corn Belt lines, and for the original Tripsacum lines used as a basis for some embodiments of the present invention:

TABLE RW-1

|  | corrected for dry weight (g) | These corn weights are for the average weight of the kernels if they had no water as a part of that weight or in other words on a dry matter basis. |
| --- | --- | --- |
| B73 | 0.227 | |
| Mo17 | 0.292 | |
| B73 × Mo17 | 0.205 | |
| Pioneer 3489 | 0.354 | |

The average kernel weight for 95 ears of the original Tripsacum Introgressed Population was 0.136 g dry matter basis, and the range of kernel weights were from 0.057 g to 0.298 g Dry matter basis for individual kernels. About 9 ears were selected for introgression in the above embodiments, based on their nutritive characteristics, and those had individual kernel weights from 0.081 g to 0.193 g Dry matter basis In various embodiments, the present invention provides:

A corn seed that includes Tripsacum germplasm; wherein the corn seed includes nutritive content or proportions not found in seeds of *Zea Mays L.* that do not comprise the Tripsacum germplasm, and wherein the seed has a weight per seed of greater than about 0.18 grams on a 15% moisture basis.

In some embodiments, the corn seed produces a corn plant that produces seeds having an average seed weight of approximately 0.18 grams or greater on a 5% moisture basis, and an oleic-acid content of approximately 50% or greater, relative to the total fatty acid content of the seed.

In some embodiments, the corn seed produces a corn plant that produces seeds having a substantially yellow and/or white seed coat.

Another aspect of the invention is a corn-seed product consisting of a substantially homogeneous assemblage of corn seeds, the se eds including seeds from a corn plant grown from one of the corn seeds described above, and the seeds having an average weight per seed of about 0.18 grams or greater on a 15% moisture basis.

In some embodiments, the substantially homogeneous assemblage of corn seeds include a protein content by weight of approximately 10% or greater on a 15% moisture basis.

In some embodiments, the substantially homogeneous assemblage of corn seeds include a protein content by weight of approximately 10% or greater on a 15% moisture basis, and an oil content by weight of approximately 4% or greater on a 15% moisture basis.

In some embodiments, the substantially homogeneous assemblage of corn seeds include an oil content by weight of approximately 5% or greater on a 15% moisture basis. In some embodiments, the oil content by weight is approximately 6% or greater on a 15% moisture basis. In some embodiments, the oil content by weight is approximately 7% or greater on a 15% moisture basis.

In some embodiments, the substantially homogeneous assemblage of corn seeds include an oleic-acid content of approximately 50% or greater, relative to the total fatty acid content of the assemblage of corn seeds.

Another aspect of the invention is a corn-seed oil product derived from a substantially homogeneous assemblage of corn seeds, the seeds including seeds from a corn plant grown from one of the corn seeds described above. In some embodiments, the product has an oleic-acid content of approximately 50% or greater, relative to the total fatty acid content of the oil product. In some embodiments, the oil product has an oleic-acid content of approximately 55% or greater, relative to the total fatty acid content of the oil product. In some embodiments, the oil product has an oleic-acid content of approximately 60% or greater, relative to the total fatty acid content of the oil product. In some embodiments, the oil product has an oleic-acid content of approximately 65% or greater, relative to the total fatty acid content of the oil product. In some embodiments, the oil product has an oleic-acid content of approximately 70% or greater, relative to the total fatty acid content of the oil product.

In some embodiments, the corn seed as described above produces a corn plant that produces seeds having an average seed weight of approximately 0.15 grams or greater at 15% moisture, and a protein content by weight of approximately 10% or greater. In some such embodiments, the average seed weight is approximately 0.18 grams or greater at 15% moisture, and a protein content by weight of approximately 10% or greater. In some such embodiments, the average seed weight is approximately 0.20 grams or greater at 15% moisture, and a protein content by weight of approximately 12% or greater. In some such embodiments, the average seed weight is approximately 0.18 grams or greater at 15% moisture, and a protein content by weight of approximately 12% or greater.

In some embodiments, the corn seed as described above produces a corn plant that produces seeds having an average seed weight of approximately 0.15 grams or greater, and a protein content by weight at 15% moisture of approximately 10% or greater, and an oil content by weight of approximately 4% or greater. In some such embodiments, the oil content by weight of approximately 5% or greater. In some such embodiments, the oil content by weight of approximately 6% or greater. In some such embodiments, the oil content by weight of approximately 7% or greater.

In some embodiments, the corn seed as described above produces a corn plant that produces seeds having an average seed weight of approximately 0.15 grams or greater, and an oil content by weight at 15% moisture of approximately 4% or greater.

In some embodiments, the corn seed as described above produces a corn plant that produces seeds having a substantially yellow and/or white seed coat.

In some embodiments, the corn seed as described above produces a corn plant that produces seeds having a starch content that has a peak onset temperature of gelatinization of approximately 64 degrees centigrade or lower, as measured by Differential Scanning Calorimetry with the. following conditions: a ratio of 1:2 starch to water, a heating range beginning at 30 degrees Celsius and ending at 110 degrees Celsius.

In some embodiments, the corn seed as described above produces a corn plant that produces seeds having a starch content that has a peak height index of gelatinization of approximately 1.3 or higher.

In some embodiments, the corn seed as described above produces a corn plant that produces seeds having a starch, content that has a percentage retrogradation of approximately 40 percent or lower.

In some embodiments, the corn seed as described above produces a corn plant that produces seeds having a starch content that has an enthalpy value of gelatinization of approximately 2.6 calories per gram or less.

Another aspect of the invention is a corn plant produced from the seed as described above or regenerable parts of the seed. Another aspect of the invention are seed of such corn plant. Another aspect of the invention is pollen of such plant. Another aspect of the invention is seed of a corn plant pollinated by such pollen. Another aspect of the invention is an ovule of such corn plant. Another aspect of the invention is a corn plant having all the physiological and morphological characteristics of such plant. Another aspect of the invention is a tissue culture of regenerable cells, the cells including genetic material derived, in whole or in part, from such plant, wherein the cells regenerate plants having the morphological and physiological characteristics of the respective inbred corn lines so designated. Another aspect of the invention is such a tissue culture, comprising cultured cells derived, in whole or in part, from a plant part selected from the group consisting of leaves, roots, root tips, root hairs, anthers, pistils, stamens, pollen, ovules, flowers, seeds, embryos, stems, buds, cotyledons, hypocotyls, cells and protoplasts. Another aspect of the invention is a corn plant produced from such tissue culture. Yet another aspect of the invention is a corn-seed product comprising a substantially homogeneous assemblage of corn seeds from such corn plant.

Still another aspect of the invention is a method for producing a white-coated or yellow-coated corn seed having an oleic-acid content of approximately 560% or greater by weight, comprising: crossing a first parent that comprises Tripsacum germplasm encoding the oleic-acid content with a second parent that comprises a genetic determinant for yellow or white seed color.

In some embodiments of the method, the first parent is true-breeding for a yellow or white seed color, and the second parent is true-breeding for a yellow or white seed color.

In some embodiments of the method, the first parent includes genetic material derived from a plant of *Tripsacum dactyloides L.*

In some embodiments, the method further includes selecting seeds based on their total saturated fatty-acid content from a plant grown from seed resulting from the crossing, and introgressing in a breeding program using the selected seeds.

In some embodiments, the method further includes selecting seeds based on their oleic-acid content from a plant grown from seed resulting from the crossing, and introgressing in a breeding program using the selected seeds.

Still another aspect of the invention is a corn-seed product comprising: a substantially homogeneous assemblage of corn seeds having an average weight per seed of about 0.18 grams or greater on a 15% moisture basis, and a protein content by weight of approximately 10% or greater on a 15% moisture basis.

In some embodiments of the corn-seed product, the protein content by weight is approximately 12% or greater on a 15% moisture basis, and In some embodiments of the corn-seed product, the substantially homogeneous assemblage of corn seeds has an oil content by weight of approximately 4% or greater on a 15% moisture basis, and wherein the protein content by weight is approximately 12% or greater on a 15% moisture basis, and In some embodiments of the corn-seed product, the substantially homogeneous assemblage of corn seeds comprise an oil content by weight of approximately 5% or greater on a 15% moisture basis.

In some embodiments of the corn-seed product, the substantially homogeneous assemblage of corn seeds comprise an oil content by weight of approximately 6% or greater on a 15% moisture basis.

In some embodiments, the present invention provides a corn seed having a saturated fatty acid content of approximately 15% or greater, relative to the total fatty acid content of the seed. In some embodiments, the seed includes Tripsacum germplasm. In some embodiments, the seed includes *Tripsacum dactyloides L.* germplasm. In some embodiments, the saturated fatty-acid content of the seed is approximately 16% or greater. In some embodiments, the saturated fatty-acid content of the seed is approximately 17% or greater. In some embodiments, the saturated fatty-acid content of the seed is approximately 18% or greater. In some embodiments, the saturated fatty-acid content of the seed is approximately 19% or greater. In some embodiments, the saturated fatty-acid content of the seed is approximately, 20% or greater. In some embodiments, the saturated fatty-acid content of the seed is approximately 21% or greater. In some embodiments, the saturated fatty-acid content of the seed is approximately 22% or greater. In some embodiments, the saturated fatty-acid content of the seed is approximately 23% or greater. In some embodiments, the saturated fatty-acid content of the seed is approximately 24% or greater. In some of these embodiments, the corn seed produces a corn plant that produces seeds having a substantially yellow seed coat. In some of these embodiments, the corn seed produces a compliant that produces seeds having a substantially white seed coat. In some of these embodiments, the corn seed produces a corn plant that produces seeds having a substantially yellow and white seed coat.

In some embodiments, the present invention provides a corn plant grown from a seed having a saturated fatty acid content of approximately 15% or greater, relative to the total fatty acid content of the seed, wherein the plant produces seeds having a saturated fatty acid content of approximately 15% or greater, relative to the total fatty acid content of the seed. In some embodiments, the seed includes Tripsacum germplasm. In some embodiments, the seed includes *Tripsacum dactyloides L.* germplasm. In some embodiments, the plant produces seeds having saturated fatty-acid content of approximately 16% or greater. In some embodiments, the plant produces seeds having saturated fatty-acid content of approximately 17% or greater. In various other embodiments, the plant produces seeds having saturated fatty-acid content of approximately 18% or greater, approximately 19% or greater, approximately 20% or greater, approximately 21% or greater, approximately 22% or greater, approximately 23% or greater, and even approximately 24% or greater. In some of these embodiments, the corn seed produces a corn plant that produces seeds having a substantially yellow seed coat. In some of these embodiments, the corn seed produces a corn plant that produces seeds having a substantially white seed coat. In some of these embodiments, the corn seed produces a corn plant that produces seeds having a substantially yellow and white seed coat. Some embodiments of the present invention include a corn-seed product having a substantially homogeneous assemblage of corn seeds, the assemblage of corn seeds including first seeds from a corn plant grown from one of the corn seeds described in this paragraph, wherein the first seeds have an average weight per seed of greater than about 0.1 5 grams. In various: other such embodiments, the average weight per seed is greater than about 0.16 grams, about 0.17 grams, about 0.18 grams, about 0.19 grams, about 0.2 grams, about 0.21 grams, about 0.22 grams, about 0:23 grams, about 0.24 grams, about 0.26 grams, about 0.28 grams, about 0.3 grams, about 0.32 grams, about 0.34 grams, about 0.36 grams, about 0.38 grams, or about 0.4 grams. In contrast, conventional corn can achieve such average kernel weights, but does not provide the enhanced nutritive characteristics, and other Tripsacum-corn crosses have had small kernel weights, poor color (i.e., not white or yellow), and/or have lacked the combination or proportions of nutritive values achieved with the present invention.

In some embodiments, the present invention provides a corn seed and/or a corn plant grown from the seed having a saturated fatty acid content of approximately 9% or less, relative to the total fatty acid content of the seed, wherein the plant produces seeds having a saturated fatty acid content of approximately 9% or less, relative to the total fatty acid content of the seed. In some embodiments, the seed includes Tripsacum germplasm. In some embodiments, the seed includes *Tripsacum dactyloides L.* germplasm. In some embodiments the plant produces seeds having saturated fatty-acid content of approximately 8% or less. In various other embodiments, the plant produces seeds having saturated fatty-acid content of approximately 7% or less, approximately 6% or less, and even a saturated fatty-acid content of approximately 5% or less. In some of these embodiments, the corn seed produces a corn plant that produces seeds having a substantially yellow seed coat. In some of these embodiments, the corn seed produces a corn plant that produces seeds having a substantially white seed coat. In some of these embodiments, the corn seed produces a corn plant that produces seeds having a substantially yellow and white seed coat. Some embodiments of the present invention include a corn-seed product having a substantially homogeneous assemblage of corn seeds, the assemblage of corn seeds including first seeds from a corn plant grown from one of the corn seeds described in this paragraph, wherein the first seeds have an average weight per seed of greater than about 0.15 grams. In various other such embodiments, the average weight per seed is greater than about 0.16 grams, about 0.17 grams, about 0.18 grams, about 0. 19 grams, about 0.2 grams, about 0.21 grams, about 0.22 grams, about 0.23 grams, about 0.24 grams, about 0.26 grams, about 0.28 grams, about 0.3 grams, about 0.32 grams, about 0.34 grams, about 0.36 grams, about 0.38 grams, or about 0.4 grams. In contrast, conventional corn can achieve such average kernel weights, but does not provide the enhanced nutritive characteristics, and other Tripsacum-corn crosses have had small kernel weights, poor color (i.e., not white or yellow), and/or have lacked the combination or proportions of nutritive values achieved with the present invention.

In some embodiments, the present invention provides a corn seed and/or a corn plant grown from the seed having an oleic-acid content of approximately 50% or greater, relative to the total fatty acid content of the seed, wherein the plant produces seeds having an oleic-acid content of approximately 50% or greater, relative to the total fatty acid content of the seed. In some embodiments, the seed includes Tripsacum germplasm. In some embodiments, the seed includes *Tripsacum dactyloides L.* germplasm. In some embodiments, the plant produces seeds having an oleic-acid content of approximately 50% or greater. In various other embodiments, the plant produces seeds having an oleic-acid content of approximately 55% or greater, approximately 60% or greater, approximately 65% or greater, and even approximately. 70% or greater. In some of these embodiments, the corn seed produces a corn plant that produces seeds having a substantially yellow seed coat. In some of these embodiments, the corn seed produces a corn plant that produces seeds having a substantially white seed coat. In some of these embodiments, the corn seed produces a corn plant that produces seeds having a substantially yellow and white seed coat. Some embodiments of the present invention include a corn-seed product having a substantially homogeneous assemblage of corn seeds, the assemblage of corn seeds including first seeds from a corn plant grown from one of the corn seeds described in this paragraph, wherein the first seeds have an average weight per seed of greater than about 0.15 grams. In various other such embodiments, the average weight per seed is greater than about 0.16 grams, about 0.17 grams, about 0.18 grams, about 0.19 grams, about 0.2 grams, about 0.21 grams, about 0 .22 grams, about 0.23 grams, about 0.24 grams, about 0.26 grams, about 0.28 grams, about 0.23 grams, about 0.3 2 grams, about 0.34 grams, about 0.36 grams, about 0.38 grams, or about 0.4 grams.

In some embodiments, the present invention provides a corn seed and/or a corn plant grown from the seed of high-protein inbred corn lines designated GC#3892, GC#3805, GC#3978, GC#3728, GC#3963, GC#3642, GC#3781, or GC#3663, high-oil inbred corn lines designated GC#4066, GC#3886, GC#3831, GC#3833, GC#3641, GC#3839, GC#3822, GC#3930, GC#3969, GC#3696, GC#3829, GC#3713, GC#4037, GC#3100, GC#3901, GC#3809, GC#3689, GC#3640, GC#3723, GC#3821, GC#3892, GC#3697, GC#4053, GC#3711, GC#3712, GC#3823, GC#3694, GC#3838, GC#3717, GC#3687, GC#3968, GC#4151, GC#3941, GC#3695, GC#3806, GC#3926, GC#3896, GC#3808, GC#3927, GC#3719, or GC#3810, or high-protein and high-oil inbred corn lines designated GC#3847, GC#3763, GC#3913, GC#3753, GC#3820, GC#3905, GC#3815, GC#3911, GC#3646, GC#3951, GC#4026, GC#3692, GC#3929, GC#3978, GC#3807, GC#3643, GC#4090, GC#3961, GC#3922, GC#3631, GC#3812, GC#3716, GC#3691, GC#3674, GC#3714, GC#4020, GC#3636, GC#1330, GC#3747, GC#3933, GC#3932, GC#3924, GC#3762, GC#3971, GC#3904, GC#3956, GC#4158, GC#3964, GC#4030, GC#4054, or GC#1324 (together, called lines "GC inbred maize lines"). In one embodiment, the present invention provides a corn plant produced by the seed of GC inbred maize lines or regenerable parts of said seed. In one embodiment, the present invention provides seed of such a corn plant. In one embodiment, the present invention provides pollen of such a corn plant. In one embodiment, the present invention provides seed of a corn plant pollinated by the pollen. In one embodiment, the present invention provides an ovule of a corn plant produced by the seed of GC inbred maize lines or regenerable parts of said seed. In one embodiment, the present invention provides a corn plant having all the physiological and morphological characteristics of a corn plant produced by the seed of GC inbred maize lines or regenerable parts of said seed. In one embodiment, the present invention provides a tissue culture of regenerable cells, the cells including genetic material derived, in whole or in part, from high-protein GC inbred corn lines, wherein the cells regenerate plants having the morphological and physiological characteristics of the respective inbred corn lines so designated. In one embodiment, the present invention provides such a tissue culture comprising cultured cells derived, in whole or in part, from a plant part selected from the group consisting of leaves, roots, root tips, root hairs, anthers, pistils, stamens, pollen, ovules, flowers, seeds, embryos, stems, buds, cotyledons, hypocotyls, cells and protoplasts. In one embodiment, the present invention provides a corn plant regenerated from such a tissue culture, the corn plant having all the morphological and physiological characteristics of high-protein GC inbred corn lines.

In some embodiments, the present invention provides a method for producing high-protein content or high-oil content or high-protein and high-oil content corn seed. The method includes crossing a first parent corn plant with a second parent corn plant and harvesting resultant first-generation (F1) hybrid corn seed, wherein said first or second parent corn plant is one of the corn plants of NN above.

In some embodiments, the present invention provides a method for breeding and selecting corn including (a) introgressing plants of a corn line with plants of genus Tripsacum, to obtain genetic material; (b) growing corn plants from the genetic material resulting from the introgressing step of step (a) to obtain seeds; and (c) selecting from among the seed of the corn plants of step (b) those seeds having superior protein content or oil content or both. In some embodiments, the method further includes (d) creating an inbred corn line derived from the selected seeds of step (c). In some embodiments, the method further includes (e) crossing the inbred corn line with another inbred corn line to obtain hybrid seeds. In some embodiments, the method further includes (f) generating plants from the hybrid seeds resulting from step (e). In some embodiments, the method further includes (g) generating a tissue culture of regenerable cells from genetic material derived from the plants resulting from step (b), the tissue culture derived, in whole or in part, from a plant part selected from the group consisting of leaves, roots, root tips, root hairs, anthers, pistils, stamens, pollen, ovules, flowers, seeds, embryos, stems, buds, cotyledons, hypocotyls, cells and protoplasts.

In some embodiments, the present invention provides seed of a corn variety having greater than or equal to about 10% protein at 0% moisture content. In some such embodiments, the seed have greater than or equal to about 11% protein, about 12% protein, about 13% protein, about 14% protein, about 15% protein, about 16% protein, or even about 17% protein at 0% moisture content. In some such embodiments, the seed have greater than or equal to about 4% oil at 0% moisture content. On other embodiments, the oil content is greater than about 5%, 6%, or even 7%. In some such embodiments, the present invention provides seed of a corn variety according to one of the above combinations of protein and or oil content, the variety having genetic material derived from a plant of genus Tripsacum. In some embodiments, the variety has genetic material derived from a plant of *Tripsacum dactyloides L*. Some embodiments provide a first-generation (F1) corn plant and seed thereof derived from one of the seed described in this paragraph.

In some embodiments, the present invention provides a first-generation (F1) hybrid corn plant and seed thereof produced by crossing a first inbred female corn plant with a second inbred male corn plant, wherein said first or second parent corn plant is from a GC inbred corn line. Some embodiments provide such a hybrid corn plant and seed thereof, wherein an inbred corn plant from a GC inbred corn line is the female parent. Some embodiments use an inbred corn plant from a GC inbred corn line as the male parent.

In some embodiments, the present invention provides a method for producing first-generation (F1) hybrid corn seed comprising crossing a first inbred parent corn plant with a second inbred parent corn plant, wherein said first or second parent corn plant is the inbred corn plant from a GC inbred corn line, and harvesting the F1 hybrid seed produced thereby. Some embodiments provide a first-generation (F1) hybrid corn plant and seed thereof produced by growing seed produced by this method.

Various embodiments of the invention are based on density of the corn (see, e.g., table 3 above).

The present invention thus provides enhanced grain and oil quality of corn.

Corn is the most important feed grain in the United States. Corn production in 1995 was 10,962 million bushels. Fifty-three percent of this grain was used for feed; 17% for food, seed, and industrial uses; 25% was exported (mainly for feed); and 5% was in ending stocks.

Conventional corn kernels are composed of approximately 73% starch, 10% protein, and 5% oil, with the remainder as fiber, vitamins, and minerals. Among feed grains, corn is one of the most concentrated sources of energy, containing more metabolized energy or total digestible nutrients because of its high starch-low fiber content.

The lipid portion of the grain not only provides energy but essential fatty acids for animal growth. Feeding swine a diet with an elevated level of mono-unsaturated fatty acid effectively increases the level of this important lipid in the pork. This impacts on human nutrition by increasing the mono-unsaturated lipids and decreasing the saturated fats consumed in the human diet. Unsaturated fatty acids in the poultry diet increases the absorption of oxycarotenoids (pigments responsible for yellow color of skin and egg yolks), which improves the consumer acceptability of poultry products.

Improvements in crops by plant breeding are usually followed by a decrease in genetic diversity, especially in the materials that ultimately reach commercial production. On a worldwide basis only 5% of available corn germplasm is used commercially. From biochemical data, U.S. maize cultivation and breeding appear to remain heavily dependent upon usage of the inbred lines B73, A632, Oh43, and Mo17, or closely-related derivatives. In contrast to many other crops, corn breeders have continued to focus on short-term breeding goals largely because of the predominance of the private sector in corn breeding and its need for short-term results. This pattern has resulted in the development of a very narrow genetic base of corn produced on the farm, with many companies selling closely related hybrids. This makes it difficult to develop hybrids for new market demands.

According to Ertle and Orman, 1994, there is limited variability for feed quality in present-day hybrids, or elite breeding materials, as shown by the composition trait values in 7,399 samples collected from 27 locations in North America from 1987 to 1993 and analyzed for protein, oil, and starch composition. There is also limited variability in hybrids entered in the Iowa Corn Yield Tests since 1988.

To find sources of genetic variability, corn lines introgressed with genes from Tripsacum, a wild relative of corn, were evaluated for grain and oil quality traits. Lines with enhanced traits were improved by traditional plant breeding techniques of selfing, crossing to public Corn Belt hybrids, and backcrossing to the parental lines.

Grain Quality of Corn Belt lines

TABLE x1

Composition of Corn Belt Lines

| Item | Protein[1] | Oil[1] | Starch[1] | Density[1] |
|---|---|---|---|---|
| B73 | 11.9 | 3.4 | 71.8 | 1.278 |
| Mo17 | 11.9 | 3.3 | 71.6 | 1.294 |
| B73 × Mo17 | 12.9 | 3.8 | 70.4 | 1.291 |
| Mo17 × B73 | 12.9 | 3.5 | 69.0 | 1.307 |
| Pioneer 3394 | 11.4 | 3.3 | 71.5 | 1.302 |
| Pioneer 3489 | 9.1 | 4.0 | 71.9 | 1.263 |

[1]NIT prediction on a dry matter (0% moisture) basis.

TABLE x2

Premium Grain Value

| Item | EPV[2]($) | Premium[3]($) |
|---|---|---|
| Pioneer 3394 | 2.57 | −0.15 |
| Pioneer 3489 | 2.55 | −0.17 |

[1]Estimated Premium value as calculated from the formula in Nutrient content and Feeding value of Iowa Corn Current Statistics with corn priced at $2.72/Bu, 8.0% protein, 3.5% oil, 59.5% starch, oil refining loss at 2.5%, Distillers dried grain priced at $145/ton, 9% moisture, 44% protein content of soymeal, soybean meal priced at $214/ton, feed additive priced at $0.1/LB, weight of feed additives 60%, and 16% protein content of feed.
[3]Premium paid per bushel over the $2.72/Bu value.

Over 6,000 introgressed lines corn lines were evaluated for fatty acid composition. Lines with the most unique profiles were selected for advancement and incorporated into a plant breeding scheme to enhance the oil quality of corn belt lines (A619, A632, B14A, B73, H99, Oh43, Mo17, and W153R) and improve the agronomic characteristics of the introgressed lines.

TABLE x3

Compositions of Introgressed Lines with Most Extreme Values

| Item | Protein[1] | Oil[1] | Starch[1] | Density[1] |
|---|---|---|---|---|
| High Protein | 18.1 | 5.4 | 63.7 | 1.340 |
| High Oil | 13.2 | 7.5 | 64.8 | 1.334 |
| High Protein and High Oil | 17.4 | 6.7 | 63.1 | 1.340 |

[1]NIT prediction on a dry matter (0% moisture) basis.
The impact on the premium value of grain from the introgressed lines (Table x3) is shown in Table x4.

TABLE x4

Premium Grain Value

| Item | EPV[2]($) | Premium[3]($) |
|---|---|---|
| High Protein | 3.38 | 0.66 |
| High Oil | 3.13 | 0.41 |
| High Protein and High Oil | 3.33 | 0.61 |

[2]Estimated Premium value as calculated from the formula in Nutrient content and Feeding value of Iowa Corn Current Statistics with corn priced at $2.72/Bu, 8.0% protein, 3.5% oil, 59.5% starch, oil refining loss at 2.5%, Distillers dried grain priced at $145/ton, 9% moisture, 44% protein content of soymeal, soybean meal priced at $214/ton, feed additive priced at $0.1/LB, weight of feed additives 60%, and 16% protein content of feed.
[3]Premium paid per bushel over the $2.72/Bu value. In addition to the lines listed in the table x4, there are 8 high protein selections with values ranges of 15.1% to 17.4% protein. 82 high oil lines with values ranges of 6.0 to 7.7% oil. 10 high protein and high oil lines crossed to Mo17 and currently in yield trials at six locations with value ranges of 12.1% protein with 5.0% oil to 18.1% protein with 5.4% oil.

Oil Quality Traits for Corn Belt Lines

TABLE x5

Fatty Acid Compositions for Corn Belt Lines

| Corn Belt | Palmitic | Stearic | Oleic | Linoleic | Linolenic | Total Saturates |
|---|---|---|---|---|---|---|
| B73 | 10.0 | 2.1 | 30.0 | 56.7 | 1.2 | 12.1 |
| A632 | 9.9 | 1.4 | 18.8 | 68.5 | 1.4 | 11.3 |
| Oh43 | 12.0 | 1.7 | 18.8 | 65.6 | 1.7 | 13.7 |
| Mo17 | 9.9 | 2.0 | 20.0 | 66.7 | 0.7 | 11.9 |

TABLE x5-continued

Fatty Acid Compositions for Corn Belt Lines

| Corn Belt | Palmitic | Stearic | Oleic | Linoleic | Linolenic | Total Saturates |
|---|---|---|---|---|---|---|
| Pioneer 3394 | 10.4 | 1.8 | 22.9 | 60.1 | 1.1 | 11.1 |
| Pioneer 3489 | 8.6 | 2.5 | 26.8 | 60.1 | 1.1 | 12.1 |

Oil Quality Traits for Introgressed Lines

TABLE x6

Fatty Acid Compositions of Introgressed Lines with Most Extreme Values

| Item | Palmitic | Stearic | Oleic | Linoleic | Linolenic | Total Saturates |
|---|---|---|---|---|---|---|
| High Oleic | 5.9 | 3.2 | 70.1 | 20.1 | 0.7 | 9.1 |
| High Total Saturates | 22.3 | 1.9 | 18.3 | 54.9 | 2.6 | 24.3 |
| Low Total Saturates | 4.9 | 1.8 | 4.5 | 47.3 | 1.0 | 6.7 |

In addition to the lines listed in Table x6, there are seven high oleic recovered introgressed lines with values ranges of 53% to 68% oleic, thirty-five high oleic lines from crosses of introgressed lines with Corn Belt lines, A619, A632, B73, Mo17, or W153R, with value ranges of 59% to 70% oleic, and nine lines from crosses of introgressed lines with Corn Belt lines were backcrossed and selfed several generations resulting in material with value ranges of 52% to 60% oleic.

High total saturated fatty acid lines not listed in Table x6 include twenty-eight recovered introgressed lines with value ranges of 19% to 22% total saturates, twenty-three introgressed lines crossed to Corn Belt lines either B73, Mo17, or W153R with value ranges of 19% to 24% total saturates, and four introgressed lines backcrossed and selfed several generations with value ranges of 16 to 18% total saturates.

Low total saturated fatty acid lines not listed in Table x6 include three recovered lines with value ranges of 8.2% to 8.4% total saturates, fourteen lines from crosses to Corn Belt lines and selfed several generations with value ranges of 7.4% to 8.1% total saturates, and two crossed lines backcrossed to Corn Belt lines and selfed several generations with value ranges of 7.4% to 8.1% total saturated fatty acid compositions.

Thus, introgressing genes from Tripsacum into Corn Belt material greatly enhances both the grain and oil quality making it possible to develop new products from corn.

The present invention thus provides a number of unique properties of corn from Tripsacum-Maize hybrids and introgressed derivative lines. Various embodiments of the present invention provide three main categories of properties:
1) Composition Quality-Protein, Oil and Starch lines
   a. High Protein
   b. High Oil
   c. High Protein and High Oil
   d. High Starch
   e. High Density of the kernel weight/cc (NIR near infrared reflectance)–dry milling
   f. Low Density (useful for wet milling for starch recovery and germ for oil)

2) Oil Quality-Fatty Acid lines
  a. High Oleic acid
  b. High Total Saturated acids
  c. Low Total Saturated acids
  d. High Oleic and High Stearic acids (new)
3) Starch Quality-Thermal Property lines
  a. Low Onset of Gelatinization ($T_0G$)
  b. Low Percent Retrogradation (%R)
  c. High Percent Retrogradation (%R)
  d. High Peak-Height Index (PHI)
  e. Low Enthalpy of Gelatinization ($\Delta HG$)
  g. Low enthalpy of Retrogradation ($\Delta HR$)
  h. Narrow Range of Gelatinization ($R_nG$)
  i. Wide Range of Gelatinization ($R_nG$)

In various embodiments, the following corn lines provide exemplary embodiments for each category listed above, which are shown below with measured values of the relevant parameter or parameters from samples of the corn lines, and a normal value for conventional corn lines is provided for comparison:

| | | Pedigree | |
|---|---|---|---|
| 1a) | High Protein | Pedigree | Normal value: 10.6(%) |
| | GC#3892 | S2 of #13S1 × A632 | 17.4 |
| | GC#3805 | S2 of #13S1 sib | 16.4 |
| | GC#3978 | S2 of (W153R × #5S1) × #13S1 | 16.2 |
| | IuuN: 2332 | #87S1 × Mo17 | 18.1 |
| 1b) | High Oil | Pedigree | Normal value: 3.6(%) |
| | GC#3886 | S2 of #13S1 × A632 | 7.7 |
| | GC#4066 | S2 of (#5S1 × Mo17) × (#5S1 × Mo17) | 7.7 |
| | GC#3831 | S2 of #13S1 × #13S1 | 7.6 |
| | GC#3641 | S2 of #15S1 × #5S1 | 7.5 |
| | GC#3833 | S2 of #13S1 × #13S1 | 7.5 |
| | P96N: 392-4 | S1 of (Mo17 × #5s1) × (#5s1 × Mo 17) | 7.7 |
| 1c) | High Protein and High Oil | Pedigree | Normal value: 10.6/3.6(%/%) |
| | GC#3892 | S2 of #13S1 × A632 | 17.4/6.7 |
| | GC#3978 | S2 of (W153R × #5S1) × #13S1 | 16.2/6.2 |
| | GC#3892 | S2 of #13S1 × A632 | 17.4/6.7 |
| | GC#3831 | S2 of #13S1 × #13S1 | 14.8/7.6 |
| 1d) | High Starch | Pedigree | Normal value: 70.9 |
| | GC#3872 | S2 of W153R × #13S1 | 74.5 |
| | GC#3850 | S2 of #13S1 × Mo17 | 73.7 |
| 1e) | High Density | Pedigree | Normal value: 1.285 |
| | GC#3904 | S2 of W153R × #13S1 | 1.358 |
| | GC#3903 | S2 of W153R × #13S1 | 1.349 |
| | GC#3805 | S2 of #13S1 × #13S1 | 1.348 |
| | GC#3956 | S2 of #13S1 × #13S1 | 1.347 |
| | GC#3940 | S2 of #13S1 × #13S1 | 1.343 |
| 1f) | Low Density | Pedigree | Normal value: 1.285 |
| | GC#3979 | S2 of (W153R × #5S1) × #13S1 | 1.106 |
| | GC#3827 | S2 of #13S1 × #13S1 | 1.117 |
| 2a) | High Oleic acid | Pedigree | Normal value: 22.9 |
| | GC#5687 | S2 of (W153R × #5s1) × #13s1 | 70.1% |
| 2b) | High Total Saturated Fatty Acids | Pedigree | Normal value: 11.6% |
| | GC#6175 (ATCC Accession number 209734) | S3 of B73 × #88S1 | 23% |
| 2c) | Low Total Saturated acids | Pedigree | Normal value: 11.6% |
| | GC#3905 | S2 of W153R × #13S1 | 6.7% |
| 2d) | High Oleic and High Stearic acids | Pedigree | Normal value: 22.9/1.8 |
| | GC#4674 | S2 of #5S1 | 67.8/7.6 |
| | GC#4679 | S2 of #5S1 | 55.0/8.4 |

-continued

| | | Pedigree | Normal value: 67.9° C. |
|---|---|---|---|
| 3a) | Low T$_0$G | | |
| | GC#166 | :#17S1 | 62.1° C. |
| | GC#187 | #17S1 × B73 | 59.6° C. |
| 3b) | Low %R | Pedigree | Normal value: 56.4% |
| | GC#7 | #5S1 | 36.4 |
| | GC#8 | #5S1 × A619 | 40.4 |
| 3c) | High %R | Pedigree | Normal value: 56.4% |
| | GC#109 | H99 × #13S1 | 85.7 |
| | GC#198 | B14A × #17S1 | 76.3 |
| 3d) | High PHI | Pedigree | Normal value: 1.1 |
| | GC#20 | #5S1 × Mo17 | 1.43 |
| | GC#43 | A632 × #5S1 | 1.35 |
| | GC#80 | #13S1 × B14A | 1.29 |
| | GC#139 | #5S1 × A632 | 1.35 |
| | GC#164 | W153R × #15S1 | 1.60 |
| 3e) | Low ΔHG | Pedigree | Normal value 3.5 cal/g |
| | GC#109 | H99 × #13S1 | 2.5 |
| 3f) | Low ΔHR | Pedigree | Normal value: 1.9 cal/g |
| | GC#1743 | S1 of B73 × #13S1 | 1.1 |
| 3g) | Narrow R$_n$G | Pedigree | Normal value: 6.3° C. |
| | GC#20 | #5S1 × Mo17 | 4.5 |
| | GC#43 | A632 × #5S1 | 4.8 |
| | GC#80 | #13S1 × B14A | 4.9 |
| | GC#139 | #5S1 × A632 | 4.6 |
| | GC#164 | W153R × #15S1 | 4.3 |
| 3h) | Wide R$_n$G | Pedigree | Normal value: 6.3° C. |
| | GC#1322 | (Mo17 × #5S1) × (#5S1 × Mo17) | 18.3 |

It is understood that the above description is intended to be illustrative, and not restrictive. Many other embodiments will be apparent to those of skill in the art upon reviewing the above description. The scope of the invention should, therefore, be determined with reference to the appended claims, along with the full scope of equivalents to which such claims are entitled.

What is claimed is:

1. A corn seed produced by the process of introgressing *Tripsacum dactyloides L.* genetic material from a *Zea mays X Tripsacum dactyloides L.* hybrid into a *Zea mays* genome, wherein said *Zea mays X Tripsacum dactyloides L.* hybrid is selected from the group consisting of recovered lines #5S1, #13S1, and #15S1 deposited as ATCC Nos. PTA-5159, PTA-5158, and PTA-5160 respectively, and wherein expression of said *Tripsacum dactyloides L.* genetic material results in the corn seed having a seed weight greater than about 0.15 grams, when measured at 15% moisture.

2. A corn seed according to claim 1, wherein the corn seed produces a corn plant that produces seeds having an average seed weight of approximately 0.18 grams or greater on a 15% moisture basis, and an oleic acid content of approximately 50% or greater, relative to the total fatty acid content of the seed.

3. A corn seed according to claim 1, wherein the corn seed produces a corn plant that produces seeds having a yellow and/or white seed coat.

4. A corn seed according to claim 1, wherein the corn seed produces a corn plant that produces seeds having an average seed weight of approximately 0.15 grams or greater at 15% moisture, and a protein content by weight of approximately 10% or greater.

5. A corn seed according to claim 1, wherein the corn seed produces a corn plant that produces seeds having an average seed weight of approximately 0.15 grams or greater, and a protein content by weight at 15% moisture of approximately 10% or greater, and an oil content by weight of approximately 4% or greater.

6. A corn seed according to claim 1, wherein the corn seed produces a corn plant that produces seeds having an average seed weight of approximately 0.15 grams or greater, and an oil content by weight at 15% moisture of approximately 4% or greater.

7. A corn seed according to claim 4, wherein the corn seed produces a corn plant that produces seeds having a yellow and/or white seed coat.

8. A corn seed according to claim 1, wherein the corn seed produces a corn plant that produces seeds having a starch content that has a peak onset temperature of gelatinization of approximately 64 degrees centigrade or lower.

9. A corn seed according to claim 1, wherein the corn seed produces a corn plant that produces seeds having a starch content that has a peak height index of gelatinization of approximately 1.3 or higher.

10. A corn seed according to claim 1, wherein the corn seed produces a corn plant that produces seeds having a starch content that has a percentage retrogradation of approximately 40 percent or lower.

11. A corn seed according to claim 1, wherein the corn seed produces a corn plant that produces seeds having a starch content that has an enthalpy value of gelatinization of approximately 2.6 or less.

12. A corn plant produced from the seed of claim 1 or parts thereof.

13. Seed of the corn plant of claim 12, wherein said seed comprises said *Tripsacum dactyloides* genetic material.

14. Pollen of the plant of claim 12, wherein said pollen comprises said *Tripsacum dactyloides* genetic material.

15. Seed, of a *Zea mays* plant pollinated by the pollen of claim 14, said seed having *Tripsacum dactyloides L.* genetic material, the expression of which results in the seed having a seed weight greater than about 0.15 grams, when measured at 15% moisture.

16. An ovule of the plant of claim 12, wherein said ovule comprises said *Tripsacum dactyloides* genetic material.

17. A corn plant having all the physiological and morphological characteristics of the plant of claim 12.

18. A tissue culture of regenerable cells, the cells including genetic material from diploid tissue of the plant of claim 12, wherein the cells regenerate plants having all the morphological and physiological characteristics of the plant of claim 12.

19. A tissue culture of claim 18, comprising cultured cells derived from a plant part selected from the group consisting of leaves, roots, root tips, root hairs, flowers, seeds, embryos, stems, buds, cotyledons, hypocotyls, cells and protoplasts.

20. A corn plant produced from the tissue culture of claim 18, said corn plant having *Tripsacum dactyloides L.* genetic material, the expression of which in the seed of said corn plant results in the seed having a seed weight greater than about 0.15 grams, when measured at 15% moisture.

21. A method for producing a white-coated or yellow-coated corn seed having an oleic acid content of approximately 50% or greater by weight relative to the total fatty acid content of the seed, comprising:

crossing a first parent that is a *Zea mays* X *Tripsacum dactyloides L.* hybrid selected from the group consisting of recovered lines #5S1, 913S1, and #15S1 deposited as ATCC Nos. PTA-5159, PTA-5158, and PTA-5160 respectively, and that comprises *Tripsacum dactyloides L.* germplasm having genetic material encoding the oleic acid content, with a second parent that comprises a genetic determinant for yellow or white seed color, wherein said second parent is *Zea mays*.

* * * * *